US007186724B2

(12) United States Patent
Hendrix et al.

(10) Patent No.: US 7,186,724 B2
(45) Date of Patent: Mar. 6, 2007

(54) HETEROCYCLIC SUBSTITUTED CARBONYL DERIVATIVES AND THEIR USE AS DOPAMINE D₃ RECEPTOR LIGANDS

(75) Inventors: James A Hendrix, Hillsborough, NJ (US); Horst Hemmerle, Bad Soden (DE); Matthias Urmann, Eschborn, DE (US); Gregory M Shutske, Pittstown, NJ (US); Jospeh T Strupczewski, Flemington, NJ (US); Kenneth J Bordeau, Kintnersville, PA (US); John G Jurcak, Bethlehem, PA (US); Thaddeus Nieduzak, Bridgewater, NJ (US); Sharon A Jackson, Whitehouse Station, NJ (US); Paul Angell, Liberty Township, OH (US); James P Carey, Cincinnati, OH (US); George Lee, Somerville, NJ (US); David Fink, Lebanon, NJ (US); Jean-Fancois Sabuco, Paris (FR); Yulin Chiang, Convent Station, NJ (US); Nicola Collar, Madison, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 10/819,037

(22) Filed: Apr. 6, 2004

(65) Prior Publication Data
US 2004/0220173 A1 Nov. 4, 2004

Related U.S. Application Data

(63) Continuation of application No. 10/078,225, filed on Feb. 19, 2002, now abandoned.

(60) Provisional application No. 60/269,672, filed on Feb. 16, 2001.

(30) Foreign Application Priority Data
Jul. 19, 2001 (GB) ................... 0117577.7

(51) Int. Cl.
*A61K 31/496* (2006.01)
*C07D 409/04* (2006.01)
*C07D 409/14* (2006.01)
*A61K 31/4535* (2006.01)
*A61K 31/454* (2006.01)
*C07D 403/04* (2006.01)

(52) U.S. Cl. ............................ 514/252.13; 514/254.04; 514/254.06; 514/254.09; 544/368; 544/370; 544/371; 544/373; 544/376; 544/121; 544/360; 544/361; 544/362; 544/131; 544/295; 546/187; 546/193; 546/194; 546/198

(58) Field of Classification Search ................ 514/183, 514/252.12, 252.13, 252.08, 254.06, 254.04, 514/254.09; 544/358, 366, 371, 376, 368, 544/370, 373
See application file for complete search history.

(56) References Cited

U.S. PATENT DOCUMENTS

| 354,411 | A | | 12/1886 | Hardcastle et al. ........... 72/325 |
| 5,116,970 | A | * | 5/1992 | New et al. .................... 544/235 |
| 5,708,018 | A | * | 1/1998 | Haadsma-Svensson et al. ............................ 514/408 |
| 6,001,834 | A | * | 12/1999 | Strupczewski et al. ... 514/254.04 |

FOREIGN PATENT DOCUMENTS

WO   WO 00/21950   4/2000

OTHER PUBLICATIONS

Joseph T. Coyle et al, Science, 2191184-1190(1983).*
Cecil's Textbook of Medicine, vol. 2,2oth Edn., pp. 1992.*
Anne Bourson et al, J. Pharmacol. & Exptal. Thera.374, 173-274(1995).*
Lingford-Hughes et al, PubMed Abstract 12697627, also cited as Br. Med.Bull., 65,209-22(2003).*
PubMed Abstract 3925957, also cited as Kelly E. et al, Biochem. 34/15,2655-62(1985).*
Kelley et al,PubMed Abstract 12117573, also cited as Physiol. Behav., 76/3, 365-77(2002).*
Bressan et al, PubMed. 12900302, also cited as Am.J.Psychiatry, 160/8, 1413-20(2003).*
Campiani et al, PubMed Abstract 12930145, also cited as J.Med. Chem.,46/18,3822-39(2003).*
PubMed Abstract 11350861, also cited as Yoshikawa T et al, Br. J. Pharmacol. 133/2,253-60(2001).*
A. Bourson et al., Determination of the Role of the 5-ht6 Receptor in the Rat Brain: A Study Using Antisense Oligonucleotides, J. of Pharmacol & Exptal Thera. vol. 374, 1995, pp. 173-274.
R.A. Bressan et al., Is regionally selective D2/D3 dopamine occupancy sufficient to atypical antipsychotic effect? an in vivo quantitative [123I] epidepride SPET study of amisulpride-treated patients, PubMed 12900302, also cited as Am.J. Psychiatry, 160/8, pp. 1413-1420 (2003).

* cited by examiner

*Primary Examiner*—Emily Bernhardt
(74) *Attorney, Agent, or Firm*—Barbara E. Kurys

(57) ABSTRACT

The invention relates to heterocyclic substituted carbonyl derivatives that display selective binding to dopamine D₃ receptors. In another aspect, the invention relates to a method for treating central nervous system disorders associated with the dopamine D₃ receptor activity in a patient in need of such treatment comprising administering to the subject a therapeutically effective amount of said compounds for alleviation of such disorder. The central nervous system disorders that may be treated with these compounds include Psychotic Disorders, Substance Dependence, Substance Abuse, Dyskinetic Disorders (e.g. Parkinson's Disease, Parkinsonism, Neuroleptic-Induced Tardive Dyskinesia, Gilles de la Tourette Syndrome and Huntington's Disease), Dementia, Anxiety Disorders, Sleep Disorders, Circadian Rhythm Disorders and Mood Disorders. The subject invention is also directed towards processes for the preparation of the compounds described herein as well as methods for making and using the compounds as imaging agents for dopamine D₃ receptors.

40 Claims, No Drawings

HETEROCYCLIC SUBSTITUTED CARBONYL DERIVATIVES AND THEIR USE AS DOPAMINE $D_3$ RECEPTOR LIGANDS

CROSS REFERENCE TO RELATED APPLICATIONS

This application is a continuation application of U.S. application Ser. No. 10/078,225 filed Feb. 19, 2002 which claims the benefit of U.S. Provisional Application No. 60/269,672 filed Feb. 16, 2001 and GB 0117577.7 filed Jul. 19, 2001, which are hereby incorporated by reference herein in their entireties.

BACKGROUND OF THE INVENTION

The subject invention relates to novel heterocyclic derivatives that selectively bind to the dopamine $D_3$ receptor. The therapeutic effect of currently available antipsychotic agents (neuroleptics) is generally believed to be exerted via blockade of $D_2$ receptors; however this mechanism is also thought to be responsible for undesireable extrapyramidal side effects (eps) associated with many neuroleptic agents. Without wishing to be bound by theory, it has been suggested that blockade of the dopamine $D_3$ receptor may give rise to beneficial antipsychotic activity without significant eps. (see for example Sokoloff et al, Nature, 1990; 347:146–151; and Schwartz et al, Clinical Neuropharmacology, Vol 16, No. 4, 295–314, 1993). This receptor is shown in high abundance in brain regions associated with emotional and cognitive functions. Compounds that selectively bind to the dopamine $D_3$ receptor are useful in treating certain central nervous system disorders. These central nervous system disorders include the following indications:

1) Psychoses (including schizophrenia)—See, for example, *Biochem Pharmacol*, 1992, 3(4), 659–66; *Clin Neuropharmacol*, 1993,16(4), 295–314; *Neuropsychopharmacology*, 1997, 16(6), 375–84; *Am J Psychiatry*, 1999,156 (4), 610–616; *Psychopharmacology (Berl)*, 1995, 120(1), 67–74.
2) Substance dependence and substance abuse—See, for example, Neuroreport,1997, 8(9–10), 2373–2377; *J Pharmacol Exp Ther*, 1996, 278(3), 1128–37; *Brain Res Mol Brain Res*, 1997, 45(2), 335–9.
3) Mood Disorders (including mania, depressive disorders and bipolar disorders)—See, for example, *Clin Neuropharmacol*, 1998, 21(3),176–80; *Am J Med Genet*, 1998, 81(2),192–4; *J Clin Psychiatry*, 1995,56(11), 514–518; *J Clin Psychiatry*, 1995, 56(9), 423–429; *Am J Med Genet*, 1995, 60(3), 234–237; *Pharmacopsychiatry*, 1999, 32(4), 127–135; *J Affect Disord*, 1999, 52(1–3), 275–290; *Am J Psychiatry*, 1999, 156(4), 610–616.
4) dyskinetic disorders (including Parkinson's Disease, Parkinsonism, Neuroleptic-Induced Tardive Dyskinesia and Gilles de la Tourette Syndrome)—See, for example, *Clin Neuropharmacol*, 2000, 23(1), 34–44; *Eur J Pharmacol*, 1999, 385(1), 39–46.
5) sleep disorders (including narcolepsy)—The $D_3$ agonist pramipexole causes narcolepsy. A $D_3$ antagonist would be useful for reversing this undesireable side effect. See *Aust Fam Physician*, 1999, 28(7), 737; *Neurology*, 1999, 52(9), 1908–1910.
6) anxiety disorders (including obsessive compulsive disorders)—See, for example, *Physiol Behav*, 1997, 63(1), 137–141; *J Clin Psychiatry*, 1995, 56(9), 423–429; *J Psychiatry Neurosci*, 2000, 25(2), 185; *J Affect Disord*, 1999, 56(2–3), 219–226.
7) nausea—Dopamine antagonists are used alone and in combination with 5HT3 antagonists. See, for example, *Support Care Cancer*, 1998, 6(1), 8–12; *Support Care Cancer*, 2000, 8(3), 233–237; *Eur J Anaesthesiol*, 1999, 16(5), 304–307.
8) dementia—See, for example, *Behav Brain Res*, 2000, 109(1), 99–111; *Neuroscience*, 1999, 89(3), 743–749.

Dopamine $D_3$ receptor ligands are also useful for the treatment of renal dysfunction. See, for example, WO 200067847.

SUMMARY OF THE INVENTION

This invention relates to a class of compounds and pharmaceutically acceptable salts thereof which are selective modulators of dopamine $D_3$ receptors. The compounds may act as agonists, partial agonists, antagonists or allosteric modulators of dopamine $D_3$ receptors, and are useful for a variety of therapeutic applications.

In another aspect, the invention relates to a method for treating central nervous system disorders associated with the dopamine $D_3$ receptor activity in a patient in need of such treatment comprising administering to the subject a therapeutically effective amount of a compound described herein for alleviation of such disorder. The central nervous system conditions or disorders that may be treated with these compounds include Psychotic Disorders, Substance Dependence, Substance Abuse, Dyskinetic Disorders (e.g. Parkinson's Disease, Parkinsonism, Neuroleptic-Induced Tardive Dyskinesia, Gilles de la Tourette Syndrome and Huntington's Disease), Nausea, Dementia, Anxiety Disorders, Sleep Disorders, Circadian Rhythm Disorders and Mood Disorders.

In yet another aspect, the subject invention is directed toward a pharmaceutical composition comprising an effective amount of a compound described herein with a pharmaceutically-acceptable carrier or diluent optionally in conjunction with one or more dopamine $D_1$, $D_2$, $D_4$, $D_5$ or 5HT receptor antagonists.

In yet another aspect, the subject invention is directed towards processes for the preparation of the class of compounds described herein.

Also within the scope of this invention are methods for using these novel compounds as imaging agents for dopamine $D_3$ receptors. Methods of using these compounds as imaging agents are presented, as are intermediates and methods for making the imaging agents.

DETAILED DESCRIPTION OF THE INVENTION

In accordance with the present invention, there are provided compounds of formula I A compound of the formula (I):

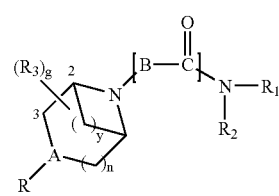

wherein

A is CH or N;

n is 1 or 2;
when n is 1, y is 0 or 2;
when n is 2, y is 0;
g is 1 or 2;
each $R_3$ is independently hydrogen, $C_1$–$C_6$alkyl, or
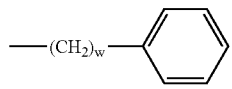
wherein w is 1, 2, or 3;
R is selected from the group consisting of (a)–(w):
a)
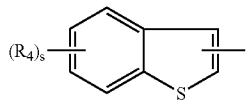
b)
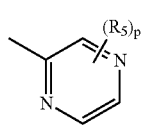
c)
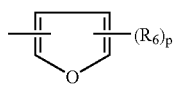
d)
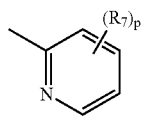
e)
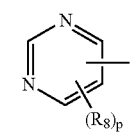
f)
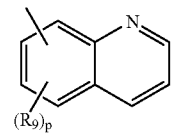
g)
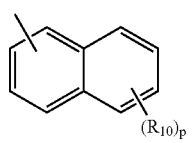
h)
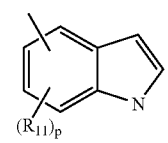
i)
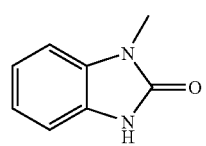
-continued
j)
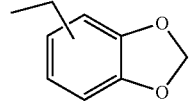
k)
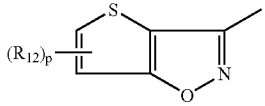
l)
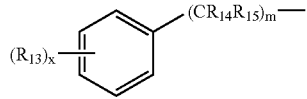
m)
—$CO_2R_{16}$
n)
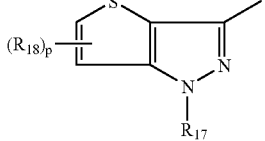
o)
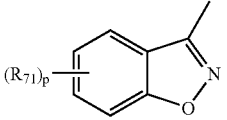
p)
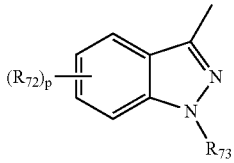
q)
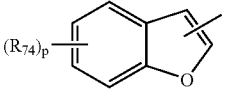
r)
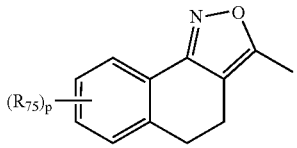
s)
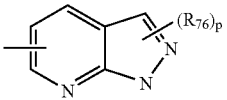
t)
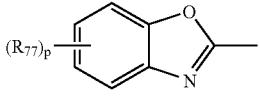
u)
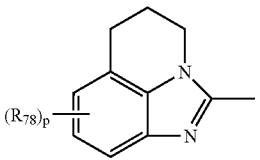

-continued

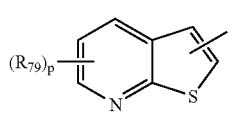  v)

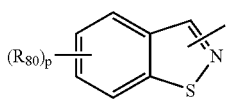  w)

wherein
  each $R_4$, $R_5$, $R_6$, $R_7$, $R_8$, $R_9$, $R_{10}$, $R_{11}$, $R_{12}$ and $R_{18}$ is independently hydrogen, $C_1$–$C_6$alkyl, halogen, trifluoromethyl, —$CO_2C_1$–$C_6$alkyl or —$CH_2OC_1$–$C_6$alkyl;
  each $R_{71}$, $R_{72}$, $R_{74}$ and $R_{80}$ is independently hydrogen, $C_1$–$C_6$alkyl, $C_1$–$C_6$alkoxy, halogen, trifluoromethyl, —$CO_2C_1$–$C_6$alkyl or —$CH_2OC_1$–$C_6$alkyl;
  $R_{73}$ is hydrogen, alkyl, pyridyl, benzyl, —$CH_2CF_3$, —$CO_2C_1$–$C_6$alkyl, phenyl optionally substituted with halogen, trifluoromethyl, trifluoromethoxy or $R_{73}$ is

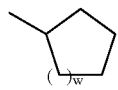

wherein w is 1, 2 or 3 as hereinbefore defined;
  each $R_{75}$ is hydrogen, halogen, $C_1$–$C_6$alkyl or $C_1$–$C_6$alkoxy;
  each $R_{76}$ is hydrogen, halogen, —CN or $C_1$–$C_6$alkyl;
  each $R_{77}$ is hydrogen, halogen, $C_1$–$C_6$alkyl or $C_1$–$C_6$alkoxy;
  each $R_{78}$ hydrogen, halogen, $C_1$–$C_6$alkyl or $C_1$–$C_6$alkoxy;
  each $R_{79}$ hydrogen, halogen, $C_1$–$C_6$alkyl or $C_1$–$C_6$alkoxy;
  p, s and x are 0, 1, or 2;
  each $R_{13}$ is independently hydrogen, $C_1$–$C_6$alkyl, halogen, benzyl, trifluoromethyl, $C_1$–$C_6$alkoxy, nitro, —CN, or —$COC_1$–$C_6$alkyl;
  $R_{16}$ is $C_1$–$C_6$alkyl;
  each $R_{14}$ and $R_{15}$ is independently hydrogen or $C_1$–$C_6$alkyl;
  $R_{17}$ is hydrogen, $C_1$–$C_6$alkyl, Ar, —COAr, —CONHAr or —$SO_2$—Ar wherein
    Ar is a phenyl group which is optionally mono- or di-substituted with substituents independently selected from $C_1$–$C_6$alkyl, halogen, trifluoromethyl, $C_1$–$C_6$alkoxy, nitro, CN and $COC_1$–$C_6$alkyl; and
  m is 0, 1, or 2;

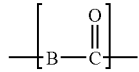

represents a group selected from (a)–(f):

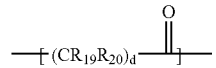  a)

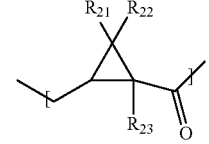  b)

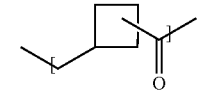  c)

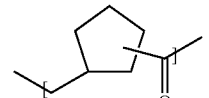  d)

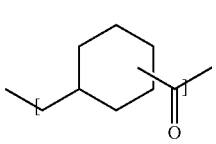  e)

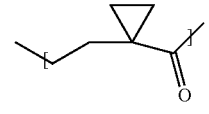  f)

wherein
  each $R_{19}$ and $R_{20}$ is independently hydrogen, hydroxy or $C_1$–$C_6$alkyl;
  $R_{21}$, $R_{22}$, and $R_{23}$ are each independently hydrogen or $C_1$–$C_3$ linear alkyl; and
  d is 3 or 4;
$R_1$ is a) hydrogen;
  b) $C_1$–$C_6$alkyl optionally mono- or di-substituted with hydroxy; or

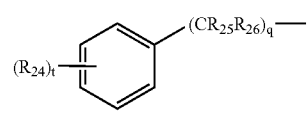  c)

wherein
  each $R_{24}$ is independently hydrogen or $C_1$–$C_6$alkyl;
  each $R_{25}$, and $R_{26}$ is independently hydrogen or $C_1$–$C_6$alkyl;
  t is 0 or 1; and
  q is 0 or 1;
$R_2$ is a group selected from (a)–(jj):

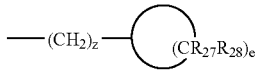  (a)

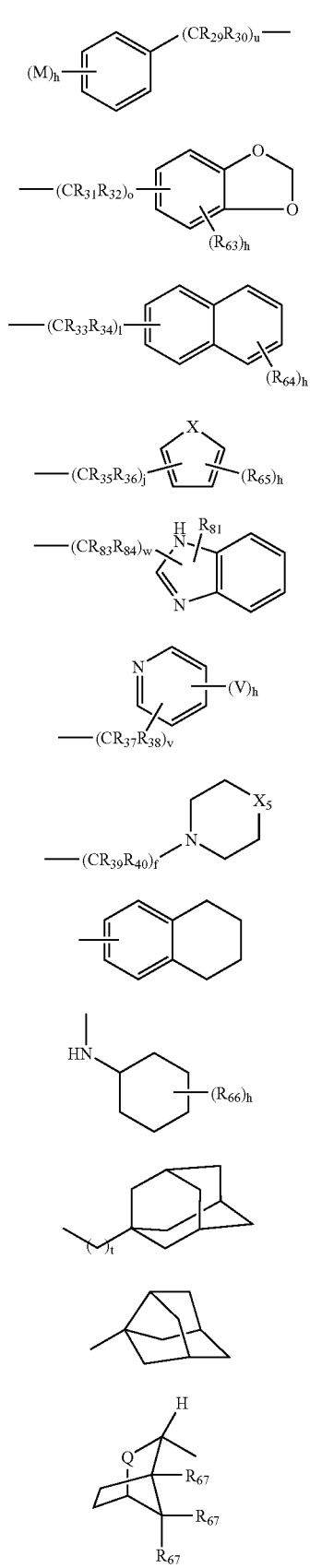
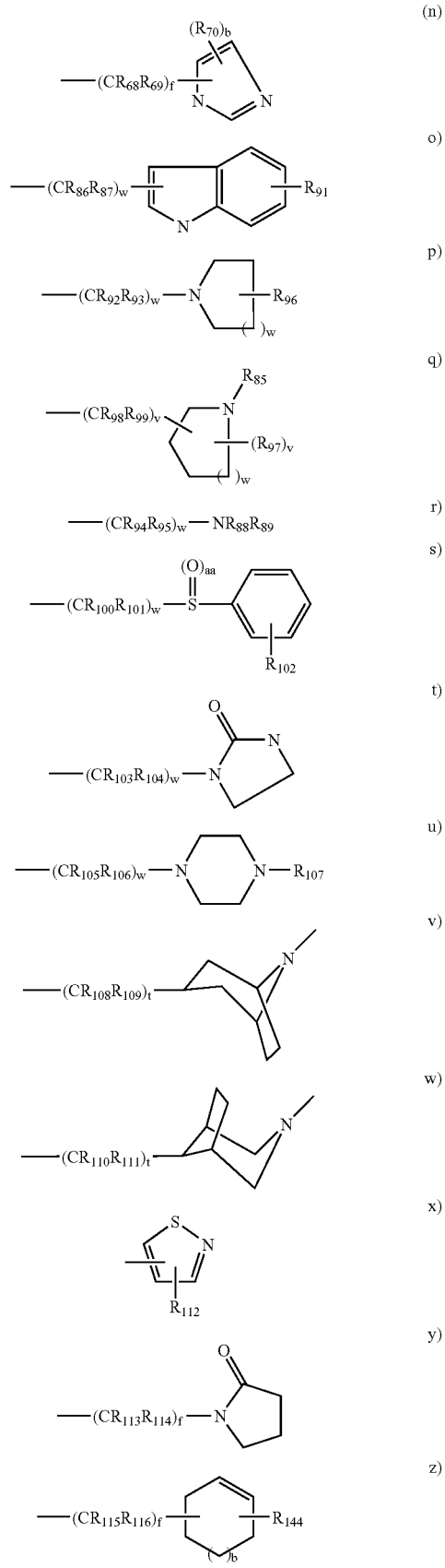

-continued

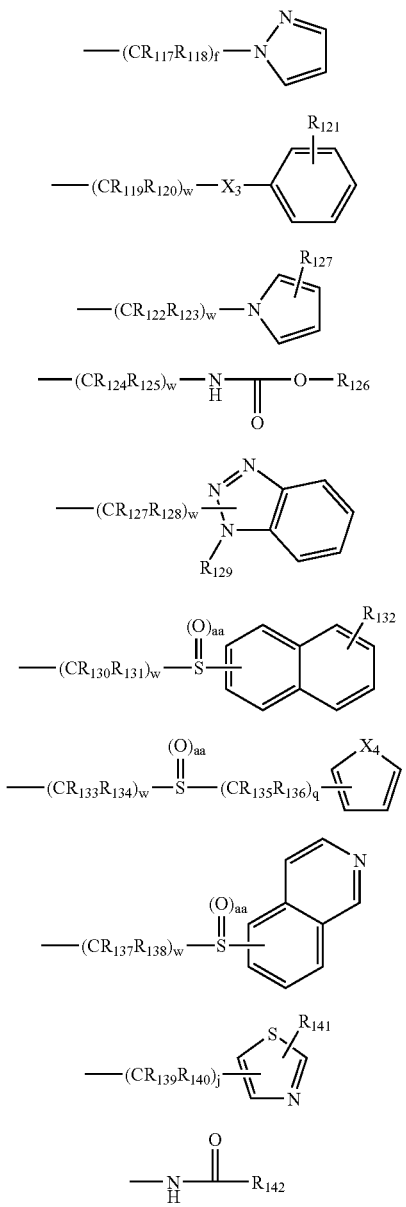

aa)

bb)

cc)

dd)

ee)

ff)

gg)

hh)

ii)

jj)

wherein
each $R_{27}$ and $R_{28}$ is independently selected from:
(1) hydrogen;
(2) $C_1$–$C_6$alkyl;
(3) $C_1$–$C_6$alkoxy;
(4) —$CO_2$—$R_{43}$ wherein $R_{43}$ is hydrogen or $C_1$–$C_6$alkyl;
(5) hydroxy;
(6) —$(CH_2)_a$—$OR_{44}$ wherein a is 1, 2 or 3 and $R_{44}$ is hydrogen or $C_1$–$C_6$alkyl;
(7) —(CO)—$NR_{45}R_{46}$ wherein $R_{45}$ and $R_{46}$ are each independently hydrogen, $C_1$–$C_2$alkyl, or $R_{45}$ and $R_{46}$ taken together form a 5-membered monocyclic ring;
z is 0 or 1;
e is 2, 3, 4, 5, 6 or 7;
h is 0, 1, 2 or 3;

u is 0, 1, 2, 3 or 4;
o is 0 or 1;
l is 0 or 1;
j is 0, 1, 2 or 3;
v is 0, 1, 2, 3 or 4;
w is 1, 2 or 3 as hereinbefore defined;
f is 1, 2, 3 or 4;
t is 0 or 1 as hereinbefore defined;
b is 0, 1 or 2;
q is 0 or 1 as hereinbefore defined;
aa is 0 or 2;
X is O, S or $NR_{90}$ wherein $R_{90}$ is hydrogen, $C_1$–$C_6$alkyl, or

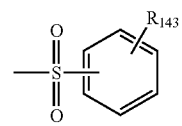

wherein $R_{143}$ is hydrogen or alkyl;
each M and V is a group independently selected from hydrogen, halogen, $C_1$–$C_6$alkyl, $C_1$–$C_6$alkoxy, trifluoromethyl, hydroxy, phenyl, phenoxy, —$SO_2NH_2$ or

or
—$NR_{48}R_{49}$ wherein $R_{48}$ and $R_{49}$ are each independently hydrogen or $C_1$–$C_2$alkyl;
each $R_{31}$, $R_{32}$, $R_{33}$, $R_{34}$, $R_{35}$, $R_{36}$, $R_{37}$, $R_{38}$, $R_{39}$, $R_{40}$, $R_{68}$, and $R_{69}$ is independently hydrogen or $C_1$–$C_6$alkyl;
each $R_{29}$, $R_{30}$ is independently hydrogen, phenyl or $C_1$–$C_6$alkyl;
each $R_{83}$, $R_{84}$, $R_{86}$, $R_{87}$, $R_{88}$, $R_{89}$, $R_{92}$, $R_{93}$, $R_{98}$, $R_{99}$, $R_{94}$, $R_{95}$, $R_{100}$, $R_{101}$, $R_{103}$, $R_{104}$, $R_{105}$, $R_{106}$, $R_{108}$, $R_{109}$, $R_{110}$, $R_{111}$, $R_{113}$, $R_{114}$, $R_{115}$, $R_{116}$, $R_{117}$, $R_{118}$, $R_{119}$, $R_{120}$, $R_{122}$, $R_{123}$, $R_{124}$, $R_{125}$, $R_{127}$, $R_{128}$, $R_{130}$, $R_{131}$, $R_{133}$, $R_{134}$, $R_{135}$, $R_{136}$, $R_{137}$, $R_{138}$, $R_{139}$ and $R_{140}$ is independently hydrogen or $C_1$–$C_6$alkyl;
each $R_{63}$, $R_{64}$ and $R_{65}$ is independently hydrogen, halogen, $C_1$–$C_6$alkyl or $C_1$–$C_6$alkoxy;
each $R_{66}$ is independently hydrogen, hydroxy, $C_1$–$C_6$alkyl or $C_1$–$C_6$alkoxy;
Q is $CH_2$, CHOH or C=O;
$X_5$ is O or S;
each $R_{67}$ is independently hydrogen or $C_1$–$C_6$alkyl;
$R_{70}$ is hydrogen, $C_1$–$C_6$alkyl, halogen, nitro or a phenyl group optionally mono-substituted with $C_1$–$C_6$alkyl, halogen or trifluoromethyl;
$R_{81}$ is hydrogen, $C_1$–$C_6$alkyl, or —$CO_2C_1$–$C_6$alkyl;
$R_{91}$ is hydrogen, halogen, $C_1$–$C_6$alkyl or $C_1$–$C_6$alkoxy;
$R_{96}$ is hydrogen, $C_1$–$C_6$alkyl or

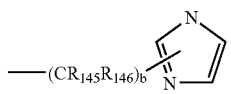

wherein $R_{145}$ and $R_{146}$ are each independently hydrogen or $C_1$–$C_6$alkyl and b is 0, 1 or 2 as hereinbefore defined;

$R_{97}$ is hydrogen or $C_1$–$C_6$alkyl;

each $R_{102}$ is independently hydrogen, halogen, $C_1$–$C_6$alkyl or $C_1$–$C_6$alkoxy;

$R_{107}$ is hydrogen or $C_1$–$C_6$alkyl;

each $R_{121}$ is independently hydrogen, halogen, $C_1$–$C_6$alkyl or $C_1$–$C_6$alkoxy;

$R_{127}$ is hydrogen or $C_1$–$C_6$alkyl;

$R_{126}$ is $C_1$–$C_6$alkyl or benzyl;

$R_{129}$ is hydrogen or $C_1$–$C_6$alkyl;

$R_{132}$ is hydrogen, $C_1$–$C_6$alkyl, halogen or $C_1$–$C_6$alkoxy;

$X_3$ is O or —$NR_{127}$ wherein $R_{127}$ is hydrogen or $C_1$–$C_6$alkyl;

$X_4$ is O, S or —$NR_{143}$ wherein $R_{143}$ is hydrogen or $C_1$–$C_6$alkyl;

$R_{141}$ is hydrogen, $C_1$–$C_6$alkyl or amino;

$R_{142}$ is benzyl or phenyl each of which may be optionally substituted with $C_1$–$C_6$alkyl, halogen or $C_1$–$C_6$alkoxy;

$R_{144}$ is hydrogen or $C_1$–$C_6$alkyl;

$R_{85}$ is hydrogen, $C_1$–$C_6$alkoxy, $C_1$–$C_6$alkyl, —$CO_2C_1$–$C_6$alkyl, $C(O)C_1$–$C_6$alkyl or a group selected from the following:

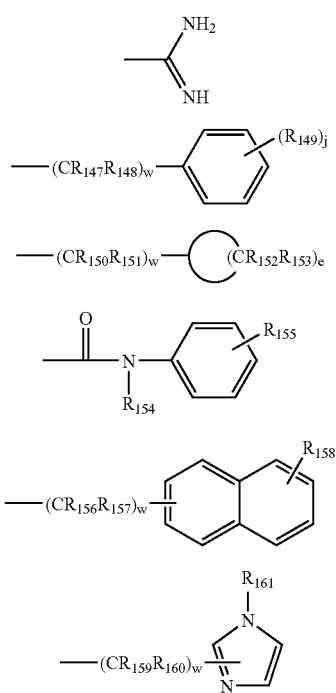

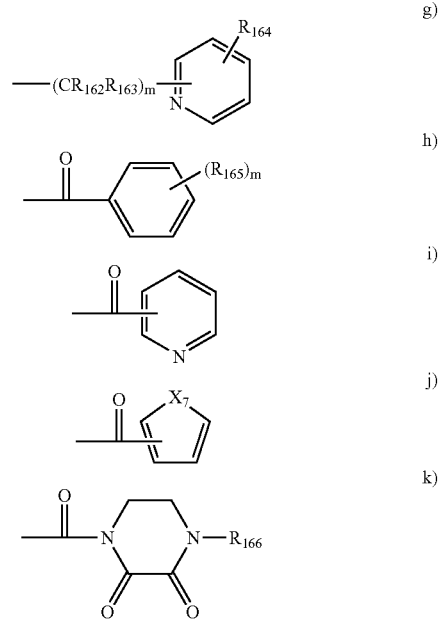

wherein j is 0, 1, 2 or 3 as hereinbefore defined;

w is 1, 2 or 3 as hereinbefore defined;

m is 0, 1 or 2 as hereinbefore defined;

e is 2, 3, 4, 5, 6 or 7 as hereinbefore defined;

each $R_{147}$, $R_{148}$, $R_{150}$, $R_{151}$, $R_{152}$, $R_{153}$, $R_{156}$, $R_{157}$, $R_{159}$, $R_{160}$, $R_{162}$ and $R_{163}$ is independently hydrogen or $C_1$–$C_6$alkyl;

$R_{149}$ is hydrogen, halogen, $C_1$–$C_6$alkyl, phenoxy, trifluoromethyl or trifluoromethoxy;

$R_{155}$ is hydrogen, halogen or $C_1$–$C_6$alkyl;

$R_{158}$ is hydrogen or $C_1$–$C_6$alkyl;

$R_{161}$ is hydrogen or $C_1$–$C_6$alkyl;

$R_{164}$ is hydrogen, halogen, $C_1$–$C_6$alkyl or trifluoromethyl;

$R_{165}$ is hydrogen, $C_1$–$C_6$alkyl or halogen;

$X_7$ is O or S or —$NR_{167}$ wherein $R_{167}$ is hydrogen or $C_1$–$C_6$alkyl;

$R_{166}$ is hydrogen or $C_1$–$C_6$alkyl;

or $R_1$ and $R_2$ are joined together to form a 5-, 6-, or 7-membered monocyclic saturated ring, and in which the ring is optionally mono- or di-substituted, the substituents independently selected from:

(1) $C_1$–$C_6$alkyl;

(2) —$CO_2$—($C_1$–$C_6$alkyl);

(3) —$NR_{50}R_{51}$ wherein $R_{50}$ and $R_{51}$ are each independently hydrogen, $C_1$–$C_6$alkyl, or a phenyl group which is optionally mono- or disubstituted with substituents independently selected from $C_1$–$C_6$alkyl, halogen or trifluoromethyl;

(4) —C(O)phenyl wherein the phenyl group is optionally mono- or disubstituted with substituents independently selected from $C_1$–$C_6$alkyl, halogen or trifluoromethyl;

(5) —$(CH_2)_mOR_{52}$ wherein $R_{52}$ is hydrogen or $C_1$–$C_2$alkyl or a phenyl group which is optionally mono- or disubstituted with substituents independently selected from $C_1$–$C_6$alkyl, halogen or trifluoromethyl, and m is 0, 1 or 2 as hereinbefore defined;

(6) —NR₅₄—COR₅₃ wherein R₅₄ is hydrogen or C₁–C₆alkyl and R₅₃ is hydrogen or C₁–C₂alkyl;
(7) =O;
(8) —CN;

(9) 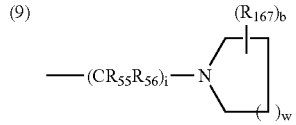

(10) 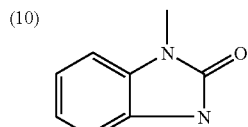

(11) 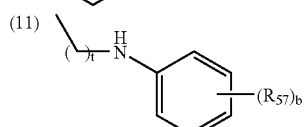

(12) 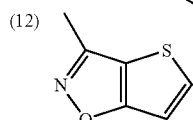

(13) 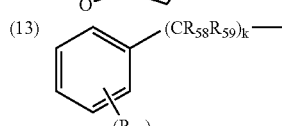

(14) 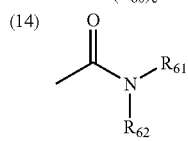

(15) 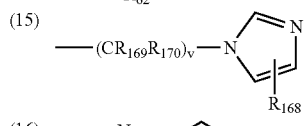

(16) 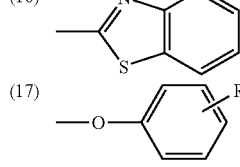

(17) 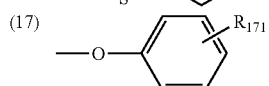

wherein
b is 0, 1 or 2 as hereinbefore defined;
w is 1, 2 or 3 as hereinbefore defined;
t is 0 or 1 as hereinbefore defined;
i is 0, 1 or 2;
v is 0, 1, 2, 3 or 4 as hereinbefore defined;
k is 0 or 1 as hereinbefore defined;
c are 0, 1 or 2;
$R_{167}$ is hydrogen or C₁–C₆alkyl;
each $R_{55}$, $R_{56}$, $R_{58}$, $R_{59}$, $R_{169}$ and $R_{170}$ is independently hydrogen or C₁–C₆alkyl;
each $R_{57}$ is independently hydrogen, halogen or C₁–C₆alkyl;
each $R_{60}$ is independently hydrogen, halogen or C₁–C₆alkyl;
$R_{61}$ and $R_{62}$ are each independently hydrogen or C₁–C₆alkyl;
$R_{168}$ is hydrogen, thienyl or furanyl;

$R_{171}$ is hydrogen, C₁–C₆alkyl, halogen, trifluoromethyl or trifluoromethoxy;
or R₁ and R₂ are joined together to form a group of formula X;

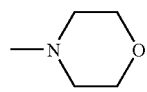
(X)

or R₁ and R₂ are joined together to form the group of formula (Y)

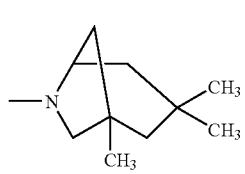
(Y)

or R₁ and R₂ are joined together to form any of the following groups:

(a) 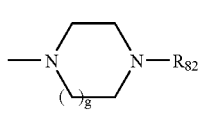

(b) 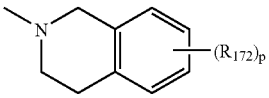

(c) 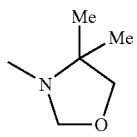

(d) 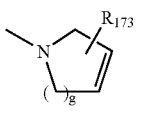

(e) 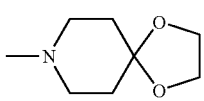

wherein
g is 1 or 2 as hereinbefore defined;
p is 0, 1 or 2 as hereinbefore defined;
$R_{172}$ is hydrogen, C₁–C₆alkyl or C₁–C₆alkoxy;
$R_{173}$ is hydrogen, C₁–C₆alkyl or phenyl optionally mono- or disubstituted with C₁–C₆alkyl or halogen; and
$R_{82}$ is a substituent selected from the following groups:
(a) C₁–C₆alkyl optionally substituted with hydroxy;
(b) C₁–C₆alkenyl;
(c) C₁–C₆alkoxy;
(d) —(CH₂)OC₁–C₆alkyl;

(e)

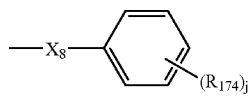

wherein $X_8$ is —$(CR_{175}R_{176})_h$— or —$(CR_{177}=CR_{188})$— wherein each $R_{174}$ is independently hydrogen, $C_1$–$C_6$alkyl, halogen, trifluoromethyl, $C_1$–$C_6$alkoxy or benzyloxy;
h is 0, 1, 2 or 3 as hereinbefore defined;
each $R_{175}$, $R_{176}$, $R_{177}$ and $R_{178}$ is independently hydrogen or $C_1$–$C_6$alkyl; and
j is 0, 1, 2 or 3 as hereinbefore defined;

(f)

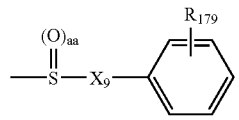

wherein $X_9$ is —$(C_{180}R_{181})_j$— or —$(CR_{184}R_{185}CR_{186}=CR_{187})$— or —$(CR_{182}=CR_{183})$—
wherein
aa is 0 or 2 as hereinbefore defined;
$R_{179}$ is hydrogen, $C_1$–$C_6$alkyl, halogen, trifluoromethyl, $C_1$–$C_6$alkoxy, benzyloxy or phenyl;
each $R_{180}$, $R_{181}$, $R_{182}$, $R_{183}$, $R_{184}$, $R_{185}$, $R_{186}$ and $R_{187}$ is independently hydrogen or $C_1$–$C_6$alkyl;
j is 0, 1, 2, or 3 as hereinbefore defined;

(g)

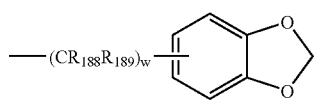

wherein w is 1, 2 or 3 as hereinbefore defined;
each $R_{188}$ and $R_{189}$ is independently hydrogen or $C_1$–$C_6$alkyl;

(h)

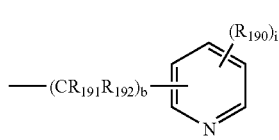

wherein
i is 0, 1 or 2 as hereinbefore defined;
each $R_{190}$ is independently hydrogen, alkyl or halogen;
b is 0, 1, or 2 as hereinbefore defined;
each $R_{191}$ and $R_{192}$ is independently hydrogen or $C_1$–$C_6$alkyl;

(i)

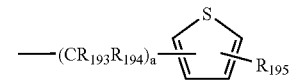

wherein
a is 1, 2 or 3 as hereinbefore defined;
each $R_{193}$ and $R_{194}$ is independently hydrogen or $C_1$–$C_6$alkyl;
$R_{195}$ is hydrogen, halogen or $C_1$–$C_6$alkyl;

(j)

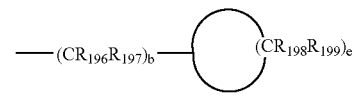

wherein
e is 2, 3, 4, 5 or 6 as hereinbefore defined;
b is 0, 1 or 2 as hereinbefore defined;
each $R_{196}$ and $R_{197}$ is independently hydrogen or $C_1$–$C_6$alkyl;
each $R_{198}$ and $R_{199}$ is independently hydrogen or $C_1$–$C_6$alkyl;

(k)

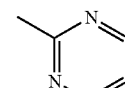

(l)

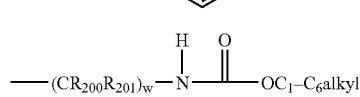

wherein
each $R_{200}$ and $R_{201}$ is independently hydrogen or $C_1$–$C_6$alkyl;
w is 1, 2 or 3 as hereinbefore defined;

(m)

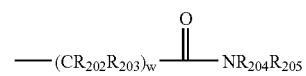

wherein
each $R_{202}$, $R_{203}$, $R_{204}$ and $R_{205}$ is independently hydrogen or $C_1$–$C_6$alkyl; and
w is 1, 2 or 3 is as hereinbefore defined;

(n)
—$(CR_{206}R_{207})_w$—$OC_1$–$C_6$alkyl
wherein
$C_1$–$C_6$alkyl is optionally substituted with hydroxy;
each $R_{206}$ and $R_{207}$ is independently hydrogen or $C_1$–$C_6$alkyl; and
w is 1, 2 or 3 as hereinbefore defined;

(o)
—$(CR_{208}R_{209})_w$—$NR_{210}R_{211}$ wherein
each $R_{208}$, $R_{209}$, $R_{210}$ and $R_{211}$ is independently hydrogen or $C_1$–$C_6$alkyl;
w is 1, 2 or 3 as hereinbefore defined;

(p)

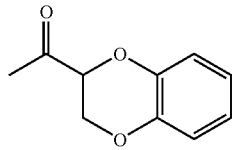

with the proviso that when n is 1; and y is 0; and $R_3$ is hydrogen or $C_1$–$C_6$alkyl; and

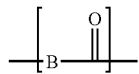

is group (a);

and R is group:
- (a) wherein $R_4$ is hydrogen, halogen or $C_1$–$C_6$alkyl, and $R_1$ is hydrogen or unsubstituted $C_1$–$C_6$alkyl,
  then $R_2$ cannot be a group of the following formula:
  - (a) wherein z is 0,
  - (b) wherein u is 0 and M is hydrogen, halogen, $C_1$–$C_6$alkyl, or trifluoromethyl,
  - (c) wherein o is 0,
  - (d) wherein l is 0,
  - (e) wherein j is 0,
  - (g) wherein v is 0, or
  - (i);
  and also when R is the group of formula (a), $R_1$ and $R_2$ cannot be joined together to form the group of formula Y or a 5-, 6-, or 7-membered monocyclic ring wherein said ring is unsubstituted or mono- or di-substituted with $C_1$–$C_6$alkyl;
- (b) and $R_1$ is hydrogen or unsubstituted $C_1$–$C_6$alkyl, then $R_2$ cannot be a group of the following formula:
  - (a),
  - (b),
  - (c) wherein o is 0,
  - (d) wherein l is 0,
  - (i),
  - (k),
  - (l), or
  - (m) wherein Q is $CH_2$;
  and also when R is the group of formula (b), $R_1$ and $R_2$ cannot be joined together to form a group of formula X or a group of formula Y or a 5-, 6-, or 7-membered monocyclic ring wherein said ring is unsubstituted or mono- or di-substituted with $C_1$–$C_6$alkyl or

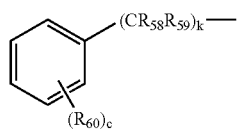

- (c) and $R_1$ is hydrogen or unsubstituted $C_1$–$C_6$alkyl, then $R_2$ cannot be a group of the following formula:
  - (c) wherein o is 0,
  - (d) wherein l is 0, or
  - (i);
- (d) and $R_1$ is hydrogen or unsubstituted $C_1$–$C_6$alkyl, then $R_2$ cannot be a group of the following formula:
  - (a),
  - (b) wherein u is 1,
  - (c) wherein o is 0,
  - (d),
  - (i),
  - (k),
  - (l), or
  - (m) wherein Q is $CH_2$;
  and also when R is the group of formula (d), $R_1$ and $R_2$ cannot be joined together to form a group of formula X or a group of formula Y or a 5-, 6-, or 7-membered monocyclic ring wherein said ring is unsubstituted or mono- or di-substituted with $C_1$–$C_6$alkyl or

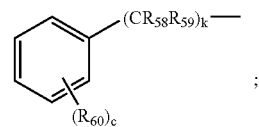

- (e) and $R_1$ is hydrogen or unsubstituted $C_1$–$C_6$alkyl, then $R_2$ cannot be a group of the following formula:
  - (a),
  - (b),
  - (c) wherein o is 0,
  - (d),
  - (i),
  - (k),
  - (l), or
  - (m) wherein 0 is $CH_2$;
  and also when R is the group of formula (e), $R_1$ and $R_2$ cannot be joined together to form a group of formula X or a group of formula Y or a 5-, 6-, or 7-membered monocyclic ring wherein said ring is unsubstituted or mono- or di-substituted with $C_1$–$C_6$alkyl or

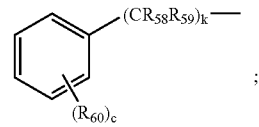

- (f) and $R_1$ is hydrogen or unsubstituted $C_1$–$C_6$alkyl, then $R_2$ cannot be a group of the following formula:
  - (a),
  - (b),
  - (c) wherein o is 0,
  - (d),
  - (i),
  - (k),
  - (l), or
  - (m) wherein Q is $CH_2$;

and also when R is the group of formula (f), $R_1$ and $R_2$ cannot be joined together to form a group of formula X or a group of formula Y or a 5-, 6-, or 7-membered monocyclic ring
wherein said ring is unsubstituted or mono- or di-substituted with $C_1$–$C_6$alkyl or

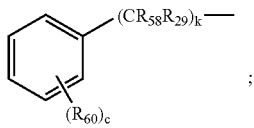

(g) and $R_1$ is hydrogen or unsubstituted $C_1$–$C_6$alkyl, then $R_2$ cannot be a group of the following formula:
(a),
(b) wherein u is 1,
(c) wherein o is 0,
(d),
(i),
(k),
(l), or
(m) wherein Q is $CH_2$;
and also when R is the group of formula (g), $R_1$ and $R_2$ cannot be joined together to form a group of formula X or a group of formula Y or a 5-, 6-, or 7-membered monocyclic ring
wherein said ring is unsubstituted or mono- or di-substituted with $C_1$–$C_6$alkyl or

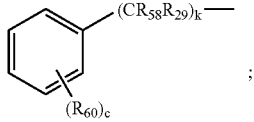

(h) and $R_1$ is hydrogen or unsubstituted $C_1$–$C_6$alkyl, then $R_2$ cannot be a group of the following formula:
(a),
(b),
(c) wherein o is 0,
(d),
(i),
(k),
(l), or
(m) wherein Q is $CH_2$;
and also when R is the group of formula (h), $R_1$ and $R_2$ cannot be joined together to form a group of formula X or a group of formula Y or a 5-, 6-, or 7-membered monocyclic ring
wherein said ring is unsubstituted or mono- or di-substituted with $C_1$–$C_6$alkyl or

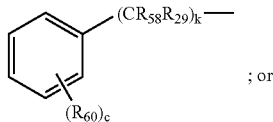

(j) then $R_1$ and $R_2$ cannot be joined together to form a group of formula Y or a 5-, 6-, or 7-membered monocyclic ring
wherein said ring is unsubstituted or mono- or di-substituted with $C_1$–$C_6$alkyl.

The subject invention is directed toward compounds or pharmaceutically acceptable salts of Formula I as depicted above in either racemic or pure stereoisomeric forms.

Terms used herein have the following meanings:

a) "Pharmaceutically acceptable salts" means either an acid addition salt or a basic addition salt which is compatible with the treatment of patients for the intended use.

"Pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents and which in comparison to their free base forms, generally demonstrate higher melting points.

"Pharmaceutically acceptable basic addition salts" means non-toxic organic or inorganic basic addition salts of the compounds of Formula (I) or any of its intermediates. Examples are alkali metal or alkaline-earth metal hydroxides such as sodium, potassium, calcium, magnesium or barium hydroxides; ammonia, and aliphatic, alicyclic, or aromatic organic amines such as methylamine, trimethylamine and picoline. The selection criteria for the appropriate salt will be known to one skilled in the art.

b) "Stereoisomers" is a general term for all isomers of the individual molecules that differ only in the orientation of their atoms in space. It includes mirror image isomers (enantiomers), geometric (cis/trans) isomers, and isomers of compounds with more than one chiral center that are not mirror images of one another (diastereoisomers).

c) "Alkyl" means a branched or straight chain alkyl or alkylene group, as is appropriate to the formula, specified by the amount of carbons in the alkyl, e.g., $C_1$–$C_6$ alkyl means a one, two, three, four, five or six carbon branched or straight chain alkyl or alkylene, as the case may be, or any ranges thereof, for example, but not limited to, C1–2, C1–3, C1–4, C1–5, C2–3, C2–4, C2–5, C2–C6, C3–C4, C3–5, C3–6, C4–5, C4–6, C5–6, etc.

d) "Patient" means a warm blooded animal, such as for example rat, mice, dogs, cats, guinea pigs, and primates such as humans.

e) "Treat" or "treating" means to alleviate symptoms, eliminate the causation of the symptoms either on a temporary or permanent basis, or to prevent or slow the appearance of symptoms of the named disorder or condition.

f) "Therapeutically effective amount" means a quantity of the compound which is effective in treating the named disorder or condition.

g) "Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

h) "Psychoses" or "Psychotic Disorders" means conditions wherein the patient experiences a major mental disorder of organic and/or emotional origin characterized by derangement of the personality and loss of contact with reality, often with delusions, hallucinations or illusions. Included under the term psychoses are the disorders schizophrenia, schizophreniform disorder, schizoaffective disorder, delusional disorder, brief psychotic disorder, shared psychotic disorder, psychotic disorder not otherwise specified, and substance-induced psychotic disorder, as defined by the Diagnostic and Statistical Manual of Mental Disorders, 4th ed., published 1994 by the American Psychiatric Association, Washington D.C. USA, incorporated herein by reference.

i) "Substance Dependence" means a condition wherein the patient exhibits a maladaptive pattern of substance use, leading to clinically significant impairment or distress. There is a pattern of repeated self-administration that usually results in tolerance, withdrawal, and compulsive drug-taking.

j) "Substance Abuse" means a condition wherein the patient exhibits a maladaptive pattern of substance use manifested by recurrent and significant adverse consequences related to the repeated use of substances. There may be repeated failure to fulfill major role obligations, repeated use in situations in which it is physically hazardous, multiple legal problems, and recurrent social and interpersonal problems. Unlike the criteria for Substance Dependence, the criteria for Substance Abuse do not include tolerance, withdrawal, or a pattern of compulsive use and instead only include the harmful consequences of repeated use.

k) "Parkinson's Disease" means a slowly progressive neurological condition, characterized by tremor, rigidity, bradykinesia, and postural instability. Other manifestations include depression and dementia.

l) "Parkinsonism" means a condition where the patient exhibits Parkinsonian signs or symptoms (i.e. tremor, muscular rigidity, or akinesia) that develop in association with the use of neuroleptic medication.

m) "Neuroleptic-Induced Tardive Dyskinesia" means a disorder characterized by involuntary movements of the tongue, jaw, trunk, or extremities which have developed in association with the use of neuroleptic medication. The involuntary movements may be chloroform, athetoid or rhythmic.

n) "Gilles de la Tourette Syndrome" means a condition manifested by motor and vocal tics. (A tic is a sudden, rapid, recurrent, nonrhythmic, stereotyped motor movement or vocalization.) The disturbance causes marked distress or significant impairment in social, occupational, or other important areas of functioning. The onset is before age eighteen years and the disturbance is not due to the physiological effects of a substance or general medical condition.

o) "Dementia" means disorders characterized by the development of multiple cognitive deficits that include memory impairment and are due to the direct physiological effects of a general medical condition, to the persisting effects of a substance, or to multiple etiologies (e.g., the combined effects of cerebrovascular disease and Alzheimer's disease). Memory impairment is required to make the diagnosis of a dementia and is a prominent early symptom. Dementia disorders share a common symptom presentation but are differentiated based on etiology. See Diagnostic and Statistical Manual of Mental Disorders, 4th ed., American Psychiatric Association, for diagnostic criteria.

p) "Anxiety Disorders" means disorders that include Panic Disorder Without Agoraphobia, Panic Disorder with Agoraphobia, Agoraphobia Without History of Panic Disorder, Specific Phobia, Social Phobia, Obsessive-Compulsive Disorder, Post-traumatic Stress Disorder, Acute Stress Disorder, Generalized Anxiety Disorder, Anxiety Disorder Due to a General Medical Condition, Substance-Induced Anxiety Disorder, and Anxiety Disorder Not Otherwise Specified, as defined by the Diagnostic and Statistical Manual of Mental Disorders, 4th ed.

q) "Sleep Disorders" means disorders that include Primary Sleep Disorders, Sleep Disorder Related to Another Mental Disorder, Sleep Disorder Due to a General Medical Condition, and Substance-Induced Sleep Disorder as defined by the Diagnostic and Statistical Manual of Mental Disorders, 4th ed. Primary Sleep Disorders are those in which none of the etiologies listed below (i.e., another mental disorder, a general medical condition, or a substance) is responsible. Primary Sleep Disorders are presumed to arise from endogenous abnormalities in sleep-wake generating or timing mechanisms, often complicated by conditioning factors. Primary Sleep Disorders in turn are subdivided into Dyssomnias (characterized by abnormalities in the amount, quality, or timing of sleep) and Parasomnias (characterized by abnormal behavioral or physiological events occurring in association with sleep, specific sleep stages, or sleep-wake transitions). A representative example of a Primary Sleep Disorder is Narcolepsy. Narcolepsy is characterized by repeated irresistible attacks of refreshing sleep, cataplexy, and recurrent intrusions of elements of rapid eye movement (REM) sleep into the transition period between sleep and wakefulness.

r) "Mood Disorders" are disorders that have a disturbance in mood as the predominant feature. As defined by the Diagnostic and Statistical Manual of Mental Disorders, 4th ed., Mood Disorders are divided into the Depressive Disorders ("unipolar depression"), the Bipolar Disorders, and two disorders based on etiology—Mood Disorder Due to a General Medical Condition and Substance-Induced Mood Disorder. The Depressive Disorders (i.e., Major Depressive Disorder, Dysthymic Disorder, and Depressive Disorder Not Otherwise Specified) are distinguished from the Bipolar Disorders by the fact that there is no history of ever having had a Manic, Mixed, or Hypomanic Episode. The Bipolar Disorders (i.e., Bipolar I Disorder, Bipolar II Disorder, Cyclothymic Disorder, and Bipolar Disorder Not Otherwise Specified) involve the presence (or history) of Manic Episodes, Mixed Episodes, or Hypomanic Episodes, usually accompanied by the presence (or history) of Major Depressive Episodes.

s) "Circadian Rhythm Disorder" means a persistent or recurrent pattern of sleep disruption leading to excessive sleepiness or insomnia that is due to a mismatch between the sleep-wake schedule required by a person's environment and his or her circadian sleep-wake pattern. The sleep disturbance causes clinically significant distress or impairment in social, occupational, or other important areas of functioning. The disturbance does not occur exclusively during the course of another Sleep Disorder or other mental disorder. The disturbance is not due to the direct physiological effects of a substance (e.g., a drug of abuse, a medication) or a general medical condition.

Preferred compounds are those wherein R is group (a) or group (k). When R is group (a), $R_4$ is further preferred to be halogen or $CF_3$. When R is group (k), $R_{12}$ is further preferred to be hydrogen, $C_1$–$C_6$alkyl, or —$CH_2OC_1$–$C_6$alkyl. $R_2$ is preferred to be group (a), (b) or (n). When $R_2$ is group (a), z is further preferred to be 0 or 1; e is further preferred to be 5; and each $R_{27}$ and $R_{23}$ is further preferred to be independently selected from hydrogen or $C_1$–$C_6$alkyl. When $R_2$ is group (b), M is further preferred to be hydrogen, $C_1$–$C_6$alkoxy or $C_1$–$C_6$alkyl and u is further preferred to be 0 or 1. When $R_2$ is group (n), $R_{70}$ is further preferred to be hydrogen and f is further preferred to be 3.

Specific embodiments of the invention include the compounds set forth in the tables herein.

Preferred embodiments of the invention are those compounds of Formula I set forth in Table 1 that exhibit enhanced D3 potency. Particularly preferred compounds include the following:

2-[4-(6-Trifluoromethyl-benzo[b]thiophen-3-yl)-piperazin-1-ylmethyl]-trans-cyclopropanecarboxylic acid (trans-4-ethyl-cyclohexyl)-amide 2-[4-(2,4-Dimethyl-phenyl)-piperazin-1-ylmethyl]-(2R, 3R)-cyclopropanecarboxylic acid (trans-4-ethyl-cyclohexyl)-amide 2-[4-(Chloro-trifluoromethyl-pyridin-2-yl)-piperazin-1-ylmethyl]-(2R, 3R)-cyclopropanecarboxylic acid (trans-4-ethyl-cyclohexyl)-amide 2-[4-(2,5-Dimethyl-phenyl)-piperazin-1-ylmethyl]-(2R, 3R)-cyclopropanecarboxylic acid (trans-4-ethyl-cyclohexyl)-amide 2-[4-(6-Trifluoromethyl-benzo[b]thiophen-3-yl)-piperazin-1-ylmethyl]-(2R, 3R)-cyclopropanecarboxylic acid (trans-4-methyl-cyclohexyl)-amide 2-(4-Thieno[2,3-d]isoxazol-3-yl-piperidin-1-ylmethyl)-(2R, 3R)-cyclopropanecarboxylic acid (trans-4-methyl-cyclohexyl)-amide 2-[4-o-Tolyl-piperazin-1-ylmethyl]-(2R, 3R)-cyclopropanecarboxylic acid (trans-4-ethyl-cyclohexyl)-amide 4-[4-(6-Fluoro-benzo[b]thiophen-3-yl)-piperazin-1-yl]-N-(trans-4-methyl-cyclohexyl)-butyramide 2-(4-Thieno[2,3-d]isoxazol-3-yl-piperidin-1-ylmethyl)-(2R, 3R)-cyclopropanecarboxylic acid (3-imidazol-1-yl-propyl)-amide 2-(4-Thieno[2,3-d]isoxazol-3-yl-piperazin-1-ylmethyl)-(2R, 3R)-cyclopropanecarboxylic acid (trans-4-methyl-cyclohexyl)-amide 2R-[4-(1-Methyl-1H-thieno[3,2-c]pyrazol-3-yl)-piperazin-1-ylmethyl]-cyclopropane-1R-carboxylic trans-(4-methyl-cyclohexyl)-amide (AVE1734)

2R-[4-(5-Trifluoromethyl-benzo[d]isoxazol-3-yl)-piperidin-1-ylmethyl]-cyclopropane-1R-carboxylic acid trans-(4-methyl-cyclohexyl)-amide. MDL 834012.

(3S-Imidazol-1-ylmethyl-piperidin-1-yl)-{2R-[4-(7-methoxy-benzo[d]isoxazol-3-yl)-piperidin-1-ylmethyl]-1R-cyclopropyl}-methanone (A002437359)

2R-[4-(1-Methyl-7-trifluoromethyl-1H-indazol-3-yl)-piperidin-1-ylmethyl]-1R-cycloproanecarboxylic acid (3-imidazol-1-yl-propyl)-amide (MDL 832654)

(3S-Imidazol-1-ylmethyl-piperidin-1-yl)-{2R-[4-(7-trifluoromethyl-benzo[d]isoxazol-3-yl)-piperidin-1-ylmethyl]-1R-cyclopropyl}-methanone (A002437360)

2R-[4-(7-Trifluoromethyl-benzo[b]thiophen-3-yl)-piperidin-1-ylmethyl]-1R-cyclopropanecarboxylic acid (trans-4-methyl-cyclohexyl)-amide (MDL 833690)

(3S-Imidazol-1-ylmethyl-piperidin-1-yl)-{2R-[4-(1-methyl-6-trifluoromethyl-1H-indazol-3-yl)-piperidin-1-ylmethyl]-1R-cyclopropyl}-methanone (A002437353)

2R-[4-(6-Trifluoromethyl-benzo[d]isoxazol-3-yl)-piperidin-1-ylmethyl]-1R-cyclopraanecarboxylic acid (3-imidazol-1-yl-propyl)-amide (A002287765)

(3S-Imidazol-1-ylmethyl-piperidin-1-yl)-{2R-[4-(6-trifluoromethyl-benzo[b]thiophen-3-yl)-piperidin-1-ylmethyl]-1R-cyclopropyl}-methanone (A002609935)

2R-[4-(6-Fluoro-7-methoxy-benzo[d]isoxazol-3-yl)-piperidin-1-ylmethyl]-1R-cyclopranecarboxylic acid (trans-4-methyl-cyclohexyl)-amide (MDL 831361)

2R-[4-(1-Methyl-1H-thieno[3,2-c]pyrazol-3-yl)-piperidin-1-ylmethyl]-1R-cycloproanecarboxylic acid (3-imidazol-1-yl-propyl)-amide (A002436291)

2R-{4-[1-(2,2,20Trifluoro-ethyl)-1H-thieno[3,2-c]pyrazol-3-yl)-piperidin-1-ylmethyl]-1R-cycloproanecarboxylic acid (3-imidazol-1-yl-propyl)-amide (A002287767)

2R-(4-Thieno[2,3-d]isoxazol-3-yl-piperazin-1-ylmethyl)-1R-cyclopropanecarboxylic acid (3-imidazol-1-yl-propyl)-amide (MDL 831493)

2R-(4-Benzo[b]thiophen-2-yl-piperidin-1-ylmethyl)-1R-cyclopranecarboxylic acid (trans-4-methyl-cyclohexyl)-amide (MDL 831148)

2R-[4-(5,6-Dihydro-4H-imidazo[4,5,1-ij]quinolin-2-yl)-piperazin-1-ylmethyl]-1R-cyclopranecarboxylic acid (trans-4-methyl-cyclohexyl)-amide (MDL 833699)

2R-(4-Thieno[2,3-b]pyridin-3-yl-piperazin-1-ylmethyl)-1R-cyclopropanecarboxylic acid (3-imidazol-1-yl-propyl)-amide (MDL 833821)

1-{2-[4-(6-Trifluoromethyl-benzo[b]thiophen-3-yl)-piperazin-1-yl]-ethyl}-cyclopropanecarboxylic acid (3-imidazol-1-yl-propyl)-amide (MDL 832231)

The compounds of the present invention may be prepared by various methods. Schemes I through VI show the different ways of preparing the compounds of Formula I.

The compounds of formula (I) of this invention can be synthesized by following or combining one or more of the steps described below, not necessarily in the order presented. Throughout the description of the synthetic steps, the definitions of R, $R_1$, $R_2$, $R_3$, g, n, y, B and A are as given above unless otherwise stated or indicated, and other nomenclatures appearing below shall have the same meanings defined in their respective first appearances unless otherwise stated or indicated.

Compounds of the present invention may be prepared according to a process which comprises (a) reacting a compound of formula (II):

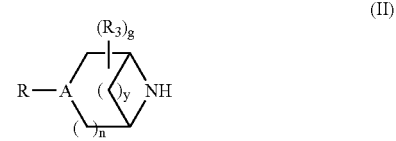

wherein R, A, n, y, $R_3$ and g are as defined in formula I with a compound of formula (III)

wherein

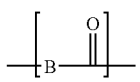

is as defined in formula I and

"LG" is a suitable leaving group selected from chlorine, bromine, iodine, mesyl, tosyl, brosyl, triflyl, nosyl, nonaflyl or tresyl:

to provide a compound of formula (IV):

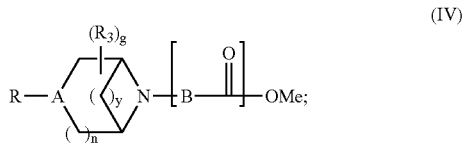
(IV)

wherein $R_3$, g, R, A, y, n and

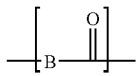

are defined as in formula I;

(b) hydrolyzing a compound of formula (IV) to provide a compound of formula (V):

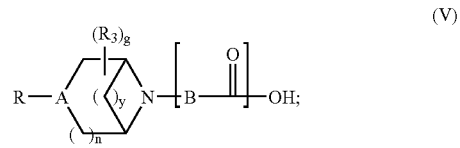
(V)

and (c) reacting a compound of formula (V) with a compound of formula (VI):

(VI)

wherein $R_1$ and $R_2$ are as defined in formula I; to provide a compound of formula (I).

Typically, the reaction in step (a) is carried out in polar solvent such as, for example, acetonitrile and an amine base such as, for example, triethylamine. The reaction is typically conducted at a temperature of about 80° C. to about 85° C. for about 1 to 3 hours.

The reaction in step (b) is typically carried out in a water miscible solvent such as, for example, methanol or 1,4-dioxane in the presence of an aqueous hydroxide base such as, for example, 5 N sodium hydroxide. The reaction is typically carried out at a temperature of about 55° C. to about 65° C. for about 2 to 3 hours.

The reaction in step (c) is typically carried out in a polar solvent such as, for example, N,N'-dimethylformamide, in the presence of a weak base such as, for example, N-methylmorpholine with a suitable coupling reagent. A suitable coupling reagent is, for example, DCC (1,3-dicyclohexylcarbodiimide), EEDQ (2-ethoxy-1-ethoxycarbonyl-1,2dihydroquinoline) or TOTU {O-[(ethoxycarbonyl)cyanomethyleneamino]-N,N,N'N'-tetramethyluronium tetrafluoroborate}. Typically, the reaction takes place at a temperature of about 20° C. to about 25° C. for about 16 to 20 hours.

Alternatively, compounds of the present invention may be prepared according to a process which comprises:

(a) reacting a compound of formula (VII) wherein $R_1$ and $R_2$ are as hereinbefore defined and "LG" is a suitable leaving group selected from chlorine, bromine, iodine, mesyl, tosyl, brosyl, triflyl, nosyl, nonaflyl or tresyl:

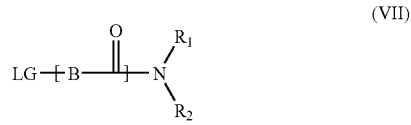
(VII)

with a compound of formula (II) to provide a compound of formula (I). This reaction is typically carried out in a polar solvent and an amine base such as acetonitrile and triethylamine, at a temperature of about 55° C. to about 65° C. for about 16 to 20 hours.

Compounds of formula (II) are either commercially available or may be prepared via synthetic methods well known in the art. For example, Scheme I describes the coupling of a benzthiophene with a commercially-available substituted piperazine. The synthesis is analogous for the un-substituted piperazine analogs. The less sterically hindered piperazine nitrogen is more reactive and cleanly gives a single product in the benzo[b]thiophene coupling. The more sterically hindered nitrogen can then be alkylated as before in the un-substituted piperazines.

SCHEME I

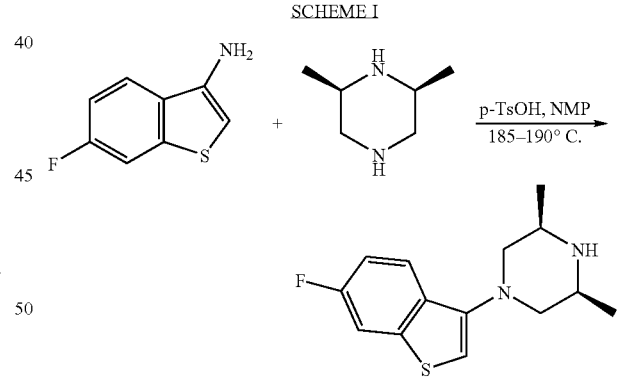

Piperidine-substituted compounds may be prepared via syntheses analogous to those shown in the following reaction Schemes II and III.

SCHEME II

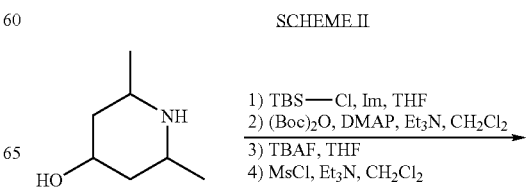

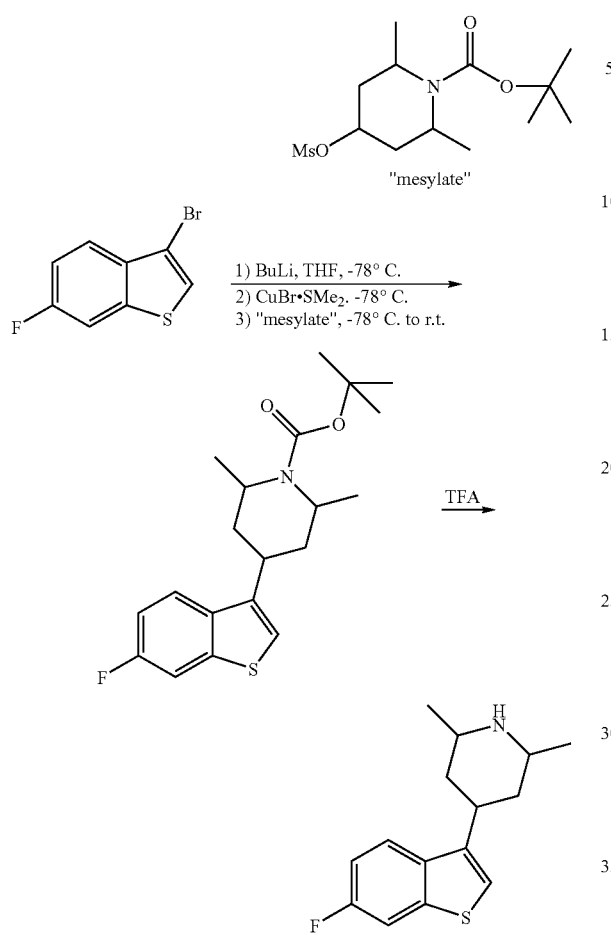

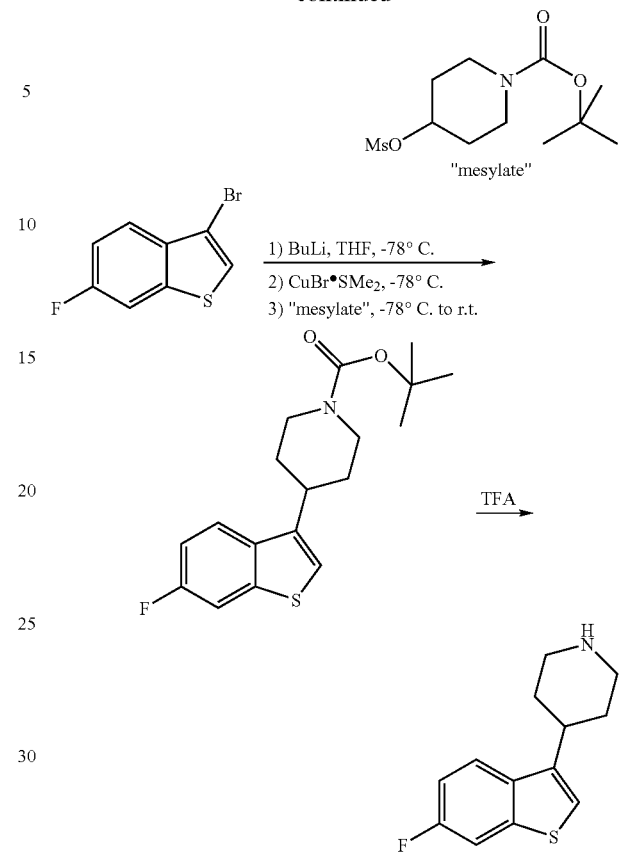

The preparation of various substituted aza- and diazacycloheptanes is described by Treiber et al. in WO 9725324.

The synthesis of compounds of formula (I) wherein the variable designated as

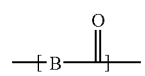

contains a carbocycle is shown in general reaction Scheme IV. For the sake of simplification, the description of synthetic schemes is presented below for compounds which contain this carbocyclic group, but it will be apparent that compounds which do not contain a carbocyclic group can be prepared by utilizing the synthetic schemes and making necessary modifications.

SCHEME III

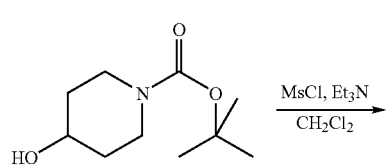

Scheme IV

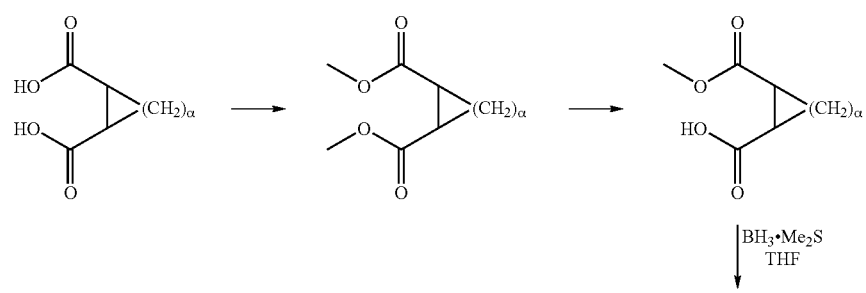

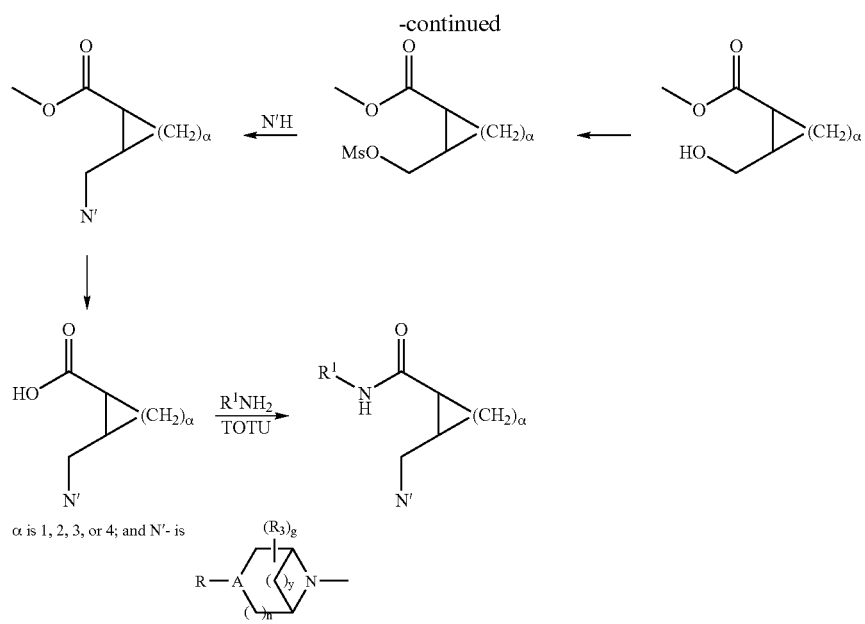

wherein R, A, R₃, y, g and n are as hereinbefore defined.

Many of the dicarboxylates or more advanced intermediates that are generically described in scheme IV are commercially available. Several of these are shown in Table 1. This table is used for illustrative purposes only and is not intended to limit the scope of the present invention in any way.

TABLE I

| Starting Materials: | | | |
|---|---|---|---|
| Structure | Name | CAS # | Supplier |
| | Dimethyl cis-1,2-cyclopropane dicarboxylate | 826-34-6 | Acros |
| | Dimethyl trans-1,2-cyclopropane dicarboxylate | 826-35-7 | Acros |
| | Dimethyl 1-methyl-trans-1,2-cyclopropane dicarboxylate | 702-92-1 | Acros |
| | Dimethyl 3-methyl-trans-1,2-cyclopropane dicarboxylate | 28363-79-3 | Acros |
| | trans-Cyclobutane-1,2-dicarboxylic acid dimethylester | | Syntec |

TABLE I-continued

Starting Materials:

| Structure | Name | CAS # | Supplier |
|---|---|---|---|
| 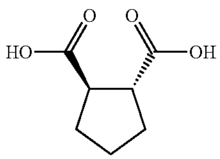 | trans-D,L-1,2-Cyclopentane-dicarboxylic acid | 1461-97-8 | Aldrich |
| 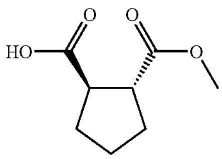 | trans-2-Carbomethoxy cyclopentane-1-carboxylic acid | | Rieke |
| 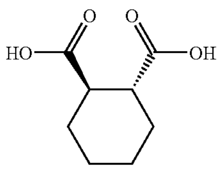 | trans-1,2-Cyclohexane dicarboxylic acid | 2305-32-0 | Aldrich Acros |
| 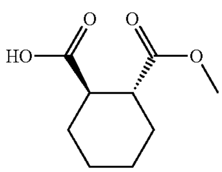 | trans-2-Carbomethoxy cyclohexane-1-carboxylic acid | | Rieke |
| 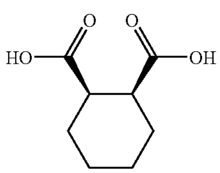 | cis-1,2-Cyclohexane dicarboxylic acid | 610-09-3 | Acros |
| 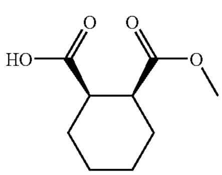 | cis-2-Carbomethoxy cyclohexane-1-carboxylic acid | | Rieke |

When not commercially available, the appropriate starting material may be obtained via standard synthetic methods.

When a compound of formula (I) is obtained as a mixture of enantiomers these may be separated by conventional methods such as crystallization in the presence of a resolving agent, or chromatography, for example using a chiral HPLC column.

Compounds of formula (I) have been found to exhibit affinity for dopamine receptors, in particular $D_3$ receptors, and are expected to be useful in the treatment of disease states which require modulation of such receptors, such as psychotic conditions. Preferred compounds of the present invention are those which have higher affinity for dopamine $D_3$ than dopamine $D_2$ receptors.

A major challenge in antipsychotic research is to produce agents with reduced side effects. Orthostatic hypotension is a common side effect in antipsychotics that is associated with the high potency that these agents have at the alpha-1 receptor (hereinafter referred to as "α-1"). A major goal of this work was to find agents with reduced α-1 potency.

The 6-trifluoromethyl benzo[b]thiophenes described herein have a clear and somewhat surprising advantage over the 6-fluoro benzo[b]thiophenes as is shown in the following table. The 6-fluoro benzo[b]thiophenes are clearly more potent at the alpha-1 receptor than are the 6-trifluoromethyl benzo[b]thiophenes. This is shown by comparing pairs of analogs that only differ in substitution at the 6-position of the benzo[b]thiophene. In every case, the 6-fluoro benzo[b]thiophene is more potent than the corresponding 6-trifluoromethyl analog. In some cases this small structural difference in substitution at the 6-position produces a dramatic change in α-1 potency. There are several examples wherein 6-fluoro analogs exhibited nanomolar potency while the corresponding 6-trifluoromethyl analog exhibited micromolar potency.

| NUM | MOLSTRUCTURE | halpha1Ki (nM) h = human | halpha1%I h = human |
|---|---|---|---|
| 826844 | | 23.4 | |
| 826804 | | | 32.8% Inh @ 1 uM |
| 826845 | | 5.44 | |
| 826805 | | | 27.8% Inh @ 1 uM |
| 826846 | | 93.9 | |
| 826806 | | | 10.3% Inh @ 1 uM |
| 826849 | | 35.2 | |

| NUM | MOLSTRUCTURE | halpha1Ki (nM) h = human | halpha1%I h = human |
|---|---|---|---|
| 826809 | | | 30.5% Inh @ 1 uM |
| 826857 | | 9.82 | |
| 826817 | | | 44.4% Inh @ 1 uM |
| 826861 | | 9.55 | |
| 826821 | | 1280 | 24% Inh @ 0.1 nM |
| 826847 | | 0.513 | |
| 826807 | | 166000 | |

-continued

| NUM | MOLSTRUCTURE | halpha1Ki (nM) h = human | halpha1%I h = human |
|---|---|---|---|
| 826848 | | 12.3 | |
| 826808 | | 126 | |
| 826850 | | 28.4 | |
| 826810 | | 200 | |
| 826851 | | 18.9 | |
| 826811 | | 223 | |

-continued

| NUM | MOLSTRUCTURE | halpha1Ki (nM) h = human | halpha1%I h = human |
|---|---|---|---|
| 826852 | | 6.16 | |
| 826812 | | 658 | |
| 826853 | | 0.258 | |
| 826813 | | 57 | |
| 826854 | | 0.0713 | |
| 826814 | | 89.3 | |
| 826855 | | 0.889 | |

-continued

| NUM | MOLSTRUCTURE | halpha1Ki (nM) h = human | halpha1%I h = human |
|---|---|---|---|
| 826815 | | 80.5 | |
| 826856 | | 15.3 | |
| 826816 | | 249 | |
| 826858 | | 9.42 | |
| 826818 | | 124 | |
| 826859 | | 4 | |

-continued

| NUM | MOLSTRUCTURE | halpha1Ki (nM) h = human | halpha1%I h = human |
|---|---|---|---|
| 826819 | | 49 | |
| 826860 | | 0.516 | |
| 826820 | | 129 | |
| 826862 | | 0.637 | |
| 826822 | | 32.2 | |
| 826863 | | 32.2 | |
| 826823 | | 148 | |

Especially preferred compounds of the instant invention are those with a reduced liability for α-1 receptor binding while at the same time having a higher affinity for dopamine $D_3$ than dopamine $D_2$ receptors.

Receptor affinity can be measured using standard methodology such as is described below.

[N-Methyl-$^3$H]Spiroperidol Binding to Cloned Human Dopamine $D_3$ Receptors

Purpose

This assay measures the in vitro activity of compounds on cloned human dopamine ($D_3$) receptors and predicts the direct dopamine-blocking properties of putative neuropsychiatric agents at human dopamine $D_3$ receptors.

Methods

A. Cloning

The $D_3$ gene was isolated from a human striatal cDNA library (Stratagene). The gene was sequenced and subcloned into the expression vector RC/RSV (Invitrogen). CHO (Chinese Hamster Ovary) cells were stably transfected with 10 μg of the $D_3$/RSV plasmid using the DOTAP method from Boehringer Mannheim and 72 clones that were G418 resistant were isolated. Using mRNA and binding displacement data a single high expressing clone was identified. This clone was then grown in large batches for the purpose of developing a 96 well format assay.

B. Cell Culture

1. One plate (10 cm) with approximately 2–3 million $D_3$ cells per plate is incubated with 1 ml of Trypsin-EDTA at room temperature for ~2 min or until cells have lifted off plates. Four ml of Ham's F12+10% Fetal Bovine Serum+1% Penicillin/Streptomycin+G418 (400 μg/ml) medium are added to resuspend cells and 1 ml of this is added to each large plate (15 cm) containing 19 ml of the same medium as mentioned above.
2. The 5 large plates are incubated at 37° C. +5% $CO_2$ for ~3 days or until the cells are confluent.
3. After these plates are confluent, they are split into 10 large plates. Medium is aspirated off, 2 ml of Trypsin-EDTA are added to each plate and plates are incubated at RT for 2 min or until cells have lifted off the plate. Eight ml of the F12 medium (same medium as #1 above) are added to each plate (10 ml total) to resuspend the cells and 5 ml are transferred to the 2 new plates containing 15 ml of the F12 media.
4. The 10 large plates are incubated at 37° C.+5% $CO_2$ for 2 days or until the cells are confluent.
5. The 10 large plates are split into 60 large plates (using Trypsin-EDTA as #3 except 4 ml of F12 medium are added to resuspend cells and 1 ml is aliquoted to 6 new plates containing 19 ml of F12 medium each).
6. Plates are incubated at 37° C.+5% $CO_2$ for ~3 days or until cell are confluent.
7. The 60 large plates are then split into 60 roller bottles (100–150 million cells/bottle). Medium is aspirated off, 2 ml of Trypsin-EDTA are added to each plate and incubated at RT for ~2 minutes or until cells have lifted off plates. Eight ml of F12 medium are added to each plate to resuspend cells and the entire 10 ml are added to 1 roller bottle containing 90 ml of the F12 medium.
8. The 60 roller bottles are immediately placed on their sides and transferred to the roller bottle incubator. They are incubated at 37° C.+5% $CO_2$ for ~3–5 days. Cells are spun at 30–40% motor speed in the Forma incubator.
9. Medium is poured off and cells are washed 2× in PBS.
10. Cells are then scraped off in 20 ml of PBS and the bottles are rinsed again with 5 ml of PBS to remove any remaining cells. Cells are stored on ice before membrane prepration.
11. The yield for 60 $D_3$ roller bottles has varied from ~260–500 mg.

Note: All tissue culture reagents are from Gibco-BRL.

C. Membrane Preparation

The cells are harvested into 250 ml centrifuge tubes with 100 volumes of cold hosphate buffered saline (PBS) and spun down (1200×G for 10 min at 4° C.). The medium is removed and 100 ml PBS are added to each centrifuge tube, cells are resuspended and spun down again. The PBS is removed and the final pellet is homogenized in an appropriate volume of 10% DMSO with a polytron on ice at a medium setting.

D. Lowry Protein Assay

A 200 μl sample membrane homogenate is added to 200 μl of 1% SDS, vortexed and allowed to stand for 5 min. Aliquots (25, 50 and 100 μl) of this mixture are assayed in duplicate following the standard Bio-Rad DC protein assay protocol (kit catalog number 500-0112) and using reagent S. Absorbance readings are made at 750 nm (note: the most accurate protein OD readings are between 0.1–0.5 units). The protein concentration is calculated using a standard curve generated concurrently with bovine serum albumin as standard.

E. Storage/Freezing Conditions

Following the determination of the protein concentration and Scatchard analysis, the protein is diluted into distilled water with 10% DMSO to the appropriate volume based on expression levels (Bmax). The concentrated protein is then aliquoted into 1.5 ml screw top cap Eppendorf tubes and placed into a −80° C. freezer.

F. Binding Assay Reagents 1. 0.5M Tris Buffer, pH 7.7
    a) 44.4 g Tris HCl 26.5 g Tris Base q.s. to 1 Liter (0.5 M Tris buffer, pH 7.7 at 37° C.)
    b) make a 1:10 dilution in distilled $H_2O$ (0.05 M. Tris buffer, pH 7.7)
2. Tris Buffer containing physiological salts
    a) Stock buffer
       NaCl 7.014 g
       KCl 0.372 g
       $CaCl_2$ 0.222 g
       $MgCl_2$ 0.204 g
       q.s. To 100 ml with 0.5 M. Tris Buffer
    b) Dilute 1:10 in distilled $H_2O$ This yields 0.05 M. Tris HCl, pH 7.7, containing NaCl (120 mM), KCl (5 mM), $CaCl_2$ (2 mM) and $MgCl_2$ (1 mM)

Optional: add 0.1% ascorbic acid and check pH (in assays with compounds that may oxidize.

3. a) 1.0% polyethyleneimine stock in 0.5M Tris (reagent 1.a) b) Dilute 1:10 in distilled $H_2O$
4. [N-methyl-$^3$H]-Spiroperidol (60–90 Ci/mmol) is obtained from New England Nuclear; catalog #NET-856.

For $K_i$ determinations: [$^3$H]NMSP is made up to a concentration of 2.7 nM in buffer 2b, such that when 150 μl is added to each tube a final concentration of 0.4 nM is attained in the 1 ml assay. Samples of total CPM added are taken for each experiment to calculate the total ligand concentration.

5. S(−)-Eticlopride is obtained from Research Biochemicals International (RBI catalog number E-101). A refrigerated stock (good for up to a month) solution of S(−)-eticlopride is made at a concentration of 30 µM in buffer 2b. One hundred microliters are added to 3 wells for the determination of nonspecific binding (this yields a final concentration of 3 µM in the 1 ml assay).

6. Test Compounds

For most assays, a 100 µM stock solution of the test compound is made up in a suitable solvent (usually <0.1% acetic acid) and serially diluted with buffer 2b, such that when 100 µl of drug is combined with the total 1 ml assay, final concentrations ranging from $10^{-5}$–$10^{-8}$ M are attained. Characteristically eight concentrations are studied for each assay; however, higher or lower concentrations may be used, depending on the potency of the drug.

G. Binding Assay

750 µl Tissue

150 µl [$^3$H]NMSP

100 µl vehicle (for total binding) or 30 µM (−)eticlopride (for nonspecific binding) or appropriate drug concentration.

The 96-Well Packard Unifilters GF/B are incubated for >1 h at 25° C. in 0.1% polyethylamine (from 3,b). The cold tissue is added last and mixed on a orbital shaker for a few seconds and is then incubated at 37° C. for 30 min in a shaking water bath. The assay is stopped by rapid filtration through Packard Unifilter plates. The filter membranes are then washed with 15 ml of ice-cold 0.05 M Tris buffer. The filters are then dried (~15 min under a heat lamp or incubated for 15 min in a 60° C. oven) and a bottom seal is applied. Then 40 µl of Packard Microscint 20 scintillation cocktail is added and a permanent topseal (Type P) is applied and heat sealed. The plates are then shaken on an orbital shaker for 1 h and placed in the Packard Topcount and counted for at least 5 minutes for each point.

Specific binding is defined as the difference between total binding and the binding in the presence of 3 µM S-(−)-eticlopride. Total binding is approximately 10% of the total added ligand. Cheng-Prusoff determination ($K_i$'s) are performed using Prism software using a one-site competition curve analysis where the top and the bottom of the non-linear regression are held constant at 0% and 100% percent inhibition. The percent inhibition at each drug concentration is the mean of duplicate determinations.

[N-Methyl-$^3$H]Spiroperidol Binding to Cloned Human Dopamine D$_2$Long Receptors Purpose:

This assay measures the in vitro activity of drugs on cloned human dopamine D$_2$Long receptors and predicts the direct dopamine-displacing properties of neuropsychiatric cardiovascular and renal agents at human dopamine D$_2$ receptors.

Methods:

A. Cloning

The D$_2$L gene was isolated from a human striatal (caudate/putamen) cDNA library. The gene was sequenced and sub-cloned into the expression vector pRC/RSV (Invitrogen). CHO (Chinese Hamster Ovary) cells were stably transfected and 72 clones that were geneticin (G418) resistant were isolated. Using mRNA and binding data a single high expressing cell line was identified (#44). This cell line was then grown in suspension culture for the purpose of developing a 96 well format assay.

B. Cell Culture Conditions

1. Medium for adherent CHO cultures:

Ham's F12+10% fetal bovine serum (FBS)+400 µg/ml geneticin (G418)+10 ml/L penicillin-streptomycin (pen-strep)

2. Cells are transferred to suspension culture when at least 1.5 million cells are available (this allows for 300,000 cells/ml in a 50 ml spinner flask; this is the ideal suspension density). Cell are removed from flasks with trypsin, spun down (1000×G) and resuspended in fresh medium:

50% CHO-SFM II+50% Ham's F12 w/10% FBS (final FBS conc. 5%)+400 µg/ml G418+pen-strep (10 ml/L)

3. After the transfer to suspension culture, growth is monitored and cell viability is assessed using trypan blue exclusion. Total and viable cell count on 5 sectors of the hemocytometer are recorded. When the viable cell density reaches 600,000 cell/ml, the volume is doubled.

4. After 1 week of growth in the 50/50 medium, the cells are spun down and transferred to a new spinner flask and replaced with 75% CHO-SFM II/25% Ham's F12+10% FBS plus the pen-strep and G418. Thereafter every 3 days, the medium is replaced with new medium containing a decreasing amount of FBS as follows:

| ml of CHO SFM:ml of Ham'S F12 | Final % FBS conc. |
| --- | --- |
| 87.50:12.5 | 1.25 |
| 93.75:6.25 | 0.625 |
| 99.00:1.00 | 0.1 |

5. The final maintenance culturing medium is made up as follows:

A stock mixture of 10 ml of pen-strep, 0.5 ml of 400 mg/ml (active; final concentration: 200 mg/ml) G418 and 1 ml of FBS are mixed and filtered and refrigerated. A volume (11.5 ml) of this mixture is added to a freshly opened 1 L bottle of CHO-SFM II.

C. Membrane Preparation

The cells are harvested into 250 ml centrifuge tubes with 100 volumes of cold phosphate buffered saline (PBS) and spun down (1200×G for 10 min at 4° C.). The medium is removed and 100 ml PBS are added to each centrifuge tube, cells are resuspened and spun down again. The PBS is removed and the final pellet is homogenized in an appropriate volume of PBS with a polytron on ice at a medium setting.

D. Lowry Protein Assay

A 200 µl sample membrane homogenate is added to 200 µl of 1% SDS, vortexed and allowed to stand for 5 min. Aliquots (25, 50 and 100 µl) of this mixture are assayed in duplicate following the standard Bio-Rad DC protein assay protocol (kit catalog number 500-0112) and using reagent S. Absorbance readings are made at 750 nm (note: the most accurate protein OD readings are between 0.1–0.5 units). The protein concentration is calculated using a standard curve generated concurrently with bovine serum albumin as standard.

E. Storage/Freezing Conditions

Following the determination of the protein concentration, the protein is diluted into distilled water with 10% DMSO to the appropriate volume based on expression levels (Bmax).

The concentrated protein is aliquoted into 1.5 ml screw top eppendorf tubes and placed into a −80° C. freezer.

F. Binding Assay Reagents
1. 0.5M Tris Buffer, pH 7.7
   a) 44.4 g Tris HCl
      26.5 g Tris Base
      q.s. to 1 Liter (0.5 M Tris buffer, pH 7.7 at 37° C.)
   b) make a 1:10 dilution in distilled $H_2O$ (0.05 M. Tris buffer, pH 7.7)
2. Tris Buffer containing physiological salts
   a) Stock buffer
      NaCl 7.014 g
      KCl 0.372 g
      $CaCl_2$ 0.222 g
      $MgCl_2$ 0.204 g
      q.s. To 100 ml with 0.5 M. Tris Buffer
   b) Dilute 1:10 in distilled $H_2O$ This yields 0.05 M. Tris HCl, pH 7.7, containing NaCl (120 mM), KCl (5 mM), $CaCl_2$ (2 mM) and $MgCl_2$ (1 mM)

Optional: add 0.1% ascorbic acid and check pH (in assays with compounds that may oxidize.

3. a) 1.0% polyethyleneimine stock in 0.5M Tris (reagent 1.a) b) Dilute 1:10 in distilled $H_2O$
4. [N-methyl-$^3$H]-Spiroperidol (60–90 Ci/mmol) is obtained from New England Nuclear; catalog #NET-856.

For $K_i$ determinations: [$^3$H]NMSP is made up to a concentration of 2.7 nM in buffer 2b, such that when 150 µl is added to each tube a final concentration of 0.4 nM is attained in the 1 ml assay. Samples of total CPM added are taken for each experiment to calculate the total ligand concentration.

5. S(−)-Eticlopride is obtained from Research Biochemicals International (RBI catalog number E-101). A refrigerated stock (good for up to a month) solution of S(−)-eticlopride is made at a concentration of 30 µM in buffer 2b. One hundred microliters are added to 3 wells for the determination of nonspecific binding (this yields a final concentration of 3 µM in the 1 ml assay).

6. Test Compounds
   For most assays, a 100 µM stock solution of the test compound is made up in a suitable solvent (usually <0.1% acetic acid) and serially diluted with buffer 2b, such that when 100 µl of drug is combined with the total 1 ml assay, final concentrations ranging from $10^{-5}$–$10^{-8}$ M are attained. Characteristically eight concentrations are studied for each assay; however, higher or lower concentrations may be used, depending on the potency of the drug.

G. Binding Assay
   750 µl Tissue
   150 µl [$^3$H]NMSP
   100 µl vehicle (for total binding) or 30 µM (−)eticlopride (for nonspecific binding) or appropriate drug concentration.

The 96-Well Packard Unifilters GF/B are incubated for >1 h at 25° C. in 0.1% polyethylamine (from 3,b). The cold tissue is added last and mixed on a orbital shaker for a few seconds and is then incubated at 37° C. for 30 min in a shaking water bath. The assay is stopped by rapid filtration through Packard Unifilter plates. The filter membranes are then washed with 15 ml of ice-cold 0.05 M Tris buffer. The filters are then dried (~15 min under a heat lamp or incubated for 15 min in a 60° C. oven) and a bottom seal is applied. Then 40 µl of Packard Microscint 20 scintillation cocktail is added and a permanent topseal (Type P) is applied and heat sealed. The plates are then shaken on an orbital shaker for 1 h and placed in the Packard Topcount and counted for at least 5 minutes for each point.

Specific binding is defined as the difference between total binding and the binding in the presence of 3 µM S-(−)-eticlopride. Total binding is approximately 10% of the total added ligand. Cheng-Prusoff determination ($K_i$'s) are performed using Prism software using a one-site competition curve analysis where the top and the bottom of the non-linear regression are held constant at 0% and 100% percent inhibition. The percent inhibition at each drug concentration is the mean of duplicate determinations.

| | $^3$H]PRAZOSIN BINDING TO CLONED HUMAN ALPHA-1A ADRENERGIC RECEPTORS ($\alpha_{1a}$) EXPRESSED IN CHINESE HAMSTER OVARY CELLS (CHO) |
|---|---|
| Purpose: | This in vitro assay is designed as a screen to identify compounds displaying a affinity for the human $\alpha_{1a}$ adrenoceptor subtype expressed in the membrane fragments of CHO cells. The assay measures the ability of the test compounds to displace [$^3$H] prazosin from $\alpha_{1a}$ sites. The identification of multiple vascular $\alpha_1$-addrenoceptors ($\alpha_{1a}$, $\alpha_{1b}$, $\alpha_{1d}$) in vitro has provided impetus to define the role(s) of these subtypes in cardiovascular regulation in vivo (Vargas and Gorman, 1995). Hemodynamic studies in the unanesthetized rat suggest that vascular $\alpha_{1a}$ receptors are the major subtype involved in the sympathetic regulation of peripheral resistance and systemic arterial pressure (Piascik et al., 1989). Additional evidence for an involvement of peripheral $\alpha_{1a}$ receptors in the maintenance of arterial pressure was demonstrated by the findings that the selective $\alpha_{1a}$ antagonist 5-MU dose dependently lowered resting arterial pressure in awake conscious dogs (Piascik et al., 1989). A demonstrated inability of the irreversible antagonist, chloroethylclonidine, to reduce arterial pressure in rats when administered intravenously, is strong evidence against the role of $\alpha_{1b}$ and $\alpha_{1d}$ receptors in the acute regulation of arterial pressure (Vargas et al., 1993). Therefore, the binding of compounds to $\alpha_{1a}$ adrenergic receptors is believed to be a good measure of a compound's potential to cause orthostatic hypotension and sedation as side effects. Prazosin is a potent antagonist of the human $\alpha_{1a}$-adrenoceptor subtype, which has been cloned and is expressed in the membrane fragments of CHO cells. |
| h$\alpha_{1a}$receptor: | The cloning of the human $\alpha_{1a}$ cDNA was accomplished first by screening a human prostate cDNA library (Clontech), from which a |

[³H]PRAZOSIN BINDING TO CLONED HUMAN ALPHA-1A ADRENERGIC RECEPTORS ($\alpha_{1a}$) EXPRESSED IN CHINESE HAMSTER OVARY CELLS (CHO) -continued

| | |
|---|---|
| | portion of the coding region was obtained. This DNA fragment was then used to screen a human leukocyte genomic library (Clontech), and the rest of the coding sequence was obtained. Later these two fragments were spliced together. The entire coding sequence was then fully sequenced including matching PCR sequence with original genomic coding sequence, thus ensuring splice sites were joined correctly (Schwinn et al., 1995). Once sequenced, the gene was subcloned into the expression vector pcDNA3 (Invitrogen). Plasmid DNA was then used for transfection into CHO cells and G418 resistant clones were isolated. A clone expressing high levels of the h$\alpha_{1a}$ receptor (as determined by mRNA and receptor binding data) was chosen and pharmacologically characterized. |
| Culture Media: | Media Ingredients for Adherent $\alpha_{1a}$ expressing CHO Culture:<br>A. HAM's F-12 (Cellgro)<br>B. 10% 0.2 micron filtered Fetal Bovine Serum (FBS)(Cellgro)<br>C. 1% 0.2 micron filtered Penicillin-Streptomycin (Cellgro)<br>D. G418 0.2 micron filtered (Geneticin 400 µg/ml)(Cellgro)<br>Cells are cultured using established methods and procedures in either 150 × 25 mm culture plates (scale up to 100 plates) or a combination of these plates and 70 roller bottles. One culturing/harvest cycle typically requires 2 weeks and yields between 100–400 mg protein. Plates or bottles are incubated at 37° C. + 5% $CO_2$. |
| Storage: | Cells are harvested by mechanical scraping, washed using PBS, collected in 250 ml Corning polypropylene centrifuge tubes, spun down (1500 RPM) and resuspended in d$H_2O$ 10% DMSO (final volume per harvest is approximately 50 ml). Protein determination is made using the Biorad DC Assay Kit. Finally, the appropriate volume is aliquoted into a 2 ml Corning Cryovial (10 mg/1–1.5 ml) which is stored at −80° C. |
| Current Lot Data: | $\alpha_{1a}$ (clone #7)<br>Batch 1/14/98<br>Receptor Concentration   2418 fmoles/mg protein<br>$K_d$   0.18 nM<br>Volume   1.5 ml/cryovial<br>Protein Concentration   approx. 10 mg/1.5 ml |
| Assay Requirement: | 0.5 cryovials per 96 well plate (assay volume = 200 µl/well) |
| [³H]-Ligand: | [7-methoxy-³H]-Prazosin: 1.0 nM (NEN, NET-823) 70–87 Ci/mmol |
| Materials: | Phentolamine mesylate (Research Biochemicals Int. #P-131)<br>96 well flat bottom plates (Beckman)<br>Unifilter GF/B Plate (Packard)<br>Polyethylenimine (Sigma #P-3134)<br>TomTec or Packard Filtermate 196 Cell Harvesters<br>Packard TopCount Scintillation Counter |
| Buffers: | A: 50 mM Tris HCl; 0.1% ascorbate, pH 7.7 (incubation buffer)<br>B: 50 mM Tris HCl; pH 7.7 (wash buffer) |
| Procedure: | Assay additions are as follows (in the order indicated):<br>Total Binding = 50 µl buffer A + 50 µl [³H]prazosin + 100 µl membrane<br>Nonsp. Bd. = 50 µl 10 µM phentolamine + 50 µl [³H]prazosin + 100 µl membrane<br>Test Cpd. = 50 µl compound + 50 µl [³H]prazosin + 100 µl membrane<br>Compounds to be evaluated are weighed out to yield a 10 mM stock solution in DMSO in a 24 well polystyrene plate. This is diluted to a 0.5 mM stock in d$H_2O$. Serial dilutions in Buffer A are made from which 50 µl additions to the plate are made in duplicate in order to achieve the final concentrations desired. Typically, one 96 well plate is used to evaluate 11 compounds at 4 concentrations ($10^{-6}$–$10^{-9}$ M) in duplicate. Total binding and nonspecific binding are determined in quadruplicate. Usually one standard is run with each assay.<br>[³H]Prazosin is made up in Buffer A such that when 50 µl are added per well the final concentration is 1.0 nM in a final assay volume of 200 µl. The final concentration should be verified by running a sample in a scintillation counter prior to adding the [³H]prazosin to the 96 well plate. Note: The radioactivity should be prepared just before the additions are made so that it is not allowed to sit on the bench for very long.<br>Packard GF/B Plate Pretreatment: The filter plates are presoaked for at least 30 min in ice cold Buffer B containing 0.05% polyethyleneimine (200 µl/200 ml) to maximize filtration efficiency and minimize filter blank binding.<br>Incubation & Filtration: Once buffer, compounds, [³H]prazosin and membrane have been added (and mixed), the 96 well plates are incubated for 40 min at 37° C. and spaced 3–5 min apart. At 40 min, the plates are filtered using a Tomtec Automated Cell Harvester. Filtration is immediately followed by washes of ice cold Buffer B (total vol. ~7 ml).<br>Drying and Counting: Each filter plate is dried under a heat lamp for 15 min. The back of the plate is sealed and 40 µl of Packard microscint |

| | [3H]PRAZOSIN BINDING TO CLONED HUMAN ALPHA-1A ADRENERGIC RECEPTORS ($\alpha_{1a}$) EXPRESSED IN CHINESE HAMSTER OVARY CELLS (CHO) |
|---|---|
| | fluid are added per well. Using Packard film, each plate is heat sealed prior to being counted in a Packard Topcount Scintillation counter. A program has been written that counts each plate twice sending DPM, CPM and TSIS data to disk and printer.<br>Analysis of Results: Raw DPM and CPM data are captured on disk and are imported into one of several software packages (Graphpad Prism Ver 2.0, Excel) residing on the LAN. Specific binding is defined as the difference between total binding and the binding in the presence of 10 μM phentolamine. Total binding is less than 10% of the total added ligand. Software using one-site competition curve analysis is employed in the calculation of $IC_{50}$ and $K_I$ (Cheng-Prusoff equation, 1973). The top and bottom of the non-linear regression are held constant at 0% and 100% inhibition. The percent inhibition at each drug concentration is the mean of duplicate determinations. |
| References: | Vargas, H. M and A. J. Gorman. Life Sciences. Vol. 57, No. 25, pp. 2291–2308, 1995.<br>Morrow, A. L. and I. Creese. Mol. Pharmacol. 29: 321–330, 1986.<br>Piascik, M. T., J. W. Kusiak, and K. W. Barron. Eur. J. Pharmacol. 11: 101–107, 1989.<br>Vargas, H. M., D. Cunningham, L. Zhou, H. B. Hartman and A. J. Gorman. J. Pharmacol. Exp. Ther. 267: 264–272, 1993. |

The functional activity of compounds of the invention (i.e. whether they are antagonists, agonists or partial agonists) can readily be determined using the microphysiometer test method that follows:

Chinese Hamster Ovary (CHO) cells, expressing the human dopamine D3 receptor, were grown on the surface of a capsule cup. Cups are assembled and placed on the microphysiometer, and buffer (Dulbecco's Modified Eagle's Medium without sodium bicarbonate and without serum) is perfused through the cup assembly until a stable baseline is achieved (4 hours). Buffer perfusion rate and solution changes are controlled by a computer. Intracellular acidification rate is measured in each of the 8 cup assemblies and recorded by the computer. Buffer containing test compound (10 nM, 100 nM, and 1 uM) was perfused through the cup assembly for 20 min, then buffer containing quinpirole (a D3 agonist) (10 nM) and test compound (same concentrations) is perfused for an additional 1 min. This is followed by a recovery period of 10–60 min where buffer alone is perfused through the cups. Quinpirole increases acidification rate. A D3 antagonist will inhibit this acidification rate in a concentration dependent manner.

$D_3$ antagonists are of potential use as antipsychotic agents for example in the treatment of schizophrenia, schizoaffective disorders, psychotic depression and mania. Conditions which may be treated by $D_3$ agonists include include dyskinetic disorders such as Parkinson's disease, neuroleptic-induced parkinsonism and tardive dyskinesias; depression; anxiety; dementia; circadian rhythm disorders, and drug (e.g. cocaine) dependency.

$D_3$ receptor ligands are also useful for treating renal dysfunction.

In accordance with yet another embodiment of the present invention, there is provided a method of modulating the activity of dopamine $D_3$ receptors, said method comprising: contacting cell-associated dopamine $D_3$ receptors with a concentration of a compound of formula IB, or a physiologically acceptable salt thereof, sufficient to modulate the activity of said dopamine $D_3$ receptor. As employed herein, a compound of formula IB shall refer to the compound of formula I except that the proviso therein is deleted therefrom.

As employed herein, the phrase "modulating the activity of dopamine $D_3$ receptors" refers to a variety of therapeutic applications. Said therapeutic applications refer to the treatment of conditions or disorders which include dyskinetic disorders, psychoses, anxiety disorders, mood disorders, dementia, sleep disorders, nausea substance dependence, substance abuse and nausea.

The instant invention also provides a method of treating conditions or disorders of the central nervous system comprising administering to a patient in need thereof a therapeutically effective amount of a compound of formula I, IA, or IB or a pharmaceutically acceptable salt thereof. The compounds of formula IA are preferred for this method. As employed herein, a "compound of formula IA" shall refer to the compound of formula I except that the proviso therein i.e. "Proviso A" is deleted therefrom and inserted therefor is the following proviso (hereinafter referred to as "Proviso B"):

"when n is 1; and y is 0; and $R_3$ is hydrogen or $C_1$–$C_6$alkyl; and

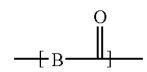

is a group of formula (a); and R is group:
(a) wherein $R_4$ is hydrogen, halogen or $C_1$–$C_6$alkyl, and $R_1$ is hydrogen or unsubstituted $C_1$–$C_6$alkyl, then $R_2$ cannot be a group of the following formula:
(a) wherein z is 0,
(b) wherein u is 0 and M is hydrogen, halogen, $C_1$–$C_6$alkyl, or trifluoromethyl,
(c) wherein o is 0,
(d) wherein l is 0,
(e) wherein j is 0,
(g) wherein v is 0, or
(i);
and also when R is the group of formula (a), $R_1$ and $R_2$ cannot be joined together to form the group of formula Y or a 5-, 6-, or 7-membered monocyclic ring wherein said ring is unsubstituted or mono- or di-substituted with $C_1$–$C_6$alkyl;

(b) and $R_1$ is hydrogen or unsubstituted $C_1$–$C_6$alkyl, then $R_2$ cannot be a group of the following formula:
(a),
(b),
(d) wherein l is 0,
(k),
(l), or
(m) wherein Q is $CH_2$;
and also when R is the group of formula (b), $R_1$ and $R_2$ cannot be joined together to form a group of formula X or a group of formula Y or a 5-, 6-, or 7-membered monocyclic ring
wherein said ring is unsubstituted or mono- or di-substituted with $C_1$–$C_6$alkyl or

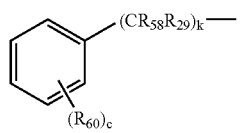

(d) and $R_1$ is hydrogen or unsubstituted $C_1$–$C_6$alkyl, then $R_2$ cannot be a group of the following formula:
(a),
(b) wherein u is 1,
(d),
(k),
(l), or
(m) wherein Q is $CH_2$;
and also when R is the group of formula (d), $R_1$ and $R_2$ cannot be joined together to form a group of formula X or a group of formula Y or a 5-, 6-, or 7-membered monocyclic ring
wherein said ring is unsubstituted or mono- or di-substituted with $C_1$–$C_6$alkyl or

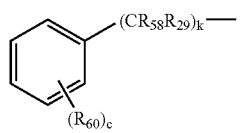

(e) and $R_1$ is hydrogen or unsubstituted $C_1$–$C_6$alkyl, then $R_2$ cannot be a group of the following formula:
(a),
(b),
(d),
(k),
(l), or
(m) wherein Q is $CH_2$;
and also when R is the group of formula (e), $R_1$ and $R_2$ cannot be joined together to form a group of formula X or a group of formula Y or a 5-, 6-, or 7-membered monocyclic ring
wherein said ring is unsubstituted or mono- or di-substituted with $C_1$–$C_6$alkyl or

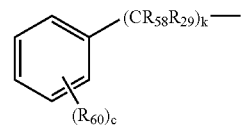

(f) and $R_1$ is hydrogen or unsubstituted $C_1$–$C_6$alkyl, then $R_2$ cannot be a group of the following formula:
(a),
(b),
(d),
(k),
(l), or
(m) wherein Q is $CH_2$;
and also when R is the group of formula (f), $R_1$ and $R_2$ cannot be joined together to form a group of formula X or a group of formula Y or a 5-, 6-, or 7-membered monocyclic ring
wherein said ring is unsubstituted or mono- or di-substituted with $C_1$–$C_6$alkyl or

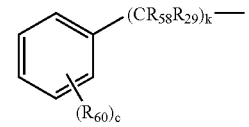

(g) and $R_1$ is hydrogen or unsubstituted $C_1$–$C_6$alkyl, then $R_2$ cannot be a group of the following formula:
(a),
(b) wherein u is 1,
(d),
(k),
(l), or
(m) wherein Q is $CH_2$;
and also when R is the group of formula (g), $R_1$ and $R_2$ cannot be joined together to form a group of formula X or a group of formula Y or a 5-, 6-, or 7-membered monocyclic ring
wherein said ring is unsubstituted or mono- or di-substituted with $C_1$–$C_6$alkyl or

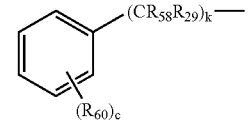

(h) and $R_1$ is hydrogen or unsubstituted $C_1$–$C_6$alkyl, then $R_2$ cannot be a group of the following formula:
(a),
(b),
(d),
(k),
(l), or
(m) wherein Q is $CH_2$;
and also when R is the group of formula (h), $R_1$ and $R_2$ cannot be joined together to form a group of formula X or a group of formula Y or a 5-, 6-, or 7-membered monocyclic ring
wherein said ring is unsubstituted or mono- or di-substituted with $C_1$–$C_6$alkyl or

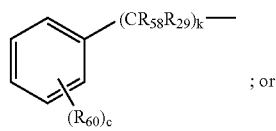

; or (j) then $R_1$ and $R_2$ cannot be joined together to form a group of formula Y or a 5-, 6-, or 7-membered monocyclic ring
wherein said ring is unsubstituted or mono- or di-substituted with $C_1$–$C_6$alkyl".

The instant invention further provides a method of treating conditions or disorders of the central nervous system comprising administering to a patient in need thereof a therapeutically effective amount of a compound of formula I, IA or IB or a pharmaceutically acceptable salt thereof, in conjunction with one or more $D_1$, $D_2$, $D_4$, DS or 5HT receptor antagonists. Compounds of formula IA are preferred for this method.

Also provided herein is a method for treating renal dysfunction comprising administering to a patient in need thereof a therapeutically effective amount of a compound of formula I, IA or IB.

In treating a patient afflicted with a condition or disorder described above, a compound of formula I, IA, or IB can be administered in any form or mode which makes the compound bioavailable in therapeutically effective amounts, including orally, sublingually, buccally, subcutaneously, intramuscularly, intravenously, transdermally, intranasally, rectally, topically, and the like. One skilled in the art of preparing formulations can determine the proper form and mode of administration depending upon the particular characteristics of the compound selected for the condition or disease to be treated, the stage of the disease, the condition of the patient and other relevant circumstances. For example, see Remington's Pharmaceutical Sciences, 18th Edition, Mack Publishing Co. (1990), incorporated herein by reference.

The compounds of Formula I, IA, or IB can be administered alone or in the form of a pharmaceutical composition in combination with pharmaceutically acceptable carriers, the proportion and nature of which are determined by the solubility and chemical properties of the compound selected, the chosen route of administration, standard pharmaceutical practice and other relevant criteria.

The compounds of formula I, IA, or IB may be administered orally, for example, in the form of tablets, troches, capsules, elixirs, suspensions, solutions, syrups, wafers, chewing gums and the like and may contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors.

The compounds of Formula I, IA, or IB may also be administered topically, and when done so the carrier may suitably comprise a solution, ointment or gel base. The base, for example, may comprise one or more of petrolatum, lanolin, polyethylene glycols, bee wax, mineral oil, diluents such as water and alcohol, and emulsifiers and stabilizers.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials.

The highly lipophilic esters, amides and carbamates of compounds I, IA, or IB are capable of sustained release in mammals for a period of several days or from about one to four weeks when formulated and administered as depot preparations, as for example, when injected in a properly selected pharmaceutically acceptable oil. The preferred oils are of vegetable origin such as sesame oil, cottonseed oil, corn oil, coconut oil, soybean oil, olive oil and the like, or they are synthetic esters of fatty acids and polyfunctional alcohols such as glycerol or propyleneglycol.

The depot compositions of formula I, IA, or IB are prepared by dissolving a highly lipophilic ester, amide or carbamate of the instant invention in a pharmaceutically acceptable oil under sterile conditions. The oil is selected so as to obtain a release of the active ingredient over a desired period of time. The appropriate oil may easily be determined by consulting the prior art, or without undue experimentation by one skilled in the art.

The dosage range at which the compounds of formula I, IA, or IB exhibit their ability to act therapeutically can vary depending upon the particular disease or condition being treated and its severity, the patient, the formulation, other underlying disease states that the patient is suffering from, and other medications that may be concurrently administered to the patient. Generally, the compounds of formula I, IA or IB will exhibit their therapeutic activities at dosages of between about 0.001 mg/kg of patient body weight/day to about 100 mg/kg of patient body weight/day.

In a further aspect, the present invention provides novel radiolabeled imaging agents of formula I, IA, or IB useful, inter alia, for imaging dopamine $D_3$ receptors in the CNS to diagnose CNS abnormalities.

In a further aspect, the present invention provides novel radiolabeled imaging agents of formula I, IA, or IB useful, inter alia, for imaging dopamine $D_3$ receptors in the CNS to diagnose CNS abnormalities.

The radiolabeled (tritiated and C-14 labeled) forms compounds of formula I, IA, or IB are useful as radioligands to determine the binding of compounds to the dopamine $D_3$ receptor. They are also useful as labeled parent compounds to determine the metabolism of the compound in animals. Preferred for this purpose are compounds of formula I and IA wherein R is group (a) with a radiolabeled $^{14}C$ in the 3-position of the benzo[b]thiophene ring, $R_4$ is trifluoromethyl, s is 1, $R_3$ is hydrogen, n is 1, y is 0, and A is N. Particularly preferred for this purpose are compounds of formula IC. As employed herein, a "compound of formula IC" shall refer to the compound of formula I wherein R is group (a) with a radiolabeled $^{14}$C in the 3-position of the benzo[b]thiophene ring, $R_4$ is trifluoromethyl in the 6-position of the benzo[b]thiophene ring, s is 1, $R_3$ is hydrogen, n is 1, y is 0, and A is N. Compounds of formula IC may be prepared in a manner analogous to that set forth in Example 33.

Imbalances in dopamine production have been implicated in a variety of mental and physical disorders, such as Parkinson's disease (PD). It is thus desirable to diagnose and monitor such imbalances and to monitor the effectiveness of drugs and substances that affect brain chemistry. New and powerful imaging methods that enable one to assess the living brain in vivo and thereby monitor brain chemistry and the effectiveness of drugs and substances that affect brain chemistry have been developed. Methods such as positron emission tomography (PET) and single photon emission computed tomography (SPECT) involve administering to a patient a radioactive tracer substance comprising a ligand that binds to the presynaptic or postsynaptic neuroreceptors in the patient's brain. Emissions (primarily gamma rays are emitted from the positrons or photons from the radioactive tracer) are measured. These emissions are indicative of the number and degree of occupancy of blocking of the neuroreceptors. The number of neuroreceptors and the degree of occupancy or blocking is calculated utilizing a mathematical model, and compared with an intra-person or inter-person control to determine the degree of drug response. Further treatment of the patient with drugs is based on the comparisons made. For these methods to be useful, however, a ligand that has a high specificity and affinity for the desired receptor is required.

It is believed that certain radioactive ligands may be selective for dopamine transporters and are thus potentially useful in evaluating changes in dopamine function in vivo and in vitro, especially for patients with Parkinson's disease (PD), which is characterized by a selective loss of dopamine neurons in the basal ganglia and substantia nigra.

Another aspect of this invention relates to methods for utilizing the compounds of the invention as CNS imaging agents. Imaging techniques are non-invasive diagnostic techniques that generally involve administering a compound with marker atoms that can be detected externally to the mammal. Generally, these methods comprise administering to a mammal a compound of the invention, dissolved or dispersed in a suitable pharmaceutical carrier or diluent. The compound of the invention selectively binds to dopamine $D_3$, thus permitting the imaging of CNS receptors and the ability to, inter alia, evaluate brain chemistry, the effectiveness of drugs, and neuronal functions. Imaging techniques suitable for practicing the present invention include, but are not limited to, single photon emission computed tomography (SPECT) and positron emission tomography (PET).

Radionuclides that are widely used in diagnostic nuclear medicine include technetium [$^{99}$Tc], iodine [$^{123}$I], carbon [$^{11}$C], and fluorine [$^{18}$F]. The radiolabeled imaging agent specifically exemplified herein contains the radionuclide $^{11}$C. It should be noted that the same or similar radiochemistry reactions can be carried out using radionuclides other than $^{11}$C.

The invention is further illustrated by the following non-limiting examples and tabulated information. These examples are understood to be illustrative only and are not intended to limit the scope of the present invention in any way. As used herein, the following terms have the indicated meanings: "g" refers to grams; "mmol" refers to millimoles; "ml" refers to milliliters; "C" refers to degrees Celsius; "TLC" refers to thin layer chromatography; "LC/MS" refers to liquid chromatography mass spectrometry; "APCI" refers to atmospheric pressure chemical ionization; "mp" refers to melting point.

EXAMPLES

Example 1

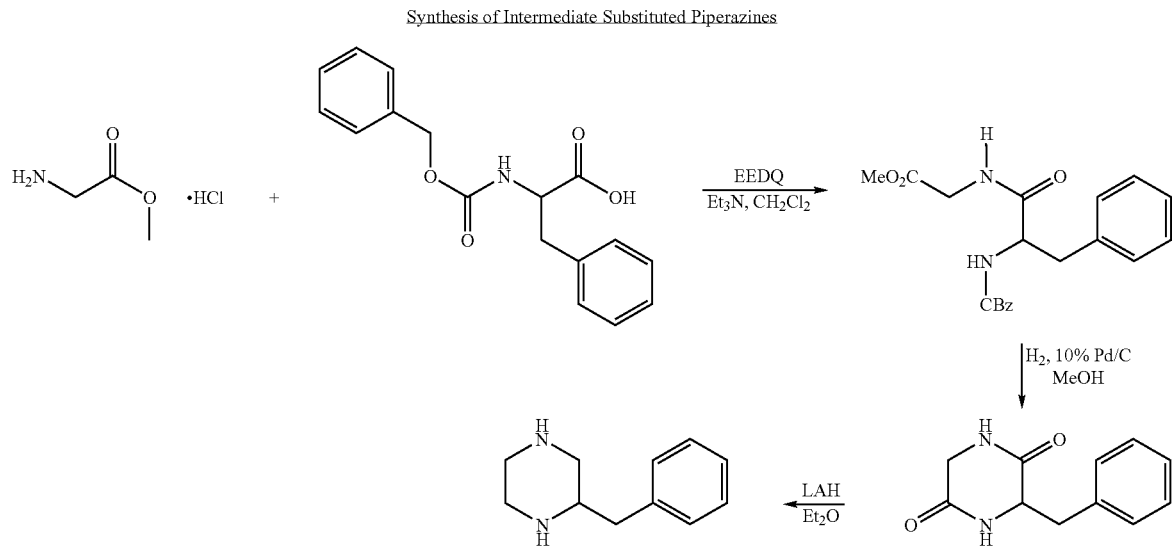

Example 1(a)

Preparation of Intermediate 3-benzyl-piperazine

To a suspension of 3-benzyl-piperazine-2,5-dione (14.98 g, 73 mmol, prepared following generally the procedure of Halpern and Westley, J. Org. Chem. 1968, 33, 864) in dry diethyl ether (500 mL) is added dropwise to a solution of lithium aluminum hydride (400 mL of a 1 M solution in diethyl ether, 400 mmol, 5.4 eq). The suspension is heated at reflux for 23 hours and then cooled to 0° C. Water (70 mL) is then cautiously added and the resulting suspension is warmed to room temperature. After 3 hours the suspension is filtered and the solid washed with diethyl ether (1 L). The filtrate is concentrated under vacuum to provide crude title compound (11.40 g, 88%) as a yellow, crystalline solid. A sample (2 g) is recrystallized from cyclohexane and then from toluene to provide the purified title compound (0.83 g) as a fine, white crystals: mp 80–81° C.

brown solid. The solid was purified via flash column chromatography (40% EtOAc in heptane) yielding 22.7 g of the olefin as a brown foam.

A 1 L Parr shaker bottle was flushed with nitrogen and charged with 10% Pd/C (4.5 g, Degussa type) and the above-obtained olefin (20.0 g, 0.110 mol) in EtOH (450 mL). The reaction was hydrogenated at 50 psi for 3.5 hours when the reaction was filtered through a celite plug and rinsed with ethanol. The bottle was recharged with fresh 10% Pd/C (4.5 g, Degussa type), the filtrate and conc. HCl (15 mL). The reaction was hydrogenated at 50 psi for 18

| Anal. Calcd. For $C_{11}H_{16}N_2$: | C, 74.96; H, 9.15; N, 15.89; |
| Found: | C, 74.84; H, 9.01; N, 16.15. |

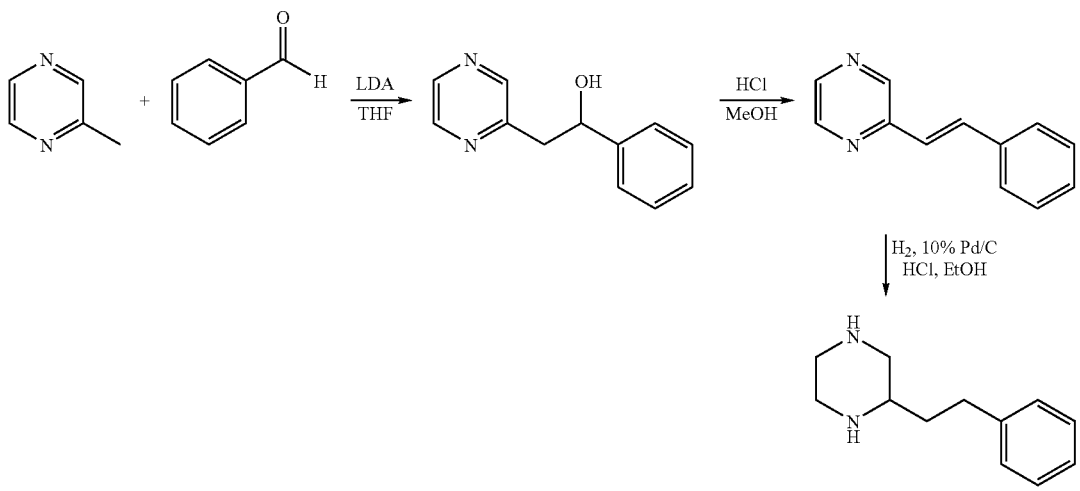

Example 1(b)

To a solution of LDA (295 mL, 0.59 mol, 2 M in heptane/THF/ethylbenzene) in anhydrous THF (300 mL) cooled to −40° C. was added 2-methylpyrazine (48.5 mL, 0.531 mol) dropwise via an addition funnel. The reaction was allowed to warm to −20° C. and was stirred for 90 minutes when a solution of benzaldehyde (54 mL, 0.531 mol) in anhydrous THF (200 mL) was added dropwise via an addition funnel. After complete addition, the reaction was allowed to warm to room temperature and was stirred for 20 hours. The reaction was then cooled in an ice bath and saturated NH$_4$Cl (500 mL) was added. The resulting mixture was extracted with EtOAc (500 mL, 250 mL). The combined extracts were dried (Na$_2$SO$_4$), filtered and concentrated to a damp, beige solid. The product was triturated with Et$_2$O and collected then dried overnight to yield 56.0 g (53%) of a light brown solid, mp 81–84° C.

A solution of the above-obtained solid (56.0 g, 0.28 mol) in MeOH (1.1 L) and conc. HCl (290 mL) was stirred at reflux for 24 hours. The reaction was cooled to room temperature and concentrated to a dark liquid. The dark liquid was cooled in an ice bath and water (1 L) was added. The resulting solution was neutralized with a saturated solution of Na$_2$CO$_3$ and the product was extracted with EtOAc (1 L, 2×500 mL). The combined extracts were dried (Na$_2$SO$_4$), filtered and concentrated to yield 46 g of a dark hours when the reaction was diluted with warm MeOH and filtered through a plug of celite. The solid was thoroughly washed with hot MeOH and the filtrate was concentrated to yield 11.2 g (39%) of the final product as the di-HCl salt, mp 297–300.

See: Tetrahedron, 30, 1974 pp667–673 and Tet. Lett. 1979, pp4483–4486

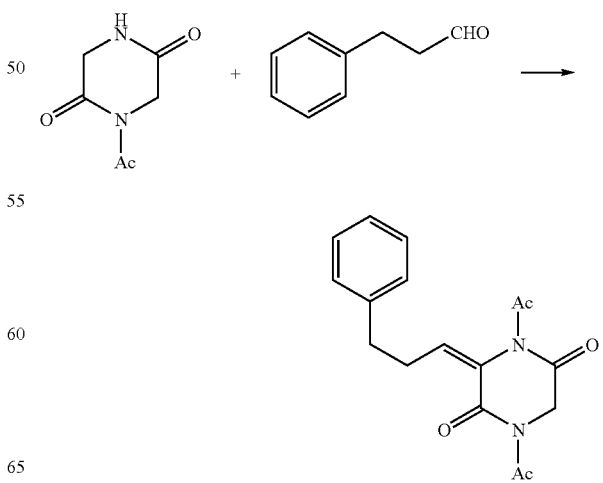

Example 1(c)

DBU (14.0 g, 92 mmol) was added to a solution of the piperazine diacetate (18.2 g, 92 mmol) and aldehyde (12.3 g, 92 mmol) in 92 mL of DMF at ambient temperature. The resulting mixture was stirred at room temperature for 5 h. The precipitated product was collected by filtration, providing 17.1 g of product.

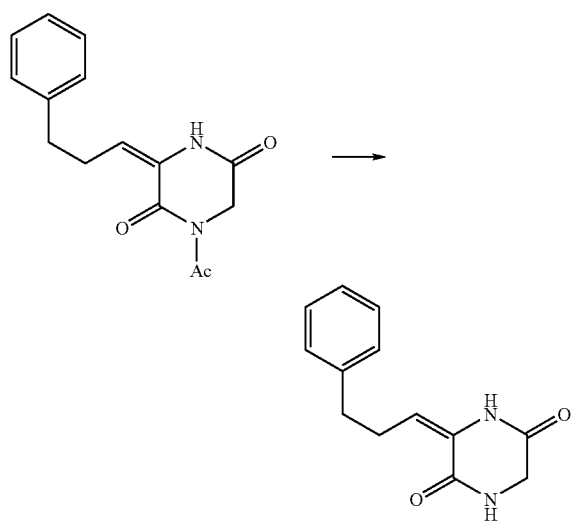

The monoacetate (17.0 g, 62.8 mmol) and hydrazine hydrate (9.4 g, 188.6 mmol) in 125 mL of DMF were stirred at room temperature for 20 h. The precipitated solid was collected by filtration, and washed with water and ethanol, leaving 13.7 g of product.

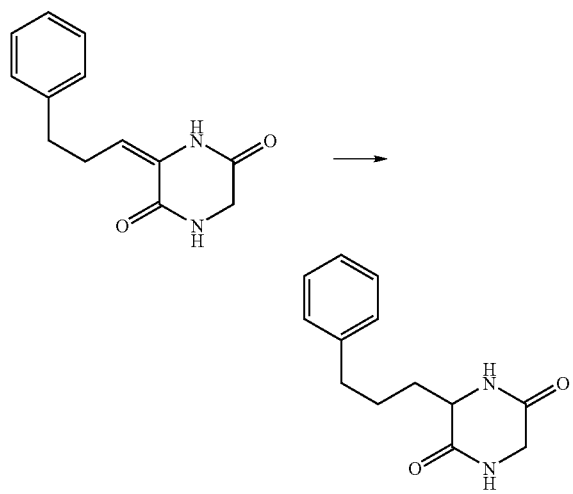

The olefin (13.6 g, 59.1 mmol) and palladium on carbon (2.7 g, 10% Pd/C, Degussa type, 50% H₂O) in 1.2 l of methanol were shaken on a Parr hydrogenation apparatus at 40 psi of hydrogen, until hydrogen uptake ceased. The mixture was diluted with dichloromethane and filtered through celite. Concentration of the filtrate provided 12.1 g of product.

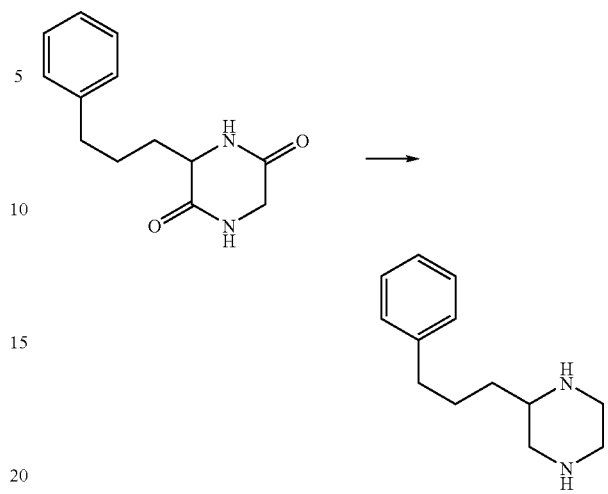

A solution of LAH (156 mL, 156 mmol, 1 M in THF) was added dropwise to a 0° C. solution of the piperazine dione (12.1 g, 52.1 mmol) in 100 ml of THF. The mixture was heated to reflux and stirred overnight. The mixture was cooled to 0° C. and 38 mL of water in 200 mL of THF was carefully added. The resulting mixture stirred for 1 h, then it was filtered, the filter cake was washed with THF, and the filtrate was concentrated in vacuo to give 7.4 g of product.

Example 2

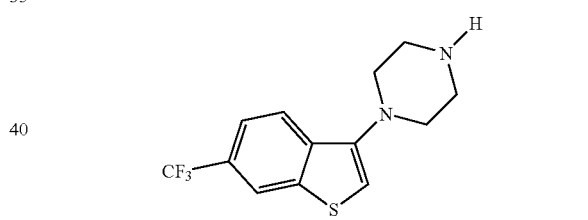

1-(6-(trifluoromethyl)-benzo[b]thien-3-yl)-piperazine hydrochloride

2a: 2–Carbomethoxy-3-amino-6-trifluoromethyl-benzo[b]thiophene:

Equip a 22-L, 3-necked, round-bottom flask with a mechanical stirrer, nitrogen bubbler, and a thermocouple probe, charge with 1.20 kg (5.55 mole) of 2-nitro-4-trifluoromethylbenzonitrile, 589.3 g (496 mL, 5.55 mole) of methyl thioglycolate, and 4.3 L of NMP. Cool the resulting yellow solution to 2° C., and add slowly, over a period of 78 min a solution prepared from 466.0 g (11.11 mole, 2.0 eq) of lithium hydroxide monohydrate in 3.36 L of water while maintaining the temperature between 2–20° C. Allow the brown slurry to warm to 21° C. over a 2 h period, and then dilute with 8.0 L of water (observe exotherm->27° C.). Stir for 40 min and cool to 18° C., collect the product by filtration, rinsing with 10 L of water, then air-drying at ambient temperature to give 1.295 kg (84.7% yield) of 2-carbomethoxy-3-amino-6-trifluoromethylbenzo[b]thiophene, as a light-yellow solid, 99.8% pure by HPLC assay.

2b: 1-(6-(trifluoromethyl)-benzo[b]thien-3-yl)-piperazine hydrochloride

Equip a 12-L, 3-necked, round-bottom flask with a mechanical stirrer, nitrogen bubbler, and a thermocouple probe, and charge with 1.14 kg (4.14 mole) of 2-carbomethoxy-3-amino-6-trifluoromethylbenzo-[b]thiophene Example 2a, 196.0 g (2.28 mole, 0.55 eq) of pipearazine, 4.0 L of NMP, and 570 mL of xylene. Heat the solution, and hold at 170–180° C. for 4 h, at which time the reaction is ca. 98% complete as determined by HPLC assay. Cool the brown solution to 168° C., and then add 1.605 kg (18.63 mole, 4.5 eq) of piperazine (temp->109° C.) following with 1.575 kg (28.28 mole, 2.0 eq) of p-toluenesulfonic acid monohydrate (observe exotherm, 109->130° C.). Connect a Dean-Stark trap to the condenser, and heat the reaction to collect an azeotrope. Remove a total of 410 mL of an aqueous distillate, while allowing the pot temperature to increase from 145 to 165° C. Monitor the progress of the reaction by GC/MS and HPLC assays. After 14 h at ca. 165° C. (>99% conversion by HPLC and GC/MS assay), cool the reaction to 30–35° C., and then quench into an extractor that contains 5 kg of ice, 12 L of water, and 8.5 L of toluene. Separate the phases, wash the organic extract with 11 L of 0.5 N NaOH, 2 L of saturated aq. NaCl., and then extract with 8 L of 1 N HCl. Dilute the acidic aqueous extract with 1 kg of ice, and basify to pH 11.2 by adding 624 g of 50% NaOH. Extract the resulting mixture with 9.5 L of toluene. Wash the toluene extract with 2 L of saturated aqueous NaCl, dry ($Na_2SO_4$), and filter. Charge the filtrate into a 22 L 3-necked, round-bottomed flask ($N_2$, mechanical stirring, temperature control probe), and add a total of 3.7 L of 1N ethereal HCl at 20–27° C. so that the mixture is positive to Congo Red indicator paper. During the HCl addition, add a total of 2.5 L of toluene to improve the stirring of the thick slurry that results. Stir at ambient temperature for 40 min, filter the slurry and wash with 4.5 L of toluene. After air drying, obtain 1.165 kg (87% yield) of 3-piperazinyl-6-trifluoromethyl-benzo[b]thiophene hydrochloride as a light pink-beige solid, 99.1% pure by GC/MS assay.

Example 3

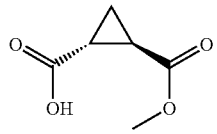

3a: trans-Cyclopropane-1,2-dicarboxylic acid monomethyl ester

Suspend trans-cyclopropane-1,2-dicarboxylic acid dimethylester (59.8 g, 0.378 mol) is suspended in 1.0N phosphate buffer (1.5 L, pH=7) add pig liver esterase (2.25 mL, 7500 units), and monitor NaOH consumption with a pH meter to control the reaction. After 3 h the consumption of 189 mL of 2N NaOH indicates the complete hydrolysis of the diester to the monomethylester. Acidified the clear solution by the addition of 5N HCl to a pH=1. Separate the enzyme by addition of dichloromethane (500 mL) and diatomaceous earth (25 g). Stir for 5 min, and then filter the mixture. Saturate the filtrate with NaCl, and extract with ethyl acetate (5 times). Combine the extracts, dry ($Na_2SO_4$) and evaporate to obtain 50.8 g (93%) of solid, mp 46–47° C., m/z=145 (M+H)$^+$

3b: (S,S)-(+)-Cyclopropane-1,2-dicarboxylic acid monomethyl ester

Add trans-cyclopropane-1,2-dicarboxylic acid monomethyl ester, Example 3a, (19.46 g) in acetone to quinine (43.8 g) in one portion. Heat the reaction to reflux, and then add methylcyclohexane (150 mL). After crystallization (5 times) from acetone/methylcyclohexane, collect 6.2 g of the diastereomeric salt ($\alpha_D$:+173, c:7.3 $CHCl_3$)

3c: (R,R)-(−)-Cyclopropane-1,2-dicarboxylic acid monomethyl ester

Concentrate the filtrate from 3b above and treat the residue with 1N $KHSO_4$ solution to yield 12.0 g of the crude (R,R) enatiomer. Dissolve this material in acetone and add 1 equivalent of quinidine in one portion. Heat the reaction to reflux, and then add methylcyclohexane. After crystallization overnight, collect 10.3 g of the diastereomeric salt ($\alpha_D$: −235, c: 8.5 $CHCl_3$)

Example 4

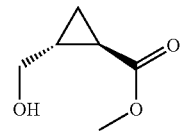

4a: trans-2-Hydroxymethyl-cyclopropanecarboxylic acid methyl ester

Add borane-methyl sulfide complex (177 mL, 0.354 mol), slowly, by means of a dropping funnel, to a stirring solution of trans-cyclopropane-1,2-dicarboxylic acid monomethyl ester (Example 3a) (25.5 g, 0.177 mol), trimethyl borate (60.3 mL, 0.531 mol) and tetrahydrofuran (150 mL) at 0° C. After complete addition, allow the reaction to come to ambient temperature and stir for 2 h more. Pour the reaction mixture into a stirring solution of 50% aqueous sodium chloride solution (1.5 L)-concentrated HCl (10 mL). Extract the mixture with ethyl acetate (EtOAc) (3 times), combine the extracts, dry ($Na_2SO_4$) and concentrate the solvent to obtain a colorless oil: 22.6 g.

4b: (S,S)-(+)-2-Hydroxymethyl-cyclopropanecarboxylic acid methyl ester

Follow the procedure of Example 4a, and substitute (S,S)-(+)-cyclopropane-1,2-dicarboxylic acid monomethyl ester (Example 3b) therein to obtain the title compound, $\alpha_D$: +54, c: 1.5 $CHCl_3$ (Tetrahedron Asymmetry Vol.6, No.3, pp.683–684, 1995)

4c: (R,R)-(−)-2-Hydroxymethyl-cyclopropanecarboxylic acid methyl ester

Follow the procedure of Example 4a, and substitute (R,R)-(−)-cyclopropane-1,2-dicarboxylic acid monomethyl ester (Example 3c) therein to obtain the title compound ($\alpha_D$: −78.6, c: 4.3 $CHCl_3$)

Example 5

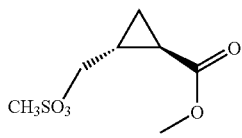

5a: trans-2-Methanesulfonyloxymethyl-cyclopropanecarboxylic acid methyl ester Add, dropwise, triethylamine (7.74 mL, 56 mmol) and 4-dimethylaminopyridine (0.013 g, 0.106 mmol) in dichloromethane (30 mL) to a stirred solution of trans-2-hydroxymethyl-cyclopropanecarboxylic acid methyl ester (Example 4a) (2.4 g, 18.64 mmol), at 0–5° C. After 0.5 h, pour the reaction mixture into water and extract the mixture with dichloromethane (3 times). Wash the combined extracts with 1N $KHSO_4$, dry ($Na_2SO_4$) and concentrate to yield 4.29 g of a pale yellow oil, which solidifies when stored at 0° C., m/z=209 $(M+H)^+$

5b: (S,S)-(+)-2-Methanesulfonyloxymethyl-cyclopropanecarboxylic acid methyl ester Follow the procedure of Example 5a, and substitute (S,S)-(+)-2-hydroxymethyl-cyclopropanecarboxylic acid methyl ester (Example 4b) therein to obtain the title compound ($\alpha_D$: +75, c: 4.7 $CHCl_3$)

5c: (R,R)-(−)-2-Methanesulfonyloxymethyl-cyclopropanecarboxylic acid methyl ester Follow the procedure of Example 5a, and substitute (R,R)-(−)-2-hydroxymethyl-cyclopropanecarboxylic acid methyl ester (Example 4c) therein to obtain the title compound ($\alpha_D$: −74.4, c: 5.9 $CHCl_3$).

Example 6

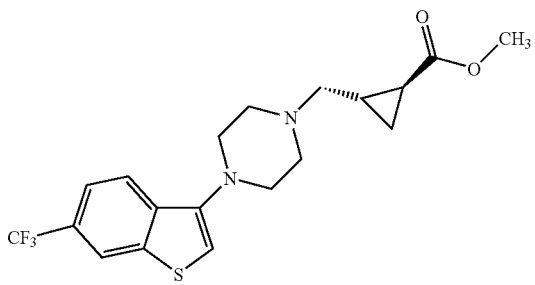

6a: trans-2-[4-(6-Trifluoromethyl-benzo[b]thiophen-3-yl)-piperazin-1-ylmethyl]-cyclopropanecarboxylic acid methyl ester Heat at reflux for 16 h, a mixture of 1-(6-trifluoromethyl-benzo[b]thiophen-3-yl)-piperazine, free base of Example 2b, (23.0 g, 71.3 mmol), trans-2-methanesulfonyloxymethyl-cyclopropanecarboxylic acid methyl ester (Example 5a) (15.3 g, 73.5 mmol), and triethylamine (40 mL, 288 mmol) in acetonitrile (600 mL). Concentrate the reaction mixture under reduced pressure and dilute the resultant oil with EtOAc (30 mL). Filter the resulting precipitate (unreacted starting piperazine) away and purify the filtrate by column chromatography over silica gel (EtOAc/heptane/MeOH/triethylamine, 20:20:1). Concentration of the appropriate fractions gives 18.0 g of colorless oil, m/z=413 $(M+H)^+$.

6b: (S,S)-(+)-2-[r4-(6-Trifluoromethyl-benzo[b]thiophen-3-yl)-piperazin-1-ylmethyl]-cyclopropanecarboxylic acid methyl ester Follow the procedure of Example 6a, and substitute (S,S)-(+)-2-methanesulfonyloxymethyl-cyclopropanecarboxylic acid methyl ester (Example 5b) therein to obtain the title compound ($\alpha_D$: +48, c: 2.8 EtOH).

6c: (R,R)-(−)-2-[4-(6-Trifluoromethyl-benzo[b]thiophen-3-yl)-piperazin-1-ylmethyl]-cyclopropanecarboxylic acid methyl ester Follow the procedure of Example 5, and substitute (R,R)-(−)-2-methanesulfonyloxymethyl-cyclopropanecarboxylic acid methyl ester, Example 5c, therein, to obtain the title compound ($\alpha_D$: −49.3, c: 3.5 $CHCl_3$).

Example 7

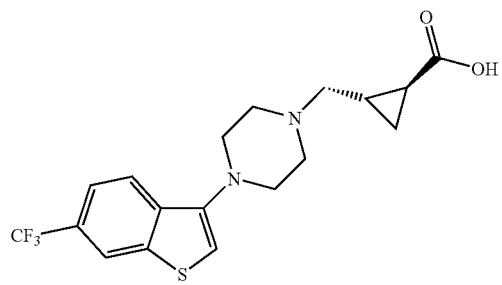

7a: trans-2-[4-(6-Trifluoromethyl-benzo[b]thiophen-3-yl)-piperazin-1-ylmethyl]-cyclopropanecarboxylic acid Add 5N NaOH solution (425 mL, 226 mmol) to a solution of trans-2-[4-(6-trifluoromethyl-benzo[b]thiophen-3-yl)-piperazin-1-ylmethyl]-cyclopropanecarboxylic acid methyl ester, Example 6a, (18.0 g, 45.1 mmol) in dioxane/methanol (400 mL, 3:1) and heat the reaction at 60° C. for 6 h. Selectively remove most of the methanol and acidify the remaining dioxane solution to pH 5–6 with 2N acetic acid. Collect the desired compound, which precipitates from solution, to obtain 14.08 g (81%) of colorless crystals, m/z=385 $(M+H)^+$

7b: (S,S)-(+)-2-[4-(6-Trifluoromethyl-benzo[b]thiophen-3-yl)-piperazin-1-ylmethyl]-cyclopropanecarboxylic acid Follow the procedure of Example 7a, and substitute (S,S)-(+)-2-[4-(6-trifluoromethyl-benzo[b]thiophen-3-yl)-piperazin-1-ylmethyl]-cyclopropanecarboxylic acid methyl ester (Example 6b) therein to obtain the title compound ($\alpha_D$: +55, c: 1.05 EtOH).

7c: (R,R)-(−)-2-[4-(6-Trifluoromethyl-benzo[b]thiophen-3-yl)-piperazin-1-ylmethyl]-cyclopropanecarboxylic acid Follow the procedure of Example 7a, and substitute (R,R)-(−)-2-[4-(6-trifluoromethyl-benzo[b]thiophen-3-yl)-piperazin-1-ylmethyl]-cyclopropanecarboxylic acid methyl ester (Example 5c) therein to obtain the title compound ($\alpha_D$: −40.5, c: 0.79 CHCl$_3$).

Example 8

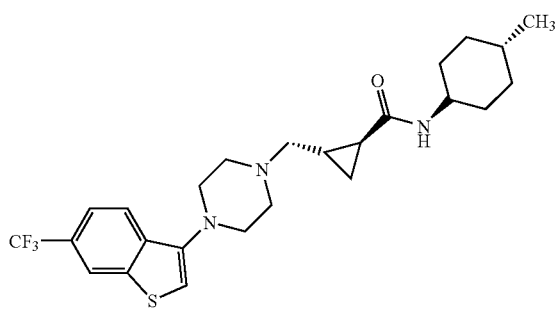

8a: trans-2-[4-(6-Trifluoromethyl-benzo[b]thiophen-3-yl)-piperazin-1-ylmethyl]-cyclopropanecarboxylic acid trans-(4-methylcyclohexyl)-amide Stir a solution of trans-2-[4-(6-trifluoromethyl-benzo[b]thiophen-3-yl)-piperazin-1-ylmethyl]-cyclopropanecarboxylic acid (Example 7a) (1.99 g, 5.0 mmol), and O-[(ethoxycarbonyl)-cyanomethylenamino]-N,N,N',N'-tetramethyluronium-tetrafluoroborate (TOTU, 2.05 g, 6.3 mmol) in DMF (50 mL) at 20° C. for 0.5 h. Add N-methylmorpholine (0.58 mL, 5.3 mmol), after which add trans-4-methylcyclohexylamine (1.13 g, 10 mmol), and stir the reaction for 5 h. Concentrate the reaction under reduced pressure to obtain an oil. Purify by column chromatography over silica gel (EtOAc/heptane/methanol/triethylamine, 20:20:1:1) to obtain 1.86, (76%) of colorless crystals LC/MS, m/z=480 (M+H)$^+$.

8b: (S,S)-(+)-2-[4-(6-Trifluoromethyl-benzo[b]thiophen-3-yl)-piperazin-1-ylmethyl]-cyclopropanecarboxylic acid trans-(4-methylcyclohexyl)-amide Follow the procedure of Example 8a, and substitute (S,S)-(+)-2-[4-(6-trifluoromethyl-benzo[b]thiophen-3-yl)-piperazin-1-ylmethyl]-cyclopropanecarboxylic acid (Example 7b) therein to obtain the title compound, LC/MS, m/z=480 (M+H)$^+$.

8c: (R,R)-(−)-2-[4-(6-Trifluoromethyl-benzo[b]thiophen-3-yl)-piperazin-1-ylmethyl]-cyclopropanecarboxylic acid trans-(4-methylcyclohexyl)-amide Follow the procedure of Example 8a, and substitute (R,R)-(−)-2-[4-(6-trifluoromethyl-benzo[b]thiophen-3-yl)-piperazin-1-ylmethyl]-cyclopropanecarboxylic acid (Example 7c) therein to obtain the title compound LC/MS, m/z=480 (M+H)$^+$.

Example 9

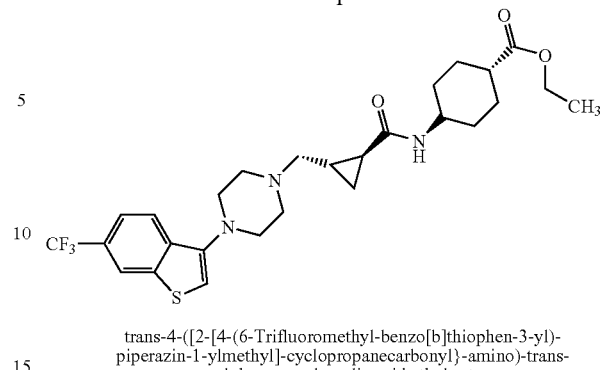

trans-4-([2-[4-(6-Trifluoromethyl-benzo[b]thiophen-3-yl)-piperazin-1-ylmethyl]-cyclopropanecarbonyl}-amino)-trans-cyclohexanecarboxylic acid ethyl ester Follow the procedure of Example 8a, and substitute trans-4-amino-cyclohexane carboxylic acid ethyl ester (J.Med.Chem. (1971), 14(7), 600–614) for trans-4-methyl-cyclohexylamine therein to obtain the title compound LC/MS, m/z=538 (M+H)$^+$.

Example 10

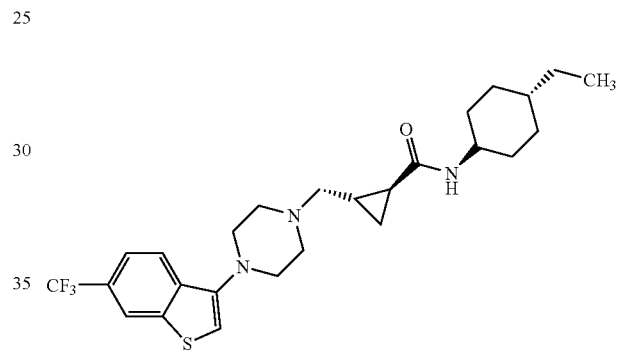

trans-2-[4-(6-Trifluoromethyl-benzo[b]thiophen-3-yl)-piperazin-1-ylmethyl]-cyclopropanecarboxylic acid trans-(4-ethylcyclohexyl)-amide Follow the procedure of Example 8a, and substitute trans-4-ethylcyclohexylamine for trans-4-methylcyclohexy-lamine therein to obtain the title compound LC/MS, m/z=494 (M+H)$^+$.

Example 11

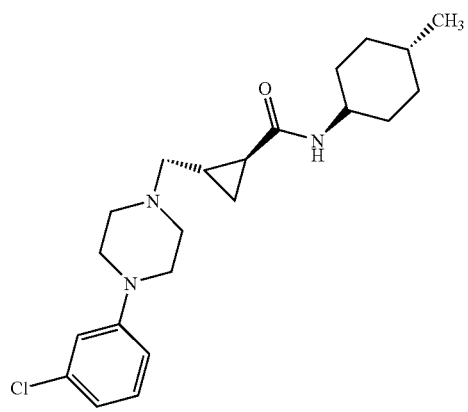

trans-2-[4-(3-Chloro-phenyl)-piperazin-1-ylmethyl]-cyclopropanecarboxylic acid trans-(4-methylcyclohexyl)-amide

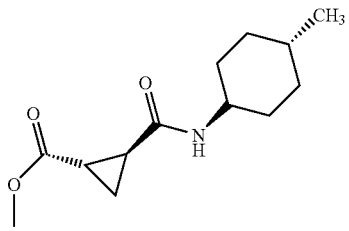

11a: trans-2-(4-Methyl-cyclohexylcarbamoyl)-cyclopropanecarboxylic acid methyl ester Stir a solution of trans-cyclopropane-1,2-dicarboxylic acid monomethyl ester (Example 3a) (3.0 g, 20.8 mmol) and TOTU (8.5 g, 26 mmol) in DMF (300 mL) at ambient temperature for 20 min at which time add N-methylmorpholine (2.4 mL 22.9 mmol) and trans 4-methylcyclohexylamine 3.06 g, 27.0 mmol). After 3 h, remove the solvent and dissolve the residue in H₂O/EtOAc. Extract the aqueous layer 3 more times with EtOAc and combine the extracts. Wash the extract with saturated NaHCO₃ solution, brine and dry over MgSO₄. Concentrate the solvent to afford the crude product, and purify by column chromatography over silica gel to give 4.76 g (95%) of colorless crystals, m/z=240 (M+H)⁺.

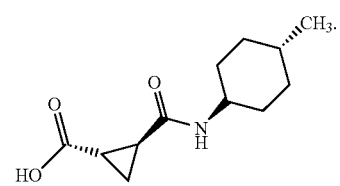

11b: trans-2-trans-2-Methylcyclohexylcarbamoyl)-cyclopropanecarboxylic acid

Stir a solution of trans-2-(4-methyl-cyclohexylcarbamoyl)-cyclopropane-carboxylic acid monomethyl ester (Example 11a) (4.5 g, 19.8 mmol), 5N NaOH (40 mL) and MeOH/dioxane overnight. Concentrate the reaction mixture under vacuum, cool the resulting solution and acidify to pH 5. Collect the precipitate, wash (H₂O) and dry under vacuum at 40° C. to obtain 3.7 g (87%) of solid.

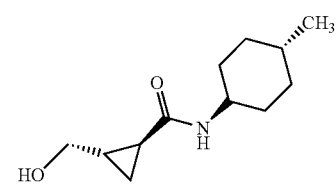

11c: trans-2-Hydroxymethyl-cyclopropanecarboxylic acid trans-(4-methylcyclohexyl)-amide Stir a solution, under argon, at 0° C., of trans -2 trans-2-methylcyclohexylcarbamoyl)-cyclopropanecarboxylic acid (Example 11b) (3.69 g, 16.4 mmol), trimethyl borate (5.6 mL, 50 mmol), and add slowly 2N borane dimethylsulfide complex in THF (16.4 mL, 32.8 mmol). Continue to stir the reaction at 0° C. for 1 h, and then at ambient temperature for 2 h. Carefully pour the reaction mixture into ice-H₂O and acidify with 2N HCl. Extract the mixture with EtOAc (3 times), wash with brine, dry over MgSO₄ and concentrate to obtain 2.85 g (83%) of product as a solid.

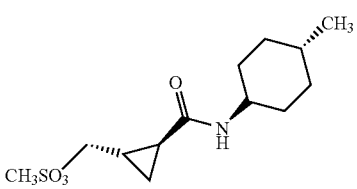

11d: Methane sulfonic acid 2-(trans-4-methylcyclohexylcarbamoyl)-trans-cyclopropylmethyl ester Add, dropwise, to a stirring suspension at −20° C. of trans-2-hydroxymethyl-cyclopropanecarboxylic acid trans-(4-methylcyclohexyl)-amide (Example 11c) (2.85 g, 13.5 mmol), triethylamine (3.74 mL, 27.0 mmol) and 4-(dimethylamino)pyridine (0.1 g, 0.82 mmol) in dichloromethane (100 ml) a solution of methanesulfonic acid (1.59 mL, 20.3 mmol) in DCM (10 mL). When the reaction is complete, pour the mixture into ice water and extract the mixture with DCM. Combine the extracts, wash with 0.1N KHSO4, brine, dry over MgSO₄ and concentrate under vacuum. Treat the residue with a mixture of isopropanol/heptane and collect the precipitate by filtration to obtain 2.91 g (74%) of solid, MS m/z=290 (M+H)⁺.

11e: trans-2-[4-(3–Chloro-phenyl)-piperazin-1-ylmethyl]-cyclopropanecarboxylic acid trans-(4-methylcyclohexyl)-amide Reflux a solution of methane sulfonic acid 2-(trans-4-methyl-cyclohexylcarbamoyl)-trans-cyclopropylmethyl ester (Example 11d) (30.0 mg, 0.1 mmol), t-(3-chlorophenyl)-piperazine hydrochloride (29.0 mg, 0.13 mmol) triethylamine (0.05 mL, 0.4 mmol) in acetonitrile (5 ml) for 15 h. Concentrate the reaction mixture under vacuum and chromatograph the residue over silica gel to obtain 11.3 mg (28%) of solid, LC/MS, m/z=390 (M+H)⁺.

Example 12

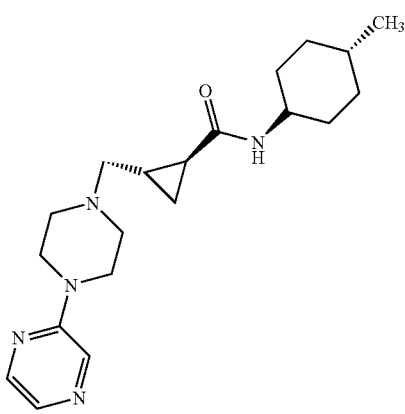

trans-2-[4-(pyrazin-2-yl)-piperazin-1-ylmethyl]-cyclopropanecarboxylic acid trans-(4-methylcyclohexyl)-amide Follow the procedure of Example 11e, and substitute 1-(pyrazin-2-yl)-piperazine hydrochloride for 1-(3-chlorophenyl)-piperazine hydrochloride therein to obtain the title compound LC/MS, m/z=358 (M+H)$^+$.

Example 13

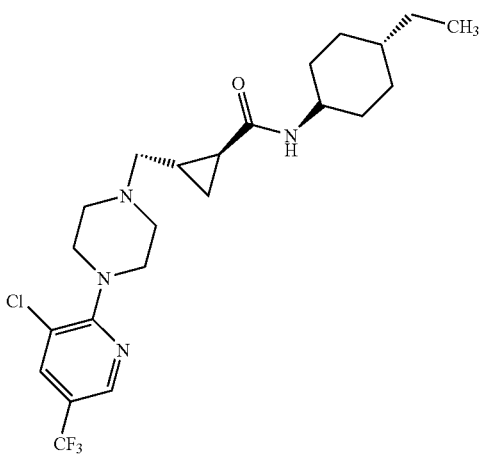

trans-2-[4-(3-Chloro-5-trifluoromethyl-pyridin-2-yl)-piperazin-1-ylmethyl)-cyclopropanecarboxylic acid trans-(4-ethylcyclohexyl)-amide

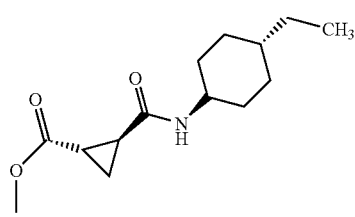

13a: trans-2-(4-Ethyl-cyclohexylcarbamoyl)-cyclopropanecarboxylic acid methyl ester Follow the procedure of Example 11a, and substitute trans-(4-ethylcyclohexylamine) for trans-(4-methylcyclohexylamine) therein to obtain the title compound, m/z=254 (M+H)$^+$.

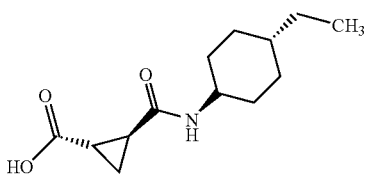

13b: trans-2-(trans-2-Ethylcyclohexylcarbamoyl)-cyclopropanecarboxylic acid

Follow the procedure of Example 11b, and substitute trans-2-(4-ethyl-cyclohexylcarbamoyl)-cyclopropanecarboxylic acid monomethyl ester (Example 13a) for trans-2-(4-methyl-cyclohexylcarbamoyl)-cyclopropanecarboxylic acid monomethyl ester therein to obtain the title compound.

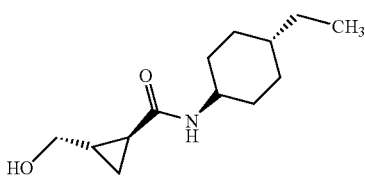

13c: trans-2-Hydroxymethyl-cyclopropanecarboxylic acid trans-(4-ethylcyclohexyl)-amide Follow the procedure of Example 11c, and substitute trans-2-(4-ethylcyclohexylcarbamoyl)-cyclopropanecarboxylic acid (Example 13b) for trans-2-(4-methyl-cyclohexylcarbamoyl)-cyclopropane carboxylic acid therein to obtain the title compound.

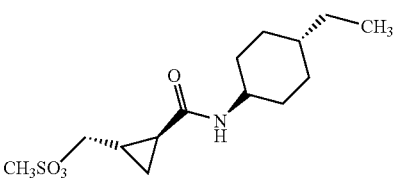

13d: Methane sulfonic acid 2-(trans-4-ethyl-cyclohexylcarbamoyl)-trans-cyclopropylmethyl ester Follow the procedure of Example 11d, and substitute trans-2-hydroxymethyl-cyclopropanecarboxylic acid trans-(4-ethylcyclohexyl)-amide, Example 13c for methane sulfonic acid 2-(trans-4-methyl-cyclohexylcarbamoyl)-trans-cyclopropylmethyl ester therein, to obtain the title compound, m/z=304 (M+H)$^+$.

13e: trans-2-[4-(3-Chloro-5-trifluoromethyl-pyridin-2-yl)-piperazin-1-ylmethyl)-cyclopropanecarboxylic acid trans-(4-ethylcyclohexyl)-amide Follow the procedure of Example 11e, and substitute methane sulfonic acid 2-(trans-4-ethyl-cyclohexylcarbamoyl)-trans-cyclopropylmethyl ester (Example 13d) for 2-(trans-4-methyl-cyclohexylcarbamoyl)-trans-cyclopropylmethyl ester and 4-(3-chloro-5-trifluoromethyl-pyridin-2-yl)-piperazine hydrochloride for 1-(3-chloro-phenyl)-piperazine hydrochloride therein to obtain the title compound LC/MS m/z=473 (M+H)+.

Example 14

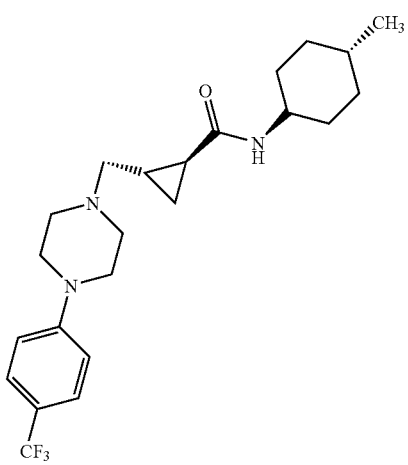

trans-2-[4-(4-Trifluoromethyl-phenyl)-pierazin-1-ylmethyl]cyclopropanecarboxylic acid trans-(4-methylcyclohexyl)-amide Follow the procedure of Example 11e, and substitute 1-(4-trifluoromethyl-phenyl)-piperazine hydrochloride for 1-(3-chloro-phenyl)-piperazine hydrochloride therein to obtain the title compound MS, m/z=424 (M+H)+, 85.2% pure by HPLC assay.

Example 15

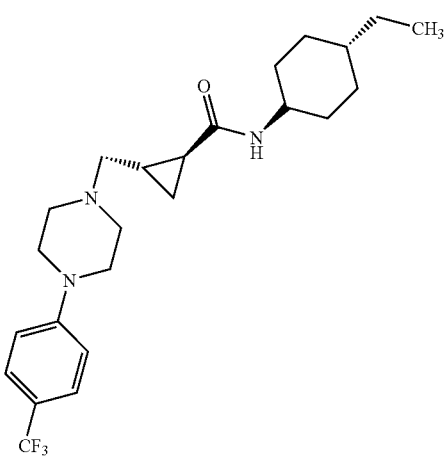

trans-2-[4-(4-Trifluoromethyl-phenyl)-pierazin-1-ylmethyl]cyclopropanecarboxylic acid trans-(4-ethylcyclohexyl)-amide Follow the procedure of Example 11e, and substitute methane sulfonic acid 2-(trans-4-ethyl-cyclohexylcarbamoyl)-trans-cyclopropylmethyl ester (Example 13d) for methane sulfonic acid 2-(trans-4-methyl-cyclohexylcarbamoyl)-trans-cyclopropylmethyl ester and 4-(4-trifluoromethyl-phenyl)-piperazine hydrochloride for 1-(3-chloro-phenyl)-piperazine hydrochloride therein to obtain the title compound MS m/z=438 (M+H)+, 78.5% pure by HPLC assay.

Example 16

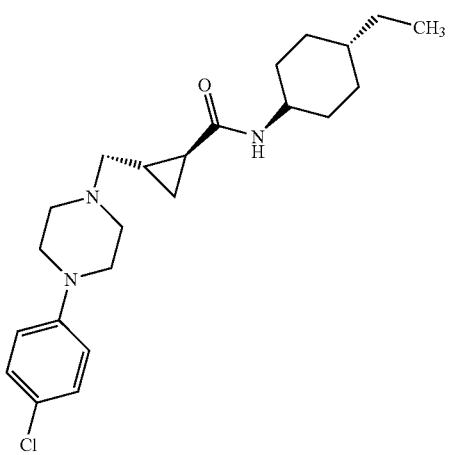

trans-2-[4-(4-Chlorophenyl)-pierazin-1-ylmethyl]cyclopropanecarboxylic acid trans-(4-ethylcyclohexyl)-amide Follow the procedure of Example 11e, and substitute methane sulfonic acid 2-(trans-4-ethyl-cyclohexylcarbamoyl)-trans-cyclopropylmethyl ester, Example 13d for 2-(trans-4-methyl-cyclohexylcarbamoyl)-trans-cyclopropylmethyl ester and 4-(4-chlorophenyl)-piperazine hydrochloride for 1-(3-chloro-phenyl)-piperazine hydrochloride therein, to obtain the title compound LC/MS, m/z=404 (M+H)+.

Example 17

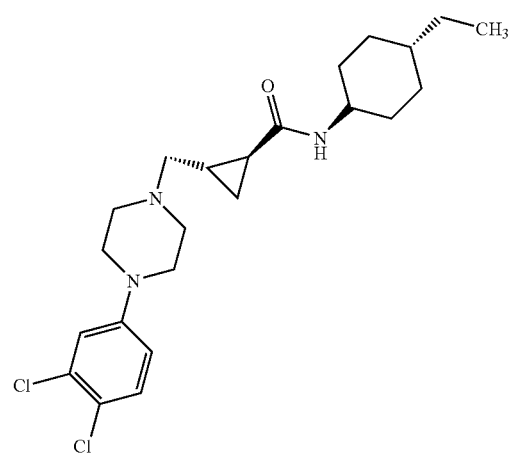

trans-2-[4-(3,4-Dichlorophenyl)-pierazin-1-ylmethyl]cyclopropanecarboxylic acid trans-(4-ethylcyclohexyl)-amide Follow the procedure of Example 11e, and substitute methane sulfonic acid 2-(trans-4-ethyl-cyclohexylcarbamoyl)-trans-cyclopropylmethyl ester (Example 13d) for 2-(trans-4-methyl-cyclohexylcarbamoyl)-trans-cyclopropylmethyl ester and 4-(3,4-dichlorophenyl)-piperazino hydrochloride for 1-(3-chloro-phenyl)-piperazine hydrochloride therein to obtain the title compound LC/MS, m/z=438 (M+H)$^+$.

Example 18

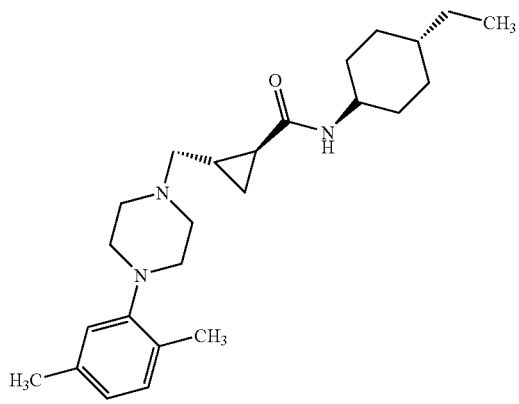

trans-2-[4-(2,5-Dimethylphenyl)-pierazin-1-ylmethyl]cyclopropanecarboxylic acid trans-(4-ethylcyclohexyl)-amide Follow the procedure of Example 11e, and substitute methane sulfonic acid 2-(trans-4-ethyl-cyclohexylcarbamoyl)-trans-cyclopropylmethyl ester (Example 13d) for 2-(trans-4-methyl-cyclohexylcarbamoyl)-trans-cyclopropylmethyl ester and 4-(2,5-dimethylphenyl)-piperazine hydrochloride for 1-(3-chloro-phenyl)-piperazine hydrochloride therein to obtain the title compound LC/MS, m/z=398 (M+H)$^+$.

Example 19

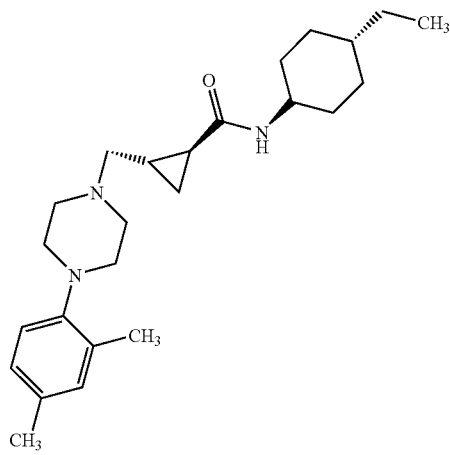

trans-2-[4-(2,5-Dimethylphenyl)-pierazin-1-ylmethyl]cyclopropanecarboxylic acid trans-(4-ethylcyclohexyl)-amide Follow the procedure of Example 11e, and substitute methane sulfonic acid 2-(trans-4-ethyl-cyclohexylcarbamoyl)-trans-cyclopropylmethyl ester (Example 13d) for 2-(trans-4-methyl-cyclohexylcarbamoyl)-trans-cyclopropylmethyl ester and 4-(2,5-dimethylphenyl)-piperazine hydrochloride for 1-(3-chloro-phenyl)-piperazine hydrochloride therein, to obtain the title compound LC/MS, m/z=398 (M+H)$^+$.

Example 20

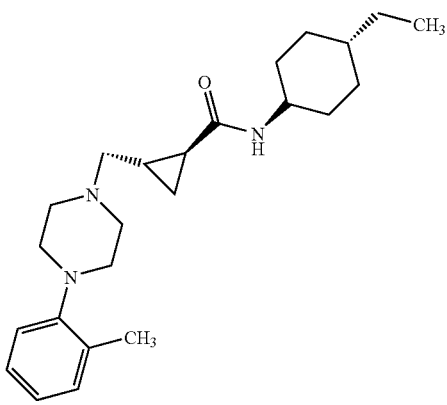

trans-2-[4-(2-Methylphenyl)-pierazin-1-ylmethyl]cyclopropanecarboxylic acid trans-(4-ethylcyclohexyl)-amide Follow the procedure of Example 11e, and substitute methane sulfonic acid 2-(trans-4-ethyl-cyclohexylcarbamoyl)-trans-cyclopropylmethyl ester (Example 13d) for 2-(trans-4-methyl-cyclohexylcarbamoyl)-trans-cyclopropylmethyl ester and 4-(2-methylphenyl)-piperazine hydrochloride for 1-(3-chloro-phenyl)-piperazine hydrochloride therein to obtain the title compound LC/MS, m/z=384 (M+H)$^+$.

Example 21

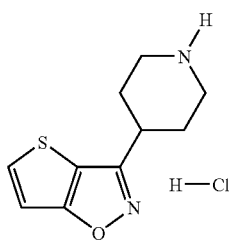

3-Piperidinyl-4-yl-thieno[2,3-d]isoxazole hydrochloride

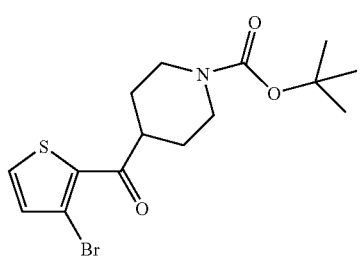

21a: 4-(3-Bromo-thiophene-2-carbonyl)-piperidine-1-carboxylic acid tert-butyl ester Stir a solution, under nitrogen, of 3-bromothiophene (21.0 mL, 0.224 mol) in tetrahydrofuran (1.0 L) at −78° C., and add a 2.0 M solution of lithium diisopropylamide in heptane/tetrahydrofuran/ethylbenzene (112 mL, 0.224 mol) for 45 min. Add, dropwise, over 2 h, a solution of 4-(N-methoxy-N-methylcarboxamido)-1-piperidinecarboxylic acid 1,1-dimethylethyl ester (prepared according to U.S. Pat. No. 5,134,139) (79.4 g, 0.291 mol) in tetrahydrofuran (800 mL). Stir for 2 h, add a saturated ammonium chloride solution, and stir for an additional 0.5 h. Filter the resulting solid, and pour the filtrate into water (800 mL). Extract the aqueous mixture with ether and concentrate to obtain a dark liquid. Pour the liquid into water (400 mL), add NaCl and extract the aqueous mixture with ether. Wash the extract with water, brine, and dry over $Na_2SO_4$. Filter and concentrate to obtain the crude product. Chromatograph the product over silica gel (pet.ether/ether, 4:1) to obtain 41.5 g (50%) of white solid.

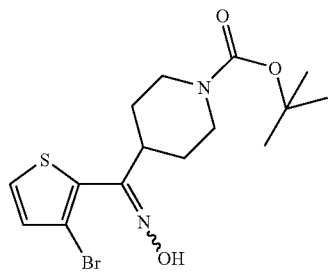

21b: 4-[(3-Bromo-thiophen-2-yl)-hydroxyimino-methyl-piperidine-1-carboxylic acid tert-butyl ester Stir a mixture of 4-(3-bromo-thiophene-2-carbonyl)-piperidine-1-carboxylic acid tert-butyl ester (Example 21a) (41.5 g, 0.11 mol), hydroxylamine hydrochloride (15.4 g, 0.23 mol) and pyridine (190 mL) at ambient temperature overnight. Pour the reaction into water (500 mL) and extract with dichloromethane (3 times). Wash the combined extracts with saturated $CuSO_4$ solution (2 times), dry ($MgSO_4$) and concentrate to a green solid. Dissolve the solid in toluene (175 mL) and let stand at ambient temperature for 3 h. Collect the resulting crystals that form and wash with toluene (60 mL). Concentrate the filtrate and again dissolve the residue in toluene and proceed to collect additional crystals to obtain a total yield of 25 g (58%) of the title compound as a light, green solid.

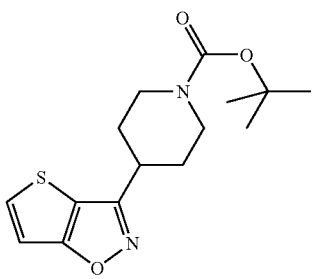

21c: 4-Thieno[2,3-d]isoxazol-3-yl-piperidine-1-carboxylic acid tert-butyl ester Add to a stirring solution of 4-[(3-bromo-thiophen-2-yl)-hydroxyimino-methyl]piperidine-1-carboxylic acid tert-butyl ester (Example 21b) (25 g., 64.2 mmol) in 2-methoxyethanol (200 mL), a solution of potassium hydroxide (7.2 g, 128.4 mmol) in water (20 mL). Heat the reaction to 60° C. and then add copper powder (1.25 g). Stir at 60–70° C. for 6 h and then at ambient temperature overnight. Pour the reaction mixture into water (500 mL) and extract with EtOAc (3 times). Concentrate to a dark residue and purify by column. chromatography over silica gel (heptane/EtOAc, 4:1) to provide 9.8 g (50%) of a white solid.

21d: 3-Piperidinyl-4-yl-thieno[2,3-d]isoxazole hydrochloride

Add ethereal HCl (10 mL) to 4-thieno[2,3-d]isoxazol-3-yl-piperidine-1-carboxylic acid_tert-butyl ester (Example 21c) (1.0 g, 3.2 mmol) and then methanol (1 mL) to effect solution. Permit to stand at ambient temperature for 1 h and then collect 0.34 g of white solid, mp 240–241° C. From the filtrate collect 0.25 g of additional white solid, mp 263–265° C. Both samples: MS, m/z=209 (M+H)⁺.

Analysis (sample mp 263–265° C.):

| | | | |
|---|---|---|---|
| Calc. For: $C_{10}H_{12}N_2OS \cdot HCl$: | 49.08% C | 5.35% H | 11.45% N |
| Found: | 49.03% C | 5.29% H | 11.25% N |

Example 22

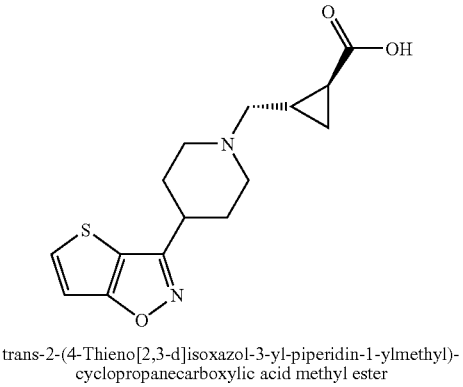

trans-2-(4-Thieno[2,3-d]isoxazol-3-yl-piperidin-1-ylmethyl)-cyclopropanecarboxylic acid methyl ester

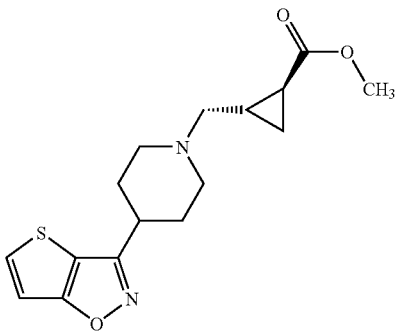

22a: trans-2-(4-Thieno[2,3-d]isoxazol-3-yl-piperidin-1-ylmethyl)-cycloproranecarboxylic acid methyl ester Reflux a solution of 3-piperidinyl-4-yl-thieno[2,3-d]isoxazole trifluoroacetate, (trifluoroacetic acid salt of Example 21d) (6.0 g, 18.6 mmol), trans-2-methanesulfonyloxymethyl-cyclopropanecarboxylic acid methyl ester (Example 5a) (3.99 g, 19.2 mmol) and triethylamine (7.6 g, 75 mmol) in acetonitrile (100 mL) for 15 h. Concentrate and purify the residue by column chromatography over silica gel (dichloromethane/EtOAc/diethylamine (8:2:1). Further purify by another chromatography dichloromethane/MeOH (95:5) to obtain 1.4 g (24%) of product, MS, m/z=321(M+H)$^+$.

22b: trans-2-(4-Thieno[2,3d]isoxazol-3-yl-piperidin-1-ylmethyl)-cyclopropanecarboxylic acid ethyl ester Add 5N NaOH (4.4 mL, 21.9 mmol) to a solution of trans-2-(4-thieno[2,3-d]isoxazol-3-yl-piperidin-1-ylmethyl)-cyclopropanecarboxylic acid methyl ester, Example 22a (1.4 g, 4.37 mmol) in dioxane/methanol (24 mL, 3:1), and heat to 60° C. for 3 h. Concentrate the reaction and treat the residue with acetic acid. After 36 h dilute the acetic acid solution with dichloromethane and wash the organic phase with 5% aqueous HCl, water and brine. Dry the organic phase and concentrate to a yellow oil. Evacuate the oil at high vacuum and 60° C. for 20 h to obtain 0.191 g of oil.

Treat the aqueous washings with NaCl and collect an additional 1.0 g of the product as a solid. MS, m/z 307 (M+H)$^+$.

Example 23

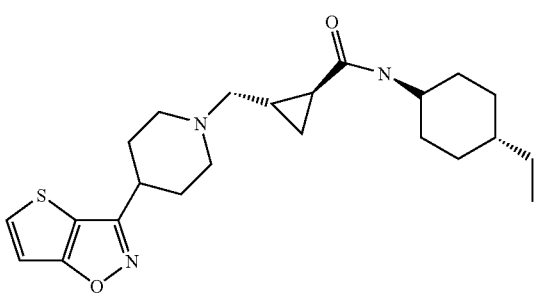

Racemic-trans-2-(4-Thieno[2,3-d]isoxazol-3-yl-piperidin-1-ylmethyl)-cyclopropanecarboxylic acid trans-(4-ethyl-cyclohexyl)-amide Add TOTU (415 mg, 1.06 mmol) to a solution of trans-2-(4-thieno[2,3-d]isoxazol-3-yl-piperidin-1-ylmethyl)-cyclopropanecarboxylic acid methyl ester (Example 22b) (300 mg, 1.0 mmol), in dimethylformamide (approximately 10 mL), and allow the reaction to stir at ambient temperature for 0.5 h. Add N-methylmorpholine (107 mg, 1.26 mmol) and trans-4-ethylcyclohexylamine (254 mg, 2.0 mmol), and stir for 6 h. Add additional equivalents of N-methylmorpholine and TOTU and continue to stir for overnight. I think again I didn't write it down Concentrate the reaction and purify the residue by column chromatography over silica gel (dichloromethane/MeOH, gradient 0→30%) to obtain 270 mg (65%), LC/MS, m/z=416 (M+H)$^+$.

Example 24

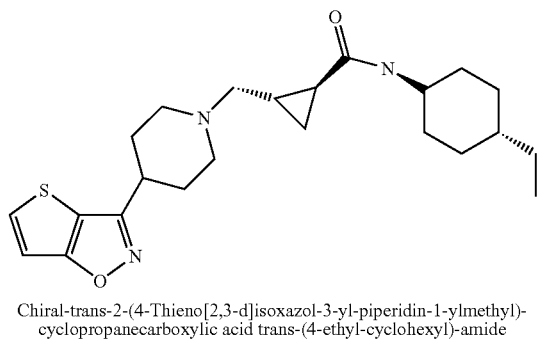

Chiral-trans-2-(4-Thieno[2,3-d]isoxazol-3-yl-piperidin-1-ylmethyl)-cyclopropanecarboxylic acid trans-(4-ethyl-cyclohexyl)-amide Dissolve racemic-trans-2-(4-thieno[2,3-d]isoxazol-3-yl-piperidin-1-ylmethyl)-cyclopropanecarboxylic acid trans-(4-ethyl-cyclohexyl)-amide (Example 23) (14 mg) in heptane/ethanol (1.5 mL, ~1:1) and make 20 separate injections of 50 μL each on to a preparative HPLC apparatus (Chiralpak AD 10μ 250×4.6 mm, heptane/ethanol, 85:15). Collect and combine fractions that elute at $t_R$=14.2 min and obtain 3.0 mg of enatiomer with an enatiomeric excess >99%.

Example 25

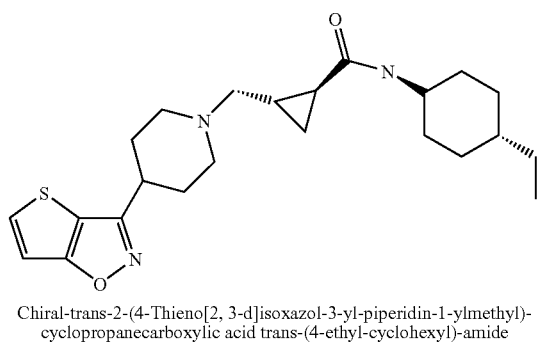

Chiral-trans-2-(4-Thieno[2, 3-d]isoxazol-3-yl-piperidin-1-ylmethyl)-cyclopropanecarboxylic acid trans-(4-ethyl-cyclohexyl)-amide Follow the procedure of Example 24, but collect and combine the fractions that elute at $t_R$=23.6 min to obtain 6.0 mg of enatiomer with opposite chirality and an enatiomeric excess >99%.

Example 26

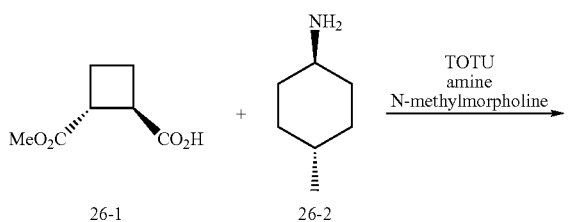

-continued

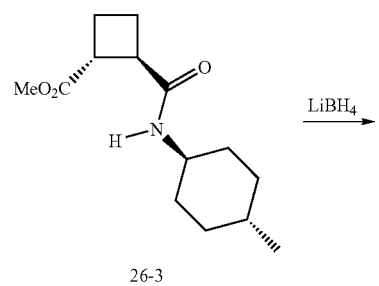

26-3

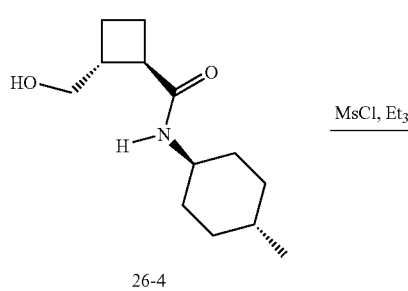

26-4

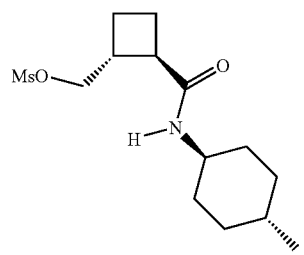

26-5

JOC 1971, 36, 3356

The cyclobutane carboxylic acid (26-1)(1.43 g, 9.05 mmol) and TOTU (3.7 g, 9.5 mmol) were combined in 90 mL of DMF and stirred at ambient temperature for 0.5 h. N-Methylmorpholine (0.96 g, 9.5 mmol) and the amine (26-2) (1.53 g, 13.5 mmol) were added and the mixture stirred at room temperature for 18 h. The mixture was diluted with ethyl acetate and the organic phase was sequentially washed with saturated sodium bicarbonate solution (3×), 10% HCl solution and brine (2×), then dried over magnesium sulfate, filtered and concentrated. The residue was dissolved in ethyl acetate and the mixture filtered. Concentration of the filtrate provided 1.5 g of the product (26-3).

Lithium borohydride 93.0 mL, 5.93 mmol, 2M in THF) was added dropwise to a solution of the ester (26-3) (1.5 g, 5.93 mmol) in 20 mL of THF at ambient temperature. The solution was stirred at room temperature for 20 h, and tehn lit was quenched by the careful addition of water. The product was extracted into ethyl acetate, and the combined organic layers were washed with water and brine, dried over magnesium sulfate, filtered and concentrated to leave 1.1 g of product. Chromatography on silica gel (40 g Biotage column) eluting with ethyl acetate and dichloromethane gave 618 mg of the alcohol (26-4).

Methanesulfonyl chloride (0.276 g, 2.41 mmol) was added dropwise to a solution of the alcohol (26-4) (0.493 g, 2.19 mmol) and triethylamine (0.332 g, 3.29 mmol) in 11 mL of dichloromethane at 0° C. The mixture was stirred at 0° C. for 1 h, and then it was stirred at ambient temperature for 2 h. The resulting solution was diluted with dichloromethane and washed with saturated sodium bicarbonate solution, water, and brine and then filtered and the filtrate was concentrated to provide 627 mg of the product (26-5).

Scheme V

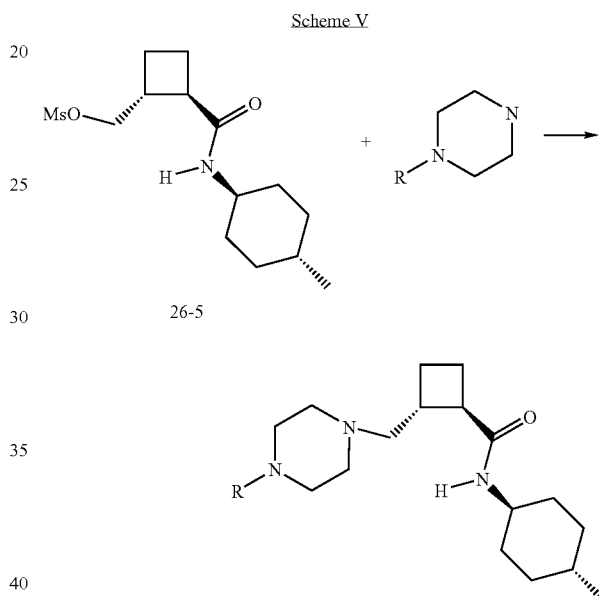

26-5

In Scheme V, R is as hereinbefore defined. For example, the mesylate (26-5) (75 mg, 0.025 mmol), potassium carbonate (52 mg, 0.038 mmol) and the amine (Example 2) (72 mg, 0.025 mmol) in 2 mL of acetonitrile were heated at 80° C. in a JKEM reaction block for 20 h. The mixture was cooled to room temperature, diluted with 6 mL of dichloromethane and 400 mg of polymer supported isocyanate resin was added (Argonaut Technologies, resin loading 1.49 mmol/gram) and the mixture shaken at ambient temperature for 20 h. The reaction mixture was deposited on a 2 g Varian strong cation exchange (SCX) column. The resin was washed twice with 4 mL ethyl acetate and thrice with 4 mL of dichloromethane. The column was further washed with 15 mL of ethyl acetate. The product was next eluted using a 4:1 mixture of 2% triethyl amine in ethyl acetate and methanol. The volatiles were removed in vacuo and the residue was chromatographed on silica gel, eluting with methanol/ethyl acetate. Concentration of the fractions containing the product provided 67 mg of product.

The following compounds were prepared using this method.

| Compound | CPD # |
|---|---|
| (structure) | 829997 |
| (structure) | 829998 |
| (structure) | 829999 |
| (structure) | 830000 |
| (structure) | 829996 |
Characterizing data for the compounds is as follows:
| CPD # | MOL WT | Amt obt | yield | basepeak | R.T. (min.) | MS % area |
|---|---|---|---|---|---|---|
| 829997 | 457.65 | 0.051 | 45 | 458.3 | 1.6 | 100 |
| 829998 | 493.63 | 0.067 | 54 | 494..3 | 1.64 | 100 |
| 829999 | 443.63 | 0.062 | 56 | 444.3 | 1.57 | 100 |
| 830000 | 430.61 | 0.040 | 37 | 431.3 | 1.44 | 100 |
| 829996 | 416.59 | 0.052 | 50 | 417.3 | 1.43 | 100 |
Example 27
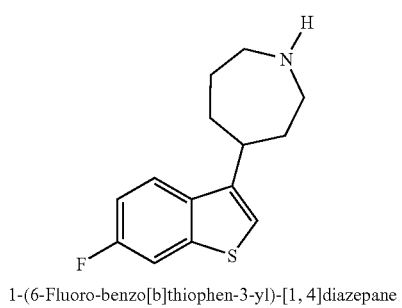
1-(6-Fluoro-benzo[b]thiophen-3-yl)-[1, 4]diazepane

27a. 3-Amino-6-fluoro-benzo[b]thiophene-2-carboxylic acid

At 50° C., add to a stirring solution of 2-carbomethoxy-3-amino-6-fluoro-benzo[b]thiophene (prepared according to U.S. Pat. No. 5,143,923), (90.1 g, 0.4 mol) in H₂O (450 mL), a 50% aqueous solution of NaOH (64 g, 0.8 mol) over 2–3 min. Heat the reaction to 70–73° C. and continue to stir for 3 h. Add 10% aqueous isopropanol (45 mL) and bring to reflux. Remove the isopropanol under N₂ and add H₂O (300 mL). Cool the reaction mixture to between 7–10° C. and add concentrated HCl (80 mL). Add H₂O (650 mL), cool to 5–7° C., filter the resulting solid, and wash the filter cake with H₂O (2×150 mL). Dry the solid under vacuum at 35° C. to obtain 80.6 g (94.7%) of solid mp 160–163° C., TLC on silica gel (dichloromethane/methanol, 3:1), R$_f$=0.69.

27b. 1-(6-Fluoro-benzo[b]thiophen-3-yl)-1,4]diazepane

Heat a solution of 3-amino-6-fluoro-benzo[b]thiophene-2-carboxylic acid (5.0 g, 24 mmol) in 1-methyl-2-pyrrolidinone (5 ml) to 100° C. for 2 h., and then, introduce a stream of nitrogen, to cool the solution to room temperature. Add homopiperazine (9.5 g, 95 mmol) and p-toluene sulfonic acid monohydrate (9.0 g, 47 mmol) and heat the mixture to 145° C. for 4 h. After that time, cool the reaction mixture to room temperature, dilute with ethyl acetate (30 mL) and wash with brine (3×15 mL). Separate the organic layer and dry over Mg SO₄. Evaporate the solvent and purify the crude product by column chromatography (SiO₂, 100 g CH₂Cl₂(MeOH 9:2, then CH₂Cl₂/MeOH/NH₄OH 9:2:0.15) to give 3.9 g (65%) of yellowish oil LC/MS (LiChrospher 5μ, RP-18, 250 mm CH₃CN/Water-gradient 20%→100% (25 min), Flow: 1.5 mL/min) t$_R$=10.74 min, m/z=250.3.

Example 28

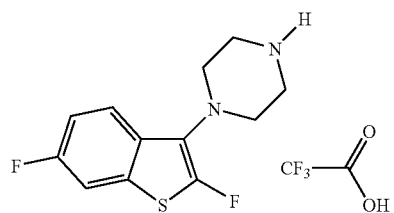

1-(2,6-Difluoro-benzo[b]thien-3-yl)-piperazine trifluoroacetate

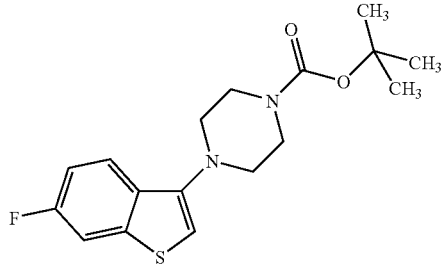

28a: 4-(6-Fluoro-benzo[b]thiophen-3-yl)-piperazine-1-carboxylic acid tert-butyl ester Add a solution of di-tert-butyl dicarbonate (5.15 g, 23.6 mmol) in CHCl₃ (15 mL), dropwise, over 45 min to a solution at −65° C. of 1-(6-fluorobenzo[b]thiophen-3-yl)-piperazine (prepared according to U.S. Pat. No. 5,143,923), (2.8 g, 11.8 mmol), 4-(dimethyl-amino)pyridine (0.1 g, 1.3 mmol), and diisopropylethylamine (4.3 mL, 3.2 g, 24.8 mmol) in CHCl₃ (50 mL). Following complete addition, stir the reaction at ambient temperature for 20 h, and then pour the reaction into a mixture of cold (5° C.) 5% aqueous NaOH/EtOAc (150/150 mL). Extract the product into EtOAc, wash the extract with H₂O, brine and concentrate to a red oil. Purify the crude oil over silica gel (EtOAc), to obtain 3.6 g, of red oil, LC/MS m/z=337 (M+H)⁺.

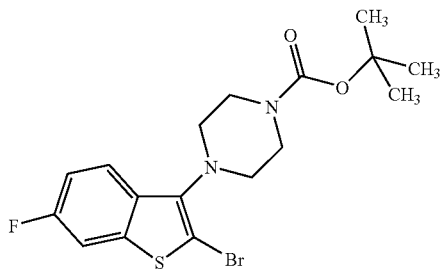

28b: 4-(2-Bromo-6-fluoro-benzo[b]thiophen-3-yl)-piperazine-1-carboxylic acid tert-butyl ester Add N-bromosuccinimide (0.59 g, 3.3 mmol) to a stirring solution of 4-(6-fluoro-benzo[b]thiophen-3-yl)-piperazine-1-carboxylic acid tert-butyl ester (Example 28a) (1.00 g, 2.97 mmol) in CHCl₃ (32.8 mL) and reflux for 30 min. Allow cooling to room temperature and filter. Evaporate the solvent and purify the residue by chromatography over silica gel (EtOAc/heptane, 9:1) to obtain 0.53 g (43%) of oil, MS, m/z=416 (M+H)⁺.

In an alternative procedure, add N-bromosuccinimide (1.319 g, 6.62 mmol) to a stirring solution of 4-(6-fluoro-benzo[b]thiophen-3-yl)-piperazine-1-carboxylic acid tert-butyl ester (Example 46a) (2.226 g, 6.62 mmol) in CCl₄ and reflux for 2 h. Allow cooling to room temperature and filter. Evaporate the solvent and purify the residue by chromatography over silica gel (EtOAc/heptane, 9:1) to obtain 2.34 g (94%) of oil.

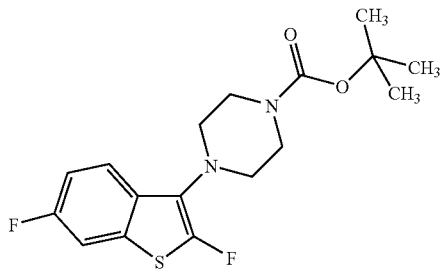

28c: 4-(2-Fluoro-6-fluoro-benzo[b]thiophen-3-yl)-piperazine-1-carboxylic acid tert-butyl ester At a temperature of −65° C. stir, under nitrogen, a solution of the 4-(2-bromo-6-fluoro-benzo[b]thiophen-3-yl)-piperazine-1-carboxylic acid tert-butyl ester (Example 28b) (15.59 g, 37.55 mmol) in anhydrous THF (247 mL) and add, dropwise, n-butyllithium in hexane (2.5M, 19.53 mL, 48.82 mmol). Stir for 30 min and then add, dropwise, N-fluorobenzenesulfonimide (17.76 g, 56.33 mmol) dissolved in anhydrous THF. Stir overnight at ambient temperature, cool the reaction to 0° C., add saturated NaCl solution and then water. Extract the mixture with EtOAc (3×'s), combine the extracts and wash with water and brine. Dry the extract (MgSO$_4$), and concentrate to obtain 11.0 g of oil. Chromatograph the oil over silica gel (ether/pet. ether, 9:1) and obtain 6.28 g (52%) of red oil, MS, m/z, 354 (M+H)$^+$.

28d: 1-(2,6-Difluoro-benzo[b]thien-3-yl)-piperazine trifluoroacetate

Stir a solution of 4-(2-fluoro-6-fluoro-benzo[b]thiophen-3-yl)-piperazine-1-carboxylic acid tert-butyl ester (Example 28c) (250 mg, 0.70 mmol) in trifluoroacetic acid (2.2 mL) at ambient temperature for 30 min. Evaporate the trifluoroacetic acid and treat the residue with ether. Stir the suspension at ambient temperature for 2 h, and filter the resulting white solid to obtain 191 mg (56%) of the trifluoroacetate salt. MS, m/z=255 (M+H)$^+$.

Examples 29–31

The following HPLC conditions are referred to in examples 29–31:

HPLC Condition I:
A) 95/5/0.1% Water/Acetonitrile/Formic Acid,
B) 5/95/0.1% Water/Acetonitrile/Formic Acid.

Column: YMC ODS-A 4×50 mm, Flow rate: 2 mL/minute.

The initial HPLC conditions consisted of 100% (A) flowing at 2 mL/minute. After the initial injection a linear gradient was performed so that at 2 minutes the HPLC conditions were 100% B. These conditions were then held for 3.4 minutes at which time the system switched back to initial conditions and equilibrated for the next analysis.

HPLC Condition II:
A) 95/5/0.1% Water/Acetonitrile/Formic Acid,
B) 5/95/0.1% Water/Acetonitrile/Formic Acid.

Column: YMC ODS-A 2×50 mm, Flow rate1 mL/minute.

The initial HPLC conditions consisted of 100% (A) flowing at 0.1 mL/minute. After the initial injection a linear gradient was performed so that at 2 minutes the HPLC conditions were 100% B. These conditions were then held for 3.5 minutes at which time the system switched back to initial conditions and equilibrated for the next analysis.

Example 29

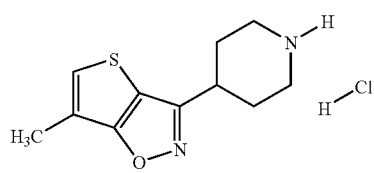

6-Methyl-3-piperidin-4-yl-thieno[2,3-d]isoxazole hydrochloride

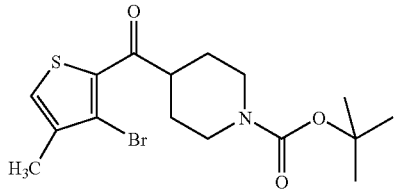

29a: Preparation of 4-[1-(3-bromo-4-methyl-thiophen-2-yl)-methanoyl]-1-piperidine-1-carboxylic acid tert-butyl ester:

Under inert conditions, add a 2.0 M solution (in tetrahydrofuran/n-heptane) of lithium diisopropylamide (29.65 mmol, 14.83 mL, 1.05 equivalents) to a cold (−78° C.) solution of 3-bromo-4-methylthiophene (28.24 mmol, 5.00 g, 1.00 equivalents) in dry tetrahydrofuran (27.33 mL). Stir at −78° C. for 1 hour and add a solution of 4-(methoxy-methyl-carbamoyl)-piperidine-1-carboxylic acid tert-butyl ester (28.24 mmol, 7.69 g, 1.00 equivalents), dropwise. Continue stirring at −78° C. for 3 hours. Quench the reaction mixture with saturated ammonium chloride (aqueous, 55 mL) and allow to warm to room temperature. Extract the reaction mixture with a mixture of ethyl acetate: diethyl ether (1:1,3 times 40 mL). Combine the extracts and dry over magnesium sulfate, filter and evaporate. Purify the residue via flash column chromatography using a mixture of n-heptane:ethyl acetate (4:1) to yield a yellow, crystalline solid (9.84 g).

MS (Cl, methane) m/e 388 (MH$^+$), LC/MS (APCI), m/e 288 (M-100), retention time 2 min. 43 sec. Condition I.

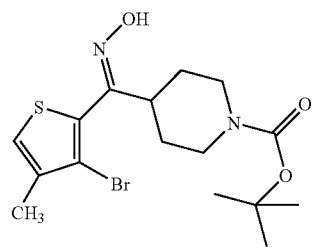

29b: Preparation of 4-[1-(3-bromo-4-methyl-thiophen-2-yl)-1-hydroxyimino-methyl]-piperidine-1-carboxylic acid tert-butyl ester:

Add ammonium hydroxide hydrochloride (50.68 mmol, 3.52 g, 2.00 equivalents) to a stirred solution of 4-[1-(3-bromo-4-methyl-thiophen-2-yl)-methanoyl]-piperidine-1-carboxylic acid tert-butyl ester (25.54 mol, 9.84 g, 1.00 equivalents) in pyridine (47.5 mL). Stir at room temperature overnight and at 70° C. for 4 hours. Cool the reaction mixture and add hydrochloric acid (3 M solution, 115 mL). Extract the reaction mixture with dichloromethane (115 mL), filter the organic layer, wash with water (100 mL), dry over magnesium sulfate, filter and evaporate. Recrystallize the resulting residue from toluene to yield a white solid (4.84 g). LC/MS (APCI), m/e 403 (MH$^+$), retention time 2 min. 32 sec. Condition I.

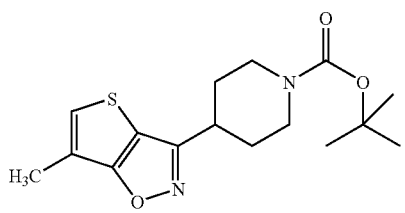

29c: Preparation of 4-(6-methyl-thieno[2,3-d]isoxazol-3-yl)-piperidine-1-carboxylic acid tert-butyl ester:

Add cesium carbonate (3.72 mmol, 1.21 g, 1.50 equivalents) and copper iodide (0.25 mmol, 47 mg, 0.10 equivalents) to a stirred solution of 4-[1-(3-bromo-4-methyl-thiophen-2-yl)-1-hydroxyimino-methyl]-piperidine-1-carboxylic acid tert-butyl ester (2.48 mmol, 1.00 g, 1.00 equivalents) in 2-methoxy ethanol (25 mL). Stir the resulting mixture at room temperature overnight and filter to remove the inorganic material. Concentrate the filtrate and partition the resulting oil between ethyl acetate (75 mL) and water (25 mL). Extract the aqueous layer with ethyl acetate (2×75 mL) and wash the combined organic layers with saturated sodium chloride (aqueous, 25 mL), dry over magnesium sulfate, filter and evaporate. Purify the residue via flash column chromatography eluting with n-heptane: ethyl acetate (4:1) to yield a white solid (588 mg). MS (Cl, methane) m/e 323 (MH$^+$), LC/MS (ESI), m/e 345 (MNa$^+$), retention time 2.05 minutes. Condition II.

29d: Preparation of 6-methyl-3-piperidin-4-yl-thieno[2,3-d]isoxazole hydrochloride:

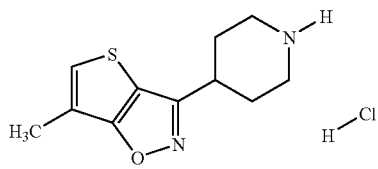

Stir a solution of 4-(6-methyl-thieno[2,3-d]isoxazol-3-yl)-piperidine-1-carboxylic acid tert-butyl ester (8.84 mmol, 2.85 g, 1.00 equivalents) in hydrochloric acid (48.75 mL, 1 M solution in diethyl ether) and methanol (2.00 mL) at room temperature for 3.5 hours. Filter the suspension, collect the white solid and dry to yield the desired product (659 mg). Allow the mother liquor to age overnight, filter, collect the white solid and dry to yield additional desired product (1.252 g). LC/MS (ESI), m/e 223 (MH$^+$), retention time 1.14 minutes. Condition II.

Example 30

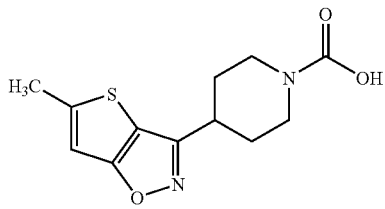

4-(5-Methyl-thieno[2,3-d]isoxazol-3-yl)-piperidine-1-carboxylic acid:

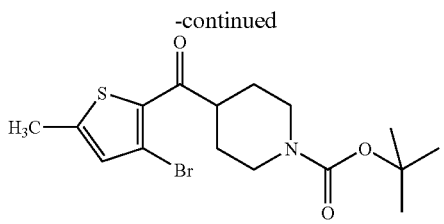

30a: Preparation of 4-[1-(3-bromo-5-methyl-thiophen-2-yl)-methanoyl]-1-piperidine-1-carboxylic acid tert-butyl ester:

Prepared essentially as in 29a except that 2-bromo-5-methyl thiophene is used as the starting material. In addition, 1.20 equivalents of lithium diisopropylamide and 1.24 equivalents of 4-(methoxy-methyl-carbamoyl)-piperidine-1-carboxylic acid tert-butyl ester are used for the reaction. Accordingly, stirring time of the reaction mixture may vary. Purification of the residue via flash column chromatography uses a gradient with a mixture of ethyl acetate: n-heptane (1:9) to ethyl acetate: n-heptane (2:8) to yield a yellow oil. LC/MS (ESI), m/e 332 (M-56) and 388 (MH$^+$), retention time 2.15 minutes. Condition II.

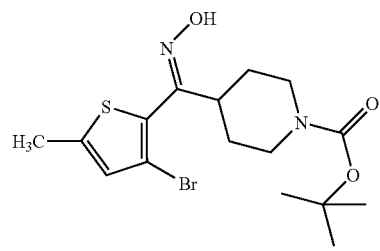

30b: Preparation of 4-[1-(3-bromo-5-methyl-thiophen-2-yl)-1-hydroxyimino-methyl]-piperidine-1-carboxylic acid tert-butyl ester:

Prepared essentially as 29b except that 4-[1-(3-Bromo-5-methyl-thiophen-2-yl)-methanoyl]-piperidine-1-carboxylic acid tert-butyl ester is used as the starting material and the reaction mixture was stirred at 70° C. for 6 hours. LC/MS (ESI), m/e 347 (M-56) and 403 (MH$^+$), retention time 2.03 minutes. Condition II.

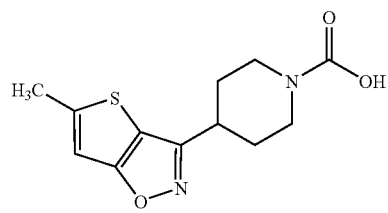

30c: Preparation of 4-(5-methyl-thieno[2,3-d]isoxazol-3-yl)-piperidine-1-carboxylic acid:

Prepared essentially as in 29c except that 4-[1-(3-bromo-5-methyl-thiophen-2-yl)-1-hydroxyimino-methyl]-piperidine-1-carboxylic acid tert-butyl ester is used as the starting material. Two other differences are: 1) 0.05 equivalents of copper iodide is used, and 2) no partition between ethyl acetate and water accompanied by subsequent extraction with ethyl acetate is required. Purification of the residue via flash column chromatography uses a mixture of ethyl acetate: n-heptane (1:4) to yield a white solid. LC/MS (ESI), m/e 345 (MNa⁺), retention time 2.12 minutes. Condition II.

Example 31

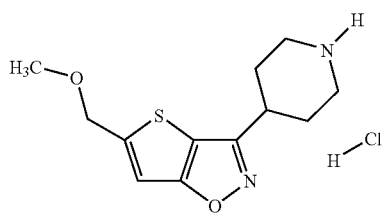

5-Methoxymethyl-3-piperidin-4-yl-thieno[2,3-d]isoxazole hydrochloride

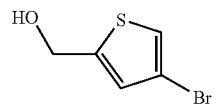

31a: Preparation of (4-bromo-thiophen-2-yl)-methanol:

Under inert conditions, add sodium borohydride (13.82 mmol, 0.523 g, 2.08 equivalents) in absolute ethanol (16 mL) dropwise over a period of 15 minutes to a stirred mixture of 4-bromothiophene-2-carboxaldehyde (26.58 mmol, 5.08 g, 1.00 equivalents) in cold (0° C.) absolute ethanol (32 mL). Stir the resulting mixture at room temperature for 2.5 hours and add glacial acetic acid dropwise until the effervescence ceases. Evaporate the resulting solution, take the residue up in diethyl ether (75 mL), wash with water (15 mL) and brine (15 mL) and dry over magnesium sulfate. Filter and evaporate to yield the product as a colorless oil (5.13 g).

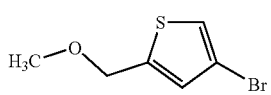

31b: Preparation of 4-bromo-2-methoxymethyl-thiophene:

Add sodium hydride (737 mg, 29.23 mmol, 1.10 equivalents, 95%) to a solution containing methyl iodide (1.65 mL, 26.57 mmol, 1.00 equivalents) and (4-bromo-thiophen-2-yl)-methanol (5.13 g, 26.57 mmol, 1.00 equivalents) in tetrahydrofuran (dry, 25 mL). Stir the resulting mixture at room temperature overnight and evaporate. Partition the residue between water (100 mL) and dichloromethane (100 mL). Extract the aqueous layer with dichloromethane (100 mL), combine the organic layers, dry over magnesium sulfate, filter and evaporate to yield the desired product as a yellow oil.

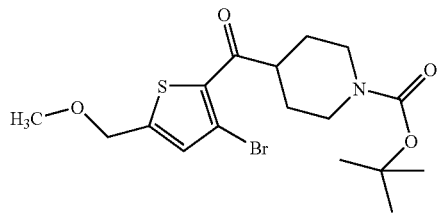

31c: Preparation of 4-[1-(3-bromo-5-methoxymethyl-thiophen-2-yl)-methanoyl]-piperidine-1-carboxylic acid tert-butyl ester:

Add lithium diisopropyl amide (13.20 mL, 26.37 mmol, 1.05 equivalents) to a stirred, cold (−78° C.) solution of 4-bromo-2-methoxymethyl-thiophene (5.20 g, 25.11 mmol, 1.00 equivalents) in tetrahydrofuran (dry, 24.30 mL). Stir at −78° C. for 1 hour and add a solution of 4-(methoxy-methyl-carbamoyl)-piperidine-1-carboxylic acid tert-butyl ester (6.84 g, 25.11 mmol, 1.00 equivalents) in tetrahydrofuran (dry, 16.40 mL), dropwise. Stir the resulting solution at −78° C. for 3 hours. Quench the reaction mixture with saturated sodium chloride (aqueous, 50 mL). Allow the resulting mixture to warm to room temperature and extract with a mixture of ethyl acetate: diethyl ether (1:1, 3×35 mL). Combine the extracts, dry over magnesium sulfate, filter and evaporate. Purify the residue via flash column chromatography eluting with a mixture of n-heptane: ethyl acetate (4:1) to yield the desired product as a yellow oil (9.47 g). LC/MS (ESI), m/e 362 (M-56) and 418 (MH⁺), retention time 2.08 minutes. Condition II.

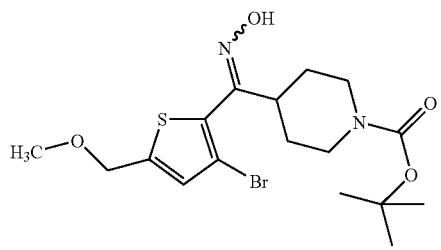

31d: Preparation of 4-[1-(3-bromo-5-methoxymethyl-thiophen-2-yl)-1-hydroxyimino-methyl]-piperidine-1-carboxylic acid tert-butyl ester:

Add hydroxylamine hydrochloride (2.29 g, 45.27 mmol, 2.00 equivalents) to a stirred solution of 4-[1-(3-bromo-5-methoxymethyl-thiophen-2-yl)-methanoyl]-piperidine-1-carboxylic acid tert-butyl ester (9.47 g, 22.64 mmol, 1.00 equivalents) in pyridine (42.40 mL). Stir the resulting solution at room temperature overnight and then at 70° C. for 4 hours. Cool the reaction mixture slightly, add hydrochloric acid (3N, 100 mL) and extract the resulting mixture with dichloromethane (100 mL). Wash the extract with water (100 mL), dry over magnesium sulfate, filter and evaporate to yield the desired product as a yellow oil (9.48 g).

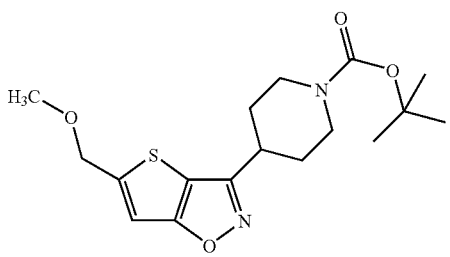

31e: Preparation of 4-(5-methoxymethyl-thieno[2,3-d]isoxazol-3-yl)-piperidine-1-carboxylic acid tert-butyl ester:

Add cesium carbonate (1.13 g, 3.46 mmol, 1.50 equivalents) and copper iodide (44 mg, 0.23 mmol, 0.10 equivalents) to a stirred solution of 4-[1-(3-bromo-5-methoxymethyl-thiophen-2-yl)-1-hydroxyimino-methyl]-piperidine-1-carboxylic acid tert-butyl ester (1.00 g, 2.31 mmol, 1.00 equivalents) in 2-methoxy ethanol (23.30 mL). Stir the resulting mixture at room temperature overnight or up to 3 days and filter through celite. Evaporate the filtrate, partition the residue between ethyl acetate (70 mL) and water (23 mL) and separate. Extract the aqueous layer with ethyl acetate (3×70 mL), combine the organic layers, dry over magnesium sulfate, filter and evaporate. Purify the residue via flash column chromatography eluting with a mixture of hexane:ethyl acetate (4:1) to yield the desired product as a yellow oil. LC/MS (ESI), m/e 375 (MNa$^+$), retention time 1.98 minutes. Condition II.

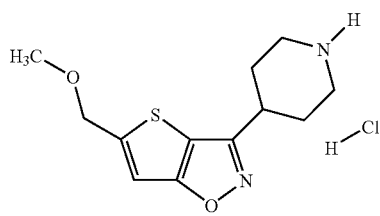

31f: Preparation of 5-methoxymethyl-3-piperidin-4-yl-thieno[2,3-d]isoxazole Hydrochloride:

Stir a solution of 4-(5-methoxymethyl-thieno[2,3-d]isoxazol-3-yl)-piperidine-1-carboxylic acid tert-butyl ester (2.21 g, 6.68 mmol, 1.00 equivalents) and hydrochloric acid (1.0 M in diethyl ether, 35 mL) overnight to form a suspension. Add additional hydrochloric acid (1.0 M in diethyl ether, 10 mL). Stir the suspension overnight, filter and wash the solid with ether. Collect the solid and dry to yield the desired product as a dark blue solid. LC/MS (ESI), m/e 253 (MH$^+$), retention time 1.17 minutes. Condition II.

Example 32

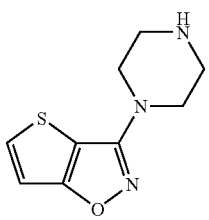

Synthesis of BOC Protected Piperazine-thienylisoxazole

3-Bromothiophene-2-carbaldehyde oxime

3-Bromothiophene-2-carbaldehyde (Maybridge) (28.7 gm, 0.15 mol) in ethanol (50 ml) was added in one portion to a solution of hydroxylamine hydrochloride (13.8 gm, 0.2 mole), sodium hydroxide (8 gm, 0.2 mol) in water (30 ml) and ethanol (100 ml). The mixture was stirred at 0° C. for 2 hours and was kept at 0° C. overnight. The reaction mixture was diluted with cold water (600 ml), and the precipitated solids were collected by filtration to provide 20.5 gm, (67%) of product. The aqueous layer was further extracted with ethyl acetate and, the combined organic layers were washed with brine, dried with magnesium sulfate filtered and concentrated in vacuo to leave an additional 6.9 g of product.

3-bromothiophene-2-hydroximidoyl chloride

To a solution of 3-bromothiophene-2-carbaldehyde oxime (10.8 gm, 52.4 mmol), hydrogen chloride (14.5 ml, 4M in dioxane) in DMF (100 ml) was added oxone (16.9 gm, 1.05 eqiv) in one portion at room temperature. The mixture was stirred at ambient temperature overnight.

At the end of the reaction, DMF solution was poured into water and product was extracted into ethyl acetate. The organic solution was washed with brine, dried over magnesium sulfate, filtered and concentrated in vacuo to 12.68 gm of product which was used in the next reaction without further purification.

(4-t-Butoxycarbonylpiperazinyl)-3-bromo-2-thienyl methanone oxime 3-bromothiophene-2-hydroximidoyl chloride (16.4 gm, 68 mmol) in tetrahydrofuran (THF, 70 ml) was added dropwise to a solution of N-(t-butoxycarbonyl)piperazine (14 gm, 1.1 equiv.), DABCO (9.5 gm, 1.25 eqiv.) in DMF (100 ml) at 0° C. over 25 minutes. The mixture was stirred for 3.5 hrs. At the end, the mixture was poured into water and was extracted with ethyl acetate. The organic was washed with brine and dried over magnesium sulfate. The solvent was removed on a rotary evaporator. The crude product (30.5 gm) was purified by chromatography on a Biotage cartridge (400 gm of silica gel), eluting with methanol in dichloromethane (0–5% of MeOH). The product thus obtained weighed 24.6 gm (85%).

(t-BOC-piperazine)3-thienylbenzisoxazole

A mixture of (4-t-Butoxycarbonylpiperazinyl)-3-bromo-2-thienyl methanone oxime (10.3 gm, 26.4 mmol), cesium carbonate (10.7 gm, 32.7 mmol), and copper iodide (500 mg) in methoxyethanol (200 ml) was stirred at room temperature overnight. The reaction mixture was diluted with ethyl acetate, the washed with water. The aqueous solution was extracted three times with ethyl acetate. the organic solution (total 600 ml) was washed with brine and was dried over magnesium sulfate then concentrated to an oil (~10 gm). This material was purified by chromatography using a Biotage cartridge (120 gm of silica gel, eluting with 0–8% Methanol in dichloromethane). The product thus obtained as light oil (5.1 gm, 62%).

Example 33

Synthesis of radiolabeled C14 intermediate useful for the preparation of certain compounds within the scope of the present invention.

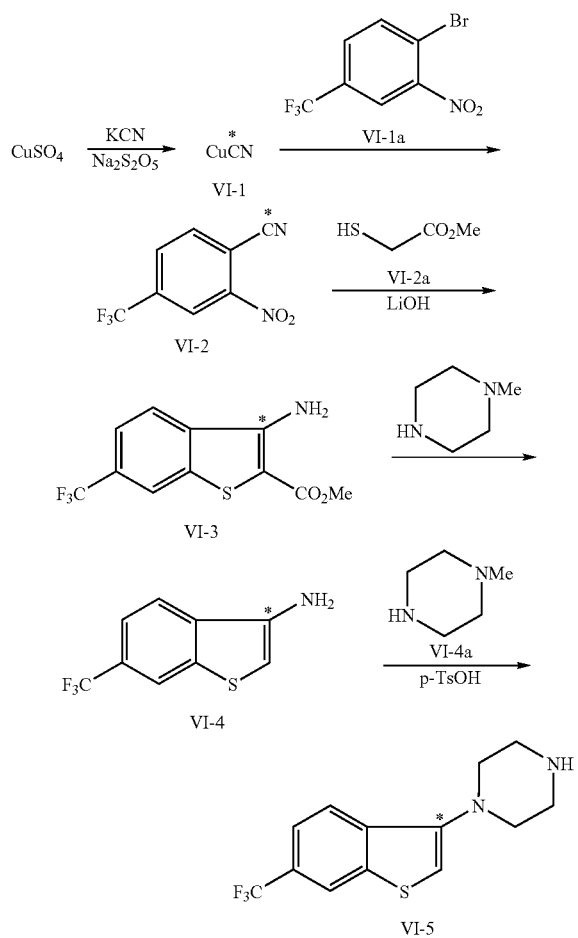

General: Analytical thin layer chromatography (TLC) was performed on E. Merck TLC plates with silica gel 60 $F_{254}$ (0.25 mm). TLC plates used in the analysis of radioactive samples were scanned on a BIOSCAN system 2000 Imaging Scanner using P-10 gas (10% methane, 90% argon). Identity of the intermediates was established by co-migration in radio-TLC and/or radio-HPLC with the standard samples of unlabeled analogues. Flash chromatography was performed using silica gel with a particle size of 40–63 µm. Specific activity was determined on a Packard Minaxi Tri-Carb Liquid Scintillation Analyzer (Model 1600 TR) using Bio-Safe II as scintillation cocktail.

Purification of compounds VI-2, VI-3, VI-4, VI-5, and VI-6 was monitored by HPLC (conditions:A) which was carried out on Waters 600 Controller, Waters 996 Photodiode Array Detector, Millennium Chromatography Manager and Beta-Ram Radioactive Flow Through Monitor System, Model 2 (IN/US Systems Inc.). Final purity determination of VI-7 by HPLC (conditions:B) was performed on Waters Model 510 Pumps, Waters 680 Gradient Controller, Waters 715 Ultra Wisp Autosampler, Waters 484 Tunable Absorbance Detector and Beta-Ram Radioactive Flow-Through Monitor System, Model 2 (IN/US Systems Inc.).

Conditions A: YMC Basic 5 µm, C18, 4.6×250 mm, mobile phase A: (v/v) 50/50 acetonitrile/0.1N ammonium formate, mobile phase B: (v/v) 75/25 acetonitrile/0.1N ammonium formate, flow rate 1.0 mL/min, uv detection at 254 nm.

| Gradient: | Time (minutes) | % MP: A | % MP: B |
|---|---|---|---|
| | 0 | 100 | 0 |
| | 15 | 100 | 0 |
| | 25 | 0 | 100 |
| | 30 | 0 | 100 |
| | 35 | 100 | 0 |

Conditions B: Ultremex 5 µm, C8, 4.6×150 mm, mobile phase (v/v/v) 50/50/0.25 acetonitrile/0.05 M potassium phosphate buffer, pH 3.0/triethylamine, flow rate 1.0 mL/min, uv detection at 210 nm.

[$^{14}$C] Copper (I) Cyanide (VI-1):

A solution of copper (II) sulfate pentahydrate (4.16 g, 16.67 mmol) in water (13.3 mL) was heated to 70° C. and a solution of sodium metabisulfite (1.94 g, 6.28 mmol) in water (3.3 mL) at 70° C. was added in one minute. Immediately a solution of [$^{14}$C] potassium cyanide (245.5 mg, 200 mCi, 3.77 mmol, S.A. 53.0 mCi/mmol) and unlabeled potassium cyanide (0.84 g, 12.9 mmol) in water (3.3 mL) at 70° C. was added in one minute. A white solid precipitated out of solution and blue color of the solution was discharged. After stirring for 10 min at 70° C., the mixture was filtered hot and the solid was washed with hot water (15 mL) and ethanol (15 mL). The white solid was dried under vacuum (0.1 mm Hg) for 27 h 45 min to prove VI-1 (1.393 g, 186.6 mCi) in 93.3% yield.

2-Nitro-4-(trifluoromethyl)-[7-$^{14}$C]benzonitrile (VI-2):

To a suspension of [$^{14}$C]copper (I) cyanide (VI-1) (1.393 g, 15.55 mmol, 186.6 mCi) in 1-methyl-2-pyrrolidinone (NMP, 10 mL) was added 4-bromo-3-nitrobenzotrifluoride (6.33 g, 23.45 mmol) and the mixture was heated at 190–195° C. for 1 h. Ethyl acetate (25 mL) and water (20 mL) were added at room temperature and the mixture was filtered through celite. To the filtrate more water (20 mL) and ethyl acetate (25 mL) were added and the aqueous layer was extracted with ethyl acetate (90 mL). The organic extract was washed with iron (III) chloride solution (50 mL) prepared by dissolving iron (III) chloride (7.468 g, 46.04 mmol) in water (50 mL).The organic extract was further washed with water (30 mL), sat. sodium chloride (15 mL), dried ($Na_2SO_4$) and the solvent was removed in vacuo. The residue was purified by flash chromatography on silica gel (hexane/ethyl acetate, 9/1–7/3) to provide an oil which was dissolved in hexane (70 mL). The solvent was removed under reduced pressure and residue was dried under vacuum for 15 h 40 min to provide VI-2 (3.01 g, 167.13 mCi, 89.6% yield) as a yellow solid. Radio-TLC (hexane/ethyl acetate, 9/1), $R_f$=0.21;HPLC (System A), RCP 99.86% (ret. time, 9.2 min).

[3-$^{14}$C]-3-Amino-2-carbomethoxy-6-trifluoromethylbenzo[b]thiophene (VI-3):

Nitrile (VI-2) (3.01 g, 13.9 mmol, 167.13 mCi) was dissolved in DMF (14 mL) and methyl thioglycolate (1.78 g, 15.94 mmol, 95%) was added in one minute. The mixture was cooled to 0–5° C. and a solution of lithium hydroxide (0.689 g, 28.77 mmol) in water (9.2 mL) was added dropwise in 12 minutes. After the addition, cooling bath was removed and the mixture was stirred at room temperature for 4 hours. Water (70 mL) was added at 0–5° C. and the mixture was stirred for 15 min at 0–5° C. the solid was collected on a filter, washed with water (20 mL) and dried under vacuum (0.1 mm Hg) for 40 h 15 min to provide VI-3 (3.469 g, 151.24 mCi, 90.49% yield). Radio-TLC (CH$_2$Cl$_2$), $R_f$=0.372; HPLC (system A), RCP 99.92% (ret. time, 16.722 min).

[3-$^{14}$C]-3-Amino-6-trifluoromethylbenzo[b]thiophene (VI-4):

To a solution of benzo[b]thiophene (VI-3) (3.469 g, 12.6 mmol, 151.2 mCi) in NMP (14 mL) was added 1-methylpiperazine (6.69 g, 66.79 mmol) and the mixture was heated at 140–145° C. for 5 h. The mixture was allowed to cool to room temperature, poured into water (60 mL) and extracted with ethyl acetate (140 mL). The organic extract was washed with water (30 mL), sat. sodium chloride (10 mL), dried (Na$_2$So$_4$) and the solvent was removed in vacuo. The residue was purified by flash chromatography on silica gel (hexane/ethyl acetate, 1/1) to yield a greenish solid which was dried under vacuum (0.1 mm HG) for 14 h to provide VI-4 (w.66 g, 146.95 mCi, 97.16% yield). ). Radio-TLC (hexane/ethyl acetate, 1/5), $R_f$=0.407; HPLC (system A), RCP 99.44% (ret. time, 10.552 min).

1-[6-(trifluoromethyl)benzo[b]thien-3-yl-[3-$^{14}$C] piperazine (VI-5):

To a solution of benzo[b]thiophene (VI-4) (2.66 g, 12.24 mmol, 146.95 mCi) in NMP (17 mL) was added piperazine (4.309 g, 50.02 mmol) and p-toluenesulfonic acid (4.76 g, 25.02 mmol) at room temperature. The mixture was heated at 17° C. for 20 m h 24 min, allowed to cool to room temperature and poured into a solution of sodium carbonate (4.70 g, 44.3 mmol) in water (60 mL). The mixture was extracted with ethyl acetate (20 mL), dried (Na$_2$SO$_4$) and the solvent was removed in vacuo. The residue was purified by flash chromatography on silica gel (CH$_2$Cl$_2$/MeOH/ NH$_4$OH, 9/1/0.2) and product was dried under vacuum (0.1 mm Hg) for 11 h 50 min. Ethanol (absolute, 30 mL) was added to the product and solvent was removed under reduced pressure. The residue was dried under vacuum (0.1 mm Hg) for 24 h 55 min to provide VI-5 (3.44 g, 144.18 mCi, 98.1% yield) as an oil. Radio-TLC (CH$_2$Cl$_2$/MeOH/ NH$_4$OH, 9/1/0.2), $R_f$=0.46; HPLC (system A), RCP 99.88% (ret. time, 5.807 min).

Example 34

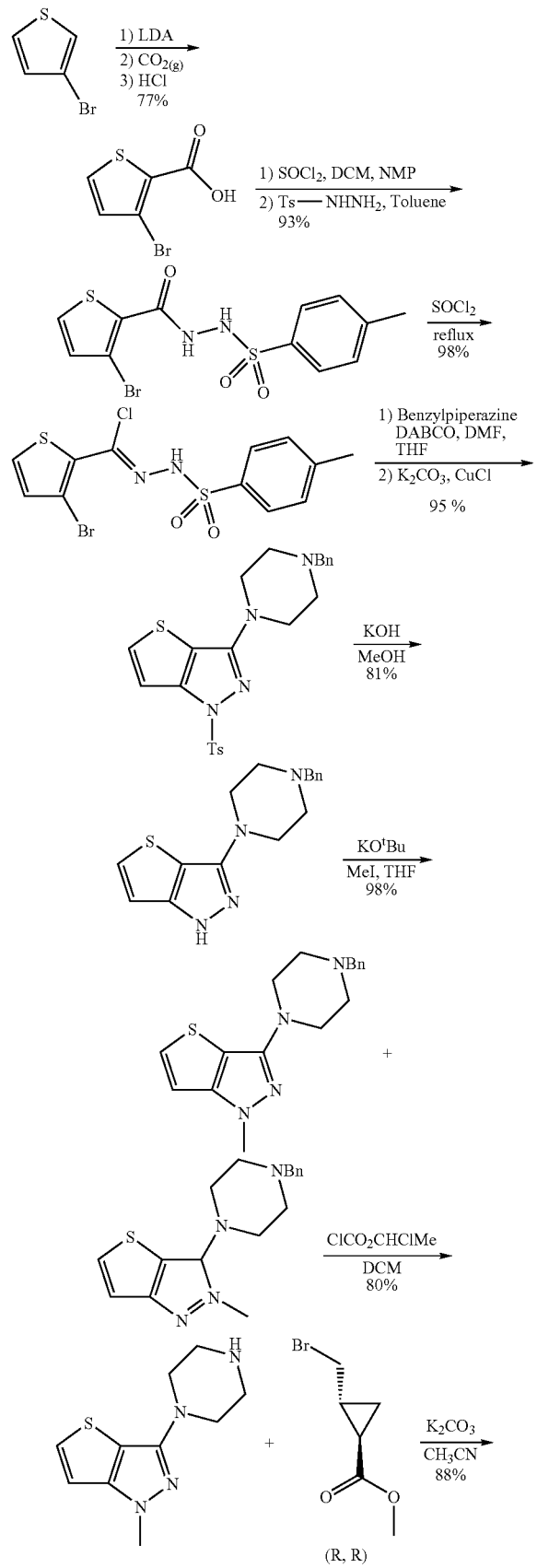

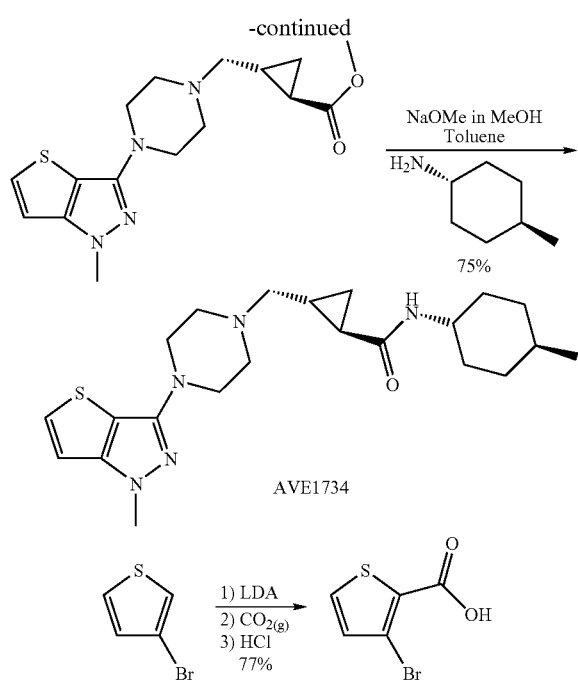

3-Bromo-thiophene-2-carboxylic acid. To a solution of 3-bromothiophene (600.0 g, 3.68 mol) in THF (3 L) cooled to −72° C. was added LDA (1.93 L, 3.86 mol, 2 N) slowly over 2 hours. The rate of LDA addition is such that the reaction temperature never exceeded 68° C. After complete addition, the solution is stirred for an additional 40 minutes. Diethyl ether (3 L) is then added via an addition funnel such that the temperature is maintained below −65° C. The addition funnel is then replaced with a dispersion tube and $CO_2$ gas is bubbled through the solution for 3 hours. Dry ice (500 g) is then added and the mixture is stirred overnight. The reaction flask is then placed in an ice bath and 6 N HCl is added slowly to prevent excessive bubbling until the pH of the solution is adjusted to 1–2. The resulting mixture is then extracted with EtOAc. The extract is washed with brine then dried over $MgSO_4$, filtered and evaporated. The product is dried under vacuum at room temperature yielding 585.15 g (77%) as an off-white solid.

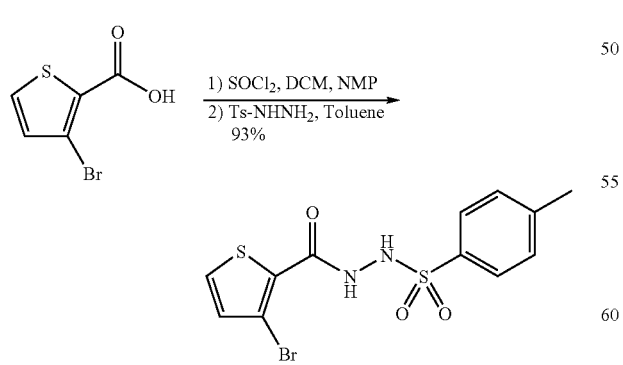

1-(3-Bromo-thiophene-2-carboxylic acid)-2-(4-toluene-sulfonyl)-hydrazine.

To a stirred suspension of the acid (285.53 g, 1.38 mol) in DCM (1.5 L) was added a catalytic amount of NMP (2 mL). Thionyl chloride (105.8 mL, 1.45 mol) is then added and the solution is refluxed until the solids have completely dissolved. The solution is further refluxed for 1 hour, cooled to room temperature and evaporated to afford a light, brown solid. The crude material is dried under vacuum overnight. The brown solid is taken up in toluene (3.5 L) and p-toluenesulfonhydrazine (402.25 g, 2.16 mol) is added. The mixture is stirred at 100° C. for 8 hours then at room temperature overnight. The resulting mixture was cooled with an ice bath and the resulting solids were collected by filtration and washed with toluene. The solids were then stirred as a slurry in 1 N HCl for 1 hour. The solids were collected by filtration and washed with copious amounts of water. The solid were dried under vacuum at 40° C. then recrystallized from toluene/isoproyl alcohol yielding 484.28 g (93%) of the desired product.

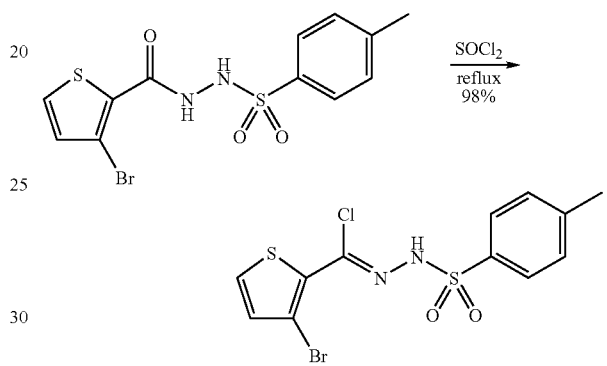

N-((4-Methylphenyl)-sulfonyl)-3-bromo-thiophene-2-carbohydrazonyl chloride. 1-(3-Bromo-thiophene-2-carboxylic acid)-2-(4-toluenesulfonyl)-hydrazine (60.80 g, 0.161 mol) was added to thionyl chloride (70.5 mL, 0.966 mol). The resulting mixture was stirred at 80° C. until the mixture becomes homogenous. The solution is then stirred at 70° C. for 30 minutes and heptane (300 mL) is added over a period of 20 minutes. The solution was cooled slowly to room temperature then cooled further to 5° C. The solids are collected by filtration, washed with heptane (3×100 mL) and dried under vacuum yielding 62.1 g (98%) of the desired product as an off-white solid.

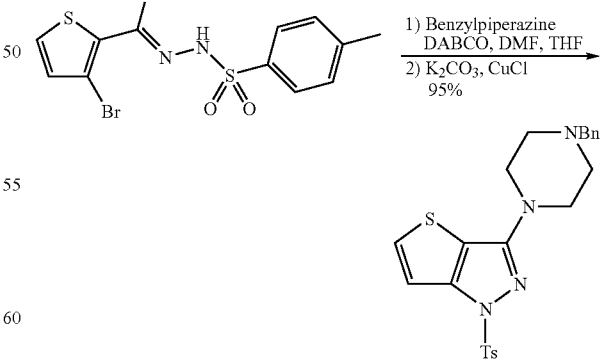

3-(4-Benzyl-piperazin-1-yl)-1-(toluene-4-sulfonyl)-1H-thieno[3,2-c]pyrazole.

To a stirred solution of DABCO (14.18 g, 112.18 mol) and benzylpiperazine (35.35 g, 0.200 mol) in DMF (200 mL)

cooled to −30° C. was added via cannula a solution of N-((4-Methylphenyl)-sulfonyl)-3-bromo-thiophene-2-carbohydrazonyl chloride (62.1 g, 0.158 mol) in THF (100 mL). The addition is controlled to prevent the reaction temperature from exceeding −30° C. After complete addition precipitation occurs and the mixture is then allowed to stir at room temperature overnight when $K_2CO_3$ (65.41 g, 0.473 mol) and CuCl (1.0 g, 0.010 mol) was added. The resulting mixture is heated to 110° C. and the THF is removed by distillation at this point. The temperature is then increased to 140° C. and the mixture is stirred for 6 hours, cooled to room temperature and stirred overnight. The mixture was then poured over water (100 mL) and EtOAc (100 mL). The EtOAC layer is then separated and the aqueous layer is extracted with EtOAC (3×500 mL). The combined EtOAC layers were washed with water (500 mL) and then filtered through celite and concentrated. The solids were collected by filtration and washed with cold water then EtOAc/heptane (1:4) and dried under vacuum yielding 66.05 g (95%) of the desired product as an off-white solid.

(2.5 L) was added a mixture of potassium t-butoxide (134.4 g, 1.2 mol) in THF (1.5 L) dropwise over a period of 1 hour while keeping the reaction temperature below 25° C. After complete addition, the mixture was cooled to −30° C. and MeI (65.4 mL, 1.05 mol) was added dropwise over a period of 30 minutes. The mixture is then slowly warmed to room temperature overnight. To the reaction mixture is slowly added saturated $NaHCO_3$ (1 L). The solution is then evaporated to remove the THF and the resulting aqueous mixture is taken up in EtOAc and washed with water and brine. The EtOAc extract is dried ($Na_2SO_4$), filtered and evaporated. The viscous concentrate is filtered through a silica gel plug with 1:1 EtOAc/heptane and evaporated yielding a viscous oil that is then dried under vacuum where it solidifies and yields 326.03 g (98%) as a 12:1 ratio of regioisomers in favor of the desired product.

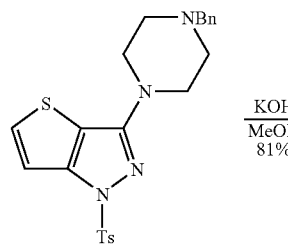

3-(4-Benzyl-piperazin-1-yl)-1H-thieno[3,2-c]pyrazole. To a stirred mixture of $KOH_{(s)}$ (56.09 g, 2.66 mol) in methyl alcohol (1.33 L) is added 3-(4-benzyl-piperazin-1-yl)-1-(toluene-4-sulfonyl)-1H-thieno[3,2-c]pyrazole (241 g, 0.532 mol). The mixture is heated at reflux for 1.25 hours, cooled to room temperature and evaporated. The residue is taked up in EtOAc (1 L) washed with water (2 L), dried ($MgSO_4$) filtered and evaporated. The residue was recrystallized from EtOAc/Heptane yielding 129 g (81%).

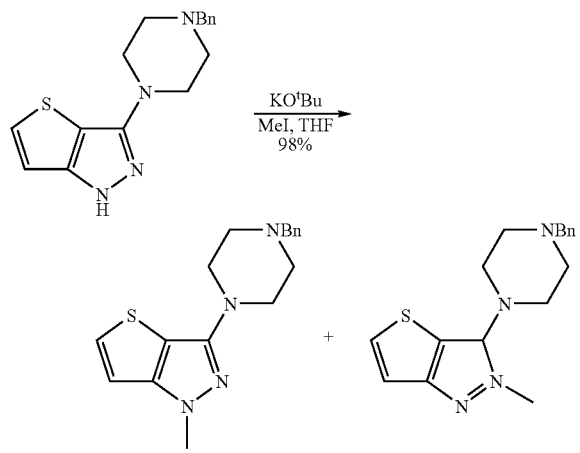

3-(4-Benzyl-piperazin-1-yl)-1-methyl-1H-thieno[3,2-c]pyrazole. To a stirred solution of 3-(4-benzyl-piperazin-1-yl)-1H-thieno[3,2-c]pyrazole (318.0 g, 1.07 mol) in THF

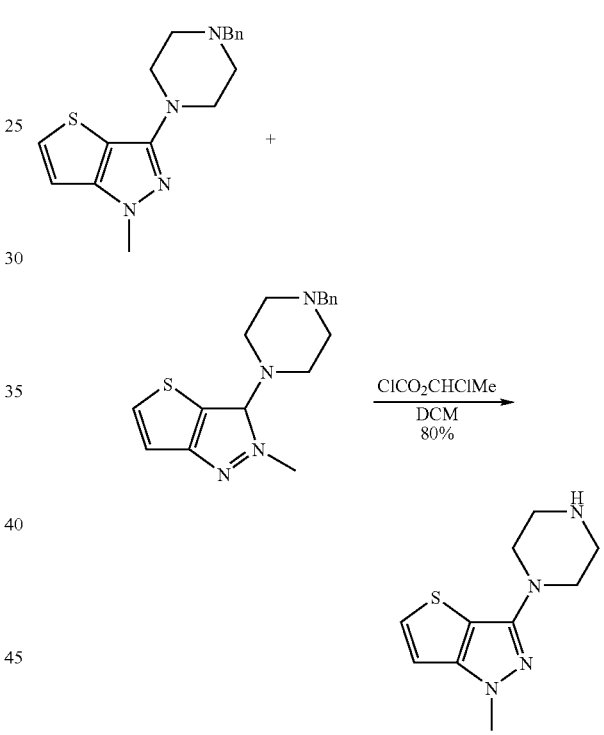

1-Methyl-3-piperazin-1-yl-1H-thieno[3,2-c]pyrazole. To a solution of a mixture of 3-(4-Benzyl-piperazin-1-yl)-1-methyl-1H-thieno[3,2-c]pyrazole and the 2-methyl analog (189.0 g, 0.60 mol) is dissolved in DCM (1.25 L) is added 1-chloroethylchloroformate (78.6 mL, 0.72 mol). The solution is heated at reflux for 1 hour when the mixture is cooled and the solvent is removed by evaporation. The residue is taken up in methanol (1 L) and heated at reflux for 30 minutes. After cooling, the solution is treated with 1 N HCl in ether (200 mL) and an additional 1 L of ether to afford the precipitation of the product. The solid is collected via filtration and washed with cold ether. The solid is recrystallized from methanol (1 L) and the HCl salt is collected by filtration, washed with ether and dried under vacuum yielding 123.04 g (80%) of the desired product as an 80:1 mixture of regioisomers in favor of the desired regioisomer as seen by NMR.

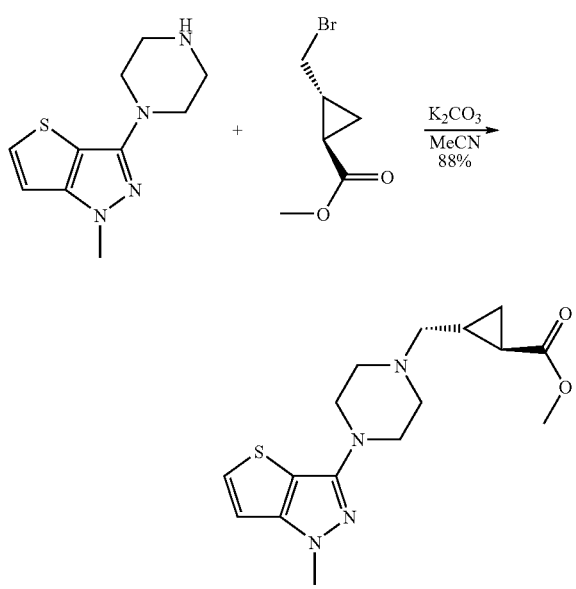

2R-[4-(1-Methyl-1H-thieno[3,2-c]pyrazol-3-yl)-piperazin-1-ylmethyl]-cyclopropane-1R-carboxylic acid methyl ester. A mixture of 1-methyl-3-piperazin-1-yl-1H-thieno[3,2-c]pyrazole (2.75 g, 12.37 mmol), 2R-bromomethyl-cyclopropane-1R-carboxylic acid methyl ester (2.41 g, 12.5 mmol) and K$_2$CO$_3$ (3.46 g, 25.0 mmol) in acetonitrile (75 mL) was heated at reflux for 1 hour and then at room temperature overnight. The mixture was diluted with EtOAc (100 mL) and then poured into water (100 mL). The layers were separated and the aqueous layer was extracted with EtOAc (50 mL). The combined organic layers were washed with brine (30 mL), dried (MgSO$_4$), filtered and evaporated. The residue was separated via column chromatography (9:1; EtOAc/MeOH) yielding 3.65 g (88%) of the desired product.

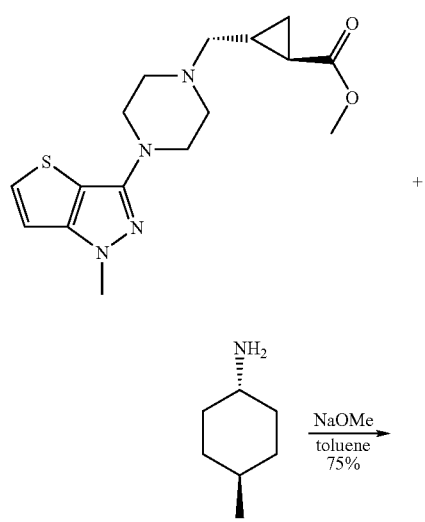

-continued

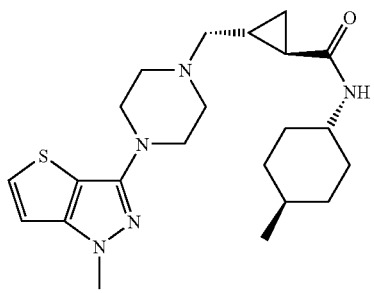

2R-[4-(1-Methyl-1H-thieno[3,2-c]pyrazol-3-yl)-piperazin-1-ylmethyl]-cyclopropane-1R-carboxylic trans-(4-methyl-cyclohexyl)-amide. To a solution of 2R-[4-(1-Methyl-1H-thieno[3,2-c]pyrazol-3-yl)-piperazin-1-ylmethyl]-cyclopropane-1R-carboxylic acid methyl ester (10.0 g, 29.9 mmol) and trans-4-methylcyclohexylamine (6.77 g, 60.0 mmol) in toluene (100 mL) was added sodium methoxide (9.72 g, 45.0 mmol, 25% in MeOH). The resulting mixture was heated to 80° C. for 21 hours. Upon cooling to room temperature, the mixture was partitioned between water (800 mL) and EtOAc (200 mL) and separated. The aqueous layer is salted out with the addition of NaCl then extracted with EtOAc (200 mL). The combined organic layers are washed with brine (50 mL), dried (Na$_2$SO$_4$), filtered and evaporated. The residue was recrystallized from toluene (100 mL) and EtOAc (20 mL) to yield 9.30 g (75%) of the desired product as a white solid, MP 185–186° C. Anal. Calcd. for C$_{22}$H$_{33}$N$_5$OS: C, 63.58; H, 8.00; N, 16.85. Found: C, 63.68; H, 8.24; N, 16.62.

Example 35

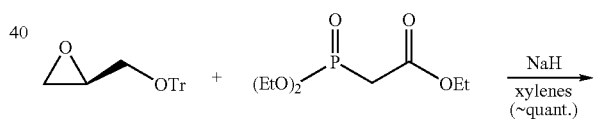

Trityloxymethyl-(1R, 2R)-cyclopropanecarboxylic acid ethyl ester. To a suspension of sodium hydride (15.20 g, 380 mmol, 60% oil dispersion) in xylenes (300 mL) was added triethylphosphonoacetate (85.07 g, 379 mmol) in a controlled manner to avoid the excessive evolution of gas and to maintain the internal temperature less than 55° C. After the complete addition, the mixture was stirred for 20 minutes when the yellow solution was added via cannula to a solution of (R)-trityl glycidyl ether (100.0 g, 316 mmol) in xylenes (300 mL). The resulting solution was heated to 125° C. for 2 hours. The resulting solution was cooled to room temperature, acidified with the addition of 10% HCl (320 mL) and extracted with EtOAc (2×300 mL). The combined extracts were washed with brine (100 mL), dried (MgSO$_4$), filtered and evaporated yielding a 175 g of a crude product as an oil. The material was carried on crude.

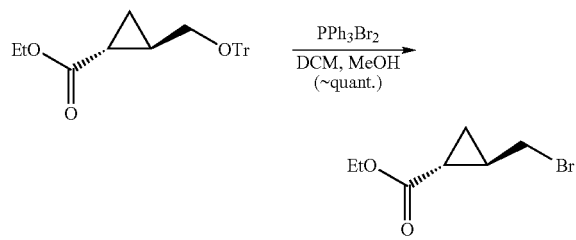

2R-bromomethyl-cyclopropane-1R-carboxylic acid methyl ester. A solution of triphenylphosphine (124.7 g, 1.34 mol) in CH$_2$Cl$_2$ (260 mL) was cooled to 5° C. when a solution of bromine (24.4 mL, 1.34 mol) in CH$_2$Cl$_2$ (65 mL) was added over 20 minutes while the temperature was maintained below 12° C. The mixture was stirred at 5° C. for 1 hour when 2 M HCl/Et$_2$O (16 mL, 32 mmol) was added followed by the addition of crude trityloxymethyl-(1R, 2R)-cyclopropane carboxylic acid ethyl ester (124 g, 0.32 mol). The resulting mixture was stirred at room temperature overnight when saturated NaHCO$_3$ (600 mL) was added. The mixture was separated and the aqueous layer was extracted with CH$_2$Cl$_2$ (200 mL). The combined organic layers were washed with water (400 mL), dried (MgSO$_4$), filtered and evaporated. The residue was diluted with heptane (200 mL) and evaporated two times to remove excess CH$_2$Cl$_2$. The residue was allowed to stand for 30 minutes when the solid impurities were removed by filtration. The filter cake was washed with heptane (2×400 mL). The combined organic layers were evaporated to provide 92.68 g of a crude yellow liquid. The crude liquid was distilled (BP=80–85° C./1.5 torr) to provide 55.19 g (84% yield for the two steps) of a colorless liquid.

Example 36

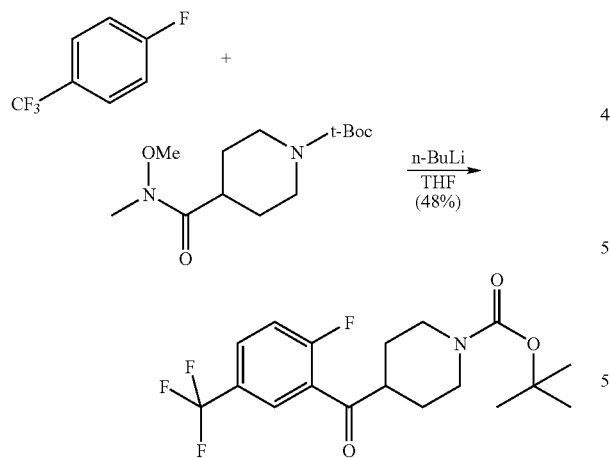

4-(2-Fluoro-5-trifluromethyl-benzoyl)-piperidine-1-carboxylic acid tert-butyl ester. A solution of 4-fluorobenzotrifluoride (25 g, 0.152M) in anhydrous THF (300 ml) was cooled to −60° C. (IPA/CO2 bath) and treated with n-butyl lithium (84 mL of a 2.0M solution in Hexane, 0.168M-1.1 eq) with a maximum rate so not to exceed 60° C. The reaction was stirred for 3 hours (temperature maintained) and then treated with a solution of 4-(methoxy-methyl-carbamoyl)-piperidine-1-carboxylic acid tert-butyl ester (51.86 g, 0.190M-1.25 eq, in 130 mL of anhydrous THF) with a maximum rate so as not to exceed −55° C. The mixture was stirred for a further two hours before allowing to warm to room temperature and stirred for 0.5 hours. The reaction was quenched with saturated ammonium chloride solution (75 mL) and the THF removed under reduced pressure. The residue was dissolved in ethylacetate (800 mL), washed with 1N Hydrochloric acid (400 ml), 5% aq NaHCO$_3$ (400 mL), water (400 mL) and brine (400 mL) successively. The organics were dried over MgSO$_4$, filtered and concentrated to give a brown oil, which on triturating in ethyl acetate gave a white solid 27.6 g (48%).

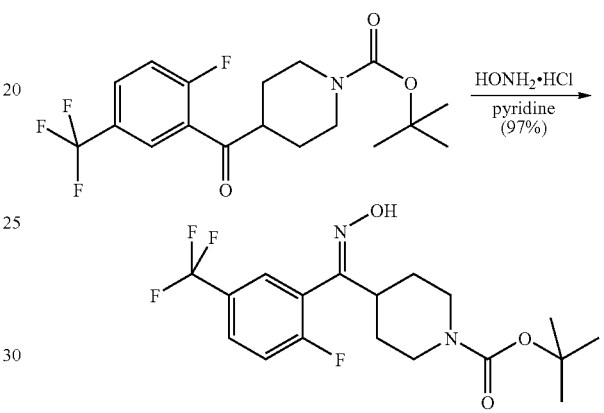

4-[(2-Fluoro-5-trifluoromethyl-phenyl)-hydroxyimino-methyl]-piperidine-1-carboxylic acid tert-butyl ester. A solution of 4-(2-fluoro-5-trifluromethyl-benzoyl)-piperidine-1-carboxylic acid tert-butyl ester (5 g, 0.013M) in pyridine (25 mL) was treated with hydroxylamine hydrochloride (1.11 g, 0.015 M-1.2 eq). The reaction was stirred under N$_2$ at room temperature for 14 hours and then poured onto ice water (250 mL). The mixture was stirred at 0° C. for 1 hour, the product was then filtered off, washed with cold water (3×15 mL) and dried in a vacuum oven at 50° C. A white solid was obtained (5.03 g, 97%).

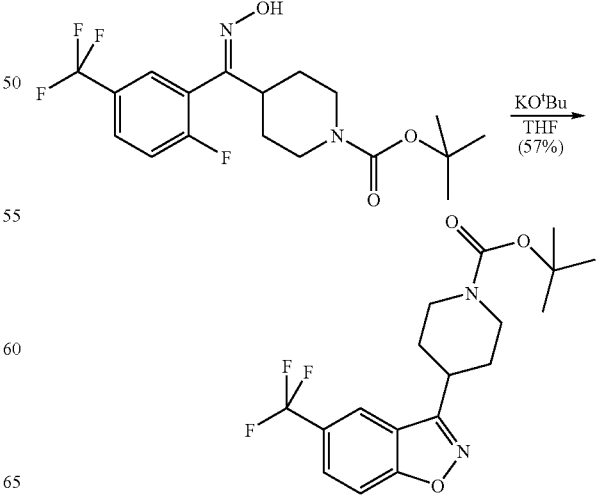

4-(5-Trifluoromethyl-benzo[d]isoxazol-3-yl)-piperidine-1-carboxylic acid tert-butyl ester. A solution of 4-[(2-Fluoro-5-trifluoromethyl-phenyl)-hydroxyimino-methyl]-piperidine-1-carboxylic acid tert-butyl ester (4.969 g, 0.013 M) in anhydrous THF (59 mL) was treated with Potassium tert-butoxide (13.4 mL of a 1M solution in THF, 0.0133 M-1.05 eq). The mixture was stirred at ambient temperature for 1 hour and. then heated to 65° C. for 2 hours. The THF was removed under reduced pressure. The residue was dissolved in ethyl acetate (100 mL), washed with H₂O (50 mL) and brine (50 mL) respectively. It was then dried over MgSO₄, filtered and concentrated to give a solid (5 g) which was purified on silica ~120 g, (eluting with ethylacetate/heptane (30:70) to give the product as a white solid (2.69 g, 57%).

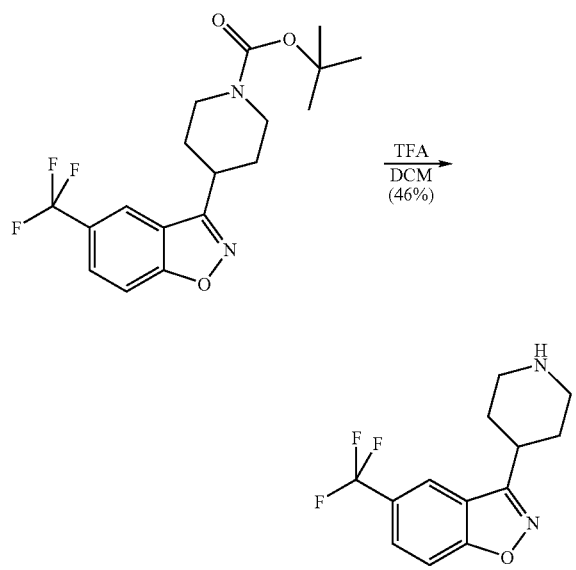

3-Piperidin-4-yl-5-trifluoromethyl-benzo[d]isoxazole. 4-(5-Trifluoromethyl-benzo[d]isoxazol-3-yl)-piperidine-1-carboxylic acid tert-butyl ester (2.69 g, 0.007M) was suspended in a 50:50 mixture of DCM/Trifluoroacetic acid (4 mL). The mixture was heated for 30 minutes at 50° C. and then concentrated to give the product as the TFA salt. This was dissolved in dichloromethane (10 mL), washed with saturated Na₂CO₃ solution (3×3 mL), dried over MgSO₄, filtered and concentrated to give the product as an oil (0.91 g, 46%)

Example 37

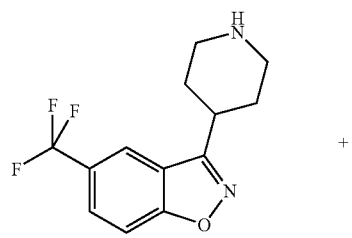

+

-continued

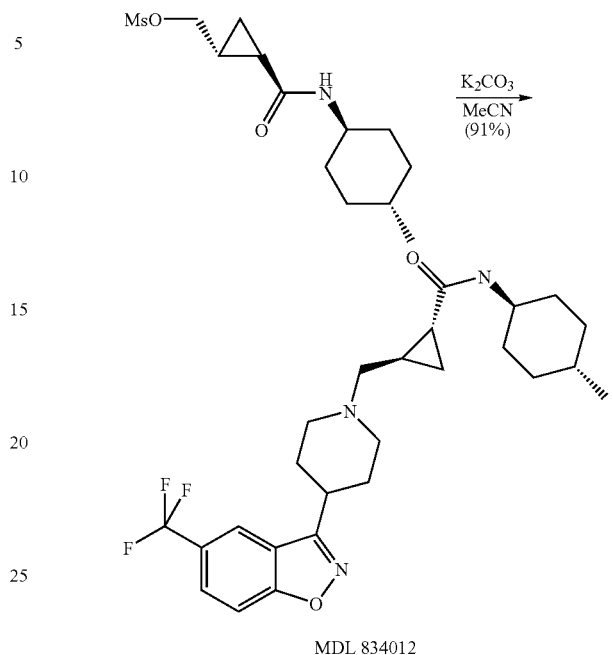

MDL 834012

2R-[4-(5-Trifluoromethyl-benzo[d]isoxazol-3-yl)-piperidin-1-ylmethyl]-cyclopropane-1R-carboxylic acid trans-(4-methyl-cyclohexyl)-amide. A solution 3-Piperidin-4-yl-5-trifluoromethyl-benzo[d]isoxazole (0.1 g, 0.37 mM) was dissolved in acetonitrile (4.5 mL) and treated with potassium carbonate (0.06 g, 0.46 mM) dissolved in water (0.5 mL). The reaction was stirred at ambient temperature for 10 minutes and then treated with methane sulfonic acid 2-(4-methyl-cyclohexyl carbomyl)-transcyclopropyl methyl ester (0.11 g, 0.38 mM-1.04 eq). Heated mixture at 56° C. for 14 hours. Product filtered off and washed with hexanes (2 mL). Dried product under vacuum to obtain the product as a white solid (0.1 18 g, 91%).

Example 38

7-Methoxy benzisoxazolyl piperidine

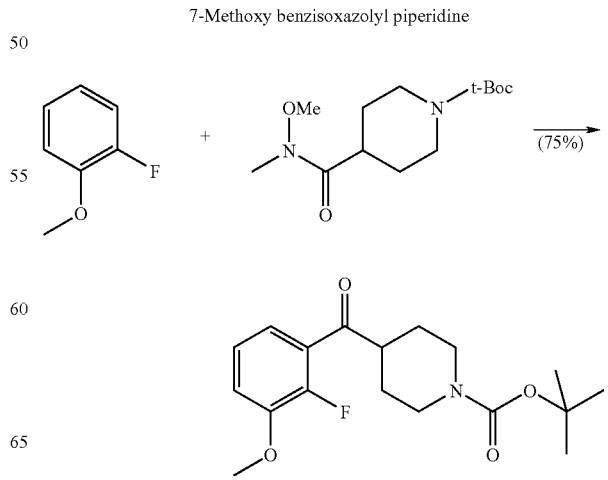

4-(2-Fluoro-3-methoxy-benzoyl)-piperidine-1-carboxylic acid tert-butyl ester. To a stirred solution of 2-fluoroanisole (6.00 g, 47.6 mmol) and anhydrous THF (125 mL) at −78° C. under nitrogen was added butyllithium (35 mL of a 1.6 M solution in hexanes, 56.0 mmol). After stirring for 13 min, N,N,N',N',N''-Pentamethyidiethylenetriamine (12.9 mL, 61.8 mmol) was added dropwise and the reaction stirred at −78° C. After 168 min, a solution of 4-(methoxy-methyl-carbamoyl)-piperidine-1-carboxylic acid tert-butyl ester (16.8 g, 61.7 mmol) in anhydrous THF (40 mL) was added dropwise over 25 min. The reaction was stirred at −78° C. for 35 min and at room temperature for 65 min. The reaction was diluted with ethyl acetate (400 mL) and washed with cold 0.5 N aqueous HCl (2×200 mL), 5% aqueous potassium carbonate (200 mL), water (200 mL), and brine (200 mL) successively. The organic phase was dried over magnesium sulfate, filtered, and the solvent removed to give 20.1 g of a yellow oil. The product was chromatographed on silica gel (350 g), using a step gradient elution of 20% ethyl acetate-jheptane to 30% ethyl acetate/heptane, to afford 12.0 g (75%) of the desired product as a white solid.

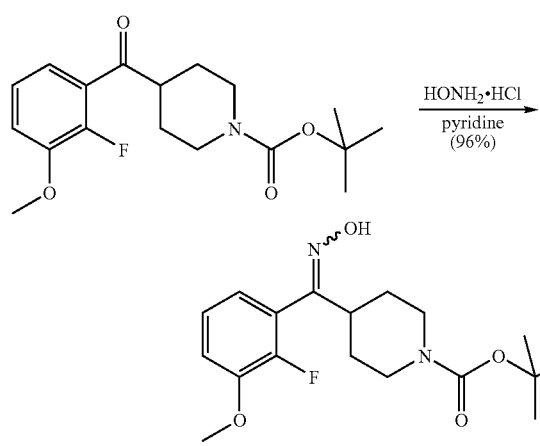

4-[(2-Fluoro-3-methoxy-phenyl)-hydroxyimino-methyl]-piperidine-1-carboxylic acid tert-butyl ester. A mixture of 4-(2-Fluoro-3-methoxy-benzoyl)-piperidine-1-carboxylic acid tert-butyl ester (11.6 g, 34.4 mmol), hydroxylamine hydrochloride (2.87 g, 41.3 mmol) and pyridine (50 mL) was stirred at room temperature under nitrogen overnight. The yellow reaction solution was poured into cold water (500 mL) and the mixture aged at 0° C. for 15 min. The product was collected by filtration, washed with water, and dried under vacuum at 50° C. to afford 11.6 g (96%) of the desired product as a white powder. Proton NMR showed product to be a 2:1 mixture of Z- to E-isomers.

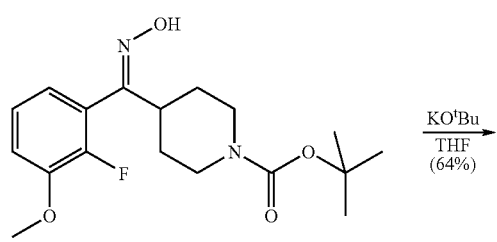

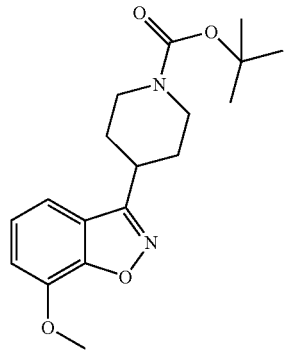

4-(7-Methoxy-benzo[d]isoxazol-3-yl)-piperidine-1-carboxylic acid tert-butyl ester (MDL 831478). To a room temperature mixture of 4-[(2-Fluoro-3-methoxy-phenyl)-hydroxyimino-methyl]-piperidine-1-carboxylic acid tert-butyl ester (5.00 g, 14.2 mmol) in THF (50 mL) under nitrogen was added potassium tert-butoxide (15.0 mL of a 1M THF solution, 15.0 mmol) rapidly and the reaction refluxed for 4 h. After cooling to room temperature, the reaction was diluted with ethyl acetate (250 mL) and washed with water (100 mL) and brine (100 mL) successively. The organics were dried over magnesium sulfate, filtered, and concentrated to give a waxy solid. Recrystallization of the solid did not remove impurities so the crude product was chromatographed on silica using a step gradient elution of 10% ethyl acetate/dichloromethane to 40% ethyl acetate/dichloromethane to afford 3.04 g (64%) of the desired product as a white powder, mp:130–132° C.

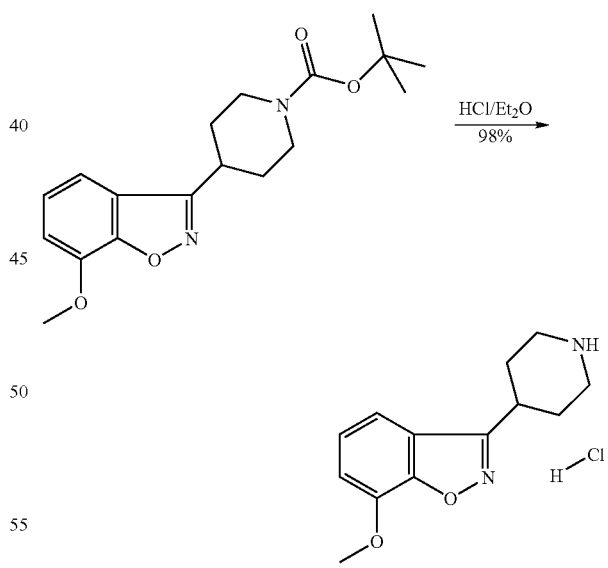

7-Methoxy-3-piperidin-4-yl-benzo[d]isoxazole hydrochloride (MDL 831587A). A mixture of 4-(7-Methoxy-benzo[d]isoxazol-3-yl)-piperidine-1-carboxylic acid tert-butyl ester (3.00 g, 9.03 mmol), HCl (35 mL of a 1 M ether solution, 35.0 mmol), and methanol (25 mL) was stirred at room temperature under nitrogen for 18 h. Ether (75 mL) was added, the mixture stirred at room temperature for 15 min, and the product collected by filtration to afford 2.37 g (98%) of the desired product as a white powder, mp: >250° C.

Example 39

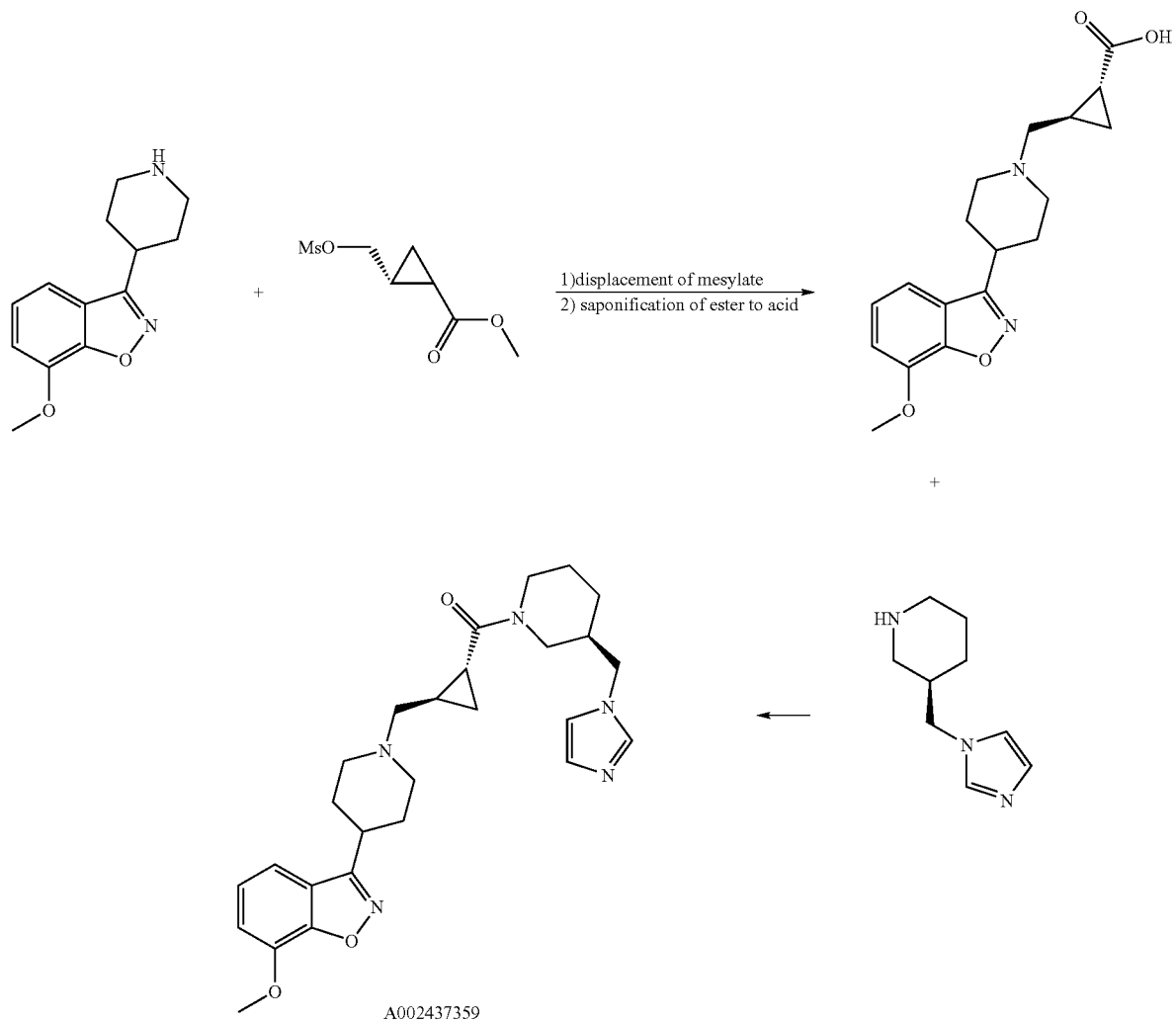

(3S-Imidazol-1-ylmethyl-piperidin-1-yl)-{2R-[4-(7-methoxy-benzo[d]isoxazol-3-yl)-piperidin-1-ylmethyl]-1R-cyclopropyl}-methanone (A002437359). The target was synthesized via the method analogous to the one described previously. 3R-Imidazol-1-ylmethyl-piperidine was obtained via the method describe by Guzi, et.al. WO 0037458.

Example 40

7-trifluoromethyl-N-methyl-indazole piperidine

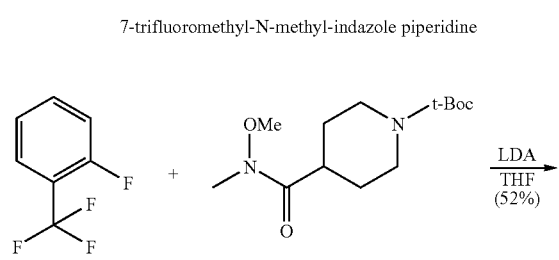

-continued

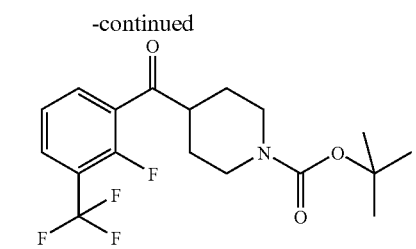

4-(2-Fluoro-3-trifluromethyl-benzoyl)-piperidine-1-carboxylic acid tert-butyl ester.

To a stirred solution of 2-fluorobenzotrifluoride (19.4 g, 118 mmol) and anhydrous THF (300 mL) at −78° C. under nitrogen was added was added LDA (65.0 mL of a 2.0 M solution in heptane/tetrahydrofuran/ethylbenzene, 130 mmol) dropwise over 25 min. After 165 min, a solution of 4-(methoxy-methyl-carbamoyl)-piperidine-1-carboxylic acid tert-butyl ester (40.1 g, 147 mmol) in anhydrous THF (100 mL) was added dropwise over 50 min and the reaction stirred at −78° C. for 20 min and at room temperature for 85 min. The reaction was quenched with saturated ammonium chloride (40 mL) and the mixture concentrated. The residue was taken up in ethylacetate (400 mL) and washed successively with 1 N HCl (200 mL), 5% aqueous potassium carbonate, water (200 mL), and brine (200 mL). The organic phase was dried over magnesium sulfate, filtered, and the solvent removed to give an amber oil. The product was chromatographed on silica gel (300 g), using a step gradient elution of 20% ethyl acetate/heptane to 60% ethyl acetate/heptane, to afford 23.2 g (52%) of the desired product as an off-white solid.

(150 mL) successively, dried over magnesium sulfate, filtered, and the solvent partially removed to give a viscid liquid. The remaining solvent was removed under high vacuum at 65° C. to provide an off-white solid. The product was chromatographed on silica, eluting with 30% ethyl acetate/heptane, to afford 6.63 g (93%) of the desired product as an off-white solid, mp: 104.7° C.

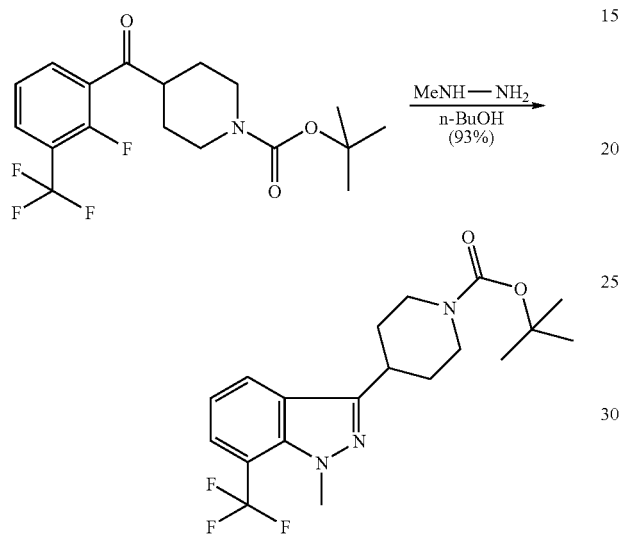

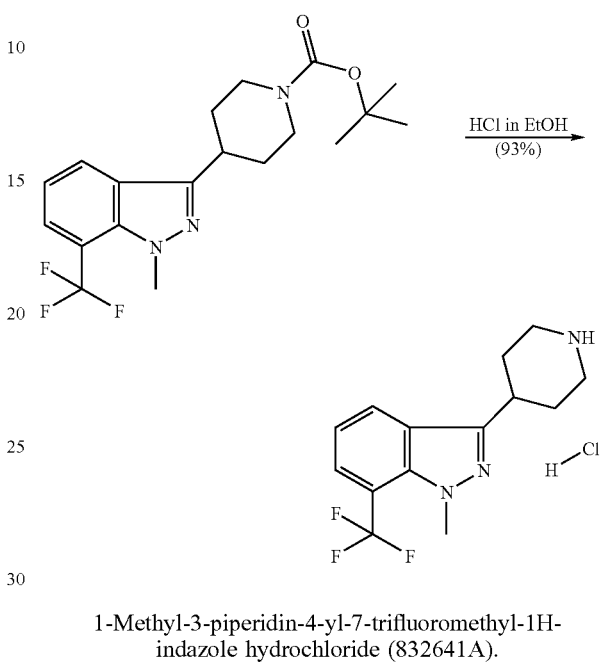

1-Methyl-3-piperidin-4-yl-7-trifluoromethyl-1H-indazole hydrochloride (832641A).

4-(1-Methyl-7-trifluoromethyl-1H-indazol-3-yl)-piperidine-1-carboxylic acid tert-butyl esters (MDL 832782). A solution of 4-(2-Fluoro-3-trifluromethyl-benzoyl)-piperidine-1-carboxylic acid tert-butyl ester (7.00 g, 18.6 mmol), methylhydrazine (1.13 g, 24.4 mmol), and n-butanol (50 mL) was heated at reflux for 135 min. The reaction was cooled to room temperature and diluted with ethyl acetate (250 mL). The oganics were washed with 5% aqueous potassium carbonate (150 mL), water (150 mL), and brine Added 1N HCl (100 mL) to a solution of 4-(1-methyl-7-trifluoromethyl-1H-indazol-3-yl)-piperidine-1-carboxylic acid tert-butyl esters (6.50 g, 16.9 mmol) in ethanol (25 mL) and the reaction stirred at room temperature overnight. The mixture was diluted with ether (350 mL) and cooled 0° C. for 20 min. The solid was collected, washed with ether, and dried at 45° C. under high vacuum to afford 4.66 g (86%) of the desired product as a white powder.

Example 41

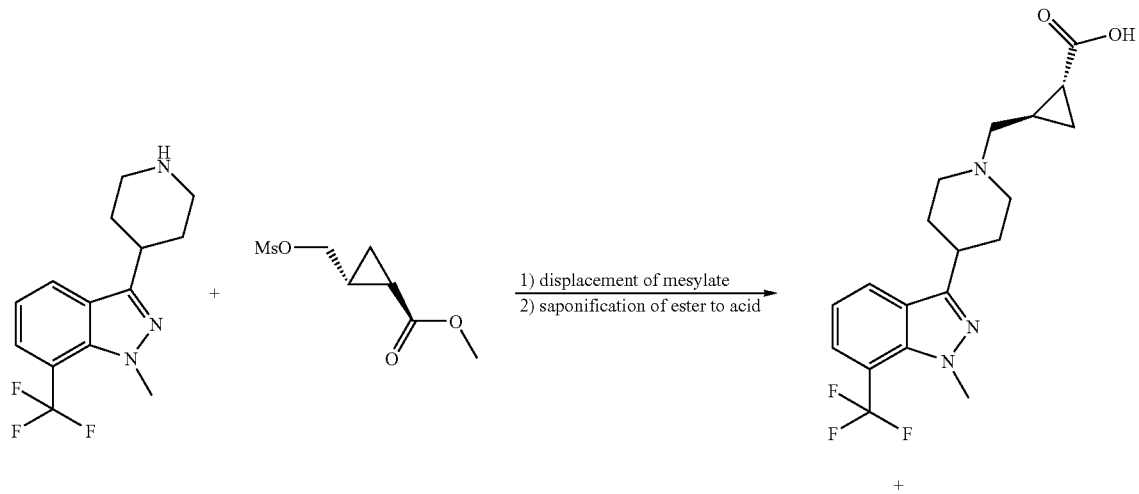

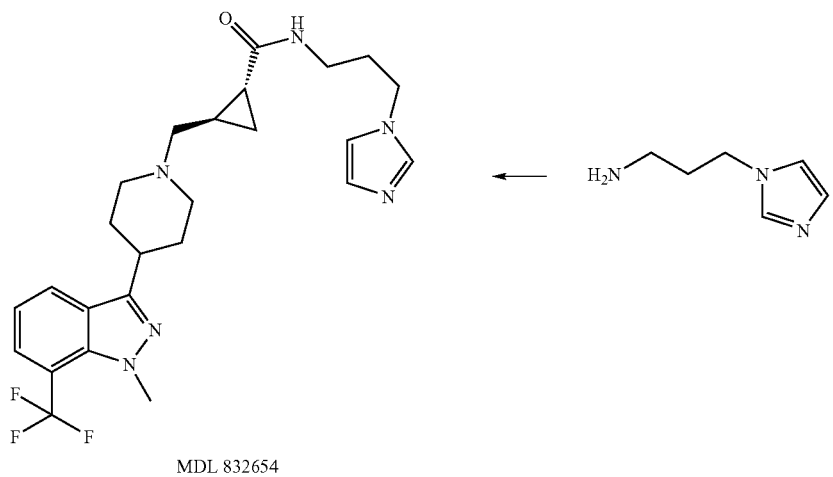

MDL 832654

2R-[4-(1-Methyl-7-trifluoromethyl-1H-indazol-3-yl)-piperidin-1-ylmethyl]-1R-cycloproanecarboxylic acid (3-imidazol-1-yl-propyl)-amide (MDL 832654). The target was synthesized via the method analogous to the one described previously.

Example 42

7-trifluoromethyl benzisoxazol piperdine

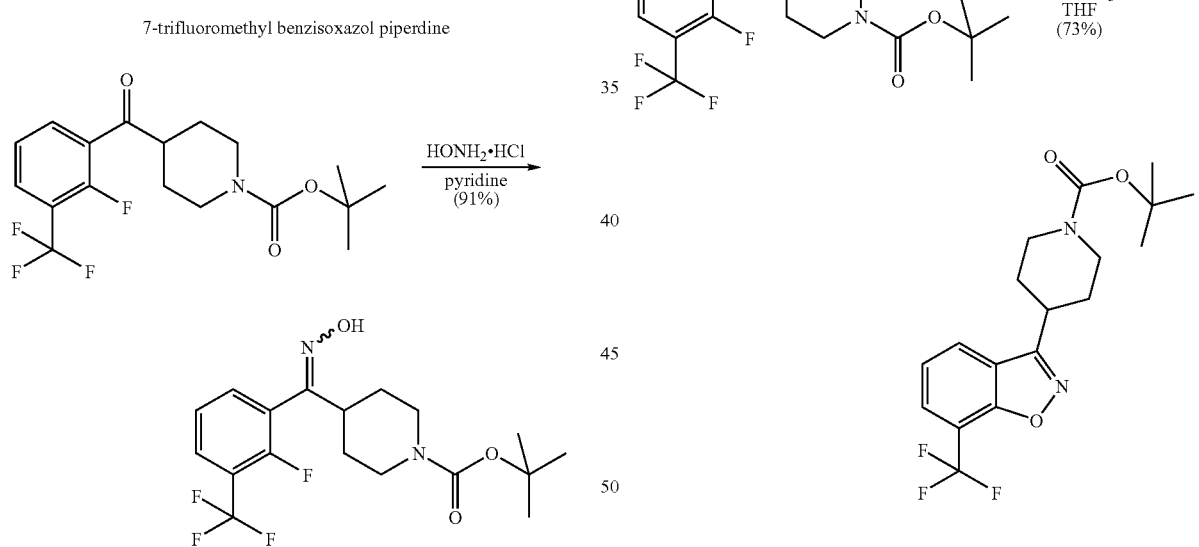

4-[(2-Fluoro-3-trifluoromethyl-phenyl)-hydroxyiminomethyl]-piperidine-1-carboxylic acid tert-butyl ester (MDL 832163). A mixture of 4-(2-Fluoro-3-trifluromethyl-benzoyl)-piperidine-1-carboxylic acid tert-butyl ester (9.00 g, 24.0 mmol), hydroxylamine hydrochloride (2.00 g, 28.8 mmol) and pyridine (50 mL) was stirred at room temperature under nitrogen overnight. The yellow reaction solution was poured into cold water (500 mL) and the mixture aged at 0° C. for 1 h. The product was collected by filtration, washed with water, and dried under vacuum at 50° C. to afford 9.54 g of a white solid. Trituration of the solid with hot 25% ethyl acetate/heptane afforded 8.50 g (91%) of the desired product as a white solid. Proton NMR showed product to be a 3.8 to 1 mixture of isomers.

4-(7-Trifluoromethyl-benzo[d]isoxazol-3-yl)-piperidine-1-carboxylic acid tert-butyl ester (MDL 832159). To a room temperature mixture of 4-[(2-fluoro-3-trifluoromethyl-phenyl)-hydroxyimino-methyl]-piperidine-1-carboxylic acid tert-butyl ester (1.40 g, 3.59 mmol) in THF (20 mL) under nitrogen was added potassium tert-butoxide (3.60 mL of a 1 M THF solution, 3.60 mmol) in one portion and the reaction heated at 60° C. for 1.5 h. After standing at room temperature overnight, the solvent was removed and the residue diluted with ethyl acetate (60 mL). The organics were washed with water (30 mL) and brine (30 mL) successively, dried over magnesium sulfate, filtered, and concentrated to give an amber solid. The crude product was chromatographed on silica using 40% ethyl acetateiheptane as eluent to afford 0.97 g (73%) of the desired product as a white solid, mp:111–113° C.

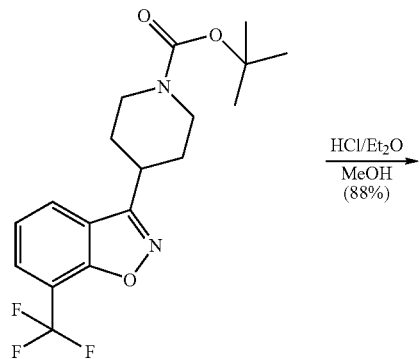

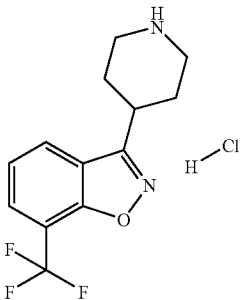

3-Piperidin-4-yl-7-trifluoromethyl-benzo[d]isoxazole (MDL 832106A). A mixture of 4-(7-trifluoromethyl-benzo[d]isoxazol-3-yl)-piperidine-1-carboxylic acid tert-butyl ester (8.00 g, 21.6 mmol), HCl (100 mL of a 1 M ether solution, 100 mmol), and methanol (50 mL) was stirred at room temperature under nitrogen overnight. The reaction was concentrated and the solid triturated with methanovether to afford 5.84 g (88%) of the desired product as a white powder, mp: 242–243° C.

Example 43

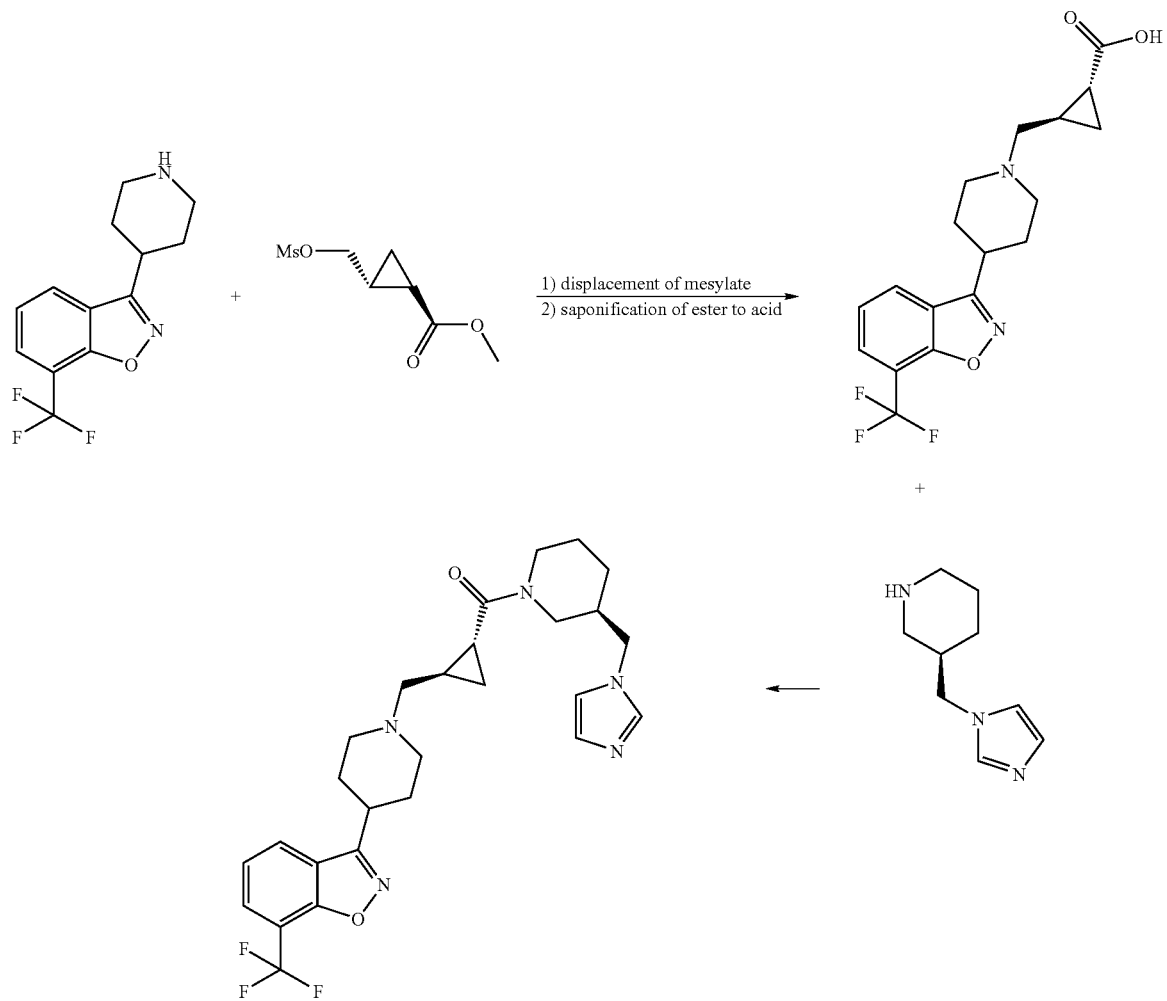

121

(3S-Imidazol-1-ylmethyl-piperidin-1-yl)-{2R-[4-(7-trifluoromethyl-benzo[d]isoxazol-3-yl)-piperidin-1-ylmethyl]-1R-cyclopropyl}-methanone (A002437360). The target was synthesized via the method analogous to the one described previously. 3R-Imidazol-1-ylmethyl-piperidine was obtained via the method describe by Guzi, et.al. WO 0037458.

Example 44

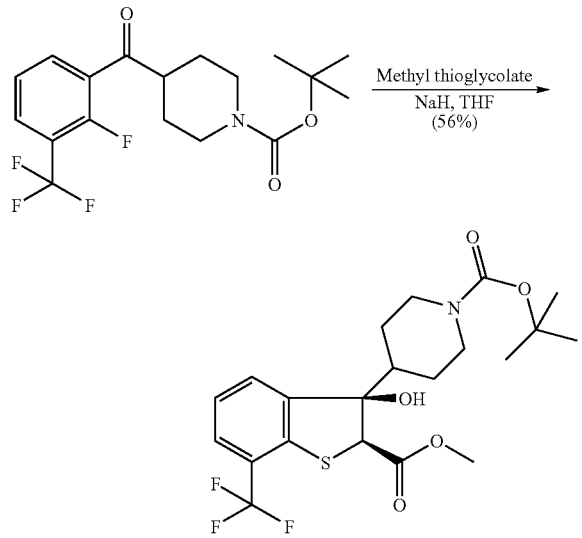

4-(3-Hydroxy-2-methoxycarbonyl-7-trifluoromethyl-2,3-dihydro-benzo[b]thiophen-3-yl)-piperidine-1-carboxylic acid tert-butyl ester (MDL 832712). To a room temperature solution of 4-(2-fluoro-3-trifluromethyl-benzoyl)-piperidine-1-carboxylic acid tert-butyl ester (9.00 g, 24.0 mmol), methyl thioglycolate (2.40 mL, 26.8 mmol), and anhydrous THF (200 mL) under nitrogen was added NaH (1.15 g of a 60% oil dispersion, 28.7 mmol) in one portion. After the gas evolution ceased, the reaction was stirred at 55° C. After 100 min, the reaction was cooled to room temperature and diluted with ethyl acetate (500 mL). The mixture was washed with water (300 mL) and brine (300 mL) successively, dried over magnesium sulfate, filtered, and the solvent removed to afford a sticky white solid. Trituration with 20% ethyl acetate/heptane afforded 6.20 g (56%) of the desired product as a white powder.

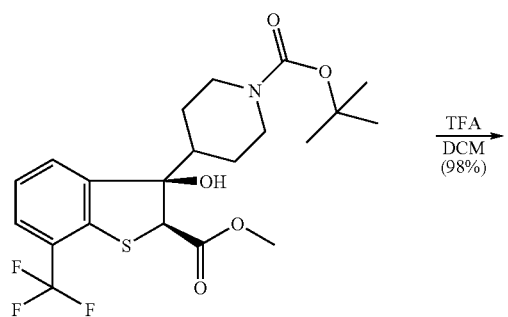

122

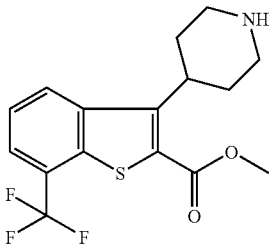

3-Piperidin-4-yl-7-trifluoromethyl-benzo[b]thiophene-2-carboxylic acid methyl ester. To a room temperature solution of 4-(3-hydroxy-2-methoxycarbonyl-7-trifluoromethyl-2,3-dihydro-benzo[b]thiophen-3-yl)-piperidine-1-carboxylic acid tert-butyl ester (6.00 g, 13.0 mmol) in DCM (30 mL) was added TFA (30 mL) causing rapid gas evolution. After 5 min, the reaction was stirred at 40° C. for 5.5 h. After cooling to room temperature, the reaction was poured into 20% aqueous potassium carbonate (400 mL) and extracted with DCM (2×200 mL). The combined extracts were dried over magnesium sulfate, filtered, and the solvent removed to give a thick oil. After drying under high vacuum 4.37 g (98%) of the desired product was obtained as a white foam.

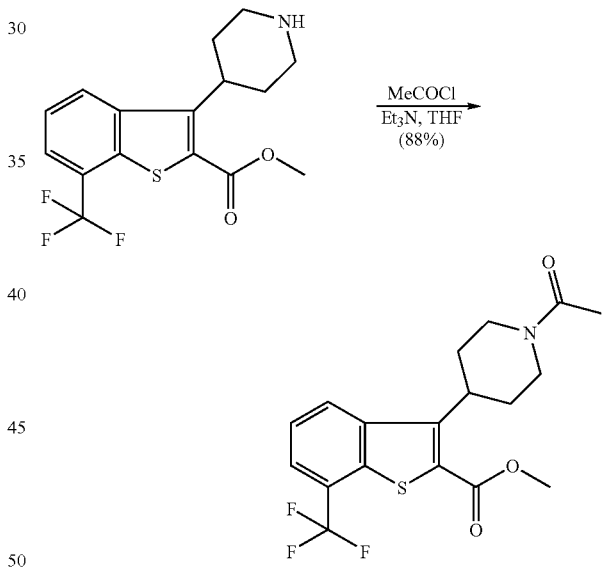

3-(1-Acetyl-piperidin-4-yl)-7-trifluoromethyl-benzo[b]thiophene-2-carboxylic acid methyl ester. To a room temperature solution of 3-piperidin-4-yl-7-trifluoromethyl-benzo[b]thiophene-2-carboxylic acid methyl ester (4.37 g, 12.7 mmol), triethylamine (2.70 mL. 19.4 mmol), and anhydrous THF (80 mL) under nitrogen was added acetyl chloride (1.10 mL, 15.5 mmol) in one portion and the reaction stirred at room temperature overnight. The reaction was diluted with ethyl acetate (300 mL) and washed with water (150 mL) and brine (150 mL) successively. The organic layer was dried over magnesium sulfate, filtered, and the solvent removed. The residue was chromatographed on silica, eluting with 10% methanol/ethyl acetate, to afford 4.28 g (88%) of the desired product as a white solid, mp: 155.2° C.

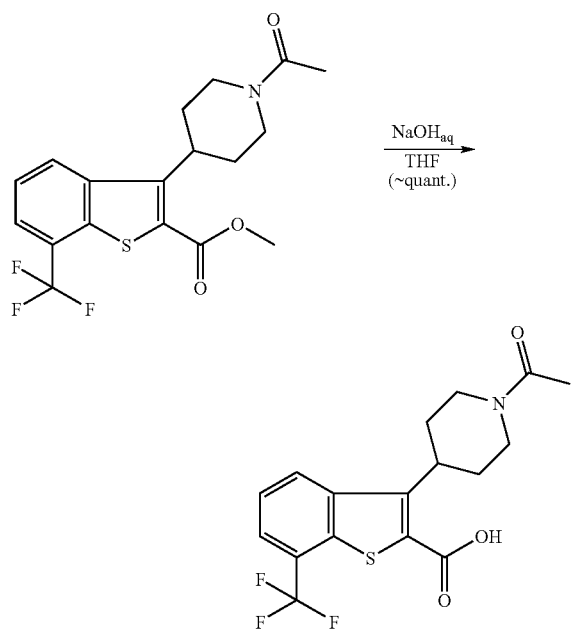

3-(1-Acetyl-piperidin-4-yl)-7-trifluoromethyl-benzo[b]thiophene-2-carboxylic acid.

To a solution of 3-(1-acetyl-piperidin-4-yl)-7-trifluoromethyl-benzo[b]thiophene-2-carboxylic acid methyl ester (4.10 g, 10.6 mmol) in THF (25 mL) was added 0.5 N aqueous sodium hydroxide (23.4 mL, 11.7 mmol) and the reaction stirred at room temperature. After 18 h, the reaction was acidified with 1 N HCl (200 mL) and the mixture extracted with DCM (2×100 mL). The organics were washed with water (100 mL), dried over magnesium sulfate, filtered, and concentrated to give 4.13 g of the desired product as a white foam.

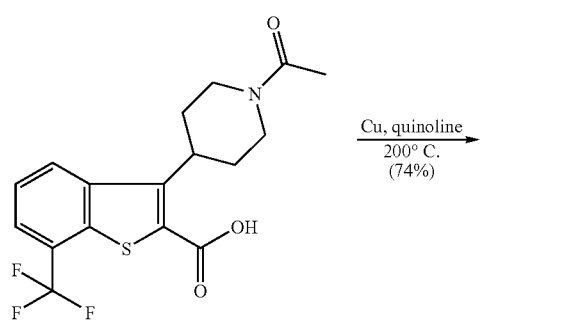

1-[4-(7-Trifluoromethyl-benzo[b]thiophen-3-yl)-piperidin-1-yl]-ethanone (MDL 832823). A mixture of 3-(1-acetyl-piperidin-4-yl)-7-trifluoromethyl-benzo[b]thiophene-2-carboxylic acid (4.13 g, 11.1 mmol), Cu powder (0.706 g, 11.1 mmol), and quinoline (20 mL) was heated to 200° C. under nitrogen. After 10 min, no gas evolution was observed and the reaction cooled at room temperature. The mixture was diluted with ethyl acetate (100 mL), filtered through a Celite bed and the filtrate washed with 1 N HCl (2×100 mL), 5% aqueous potassium carbonate (100 mL), water (100 mL), and brine (100 mL) successively. The organics were dried over magnesium sulfate, filtered, and concentrated to give an amber oil. The oil was chromatographed on silica, eluting with 10% methanol/ethyl acetate to afford 2.69 g (74%) of the desired product as a tan solid.

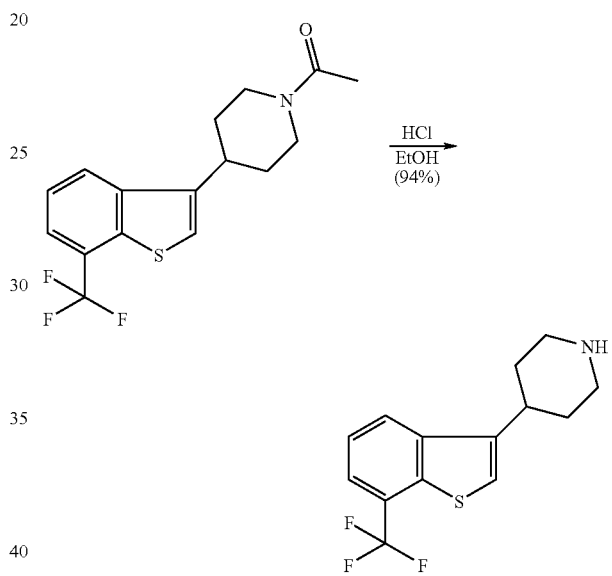

4-(7-Trifluoromethyl-benzo[b]thiophen-3-yl)-piperidine. A mixture of 1-[4-(7-trifluoromethyl-benzo[b]thiophen-3-yl)-piperidin-1-yl]-ethanone (2.95 g, 9.01 mmol), concentrated HCl (30 mL), and ethanol was heated at 80° C. for 18 h. After cooling to room temperature, the reaction was basified with 20% aqueous potassium carbonate (150 mL) and the mixture extracted with DCM (2×100 mL). The organics were washed with water (100 mL), dried over potassium carbonate, filtered, and concentrated to give 2.42 g (94%) the desired product as an amber waxy solid.

Example 45

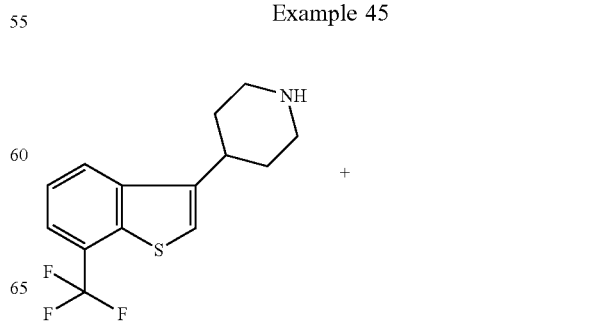

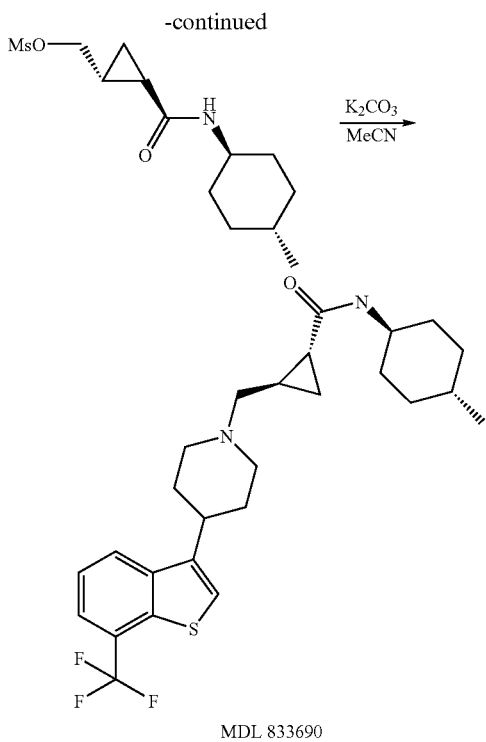

2R-[4-(7-Trifluoromethyl-benzo[b]thiophen-3-yl)-piperidin-1-ylmethyl]-1R-cyclopropanecarboxylic acid (trans-4-methyl-cyclohexyl)-amide (MDL 833690).

The target was synthesized via the method analogous to the one described above.

Example 46

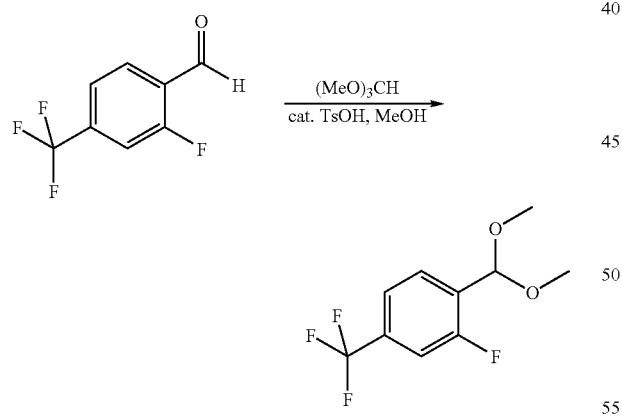

1-Dimethoxymethyl-2-fluoro-4-trifluoromethyl-benzene. A solution of 2-fluoro-4-trifluoromethylbenzaldehyde (10.0 g, 52.0 mmol), trimethyl orthoformate (55.0 g, 520 mmol) and a catalytic amount of p-toluene sulfonic acid (5 mol %) was stirred at room temperature for 24 hours. The resulting solution was saturated with the addition of solid $Na_2CO_3$ and stirred for 15 minutes. The mixture was then filtered and the solution was evaporated. The residue was diluted with ether and evaporated yielding 12.1 g (98%) of the desired product as an oil.

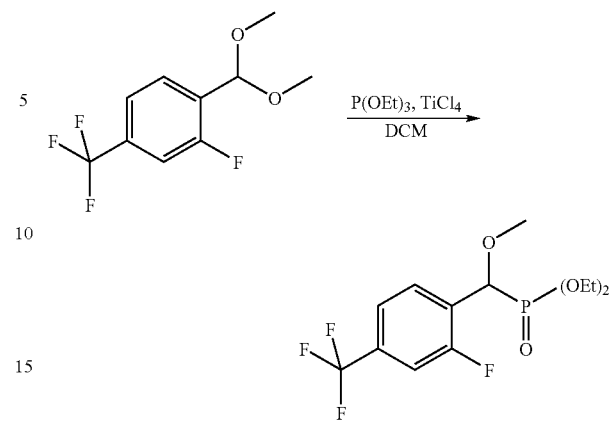

[(2-Fluoro-4-trifluoromethyl-phenyl)-methoxy-methyl]-phosphinic acid diethyl ester. To a solution of the 1-dimethoxymethyl-2-fluoro-4-trifluoromethyl-benzene (5.0 g, 21.0 mmol) and $P(OEt)_3$ (4.18 g, 25.2 mmol) in $CH_2Cl_2$ (42 mL) cooled to −78° C. was added titanium tetrachloride (42 mL, 42 mmol, 1 M in DCM) portion-wise. The resulting solution was stirred at −78° C. for 2 hours when the reaction is quenched with the addition of water (10 mL). The mixture was warmed to room temperature and separated. The aqueous layer was extracted with DCM (3×10 mL). The combined organic layers were washed with brine (25 mL), dried ($MgSO_4$), filtered and evaporated. The residue is separated via chromatography (1:1; EtOAc/DCM) yielding 6.1 g (85%) of the desired product.

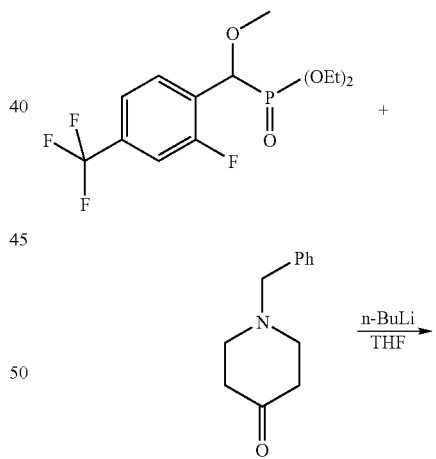

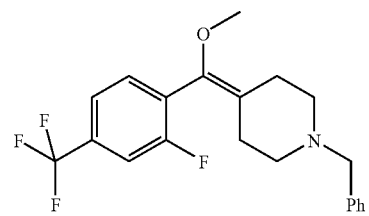

1-Benzyl-4-[(2-fluoro-4-trifluoromethyl-phenyl)-methoxy-methylene]-piperdine. To a solution of [(2-fluoro-4-trifluoromethyl-phenyl)-methoxy-methyl]-phosphinic acid diethyl ester (16.1 g, 46.5 mmol) in THF (200 mL) cooled to −78° C. was added n-Butyl lithium (32.1 mL, 51.5 mmol) drop-wise. To the resulting solution was added a solution of 1-benzyl-4-piperidone (9.71 g, 51.5 mmol) in THF (20 mL) drop-wise. The mixture was stirred at −78° C. for 3 hours and then was allowed to slowly warm to room temperature overnight. The reaction mixture was partitioned between water (50 mL) and EtOAc (200 mL) and separated. The aqueous layer was extracted with EtOAc (100 mL) and the combined organic layers were washed with brine (50 mL), dried (MgSO₄), filtered and evaporated. The residue was purified via chromatography (gradient elution, heptane to 40% EtOAc in heptane) to obtain 9.9 g (56%) of the desired product as an oil.

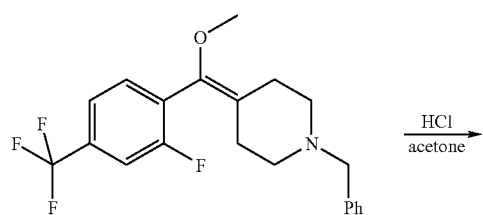

(1-Benzyl-piperidin-4-yl)-(2-fluoro-4-trifluoromethyl-phenyl)-methanone. A solution of the 1-benzyl-4-[(2-fluoro-4-trifluoromethyl-phenyl)-methoxy-methylene]-piperidine (9.9 g, 26.1 mmol) in acetone (100 mL) and conc. HCl (10 mL) in a sealed vessel was heated at 60° C. for 2 hours. Upon cooling to room temperature the solution was basified with the addition of 3 N NaOH. The resulting mixture was extracted with EtOAc (2×200 mL). The combined extracts were washed with brine (50 mL), dried (MgSO₄), filtered and evaporated yielding 8.8 g (92%) of the desired product as a solid.

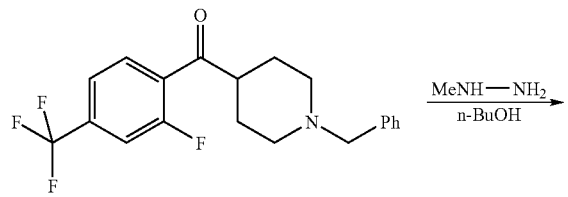

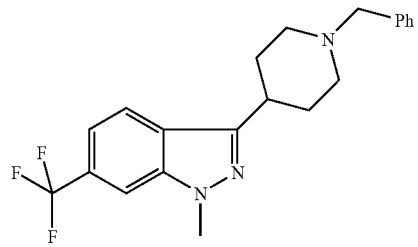

3-(1-Benzyl-piperidin-4-yl)-1-methyl-6-trifluoromethyl-1H-indazole (MDL 833796). A solution of (1-benzyl-piperidin-4-yl)-(2-fluoro-4-trifluoromethyl-phenyl)-methanone (2.0 g, 5.46 mmol), methylhydrazine (327 mg, 7.10 mmol), and n-butanol (22 mL) was heated at 120° C. in a seal vessel for 18 hours. The reaction was cooled to room temperature and basified with NaHCO₃ and extracted with EtOAc (3×50 mL). The combined organic layers were washed with brine (50 mL), dried over magnesium sulfate, filtered, and evaporated. The product was chromatographed on silica, eluting with 1:1 ethyl acetate/heptane, to afford 1.68 g (82%) of the desired product as an oil.

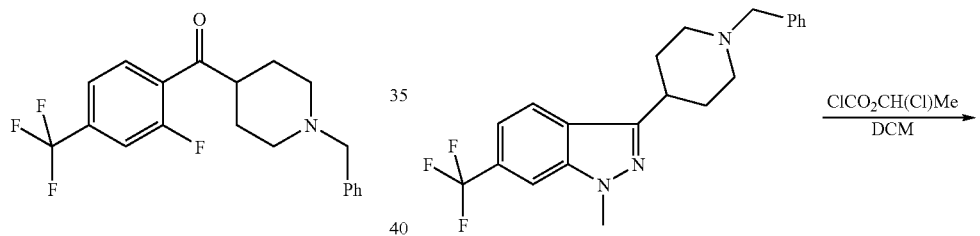

1-Methyl-3-piperidin-4-yl-6-trifluoromethyl-1H-indazole hydrochloride (MDL 833799A). To the 3-(1-benzyl-piperidin-4-yl)-1-methyl-6-trifluoromethyl-1H-indazole (1.41 g, 3.78 mmol) in DCM (20 mL) was added 1-chloroethyl chloroformate (0.49 mL, 4.50 mmol). The resulting solution was stirred at room temperature overnight when the volitiles were removed in vacuo. The residue was taken un in methanol (20 mL) and the resulting solution was heated at reflux for 1 hour. The mixture was cooled to room temperature and the solution was evaporated. The residue was taken up in EtOAc and the solid product was collected by filtration yielding 1.03 g (86%) of the HCl salt as a white solid.

Example 47

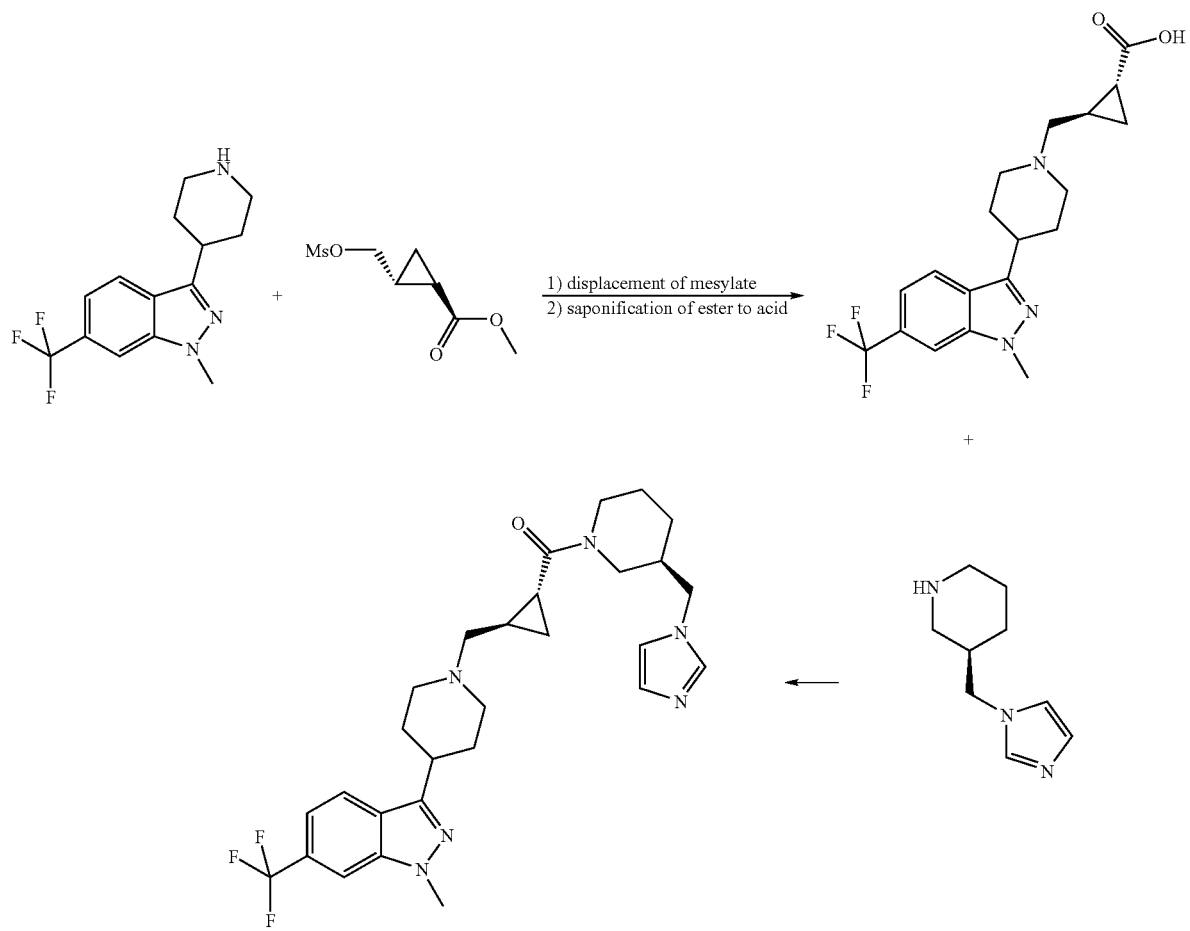

A002437353

(3S-Imidazol-1-ylmethyl-piperidin-1-yl)-{2R-[4-(1-methyl-6-trifluoromethyl-1H-indazol-3-yl)-piperidin-1-ylmethyl]-1R-cyclopropyl}-methanone (A002437353). The target was synthesized via the method analogous to the one described previously. 3R-Imidazol-1-ylmethyl-piperidine starting material was obtained via the method describe by Guzi, et.al. WO 0037458.

Example 48

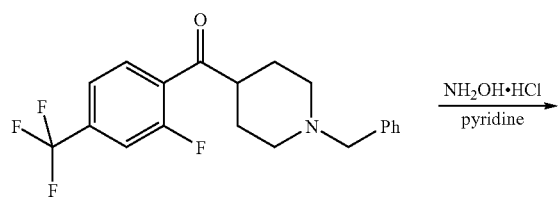

$\xrightarrow{\text{NH}_2\text{OH}\cdot\text{HCl}}_{\text{pyridine}}$

-continued

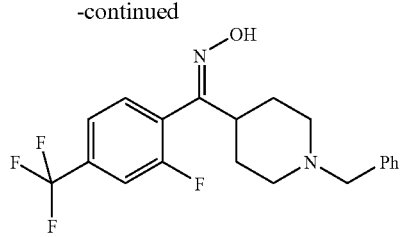

(1-Benzyl-piperidin-4-yl)-(2-fluoro-4-trifluoromethyl-phenyl)-methanone oxime. A mixture of (1-benzyl-piperidin-4-yl)-(2-fluoro-4-trifluoromethyl-phenyl)-methanone (5.0 g, 13.66 mmol), hydroxylamine hydrochloride (1.1 g, 16.39 mmol) and pyridine (50 mL) was stirred at room temperature overnight when the mixture was distilled to remove pyridine (35 mL). The solid residue was washed with heptane then ether. The resulting solid was partitioned between a saturated solution of NaHCO$_3$ and EtOAc. The organic layer was dried (MgSO$_4$), filtered and evaporated. The solid residue was washed with 3:1 heptane/EtOAc and dried under vacuum to obtain 2.1 g (40%) of the desired product as a white solid.

131

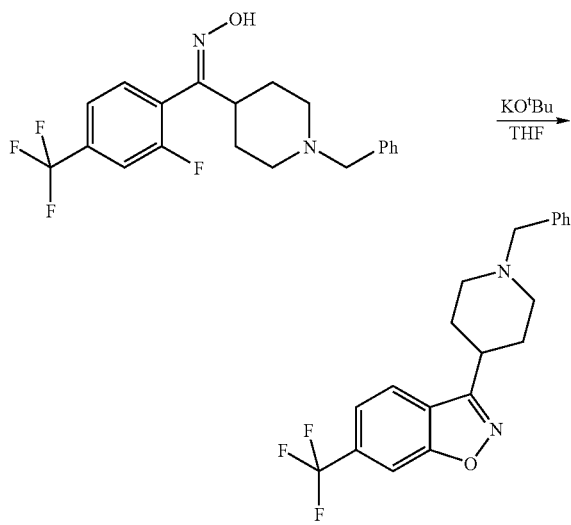

3-(1-Benzyl-piperidin-4-yl)-6-trifluoromethyl-benzo[b]isoxazole. To a room temperature mixture of (1-benzyl-piperidin-4-yl)-(2-fluoro-4-trifluoromethyl-phenyl)-methanone oxime (2.1 g, 5.51 mmol) in THF (20 mL) under nitrogen was added potassium tert-butoxide (5.78 mL of a 1M THF solution, 5.78 mmol) in one portion. The resulting solution was stirred at room temperature for 6 hours when the mixture was partitioned between water (60 mL) and ethyl acetate (60 mL). The aqueous layer was extracted with EtOAc (60 mL). The combined organic layers were washed with water (30 mL) and brine (30 mL), dried over magnesium sulfate, filtered, and concentrated to give 1.9 g (96%) as the desired product.

132

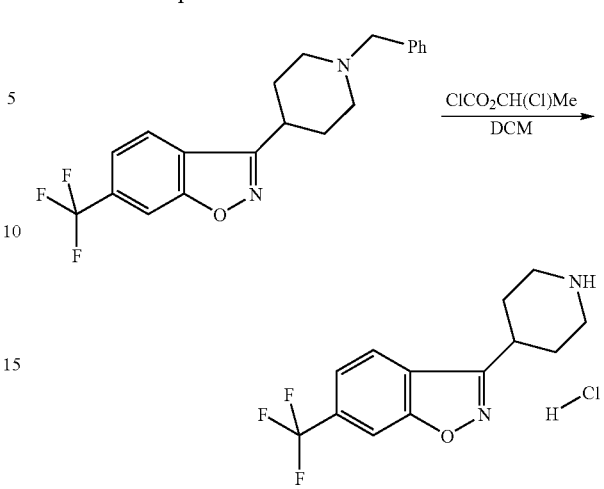

3-Piperidin-4-yl-6-trifluoromethyl-benzo[d]isoxazole hydrochloride. To the 3-(1-Benzyl-piperidin-4-yl)-6-trifluoromethyl-benzo[b]isoxazole (1.9 g, 5.27 mmol) in DCM (26 mL) was added 1-chloroethyl chloroformate (0.69 mL, 6.33 mmol). The resulting solution was stirred at room temperature overnight when the volitiles were removed in vacuo. The residue was taken un in methanol (25 mL) and the resulting solution was heated at reflux for 1 hour. The mixture was cooled to room temperature and the solution was evaporated. The residue was taken up in EtOAc and the solid product was collected by filtration yielding 1.2 g (74%) of the HCl salt as a white solid.

Example 49

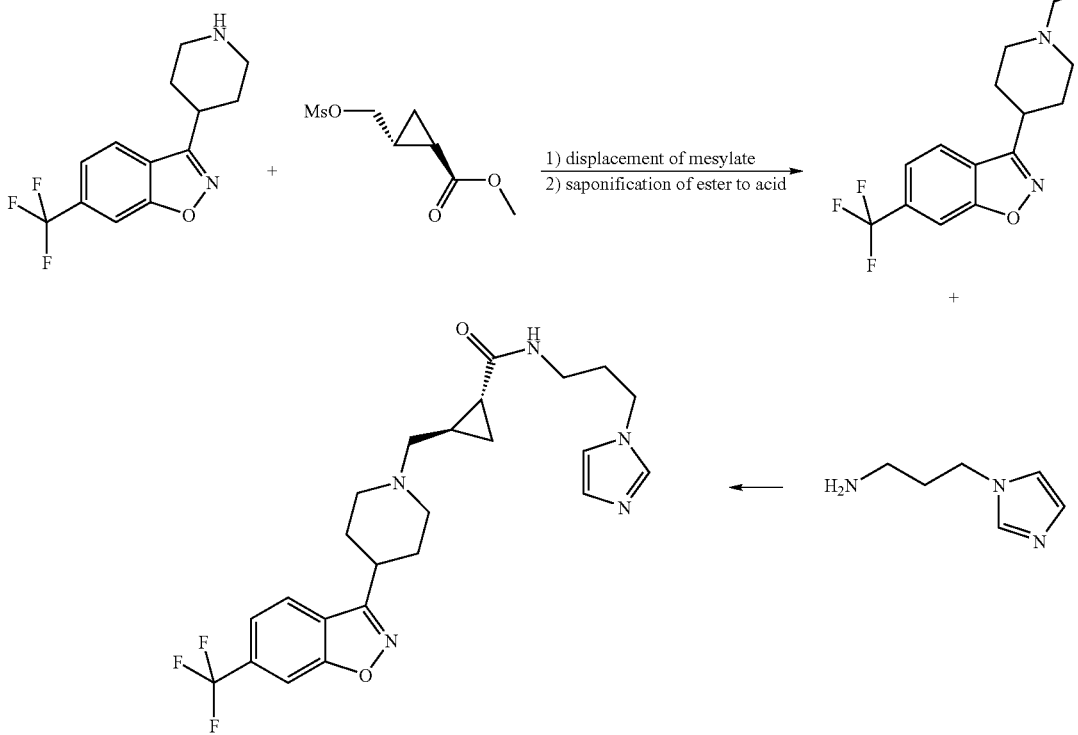

2R-[4-(6-Trifluoromethyl-benzo[d]isoxazol-3-yl)-piperidin-1-ylmethyl]-1R-cycloproanecarboxylic acid (3-imidazol-1-yl-propyl)-amide (A002287765). The target was synthesized via the method analogous to the one described previously.

Example 50

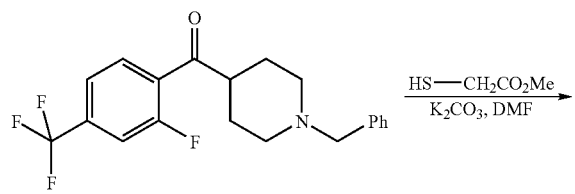

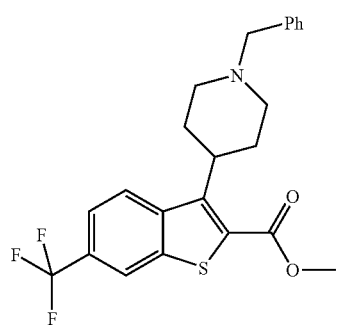

3-(1-Benzyl-piperidin-4-yl)-6-trifluoromethyl-benzo[b]thiophene-2-carboxylic acid methyl ester (MDL 833803). To a room temperature solution of (1-benzyl-piperidin-4-yl)-(2-fluoro-4-trifluoromethyl-phenyl)-methanone (7.5 g, 20.5 mmol), methyl thioglycolate (2.0 mL, 22.5 mmol), and DMF (100 mL) was added $K_2CO_3$ (5.65 g, 41.0 mmol). The reaction was stirred at 60° C. for 24 hours, cooled to room temperature and diluted with ethyl acetate (500 mL). The mixture was washed with water (2×300 mL) and brine (300 mL) successively, dried over magnesium sulfate, filtered, and the solvent removed to afford an oil. The oil was purified via chromatography (30% EtOAc in heptane) yielding 5.91 g (67%) as a solid.

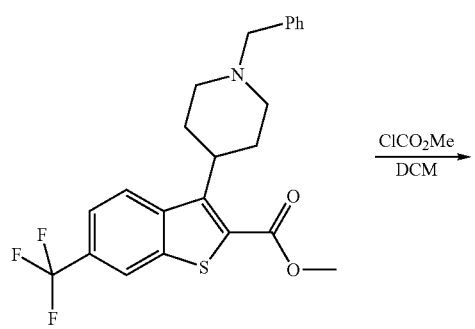

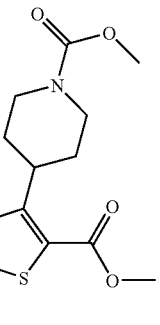

4-(2-Methoxycarbonyl-6trifluoromethyl-benzo[b]thiophen-3-yl)-piperidine-1-carboxylic acid methyl ester. To a solution of 3-(1-benzyl-piperidin-4-yl)-6-trifluoromethyl-benzo[b]thiophene-2-carboxylic acid methyl ester (5.9 g, 13.6 mmol) in DCM (50 mL) was added methyl chloroformate (1.26 mL, 16.3 mmol) drop-wise. The resulting solution was stirred overnight when the volatiles were removed in vacuo. The residue was washed with heptane to yield 4.2 g (77%) of the desired product as a white solid.

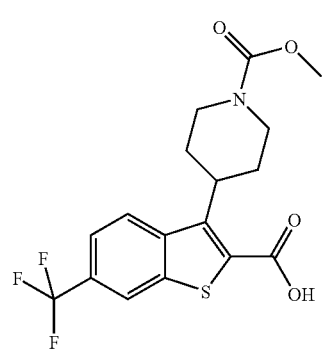

4-(2–Carboxy-6-trifluoromethyl-benzo[b]thiophen-3-yl)-piperidine-1-carboxylic acid methyl ester. To a stirred solution of 4-(2-Methoxycarbonyl-6-trifluoromethyl-benzo[b]thiophen-3-yl)-piperidine-1-carboxylic acid methyl ester (1.1 g, 2.7 mmol) in THF (7.0 mL) was added 1 N NaOH (2.97 mL). The resulting mixture was stirred at room temperature overnight when the mixture was diluted with water (50 mL) and washed with ether (100 mL). The aqueous layer was acidified with the addition of 3 N HCl and the product was extracted with EtOAc (2×150 mL). The combined organic layers were washed with brine (50 mL), dried (MgSO$_4$), filtered and evaporated yielding 960 mg (92%) of the desired product as a white solid.

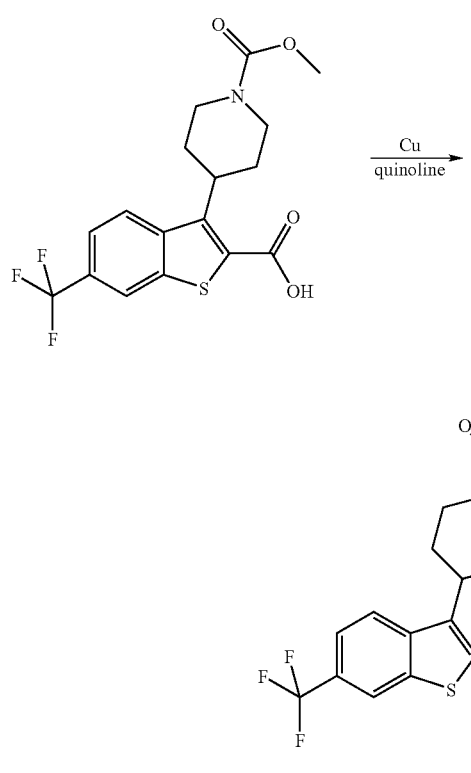

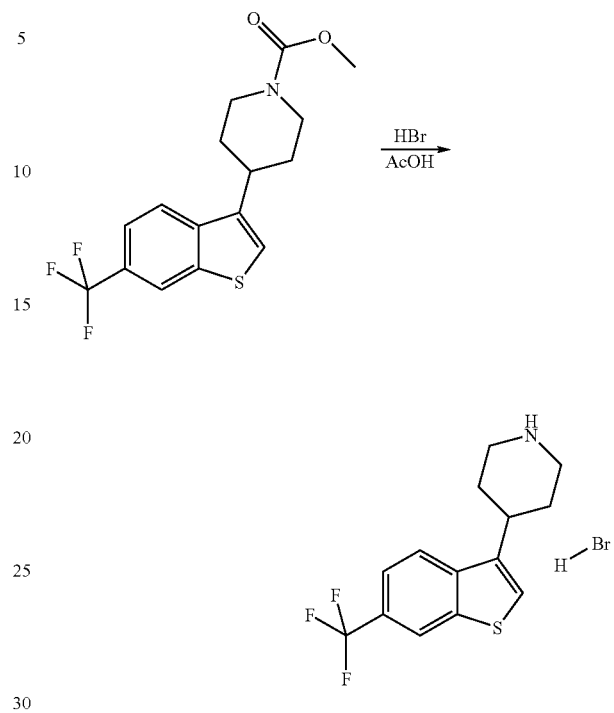

4-(6-Trifluoromethyl-benzo[b]thiophen-3-yl)-piperidine-1-carboxylic acid methyl ester. A mixture of 4-(2-carboxy-6-trifluoromethyl-benzo[b]thiophen-3-yl)-piperidine-1-carboxylic acid methyl ester (4.3 g, 11.1 mmol) and copper (705 mg, 11.1 mmol) in quinoline (28 mL) was heated at 200° C. for 45 minutes. Upon cooling to room temperature the mixture was diluted with EtOAc (50 mL) and filtered. The filtrate was washed with 5% HCl (2×20 mL), water (20 mL) and brine (20 mL), dried (MgSO₄), filtered and evaporated. The residue was separated via chromatography (30% EtOAc in heptane) yielding 3.14 g (82%) of the desired product as a white solid.

4-(6-Trifluoromethyl-benzo[b]thiophen-3-yl)-piperidine hydrobromide. A mixture of 4-(6-trifluoromethyl-benzo[b]thiophen-3-yl)-piperidine-1-carboxylic acid methyl ester (3.1 g, 9.0 mmol) in HBr (45 mL, 30% in acetic acid) was stirred at room temperature for 20 hours when the volatiles were removed in vacuo. The residue was washed with EtOAc and the product was collected by filtration yielding 3.09 g (94%) of the desired product as a white solid.

Example 51

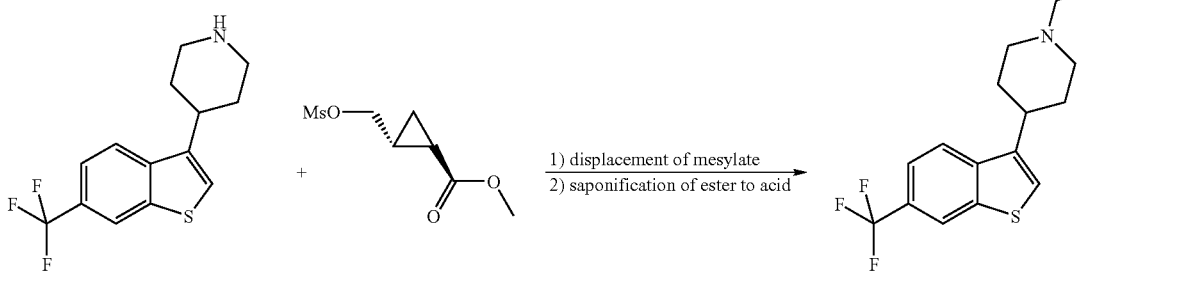

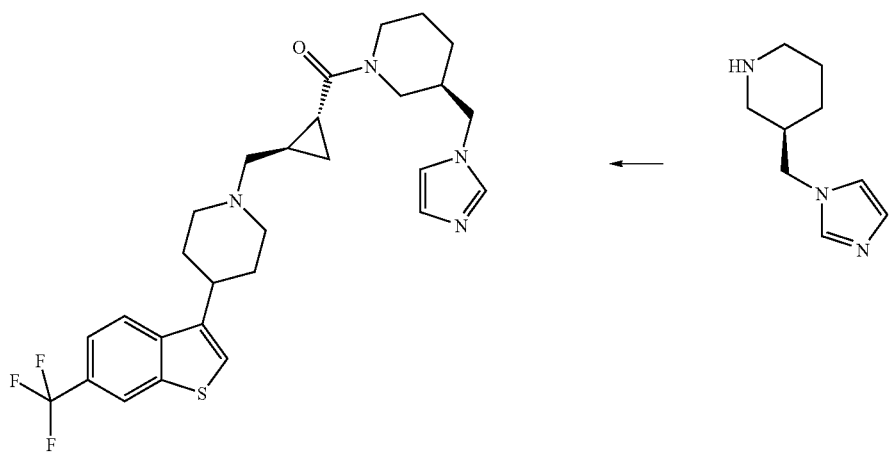

A002609935

(3S-Imidazol-1-ylmethyl-piperidin-1-yl)-{2R-[4-(6-trifluoromethyl-benzo[b]thiophen-3-yl)-piperidin-1-ylmethyl]-1R-cyclopropyl}-methanone (A002609935). The target was synthesized via the method analogous to the one described previously. 3R-Imidazol-1-ylmethyl-piperidine starting material was obtained via the method describe by Guzi, et.al. WO 0037458.

$CH_2Cl_2$ (50 mL) and washed with water (10 mL), 10% $HCl_{aq}$(10 mL), water (10 mL), saturated $NaHCO_3$ (10 mL), water (10 mL) and brine (10 mL) and dried ($MgSO_4$), filtered and evaporated. The residue was recrystallized from diethyl ether yielding 1.31 g (90%) as a white, crystalline solid, mp 117–188° C. Analysis calculated for $C_{17}H_{21}N_2FO_3$: 63.74% C, 6.61% H, 8.74% N. Found: 63.66% C, 6.64% H, 8.73% N.

Example 52

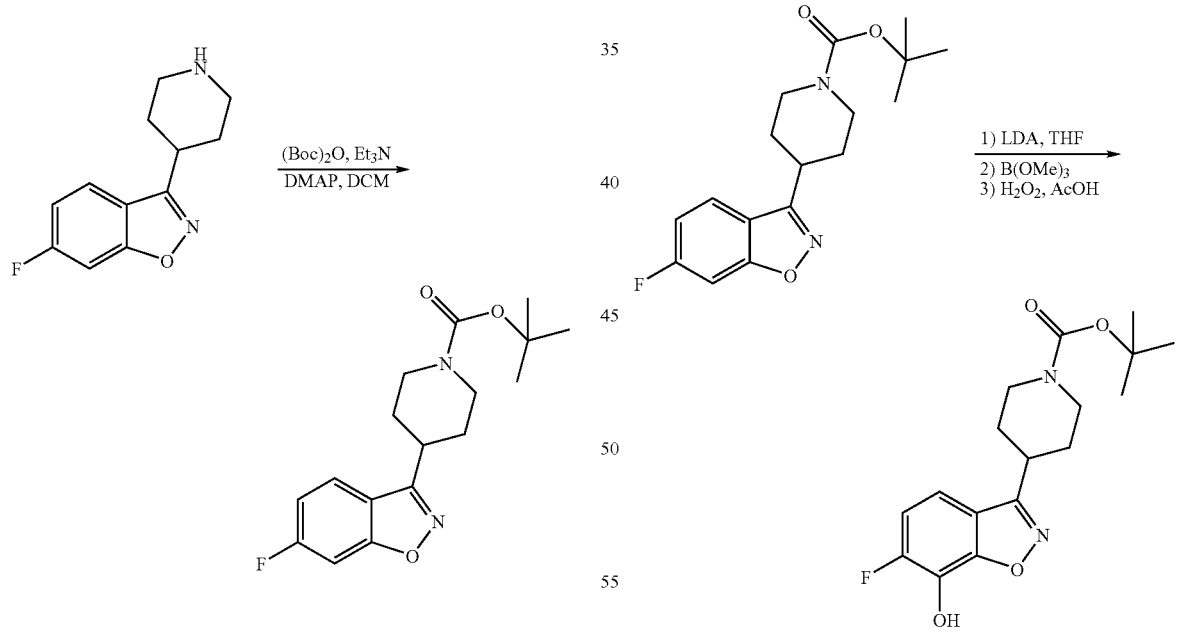

4-(6-Fluoro-benzo[d]isoxazol-3-yl)-piperidine-1-carboxylic acid tert-butyl ester (MDL 811778). To a stirred suspension of 4-(6-fluoro-benzo[d]isoxazol-3-yl)-piperidine (1.00 g, 454 mmol) in dry dichloromethane (10.0 mL) was added triethylamine (0.95 mL, 6.82 mmoles), 4-dimethylaminopyridine (55 mg, 0.454 mmoles) and di-tert-butyl dicarbonate (1.98 g, 9.09 mmoles). Gas spontaneously evolved for several minutes upon the addition of di-tert-butyl dicarbonate. The resulting solution was stirred at room temperature for 1 hour when the solution was diluted with 4-(6-Fluoro-7-hydroxy-benzo[d]isoxazol-3-yl)-piperidine-1-carboxylic acid tert-butyl ester (MDL 811820). To a stirred solution of 4-(6-fluoro-benzo[d]isoxazol-3-yl)-piperidine-1-carboxylic acid tert-butyl ester (1.00 g, 3.13 mmol) in dry tetrahydrofuran (31.3 mL) cooled to −78° C. was added lithium diisopropylamide (1.72 mL, 3.35 mmoles). The resulting solution was stirred at −78° C. for 2 hours when trimethylborate (0.44 mL, 3.84 mmoles) was added. The resulting solution was stirred at −78° C. for 1 hour then was allowed to warm to room temperature over 3 hours when hydrogen peroxide (2.00 mL) and acetic acid (1.00 mL) were added. The resulting mixture was stirred at room temperature overnight when the mixture was quenched with saturated $NH_4Cl_{aq}$ (20 mL) and 10% $HCl_{aq}$ (20 mL). The resulting mixture was extracted with $CH_2Cl_2$ (4×50 mL). The combined extracts were washed with brine (50 mL), dried ($MgSO_4$), filtered and evaporated. The residue was separated via column chromatography (1:1; $Et_2O$/Pet. ether) yielding 0.619 g (59%) of the phenol as a white, crystalline solid, mp 169–170° C. Analysis calculated for $C_{17}H_{21}N_2FO_4$; 60.70% C, 6.29% H, 8.33% N. Found: 60.72% C, 6.15% H, 8.22% N.

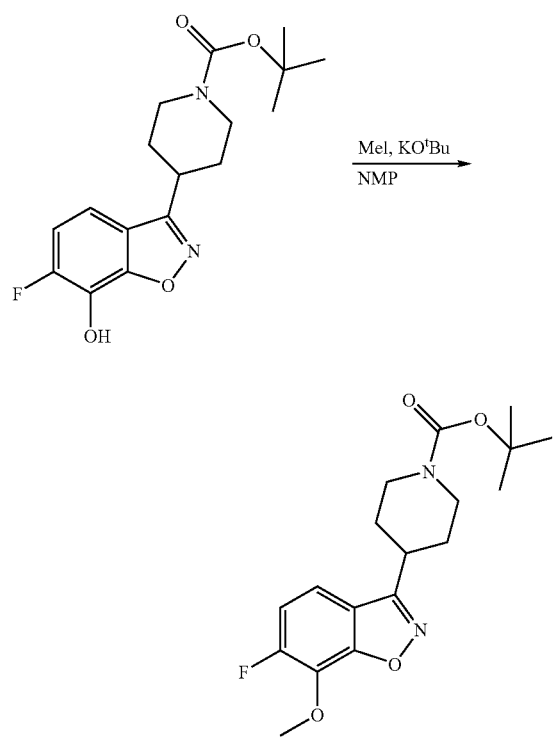

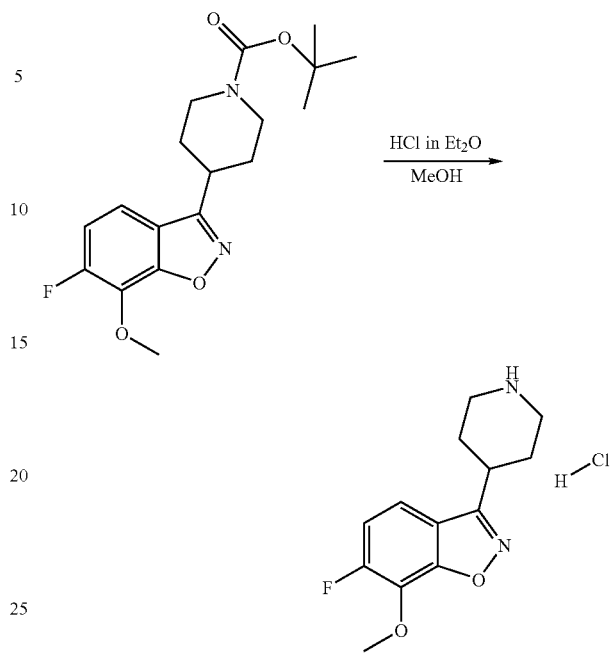

4-(6-Fluoro-7-methoxy-benzo[d]isoxazol-3-yl)-piperidine-1-carboxylic acid tert-butyl ester (MDL 811841). To a stirred solution of 4-(6-fluoro-7-hydroxy-benzo[d]isoxazol-3-yl)-piperidine-1-carboxylic acid tert-butyl ester (1.28 g, 3.80 mmol) in N-methyl-2-pyrrolidone (33 mL) was added potassium tertbutoxide (2.09 g, 17.12 mmoles). To the resulting deep red solution was added iodomethane (1.20 mL, 19.02 mmoles). The resulting yellow solution was stirred at room temperature for 6 hours when the reaction was quenched with water (55 mL) and acidified with $HCl_{aq}$. The resulting mixture was extracted with $Et_2O$ (4×110 mL). The combined extracts were washed with brine (110 mL), dried ($MgSO_4$), filtered and evaporated. The residue was separated via column chromatography (1:1; $Et_2O$/Pet. ether) yielding 1.2 g of the methyl ether. The white, solid product was further purified via recrystallization from 1:1; $Et_2O$/Pet. ether yielding 963 mg (72%) as a white, crystalline solid, mp 94–96° C. Analysis calculated for $C_{18}H_{23}N_2FO_4$: 61.70% C, 6.62% H, 7.99% N. Found: 61.75% C, 6.73% H, 7.94% N.

6-Fluoro-7-methoxy-3-piperidin-4-yl-benzo[d]isoxazole hydrochloride (MDL 811998). To a stirred solution of 4-(6-fluoro-7-methoxy-benzo[doisoxazol-3-yl)-piperidine-1-carboxylic acid tert-butyl ester (4.00 g, 11.43 mmol) in dry hydrochloric acid in diethyl ether (100 mL) was added methanol (7.62 mL). The resulting solution was stirred at room temperature for 5 hours when a white solid precipitate formed. The resulting.suspension was filtered and the white solid was wash thoroughly with ether yielding 1.76 g of the desired product as a white solid. The mother liquor precipitated yielding an additional 0.94 g of product providing a total of 2.70 g (83%) of the desired product as a pure, white solid, mp 246–248° C.

Example 53

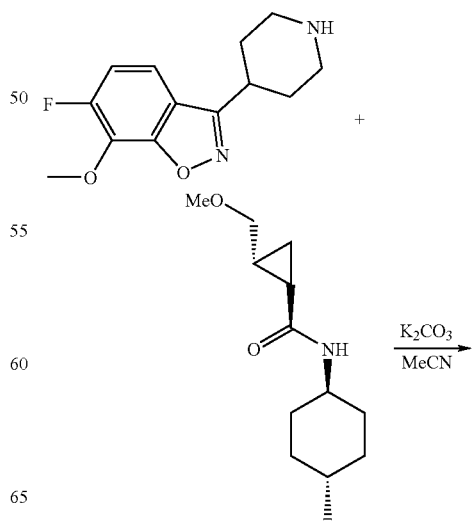

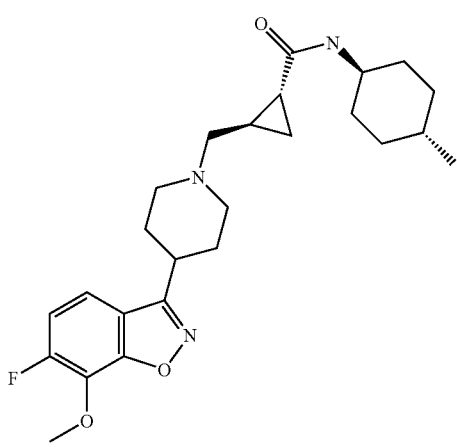

MDL 831361

2R-[4-(6-Fluoro-7-methoxy-benzo[d]isoxazol-3-yl)-piperidin-1-ylmethyl]-1R-cyclopranecarboxylic acid (trans-4-methyl-cyclohexyl)-amide (MDL 831361). The target was synthesized via the method analogous to the one described above.

Example 54

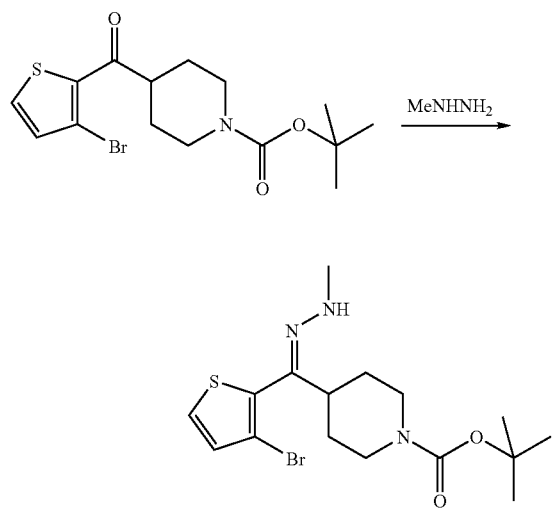

4-[(3-Bromo-thiophen-2-yl)-(methyl-hydrazono)-methyl]-piperidine-1-carboxylic acid tert-butyl ester. A mixture of 4-(thiophene-2-carbonyl)-piperidine-1-carboxylic acid tert-butyl ester (1.96 g, 5.2 mmol) in methylhydrazine (2 mL) was heated at 75° C. overnight. The excess methyl hydrazine was then removed with a vacuum pump. The residue was purified by chromatography (eluted with 0–8% of MeOH in DCM) yielding 0.95 g (45%) of the desired product.

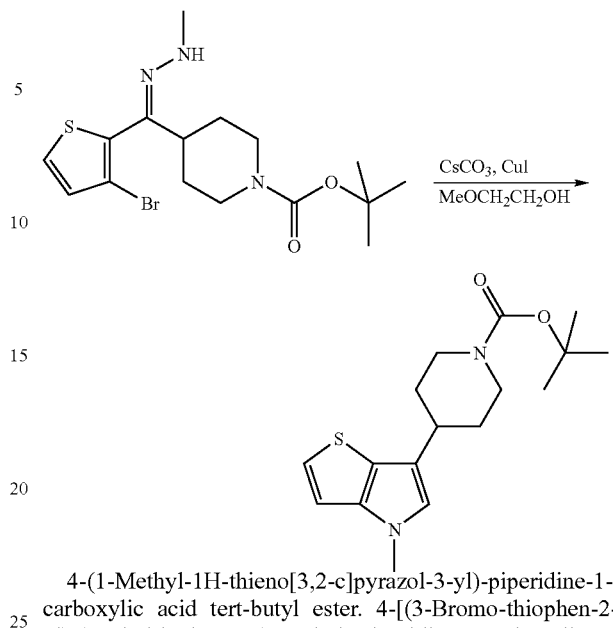

4-(1-Methyl-1H-thieno[3,2-c]pyrazol-3-yl)-piperidine-1-carboxylic acid tert-butyl ester. 4-[(3-Bromo-thiophen-2-yl)-(methyl-hydrazono)-methyl]-piperidine-1-carboxylic acid tert-butyl ester (700 mg, 1.74 mmol) was mixed with CuI (20 mg), CsCO₃ (650 mg, 1.15 eq) in methoxyethanol (10 mL). The mixture was heated to 70° C. for 2 hr. then stirred overnight at room temperature. The solvent was stripped on rotary evaporator. The residue was extracted into EtOAc then washed with brine and concentrated down to an oil. This oil was purified via chromatography (eluted with 0–10% MeOH in DCM) yielding 520 mg (68%) of the desired product.

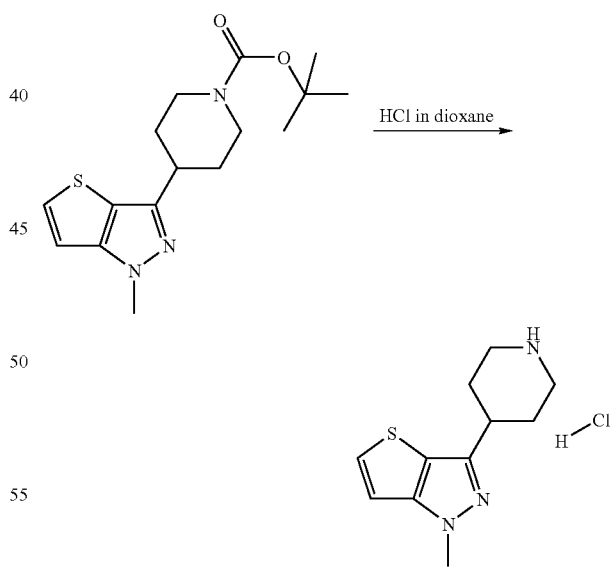

1-Methyl-3-piperidin-4-yl-1H-thieno[3,2-c]pyrazole hydrochloride (A002436287A). 4-(1-Methyl-1H-thieno[3,2-c]pyrazol-3-yl)-piperidine-1-carboxylic acid tert-butyl ester (520 mg, 1.6 mmol) was stirred at room temperature in a solution of HCl (5 mL, 4N HCl in dioxane) for 4 hours. The volatiles were removed in. vacuo and the residue was triturated with ether (twice) to yield off white solids 304 mg (74%) as the desired hydrochloride salt.

Example 55

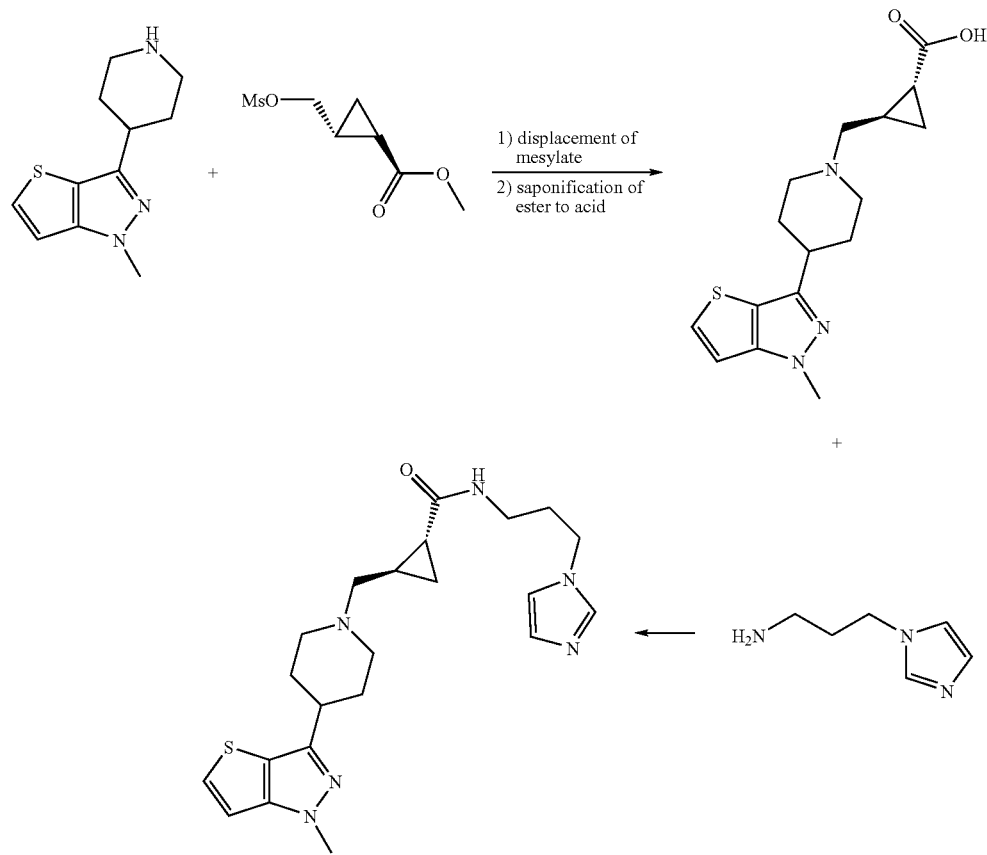

A002436291

2R-[4-(1-Methyl-1H-thieno[3,2-c]pyrazol-3-yl)-piperidin-1-ylmethyl]-1R-cyclopropanecarboxylic acid (3-imidazol-1-yl-propyl)-amide (A002436291). The target was synthesized via the method analogous to the one described previously.

Example 56

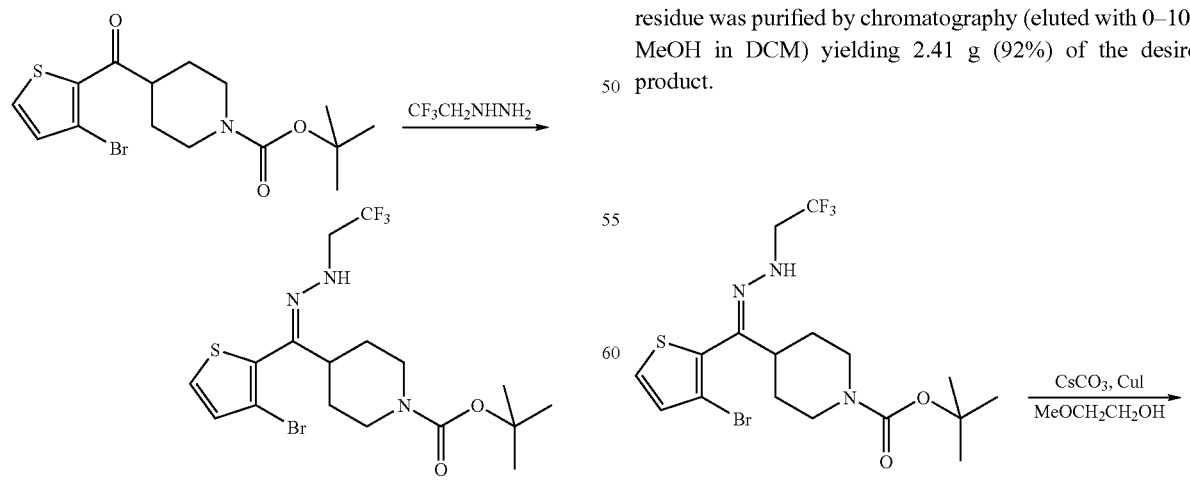

4-{(3-Bromo-thiophen-2-yl)-[(2,2,2-trifluoro-ethyl)-hydrazono]-methyl}-piperidine-1-carboxylic acid tert-butyl ester. To a mixture of 4-(thiophene-2-carbonyl)-piperidine-1-carboxylic acid tert-butyl ester (2.34 g, 6.24 mmol) in n-butanol (20 mL) was added trifluoroethylhydrazine (2.43 g, 12.4 mmol). The resulting mixture was heated at 110° C. overnight. The volatiles were then removed in vacuo. The residue was purified by chromatography (eluted with 0–10% MeOH in DCM) yielding 2.41 g (92%) of the desired product.

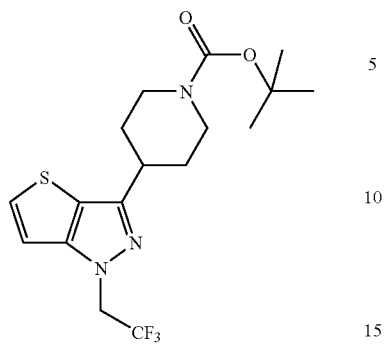

4-[1-(2,2,2-Trifluoro-ethyl)-1H-thieno[3,2-c]pyrazol-3-yl]-piperidine-1-carboxylic acid tert-butyl ester. 4-{(3-Bromo-thiophen-2-yl)-[(2,2,2-trifluoro-ethyl)-hydrazono]-methyl}-piperidine-1-carboxylic acid tert-butyl ester (2.34 g, 4.98 mmol) was mixed with CuI (50 mg), CsCO₃ (1.9 g, 1.2 eq) in methoxyethanol (25 mL). The mixture was heated to 75° C. for 1 hour. The mixture was then diluted with EtOAc and filtered. The filtrate was evaporated and the residue was purified via chromatography (eluted with 0–10% MeOH in DCM) yielding 2.03 g (>95%) of the desired product.

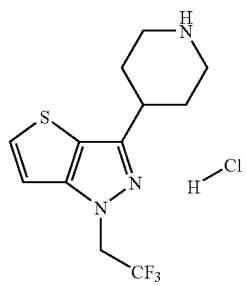

3-Piperidin-4-yl-1-(2,2,2-trifluoro-ethyl)-1H-thieno[3,2-c]pyrazole hydrochloride (833906). 4-[1-(2,2,2-Trifluoro-ethyl)-1H-thieno[3,2-c]pyrazol-3-yl]-piperidine-1-carboxylic acid tert-butyl ester (1.9 g, 4.87 mmol) was stirred at room temperature in a solution of HCl (6 mL, 4N HCl in dioxane) for 4 hours. The volatiles were removed in vacuo and the residue was triturated with ether (twice) to yield off white solids 2.1 g (74%) as the desired hydrochloride salt.

Example 57

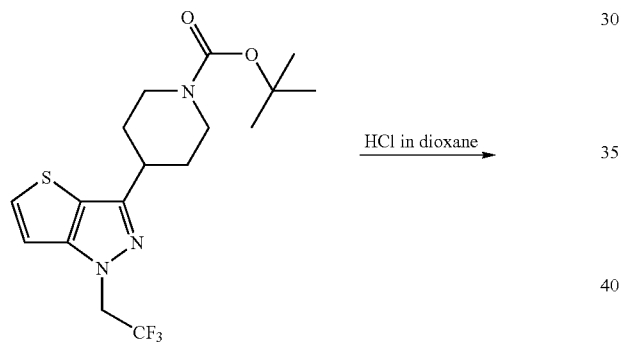

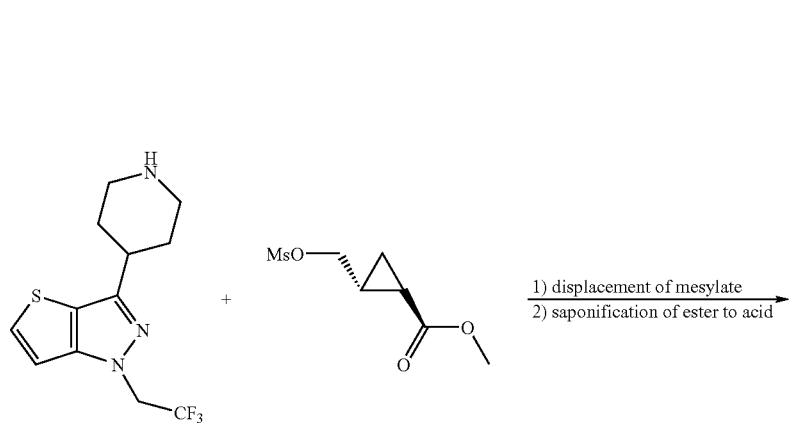

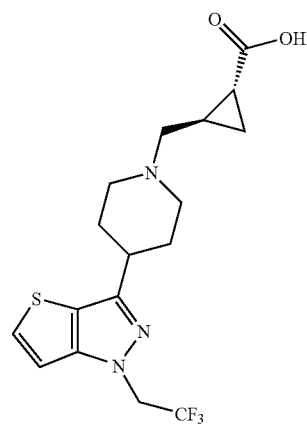

+

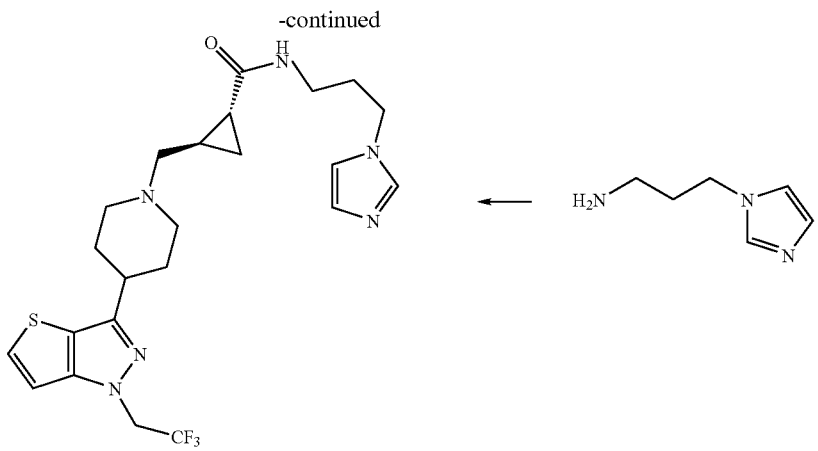

A002287767

2R-{4-[1-(2,2,20Trifluoro-ethyl)-1H-thieno(3,2-c]pyrazol-3-yl)-piperidin-1-ylmethyl]-1R-cycloproanecarboxylic acid (3-imidazol-1-yl-propyl)-amide (A002287767). The target was synthesized via the method analogous to the one described previously.

Example 58

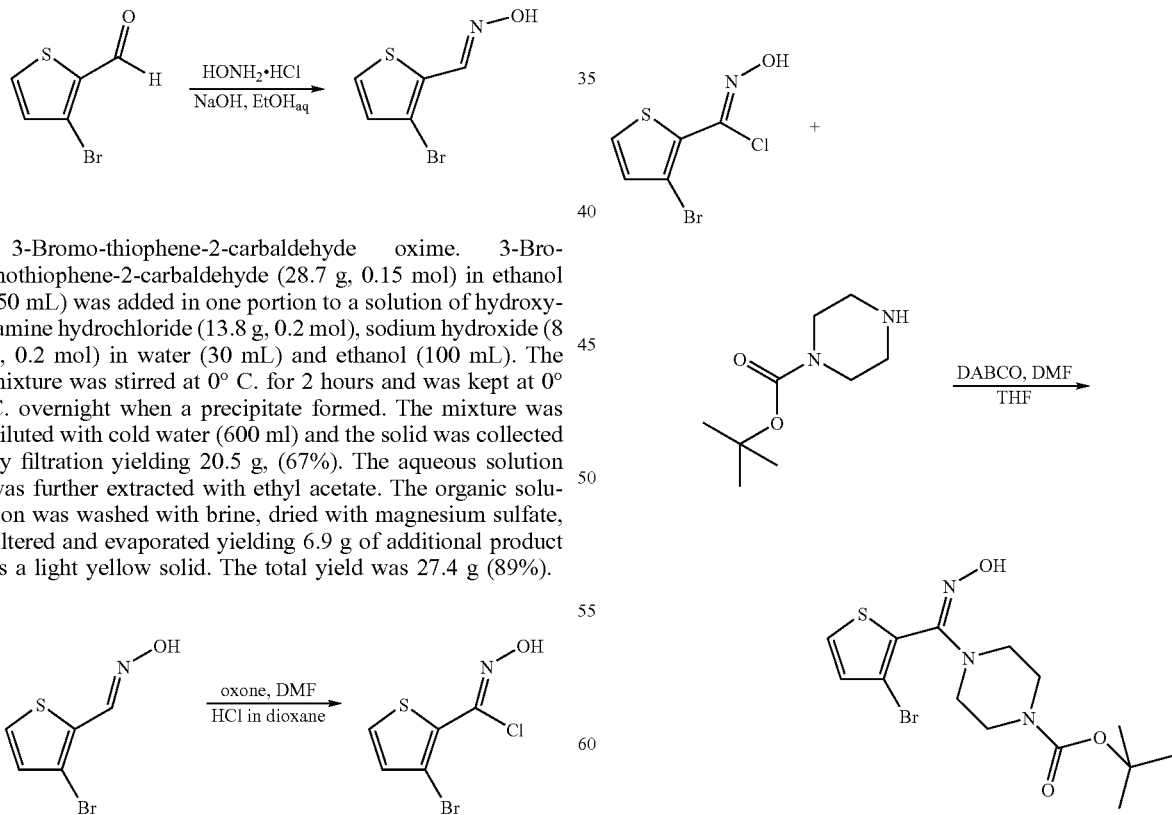

3-Bromo-thiophene-2-carbaldehyde oxime. 3-Bromothiophene-2-carbaldehyde (28.7 g, 0.15 mol) in ethanol (50 mL) was added in one portion to a solution of hydroxylamine hydrochloride (13.8 g, 0.2 mol), sodium hydroxide (8 g, 0.2 mol) in water (30 mL) and ethanol (100 mL). The mixture was stirred at 0° C. for 2 hours and was kept at 0° C. overnight when a precipitate formed. The mixture was diluted with cold water (600 ml) and the solid was collected by filtration yielding 20.5 g, (67%). The aqueous solution was further extracted with ethyl acetate. The organic solution was washed with brine, dried with magnesium sulfate, filtered and evaporated yielding 6.9 g of additional product as a light yellow solid. The total yield was 27.4 g (89%).

3-Bromo-thiophene-2-(chloro-carbaldehyde) oxime. To the solution of 3-bromo-thiophene-2-carbaldehyde oxime (10.8 g, 52.4 mmol), hydrogen chloride (14.5 mL, 4M in dioxane) in DMF (100 mL) was charged with oxone (16.9 g, 1.05 eqiv) in one portion at room temperature. The mixture was stirred at room temp overnight when the solution was poured in to water and extracted with ethyl acetate. The organic solution was washed with brine and dried over magnesium sulfate, filtered and evaporated to dryness to give a yellow solid (12.68 g, quantitative by weight) which was used in the next reaction without further purification.

4-[(3-Bromo-thiophen-2-yl)-hydroxyimino-methyl]-piperazine)-1-carboxylic acid tert-butyl ester. A solution of 3-bromo-thiophene-2-(chloro-carbaldehyde) oxime (16.4 g, 68 mmol) in THF (70 mL) was added drop-wise to a solution of N-(t-butoxycarbonyl)piperazine (14 g, 1.1 equiv.), DABCO (9.5 g, 1.25 eqiv.) in DMF (100 mL) at 0° C. over 25 minutes. The mixture was stirred at 0° C. for 3.5 hours when the mixture was poured into water and was extracted with ethyl acetate. The organic layer was washed with brine and dried over magnesium sulfate, filtered and evaporated. The crude product (30.5 g) was purified via chromatography (eluted with 0–5% of MeOH in DCM) yielding 24.6 g (85%) of the desired product.

(200 mL) was stirred at room temperature overnight. The reaction mixture was diluted with ethyl acetate and washed with water. The aqueous solution was extracted three times with ethyl acetate. The combined organic layers (total 600 ml) were washed with brine, dried over magnesium sulfate, filtered and evaporated. The residue was purified via chromatography (120 gm of silica gel, eluted with 0–8% Methanol in dichloromethane) yielding 5.1 g (62%) of the desired product as light oil.

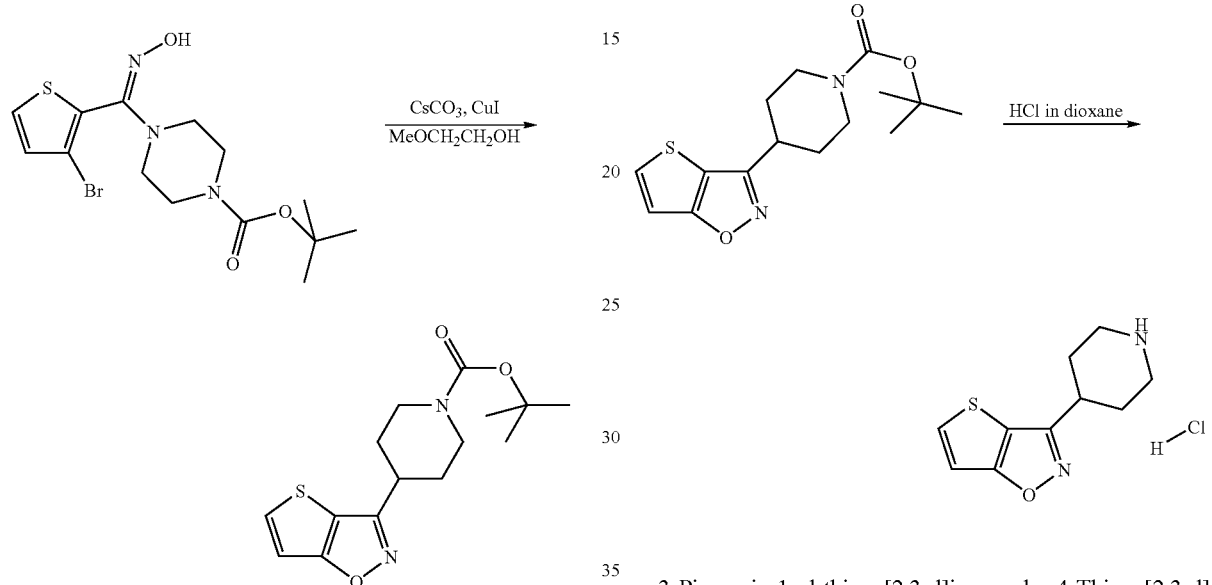

4-Thieno[2,3-d]isoxazol-3-yl-piperazine-1-carboxylic acid tert-butyl ester. A mixture of 4-[(3-bromo-thiophen-2-yl)-hydroxyimino-methyl]-piperazine)-1-carboxylic acid tert-butyl ester (10.3 g, 26.4 mmol), cesium carbonate (10.7 g, 32.7 mmol), copper iodide (500 mg) in methoxyethanol 3-Piperazin-1-yl-thieno[2,3-d]isoxazole. 4-Thieno[2,3-d]isoxazol-3-yl-piperazine-1-carboxylic acid tert-butyl ester (5.0 g, 16.2 mmol) was stirred at room temperature in a solution of HCl (25 mL, 4N HCl in dioxane) for 4 hours. The volatiles were removed in vacuo and the residue was triturated with ether (twice) to yield off white solids 3.3 g (84%) as the desired hydrochloride salt.

Example 59

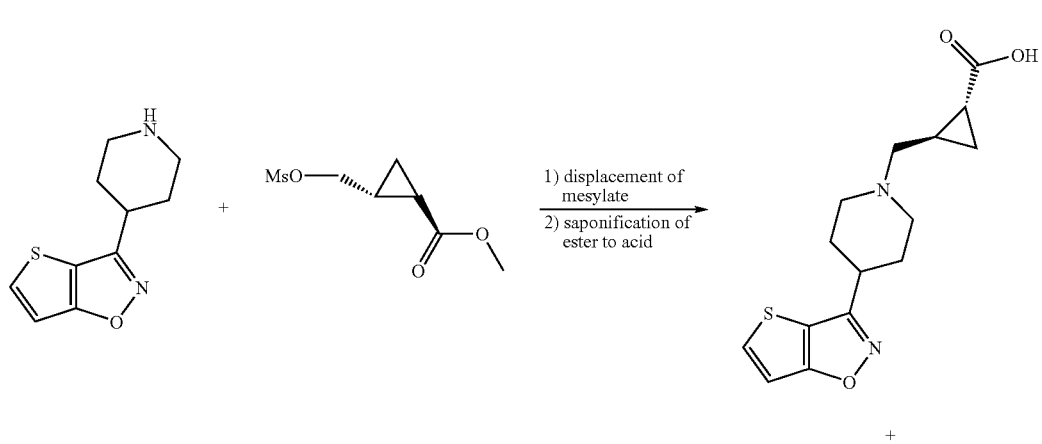

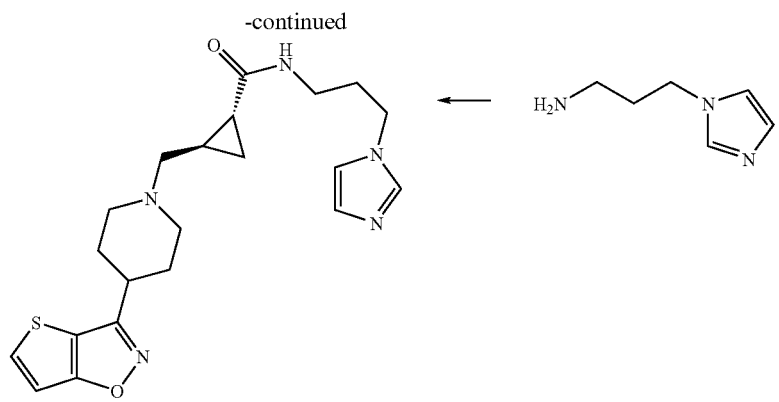

2R-(4-Thieno[2,3-d]isoxazol-3-yl-piperazin-1-ylmethyl)-1R-cyclopropanecarboxylic acid (3-imidazol-1-yl-propyl)-amide (MDL 831493). The target was synthesized via the method analogous to the one described previously.

Example 60

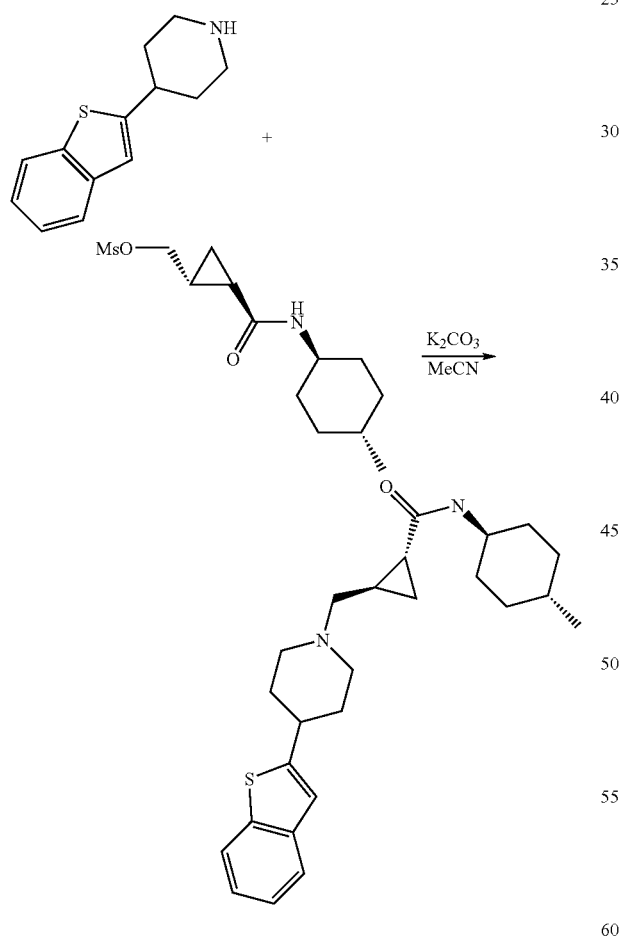

MDL 831148

2R-(4-Benzo[b]thiophen-2-yl-piperidin-1-ylmethyl)-1R-cyclopranecarboxylic acid (trans-4-methyl-cyclohexyl)-amide (MDL 831148). The target was synthesized via the method analogous to the one described above. 4-Benzo[b]thiophen-2-yl-piperidine was obtained via the method described by Bernasconi, DE 2456246.

Example 61

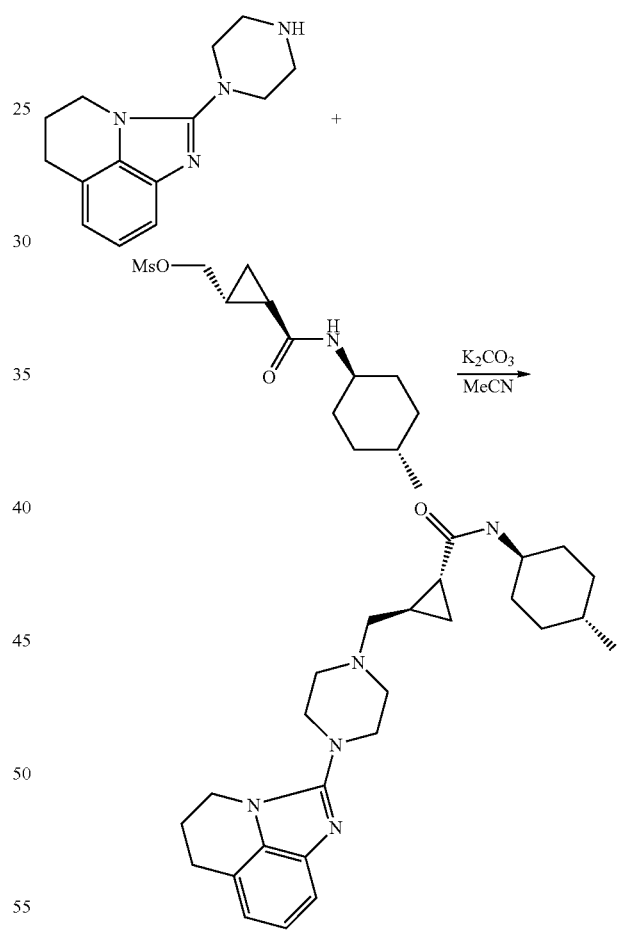

MDL 833699

2R-[4-(5,6-Dihydro-4H-imidazo[4,5,1-ij]quinolin-2-yl)-piperazin-1-ylmethyl]-1R-cyclopranecarboxylic acid (trans-4-methyl-cyclohexyl)-amide (MDL 833699). The target was synthesized via the method analogous to the one described above. 2-Piperazin-1-yl-5,6-dihydro-4H-imidazo[4,5,1-ij]quinoline was obtained via the method described by Glamkowski and Freed, EP 95-113849.

Example 62

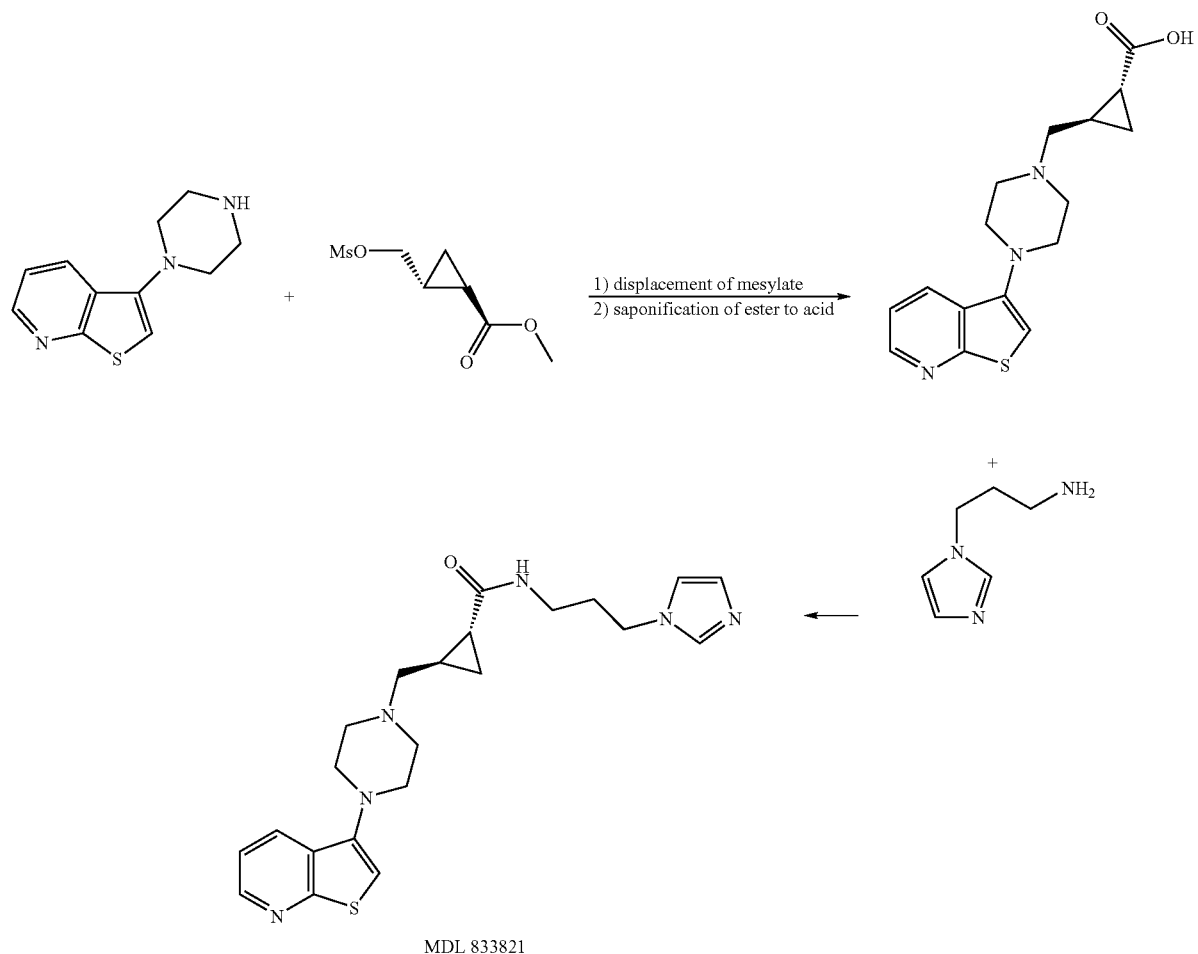

MDL 833821

2R-(4-Thieno[2,3-b]pyridin-3-yl-piperazin-1-ylmethyl)-1R-cyclopropanecarboxylic acid (3-imidazol-1-yl-propyl)-amide (MDL 833821). The target was synthesized via the method analogous to the one described above. 3-Piperazin-1-yl-thieno[2,3-b]pyridine was obtained via the method described by Hrib and Jurcak, U.S. Pat. No. 92–942,232.

Example 63

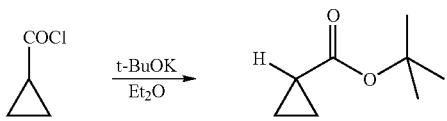

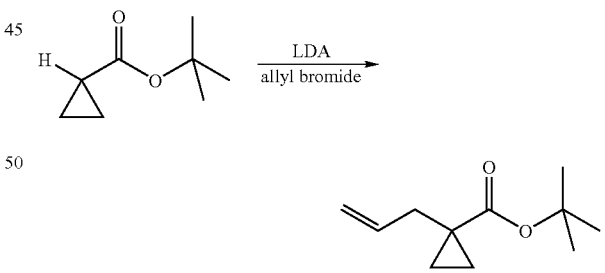

Cyclopropanecarboxylic acid tert-butyl ester. To a stirred suspension of 12.0 g (107.1 mmol) of potassium t-butoxide in 200 mL ether at 0° C. under nitrogen was added 13.4 g (128.6 mmol) of cyclopropanecarboxylic acid chloride over 5 min. After 30 min at 0° C. the mixture was stirred at ambient temperature for an additional 30 min. The reaction mixture was poured into aqueous saturated sodium bicarbonate and extracted with ether. The organic layer was dried and carefully concentrated to deliver 15.0 g (99%) of a yellow oil as the desired ester product.

1-Allyl-cyclopropanecarboxylic acid tert-butyl ester. Lithium diisopropyl amide was generated from 7.5 g (58.1 mmol) diisopropyl amine and 23.2 mL of 2.5 M n-butyl lithium in 200 mL THF at 0° C. under nitrogen. After stirring for 30 minutes at 0° C. the solution was taken to −78° C. where 7.5 g (52.8 mmol) of cyclopropanecarboxylic acid tert-butyl ester in 30 mL of THF was added dropwise over 5 min. After 4 h 12.8 g (106 mmol) of allyl bromide in 30 mL THF was added drop-wise over 10 min. to the clear golden solution. The reaction was allowed to slowly warm to room temperature. After 19 hours the reaction was poured into aqueous saturated ammonium chloride solution, extracted with ether, dried and concentrated to deliver an oil which was purified via Kugelrohr distillation (approx. 20 mm Hg; 60–75° C. oven) to deliver 5.4 g (56%) of the desired product as a clear colorless oil.

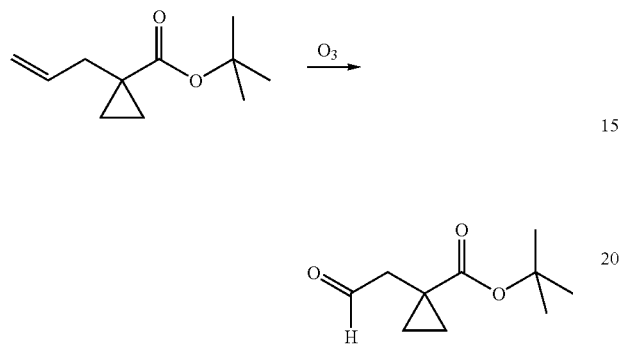

1-(2-Oxo-ethyl)-cyclopropanecarboxylic acid tert-butyl ester. A solution of 5.7 g (31.3 mmol) of 1-allyl-cyclopropanecarboxylic acid tert-butyl ester in 50 mL methanol and 50 mL dichloromethane under nitrogen was taken to −78° C. where ozone was bubbled in for 1 hour. Nitrogen was bubbled in until the familiar blue color dissipated. Three drops of pyridine followed by 2 mL of dimethyl sulfide were added and the cooling bath removed. After 2 hours the reaction was poured into aqueous saturated ammonium chloride solution, extracted with dichloromethane, dried and concentrated to deliver a quantitative yield of the desired aldehyde as an oil.

Example 64

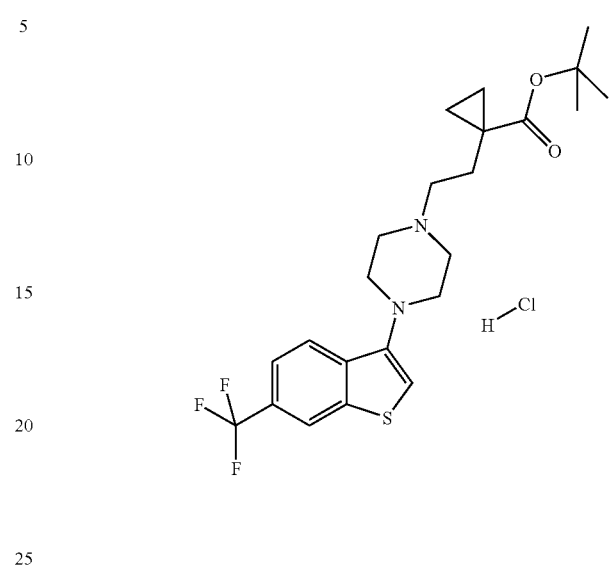

1-{2-[4-(6-Trifluoromethyl-benzo[b]thiophen-3-yl)-piperazin-1-yl]-ethyl}-cyclopropanecarboxylic acid tert-butyl ester. To a solution of 4.2 g (14.7 mmol) of 1-(6-trifluoromethyl-benzo[b]thiophen-3-yl)-piperazine in 100 mL of dichloromethane under nitrogen was added 3.5 g (19.1 mmol) of 1-(2-Oxo-ethyl)-cyclopropanecarboxylic acid tert-butyl ester. After stirring 10 minutes at room temperature 6.5 g (30.7 mmol) of sodium triacetoxyborohydride was added portion-wise. After 30 minutes 100 mL of 0.5 N aqueous sodium hydroxide was added and the reaction was stirred for 15 minutes. The organic layer was separated, dried and concentrated to deliver a paste. This was taken up in methanolic hydrogen chloride. The salt thus obtained was recrystallized from ethyl acetate/methanol to deliver 6.6 g (13.4 mmol) of the desired product as a white powder mp=187–9° C.

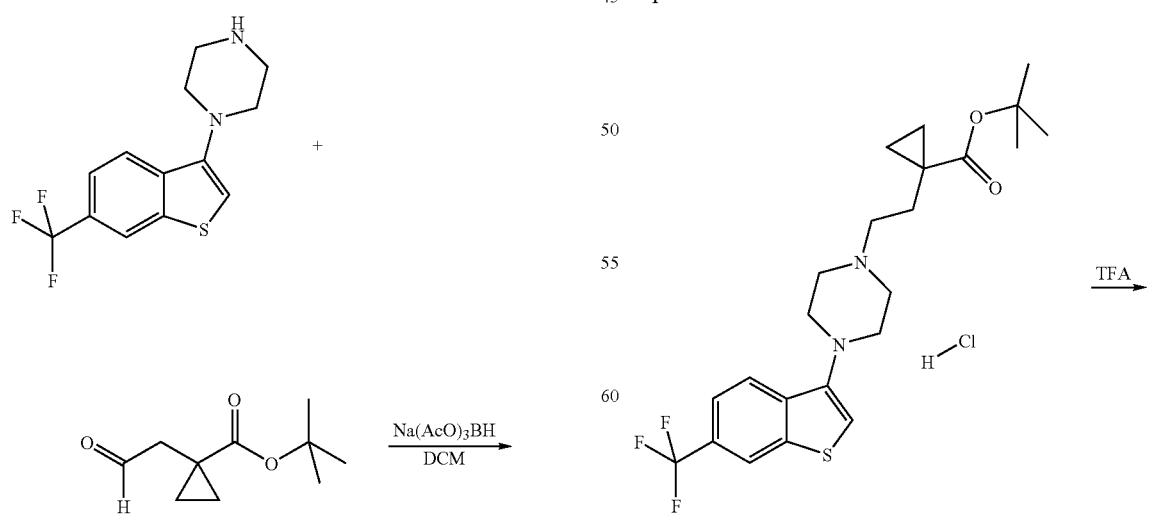

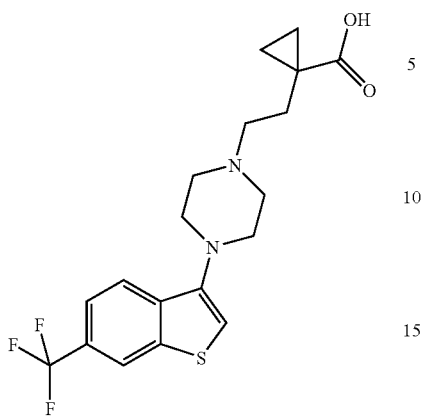

1-{2-[4-(6-Trifluoromethyl-benzo[b]thiophen-3-yl)-piperazin-1-yl]-ethyl}-cyclopropanecarboxylic acid. 1-{2-[4-(6-Trifluoromethyl-benzo[b]thiophen-3-yl)-piperazin-1-yl]-ethyl}-cyclopropanecarboxylic acid tert-butyl ester, 0.7 g (1.54 mmol), was stirred in 10 mL of trifluoroacetic acid. After 2 hours the reaction mixture was concentrated to an oil. This was taken up in methanolic hydrogen chloride. The salt thus obtained was recrystallized from ethyl acetate/methanol to deliver 0.4 g (60%) of white powder as the desired carboxylic acid mp=255–7° C.

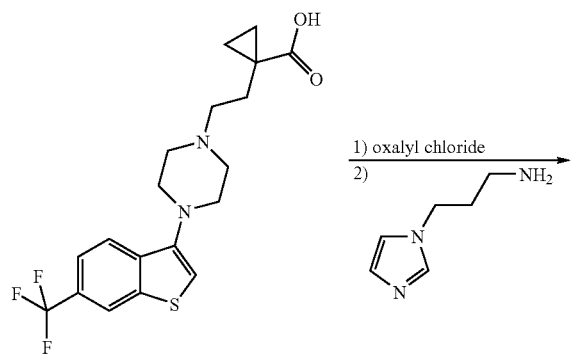

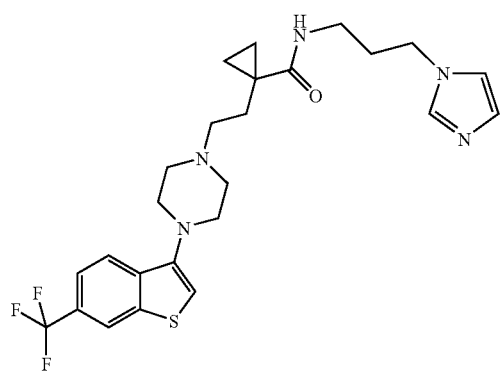

1-{2-[4-(6-Trifluoromethyl-benzo[b]thiophen-3-yl)-piperazin-1-yl]-ethyl}-cyclopropanecarboxylic acid (3-imidazol-1-yl-propyl)-amide (MDL 832231). A suspension of 0.17 g (0.39 mmol) of 1-{2-[4-(6-trifluoromethyl-benzo[b]thiophen-3-yl)-piperazin-1-yl]-ethyl}-cyclopropanecarboxylic acid in 10 mL dichloromethane under nitrogen was treated with 1 mL of oxalyl chloride followed by 3 drops of DMF. After 2 hours the reaction was concentrated to a slurry, diluted with 10 mL DMF and treated with 0.10 g (0.78 mmol) of 1-(3-aminopropyl)imidazole followed by 0.12 g (1.2 mmol) of triethylamine. After 12 hours the reaction was poured into aqueous saturated sodium bicarbonate and extracted with ethyl acetate. The organic layer was separated, dried and concentrated to deliver an oil. Chromatographic purification gave 0.075 g (38%) of the desired final product as an oil.

TABLE 2

| No. | R | n | [B-C(=O)]- | R1 | A | R2 | R3 | d3K$_i$ |
|---|---|---|---|---|---|---|---|---|
| 827055 (racemic) | 3-methyl-6-CF$_3$-benzothiophene | 2 | O=C-(CH$_2$)$_3$- | H | N | trans-4-methylcyclohexyl | CH$_2$Ph | 792 |
| 827071 (racemic) | 3-methyl-6-CF$_3$-benzothiophene | 2 | O=C-(CH$_2$)$_3$- | H | N | trans-4-(CO$_2$CH$_2$CH$_3$)cyclohexyl | (CH$_2$)$_2$Ph | 454 |
| 827074 (racemic) | 3-methyl-6-CF$_3$-benzothiophene | 2 | O=C-(CH$_2$)$_3$- | CH$_3$ | N | cyclohexyl | (CH$_2$)$_2$Ph | 267 |
| 827079 (racemic) | 3-methyl-6-CF$_3$-benzothiophene | 2 | O=C-(CH$_2$)$_3$- | CH$_3$ | N | cyclohexyl | (CH$_2$)$_3$Ph | 126 |
| 827085 (racemic) | 3-methyl-6-F-benzothiophene | 2 | O=C-(CH$_2$)$_3$- | H | N | trans-4-methylcyclohexyl | CH$_2$Ph | 126 |

TABLE 2-continued

| No. | R | n | B | R₁ | A | R₂ | R₃ | d3K₁ |
|---|---|---|---|---|---|---|---|---|
| 827086 (racemic) | 6-fluorobenzothiophen-3-yl | 2 | (CH₂)₃ with C=O | H | N | trans-4-(ethoxycarbonyl)cyclohexyl | CH₂Ph | 334 |
| 827087 (racemic) | 6-fluorobenzothiophen-3-yl | 2 | (CH₂)₃ with C=O | H | N | trans-4-ethylcyclohexyl | CH₂Ph | 178 |
| 827088 (racemic) | 6-fluorobenzothiophen-3-yl | 2 | (CH₂)₃ with C=O | H | N | 3-methylcyclohexyl | CH₂Ph | 284 |
| 827089 (racemic) | 6-fluorobenzothiophen-3-yl | 2 | (CH₂)₃ with C=O | CH₃ | N | cyclohexyl | CH₂Ph | 307 |
| 827090 (racemic) | 6-fluorobenzothiophen-3-yl | 2 | (CH₂)₃ with C=O | CH₃CH₂ | N | cyclohexyl | CH₂Ph | 346 |

TABLE 2-continued

| No. | R | n | B | $R_1$ | A | $R_2$ | $R_3$ | d3$K_i$ |
|---|---|---|---|---|---|---|---|---|
| 827101 (racemic) | 6-F-3-Me-benzothiophene | 2 | $-C(=O)-(CH_2)_3-C(CH_3)_2-$ | H | N | cyclopentyl | $CH_2Ph$ | 148 |
| 827102 (racemic) | 6-F-3-Me-benzothiophene | 2 | $-C(=O)-(CH_2)_3-C(CH_3)_2-$ | H | N | cyclohexyl | $CH_2Ph$ | 218 |
| 827105 (racemic) | 6-F-3-Me-benzothiophene | 2 | $-C(=O)-(CH_2)_3-C(CH_3)_2-$ | H | N | trans-4-methylcyclohexyl | $(CH_2)_3Ph$ | 117 |
| 827106 (racemic) | 6-F-3-Me-benzothiophene | 2 | $-C(=O)-(CH_2)_3-C(CH_3)_2-$ | H | N | trans-4-(ethoxycarbonyl)cyclohexyl | $(CH_2)_3Ph$ | 317 |
| 827107 (racemic) | 6-F-3-Me-benzothiophene | 2 | $-C(=O)-(CH_2)_3-C(CH_3)_2-$ | H | N | trans-4-ethylcyclohexyl | $(CH_2)_3Ph$ | 489 |

TABLE 2-continued

| No. | R | n | [B-C]₃ | R₁ | A | R₂ | R₃ | d3K₁ |
|---|---|---|---|---|---|---|---|---|
| 827108 (racemic) | 6-F-3-methylbenzothiophene | 2 | (CH₂)₃C(O) | H | N | 3-methylcyclohexyl | (CH₂)₃Ph | 302 |
| 827109 (racemic) | 6-F-3-methylbenzothiophene | 2 | (CH₂)₃C(O) | CH₃ | N | cyclohexyl | (CH₂)₃Ph | 78.6 |
| 827110 (racemic) | 6-F-3-methylbenzothiophene | 2 | (CH₂)₃C(O) | CH₃CH₂ | N | cyclohexyl | (CH₂)₃Ph | 208 |
| 827111 (racemic) | 6-F-3-methylbenzothiophene | 2 | (CH₂)₃C(O) | HO(CH₂)₂ | N | cyclohexyl | (CH₂)₃Ph | 143 |
| 817047 (racemic) | 6-CF₃-3-methylbenzothiophene | 2 | trans-2-methylcyclopropyl-C(O) | H | N | 4-methylcyclohexyl-C(O)-pyrrolidine | H | 2.86 |

TABLE 2-continued

| No. | R | n | | $R_1$ | | A | $R_2$ | $R_3$ | $d3K_i$ |
|---|---|---|---|---|---|---|---|---|---|
| 817048 (racemic) | 3-methyl-6-CF3-benzothiophene | 2 | acetyl-cyclopropyl-CH2- | H | | N | 4-methylcyclohexyl-C(O)N(CH2CH3)2 | H | 2.85 |
| 817049 (racemic) | 3-methyl-6-CF3-benzothiophene | 2 | acetyl-cyclopropyl-CH2- | H | | N | 4-methylcyclohexyl-C(O)NH-CH2CH2-OCH3 | H | 7.02 |
| 817050 (−)-R,R | 3-methyl-6-CF3-benzothiophene | 2 | acetyl-cyclopropyl-CH2- | H | | N | 4-methyl-1-hydroxy-1-methylcyclohexyl | H | 2.15 |
| 817051 (−)-R,R | 3-methyl-6-CF3-benzothiophene | 2 | acetyl-cyclopropyl-CH2- | H | | N | 4-methyl-1-hydroxy-1-methylcyclohexyl | H | 3.47 |

TABLE 2-continued

| No. | R | n | B | $R_1$ | A | $R_2$ | $R_3$ | d3$K_i$ |
|---|---|---|---|---|---|---|---|---|
| 817244 (racemic) | 3-methyl-6-CF$_3$-benzothiophene | 2 | cyclopropyl(CH,CH$_2$) | HO(CH$_2$)$_2$ | N | 4-methylcyclohexyl (CH$_3$ axial) | H | |
| 817569A (−)-R,R | 3-methyl-6-CF$_3$-benzothiophene | 2 | cyclopropyl(CH,CH$_2$) | H | N | 4-methylcyclohexyl (CH$_3$ axial) | H | 5.38 |
| 818499 (racemic) | 3-methyl-6-CF$_3$-benzothiophene | 2 | cyclopropyl(CH,CH$_2$) | H | N | 4-methylcyclohexyl-CH$_2$CH$_3$ | H | 22.1 |
| 818497 (racemic) | 3-methyl-6-CF$_3$-benzothiophene | 2 | cyclopropyl(CH,CH$_2$) | H | N | 1-(CH$_2$CH$_3$)-4-methyl-cyclohexan-1-ol | H | 5.52 |
| 818673 (Isomer 1) | 3-methyl-6-CF$_3$-benzothiophene | 2 | cyclopropyl(CH,CH$_2$) | CH$_2$Ph | N | 1-(CH$_2$CH$_3$)-4-methyl-cyclohexan-1-ol | H | |

TABLE 2-continued

| No. | R | n | [B—C] | R₁ | A | R₂ | R₃ | d3K₁ |
|---|---|---|---|---|---|---|---|---|
| 818674 (Isomer 2) | 3-methyl-6-CF₃-benzothiophene | 2 | cyclopropyl with CH₂OCH₃ | CH₂Ph | N | 4-methyl-1-hydroxymethyl-cyclohexyl (OH, CH₃) | H | |
| 827196 (racemic) | 4-F-phenyl | 2 | cyclopropyl with CH₂OCH₃ | H | N | trans-4-methylcyclohexyl | H | 2.35 |
| 817037 (racemic) | 2,3-diCl-phenyl | 2 | cyclopropyl with CH₂OCH₃ | H | N | trans-4-methylcyclohexyl | H | 0.98 |
| 817038 (racemic) | 4-Cl-2-methyl-1-OCH₃-phenyl | 2 | cyclopropyl with CH₂OCH₃ | H | N | trans-4-methylcyclohexyl | H | 0.952 |

TABLE 2-continued

| No. | R | n | [B-C]= | R₁ | A | R₂ | R₃ | d3K₁ |
|---|---|---|---|---|---|---|---|---|
| 817039 (racemic) | 4-CF₃-phenyl (with methyl) | 2 | cyclopropyl-CO-, CH₂- | H | N | trans-4-methylcyclohexyl | H | 14.8 |
| 817040 (racemic) | 2-methyl-benzonitrile | 2 | cyclopropyl-CO-, CH₂- | H | N | trans-4-methylcyclohexyl | H | 0.804 |
| 817045 (racemic) | 2,5-dimethylphenyl | 2 | cyclopropyl-CO-, CH₂- | H | N | trans-4-methylcyclohexyl | H | 5.36 |
| 817041 (racemic) | 2,3-dichloro-methylphenyl | 2 | cyclopropyl-CO-, CH₂- | H | N | trans-4-ethylcyclohexyl | H | 0.776 |
| 817042 (racemic) | 4-chloro-2-methyl-anisole | 2 | cyclopropyl-CO-, CH₂- | H | N | trans-4-ethylcyclohexyl | H | 0.615 |

TABLE 2-continued
| No. | R | n | $R_1$ | A | $R_2$ | $R_3$ | $d3K_i$ |
|---|---|---|---|---|---|---|---|
| 817043 (racemic) | 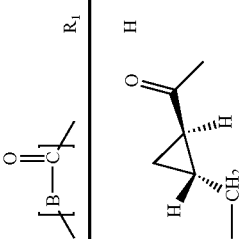 | 2 | 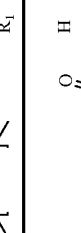 H | N |  | H | 7.2 |
| 817044 (racemic) |  | 2 | 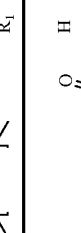 H | N |  | H | 1.1 |
| 817046 (racemic) |  | 2 | 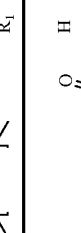 H | N |  | H | 1.92 |
| 817090 (−)-R,R |  | 2 | 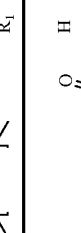 H | N |  | H | 2.17 |
| 817091 (−)-R,R |  | 2 | 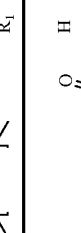 H | N |  | H | 3.98 |

TABLE 2-continued
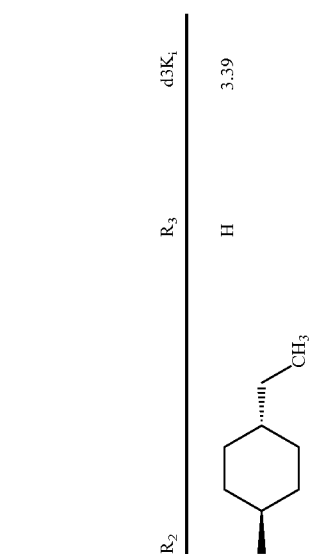
| No. | R | n | [B-C] | R₁ | A | R₂ | R₃ | d3K₁ |
|---|---|---|---|---|---|---|---|---|
| 817092 (−)-R,R |  | 2 |  | H | N |  | H | 3.39 |
| 817094 |  | 2 |  | H | N |  | H | 8.89 |
| 817095 |  | 2 |  | H | N |  | H | 0.671 |
| 817096 |  | 2 |  | H | N |  | H | 9.09 |

TABLE 2-continued

| No. | R | n | [B-C(=O)] | R₁ | A | R₂ | R₃ | d3K₁ |
|---|---|---|---|---|---|---|---|---|
| 817097 | 3,5-dichlorophenyl | 2 | 1-acetyl-2-methylcyclopropyl | H | N | trans-4-ethylcyclohexyl | H | 0.636 |
| 817098 | 4-methylindol-7-yl | 2 | 1-acetyl-2-methylcyclopropyl | H | N | trans-4-methylcyclohexyl | H | 1.06 |
| 817099 | 8-methylnaphthalen-1-yl | 2 | 1-acetyl-2-methylcyclopropyl | H | N | trans-4-methylcyclohexyl | H | 1.1 |
| 817100 | 4-methylindol-7-yl | 2 | 1-acetyl-2-methylcyclopropyl | H | N | trans-4-ethylcyclohexyl | H | 0.75 |
| 817101 | 8-methylnaphthalen-1-yl | 2 | 1-acetyl-2-methylcyclopropyl | H | N | trans-4-ethylcyclohexyl | H | 0.547 |

TABLE 2-continued

| No. | R | n | B | A | R₁ | R₂ | R₃ | d3K₁ |
|---|---|---|---|---|---|---|---|---|
| 817102 (−)-R,R | 2,4-dimethylphenyl | 2 | 1-acetyl-2-methylcyclopropyl | N | trans-4-ethylcyclohexyl | H | 7.75 |
| 827253 | 8-methylquinolinyl | 2 | 1-acetyl-2-methylcyclopropyl | N | trans-4-methylcyclohexyl | H | 15.8 |
| 827254 | 8-methylquinolinyl | 2 | 1-acetyl-2-methylcyclopropyl | N | trans-4-ethylcyclohexyl | H | 8.66 |
| 817039A (racemic) | 4-(trifluoromethyl)phenyl | 2 | 1-acetyl-2-methylcyclopropyl | N | trans-4-methylcyclohexyl | H | 35 |

TABLE 2-continued
| No. | R | n | R₁ | A | R₂ | R₃ | d3K₁ |
|---|---|---|---|---|---|---|---|
| 817090A (racemic) | 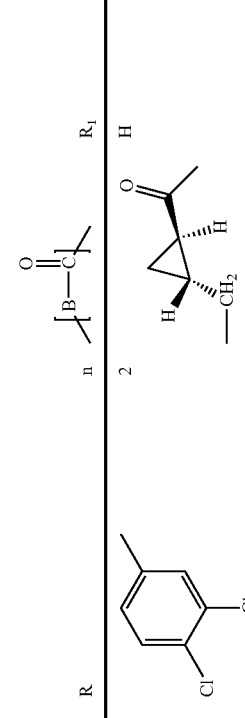 | 2 |  | N |  | H | 5.04 |
| 817571A (racemic) | 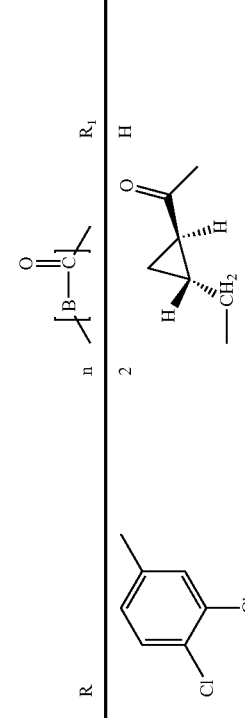 | 2 |  | N |  | H | 11.5 |
| 817092A (racemic) | 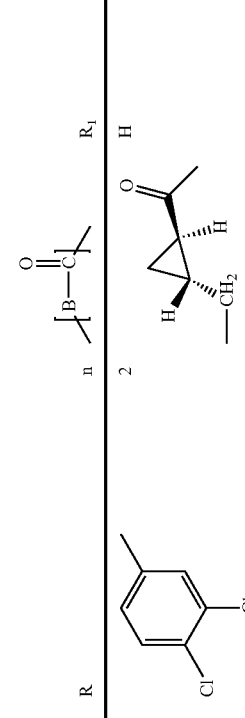 | 2 |  | N |  | H | 22.3 |
| 817570A (racemic) | 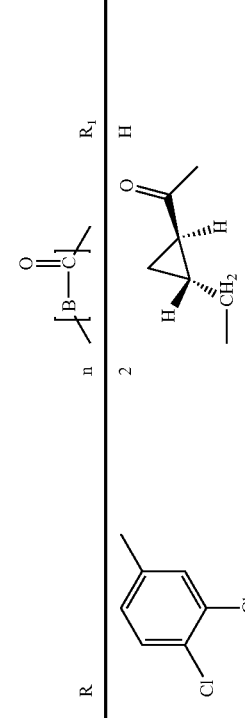 | 2 |  | N |  | H | 5.04 |
| 817478A (racemic) | 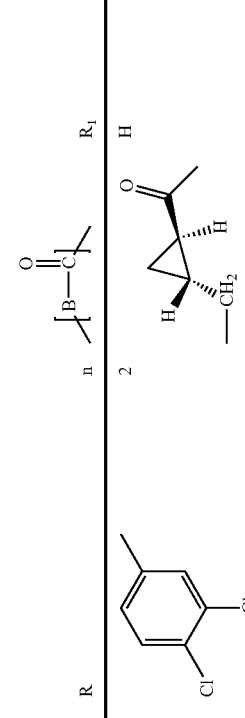 | 2 |  | N |  | H | 1.99 |

TABLE 2-continued

| No. | R | n | R₁ | A | R₂ | R₃ | d3K₁ |
|---|---|---|---|---|---|---|---|
| 817043A (racemic) | 4-(trifluoromethyl)phenyl | 2 | cyclopropyl ketone | N | trans-4-methylcyclohexyl | H | 18.6 |
| 817091A (−)-R,R | 2,4-dimethylphenyl | 2 | cyclopropyl ketone | N | trans-4-methylcyclohexyl | H | 4.04 |
| 817102A (−)-R,R | 2,4-dimethylphenyl | 2 | cyclopropyl ketone | N | trans-4-methylcyclohexyl | H | 7.57 |
| 818675DA (−)-R,R | 2-methylphenyl | 2 | cyclopropyl ketone | N | trans-4-methylcyclohexyl | H | 5.69 |
| 827201 (racemic) | benzodioxole-ethyl | 2 | cyclopropyl ketone | N | 4-methylcyclohexyl | H | 126 |

TABLE 2-continued

| No. | R | n | $B-C$ | $R_1$ | A | $R_2$ | $R_3$ | $d3K_i$ |
|---|---|---|---|---|---|---|---|---|
| 817093 (−)-R,R | 3-Cl-2-methyl-5-CF3-pyridine | 2 | cyclopropyl-CH2 (acetyl) | H | N | trans-4-methylcyclohexyl (CH3 wedge) | H | 5.97 |
| 817480A (−)-R,R | 3-Cl-2-methyl-5-CF3-pyridine | 2 | cyclopropyl-CH2 (acetyl) | H | N | trans-4-methylcyclohexyl (CH3 wedge) | H | 5.33 |
| 817566 | 3-Cl-2-methylpyridine | 2 | cyclopropyl-CH2 (acetyl) | H | N | trans-4-methylcyclohexyl (CH3 wedge) | H | 2.46 |
| 817565 | 3-Cl-2-methylpyridine | 2 | cyclopropyl-CH2 (acetyl) | H | N | 4-methylcyclohexyl (CH3 dashed) | H | 1.73 |
| 817198 | $(CH_2)_2$-phenyl | 2 | cyclopropyl-CH2 (acetyl) | H | N | 4-methylcyclohexyl (CH3 dashed) | H | 161 |

TABLE 2-continued

| No. | R | n | [structure] | R₁ | A | R₂ | R₃ | d3K₁ |
|---|---|---|---|---|---|---|---|---|
| 818427 (racemic) | 3-methylthieno-isoxazole | 2 | acetyl-cyclopropyl-CH₂ | H | N | trans-4-methylcyclohexyl | H | 6.07 |
| 817892 (−)-R,R | 3-methylthieno-isoxazole | 2 | acetyl-cyclopropyl-CH₂ | H | N | trans-4-methylcyclohexyl | H | 5.47 |
| 817893 (+)-S,S | 3-methylthieno-isoxazole | 2 | acetyl-cyclopropyl-CH₂ | H | N | trans-4-methylcyclohexyl | H | 245 |
| 817892A (−)-R,R | 3-methylthieno-isoxazole | 2 | acetyl-cyclopropyl-CH₂ | H | N | trans-4-methylcyclohexyl | H | 3.02 |
| 818574 (racemic) | 3-methylthieno-isoxazole | 2 | acetyl-cyclopropyl-CH₂ | H | N | trans-4-(CH₂CH₃)cyclohexyl | H | 9.6 |

TABLE 2-continued
| No. | R | n | R₁ | A | R₂ | R₃ | d3K₁ |
|---|---|---|---|---|---|---|---|
| 817787 (−)-R,R | 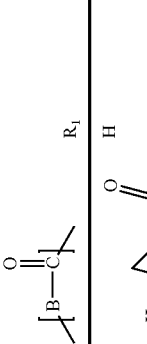 | 2 | 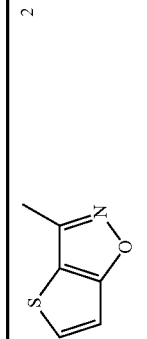 | N | 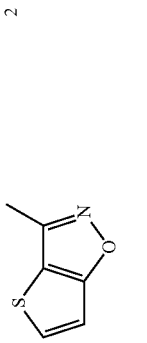 | H | 5.81 |
| 817786 (+)-S,S | 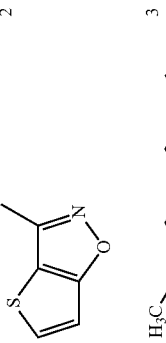 | 2 | 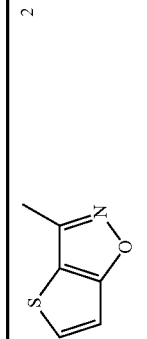 | N | 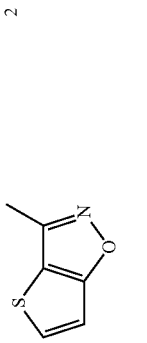 | H | 125 |
| 817787A (−)-R,R | 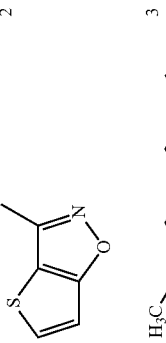 | 2 | 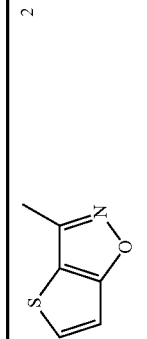 | N | 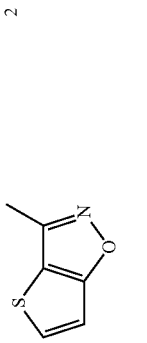 | H | 1.76 |
| 817272 (racemic) | 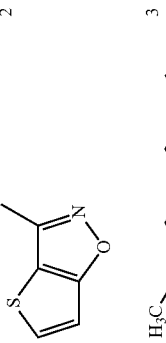 | 3 | 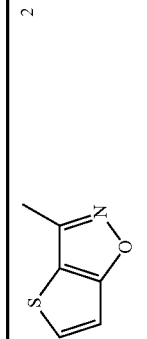 | N | 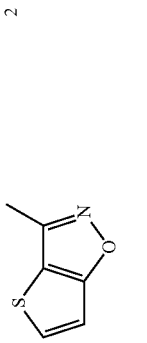 | H | 1.72 |

TABLE 2-continued
| No. | R | n | [B—C] | R₁ | A | R₂ | R₃ | d3K₁ |
|---|---|---|---|---|---|---|---|---|
| 817273 (racemic) | 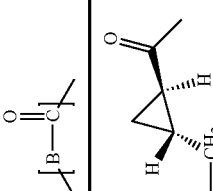 | 3 | 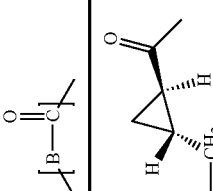 | H | N | 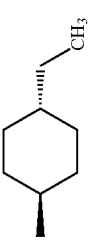 | H | 3.05 |
| 817260 (racemic) | 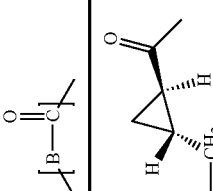 | 3 | 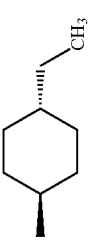 | H | N | 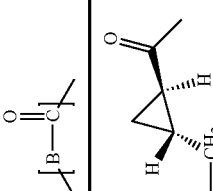 | H | 12.5 |
| 817261 (racemic) | 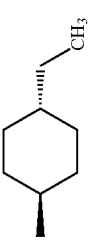 | 3 | | H | N | | H | 9.23 |

TABLE 2-continued
| No. | R | n | R₁ | A | R₂ | R₃ | d3K_i |
|---|---|---|---|---|---|---|---|
| 827731 (racemic) | 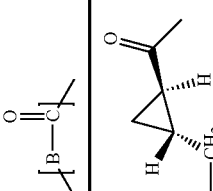 | 3 | 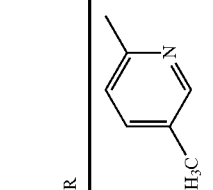 | N | 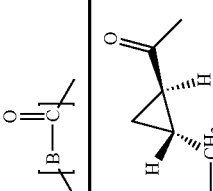 | H | 19.5 |
| 827732 (racemic) |  | 3 | 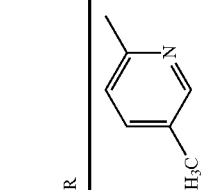 | N |  | H | 10.5 |
| 817567 (racemic) |  | 3 | 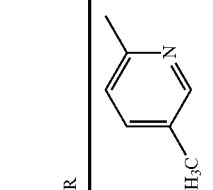 | N | 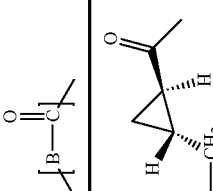 | H | 80.6 |
| 817568 (racemic) |  | 3 | 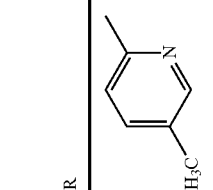 | N | 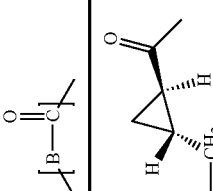 | H | 36.3 |
| 827733 (racemic) |  | 3 | 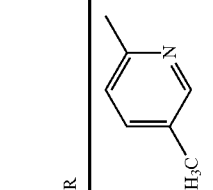 | N | 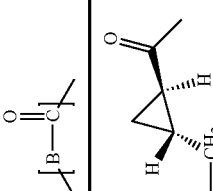 | H | 1.19 |

TABLE 2-continued
| No. | R | n | | R₁ | A | R₂ | R₃ | d3K₁ |
|---|---|---|---|---|---|---|---|---|
| 818498 (racemic) | 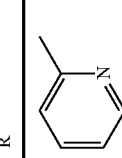 | 3 | 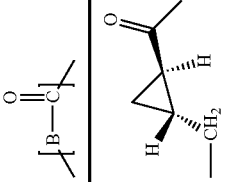 | H | N | 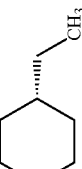 | H | 25.6 |
| 827800 (racemic) | 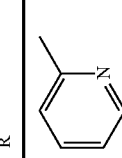 | 3 | 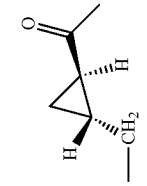 | H | N | 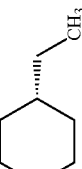 | H | 19.7 |
| 814648 | 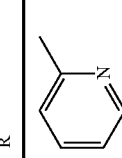 | 2 | 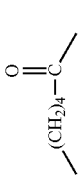 | CH₃(CH₂)₂ | N | 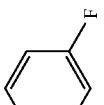 | H | 39.6 |
| 814649 | 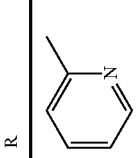 | 2 | 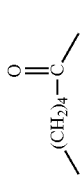 | 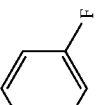 | N | 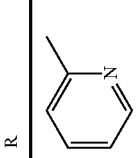 | H | 38.9 |
| 814650A | 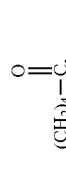 | 2 | 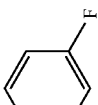 | CH₃ | N | (4-F-phenyl) | H | 18 |

TABLE 2-continued

| No. | R | n | [B-C(=O)]— | $R_1$ | [structure] | A | $R_2$ | $R_3$ | $d3K_i$ |
|---|---|---|---|---|---|---|---|---|---|
| 813384 | 6-F-benzothiophen-2-yl | 2 | —C(=O)—(CH$_2$)$_4$— | H | —N(R$_1$)R$_2$ | N | 4-F-phenyl | H | 74 |
| US 822129 | 6-F-benzothiophen-2-yl | 2 | —C(=O)—(CH$_2$)$_4$— | CH$_3$ | | N | phenyl | H | 38 |
| 822130 | 6-F-benzothiophen-2-yl | 2 | —C(=O)—(CH$_2$)$_4$— | CH$_3$CH$_2$ | | N | benzo[1,3]dioxol-5-yl | H | 51 |
| 822131 | 6-F-benzothiophen-2-yl | 2 | —C(=O)—(CH$_2$)$_4$— | CH$_3$ | | N | 4-methoxyphenyl | H | 61 |
| 822132 | 6-F-benzothiophen-2-yl | 2 | —C(=O)—(CH$_2$)$_4$— | CH$_3$CH$_2$ | | N | 2-methyl-3-hydroxyphenyl | H | 18 |

TABLE 2-continued
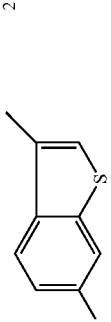
| No. | R | n | B | $R_1$ | | A | $R_2$ | $R_3$ | $d3K_i$ |
|---|---|---|---|---|---|---|---|---|---|
| 822133 | 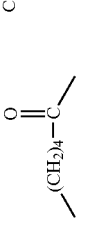 | 2 | 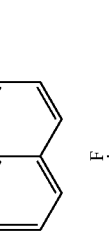 | $CH_3$ | 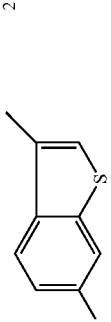 | N | 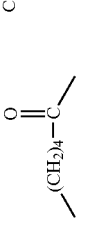 | H | 17 |
| US 822134 | 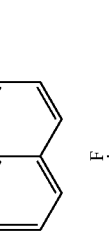 | 2 | 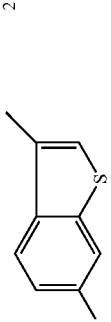 | H | 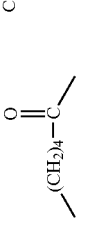 | N | 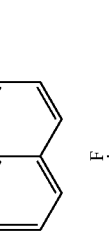 | H | 82 |
| 822135 | 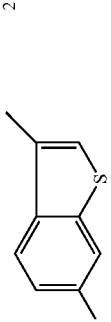 | 2 | 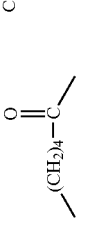 | H | 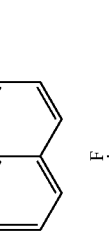 | N | 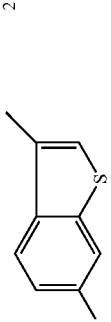 | H | 3.6 |
| 822136 | 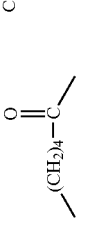 | 2 | | H | | N | 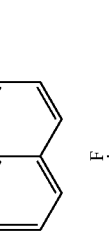 | H | 207 |
| 822137 | | 2 | | H | | N | | H | 36 |

TABLE 2-continued

| No. | R | n | B-C(=O) | R₁ | R₂ | A | R₂ | R₃ | d3K_i |
|---|---|---|---|---|---|---|---|---|---|
| 822138 | 6-F-benzothiophen-3-yl | 2 | -(CH₂)₄-C(=O)- | CH₃ | 1-naphthyl | N | | H | 81 |
| 822139 | 6-F-benzothiophen-3-yl | 2 | -(CH₂)₄-C(=O)- | CH₃ | 2-F-6-methylphenyl | N | | H | 21.2 |
| 822140 | 6-F-benzothiophen-3-yl | 2 | -(CH₂)₄-C(=O)- | CH₃ | 4-(2-methylpropan-2-yl)-methylphenyl | N | | H | 112.8 |
| 822142 | 6-F-benzothiophen-3-yl | 2 | -(CH₂)₄-C(=O)- | CH₃ | 3-phenoxy-methylphenyl | N | | H | 39.1 |
| 822143 | 6-F-benzothiophen-3-yl | 2 | -(CH₂)₄-C(=O)- | -CH₂-phenyl | 3-phenoxy-methylphenyl | N | | H | 338 |

TABLE 2-continued

| No. | R | n | B | R₁ | A | R₂ | R₃ | d3K₁ |
|---|---|---|---|---|---|---|---|---|
| 826804 | 3-methyl-6-CF₃-benzothiophene | 2 | C(=O)-(CH₂)₃-C | H | N | trans-4-methylcyclohexyl | H | 67.4 |
| 826805 | 3-methyl-6-CF₃-benzothiophene | 2 | C(=O)-(CH₂)₃-C | H | N | trans-4-(ethoxycarbonyl)cyclohexyl | H | 14.2 |
| 826806 | 3-methyl-6-CF₃-benzothiophene | 2 | C(=O)-(CH₂)₃-C | H | N | trans-4-ethylcyclohexyl | H | 40 |
| 826807 (racemic) | 3-methyl-6-CF₃-benzothiophene | 2 | C(=O)-(CH₂)₃-C | H | N | 3-methylcyclohexyl | H | 43 |
| 826808 | 3-methyl-6-CF₃-benzothiophene | 2 | C(=O)-(CH₂)₃-C | CH₃ | N | cyclohexyl | H | 17.4 |

TABLE 2-continued

| No. | R | n | B | $R_1$ | A | $R_2$ | $R_3$ | $d3K_i$ |
|---|---|---|---|---|---|---|---|---|
| 826809 | 3-methyl-6-CF3-benzothiophene | 2 | (CH2)3 | CH3CH2 | N | cyclohexyl | H | 71 |
| 826810 | 3-methyl-6-CF3-benzothiophene | 2 | (CH2)3 | HO(CH2)2 | N | cyclohexyl | H | 86.7 |
| 826820 | 3-methyl-6-CF3-benzothiophene | 2 | (CH2)3 | H | N | cyclopentyl | H | 52.8 |
| 826821 | 3-methyl-6-CF3-benzothiophene | 2 | (CH2)3 | H | N | cyclohexyl | H | 70.1 |
| 826824 | 3-methyl-6-F-benzothiophene | 3 | (CH2)3 | H | N | trans-4-methylcyclohexyl | H | 34.2 |

TABLE 2-continued

| No. | R | n | B | R₁ | A | R₂ | R₃ | d3Kᵢ |
|---|---|---|---|---|---|---|---|---|
| 826825 | 6-F-3-methylbenzothiophene | 3 | -C(O)-(CH₂)₃-C(CH₃)- | H | N | trans-4-methylcyclohexyl-CO₂CH₂CH₃ | H | 74.9 |
| 826826 | 6-F-3-methylbenzothiophene | 3 | -C(O)-(CH₂)₃-C(CH₃)- | H | N | trans-4-methylcyclohexyl-CH₂CH₃ | H | 27.4 |
| 826827 (racemic) | 6-F-3-methylbenzothiophene | 3 | -C(O)-(CH₂)₃-C(CH₃)- | H | N | 3-methylcyclohexyl | H | 39.5 |
| 826828 | 6-F-3-methylbenzothiophene | 3 | -C(O)-(CH₂)₃-C(CH₃)- | CH₃ | N | cyclohexyl | H | 14.4 |
| 826829 | 6-F-2-methylbenzothiophene | 3 | -C(O)-(CH₂)₃-C(CH₃)- | CH₃CH₂ | N | cyclohexyl | H | 15 |

TABLE 2-continued

| No. | R | n | [B-C(=O)] | R₁ | A | R₂ | R₃ | d3K₁ |
|---|---|---|---|---|---|---|---|---|
| 826830 | 6-F-3-methylbenzothiophene | 3 | —C(=O)—(CH₂)₃— | HO(CH₂)₂ | N | cyclohexyl | H | 25.1 |
| 826840 | 6-F-3-methylbenzothiophene | 3 | —C(=O)—(CH₂)₃— | H | N | cyclopentyl | H | 11 |
| 826841 | 6-F-3-methylbenzothiophene | 3 | —C(=O)—(CH₂)₃— | H | N | cyclopentyl | H | 22 |
| 822144 | 6-F-3-methylbenzothiophene | 2 | —C(=O)—(CH₂)₃— | CH₃ | N | 4-methoxyphenyl | H | 144 |
| 822145 | 6-F-3-methylbenzothiophene | 2 | —C(=O)—(CH₂)₃— | H | N | 1-naphthyl | H | 176 |

TABLE 2-continued

| No. | R | n | B | $R_1$ | A | $R_2$ | $R_3$ | $d3K_i$ |
|---|---|---|---|---|---|---|---|---|
| 822147 | 6-F-benzothiophen-3-yl | 2 | -(CH$_2$)$_3$-C(=O)- | H | N | 4-(2-(4-methylphenyl)propan-2-yl) | H | 217 |
| 822148 | 6-F-benzothiophen-3-yl | 2 | -(CH$_2$)$_3$-C(=O)- | H | N | 3-methylphenoxyphenyl | H | 41.4 |
| 826844 | 6-F-benzothiophen-3-yl | 2 | -(CH$_2$)$_3$-C(=O)- | H | N | trans-4-methylcyclohexyl | H | 0.591 |
| 826845 | 6-F-benzothiophen-3-yl | 2 | -(CH$_2$)$_3$-C(=O)- | H | N | trans-4-(ethoxycarbonyl)cyclohexyl | H | 4.42 |
| 826846 | 6-F-benzothiophen-3-yl | 2 | -(CH$_2$)$_3$-C(=O)- | H | N | trans-4-(methyl)methylcyclohexyl | H | 17.6 |

TABLE 2-continued

| No. | R | n | [B]—C(O)— | $R_1$ | A | $R_2$ | $R_3$ | $d3K_i$ |
|---|---|---|---|---|---|---|---|---|
| 826847 | 6-F-benzothiophen-3-yl | 2 | —C(O)—(CH$_2$)$_3$—CH(CH$_3$)— | H | N | 3,5-dimethylcyclohexyl | H | 1.01 |
| 826848 | 6-F-benzothiophen-3-yl | 2 | —C(O)—(CH$_2$)$_3$—CH(CH$_3$)— | CH$_3$ | N | cyclohexyl | H | 4.35 |
| 826849 | 6-F-benzothiophen-3-yl | 2 | —C(O)—(CH$_2$)$_3$—CH(CH$_3$)— | CH$_3$CH$_2$ | N | cyclohexyl | H | 54.2 |
| 826850 | 6-F-benzothiophen-3-yl | 2 | —C(O)—(CH$_2$)$_3$—CH(CH$_3$)— | HO(CH$_2$)$_2$ | N | cyclohexyl | H | 18.8 |
| 826860 | 6-F-benzothiophen-3-yl | 2 | —C(O)—(CH$_2$)$_3$—CH(CH$_3$)— | H | N | cyclopentyl | H | 3.48 |

TABLE 2-continued
| No. | R | n | B | R₁ | A | R₂ | R₃ | d3K₁ |
|---|---|---|---|---|---|---|---|---|
| 826861 | 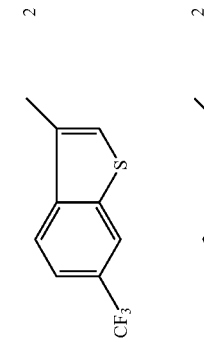 | 2 | 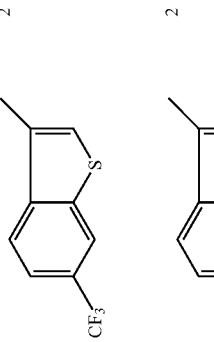 | H | N | 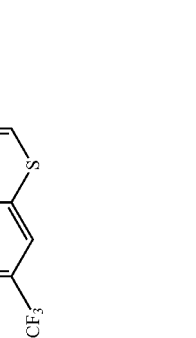 | H | 2.89 |
| US 825857 Racemic | 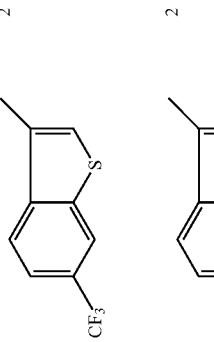 | 2 | 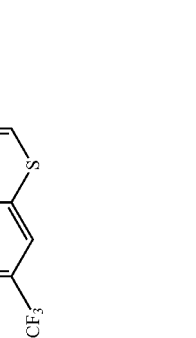 | H | N |  | H | 137 |
| 825860 Racemic | 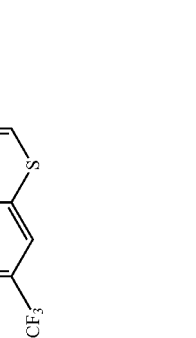 | 2 |  | H | N | 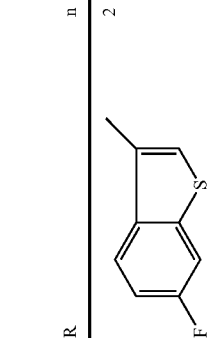 | H | 130 |
| 825870 Racemic |  | 2 | 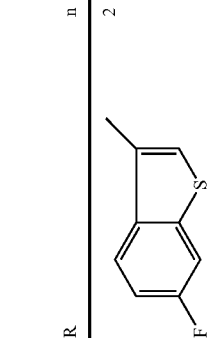 | H | N | 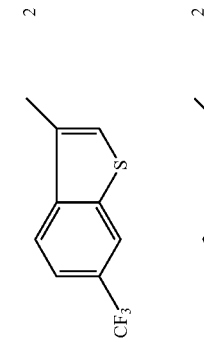 | H | 100 |

TABLE 2-continued

| No. | R | n | $R_1$ | A | $R_2$ | $R_3$ | d3$K_i$ |
|---|---|---|---|---|---|---|---|
| 825871 Racemic | | 2 | | N | | H | 137 |
| 825872 Racemic | | 2 | | N | | H | 104 |
| 825881 | | 2 | | N | | H | 189 |
| 825882 | | 2 | | N | | H | 186 |
| 825883 | | 2 | | N | | H | 140 |

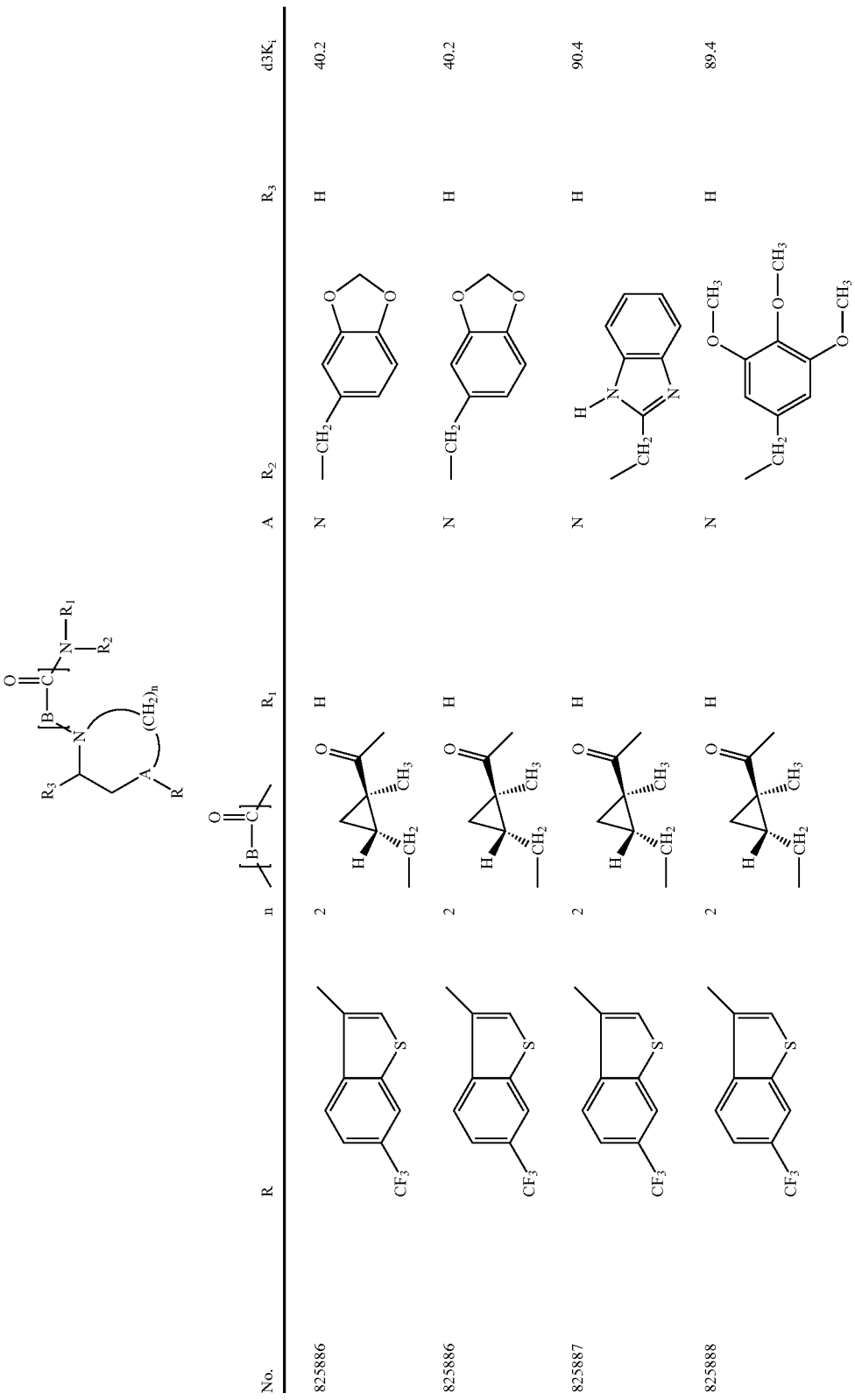

TABLE 2-continued

| No. | R | n | [B-C(=O)] | R₁ | A | R₂ | R₃ | d3K₁ |
|---|---|---|---|---|---|---|---|---|
| 825893 | 6-CF₃-3-methylbenzothiophene | 2 | cyclopropane(CH₃)(CH₂-) with C(=O) | H | N | cyclopropyl | H | 73.8 |
| 825894 | 6-CF₃-3-methylbenzothiophene | 2 | cyclopropane(CH₃)(CH₂-) with C(=O) | H | N | -CH₂-C₆H₄-N(CH₃)₂ (para) | H | 59 |
| 825895 | 6-CF₃-3-methylbenzothiophene | 2 | cyclopropane(CH₃)(CH₂-) with C(=O) | H | N | -CH₂-cyclopropyl | H | 31.7 |
| 825896 | 6-CF₃-3-methylbenzothiophene | 2 | cyclopropane(CH₃)(CH₂-) with C(=O) | H | N | -CH₂-phenyl | H | 53.3 |
| 825897 | 6-CF₃-3-methylbenzothiophene | 2 | cyclopropane(CH₃)(CH₂-) with C(=O) | H | N | -CH₂-(2-furyl) | H | 140 |

TABLE 2-continued

| No. | R | n | B-C (R1 side) | R1 | A | R2 | R3 | d3K1 |
|---|---|---|---|---|---|---|---|---|
| 825898 | 3-methyl-6-CF3-benzothiophene | 2 | cyclopropane (CH3, CH2-) | H | N | CH2-thiophene | H | 49 |
| 825899 | 3-methyl-6-CF3-benzothiophene | 2 | cyclopropane (CH3, CH2-) | H | N | CH2-C6H4-CF3 | H | 42.9 |
| 826065 | 3-methyl-6-CF3-benzothiophene | 2 | cyclopropane (CH3, CH2-) | H | N | CH2-pyridine | H | 175 |
| 822202 | 3-methyl-6-CF3-benzothiophene | 2 | cyclopropane (CH3, CH2-) | H | N | cyclopropyl | H | 8.1 |
| 826066 | 3-methyl-6-CF3-benzothiophene | 2 | cyclopropane (CH3, CH2-) | H | N | CH2-C6H4-N(CH3)2 | H | 60.3 |

TABLE 2-continued

| No. | R | n | [structure] | $R_1$ | A | $R_2$ | $R_3$ | $d3K_i$ |
|---|---|---|---|---|---|---|---|---|
| 826067 | 3-methyl-6-CF₃-benzothiophene | 2 | cyclopropyl-CH₃/CH₂- | H | N | –CH₂–cyclopropyl | H | 19.3 |
| 826068 | 3-methyl-6-CF₃-benzothiophene | 2 | cyclopropyl-CH₃/CH₂- | H | N | –CH₂–phenyl | H | 54.6 |
| 826069 | 3-methyl-6-CF₃-benzothiophene | 2 | cyclopropyl-CH₃/CH₂- | H | N | –CH₂–(2-furyl) | H | 27.2 |
| 826070 | 3-methyl-6-CF₃-benzothiophene | 2 | cyclopropyl-CH₃/CH₂- | H | N | –CH₂–(2-thienyl) | H | 12.6 |
| 826071 | 3-methyl-6-CF₃-benzothiophene | 2 | cyclopropyl-CH₃/CH₂- | H | N | –CH₂–(4-CF₃-phenyl) | H | 165 |

TABLE 2-continued
| No. | R | n | | $R_1$ | A | $R_2$ | $R_3$ | $d3K_i$ |
|---|---|---|---|---|---|---|---|---|
| 822203 | 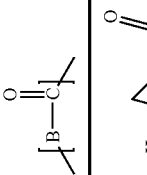 | 2 | 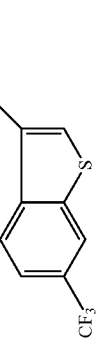 | H | N | 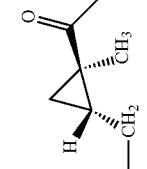 | H | 30 |
| 826072 | 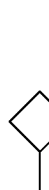 | 2 | 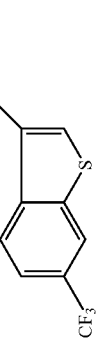 | H | N | 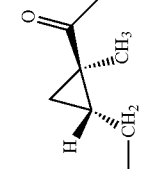 | H | 62.6 |
| 826073 | 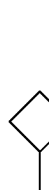 | 2 | 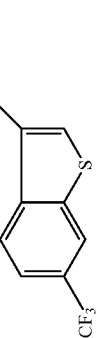 | H | N | 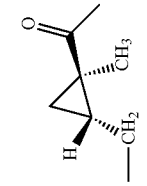 | H | 32.3 |
| 826074 | 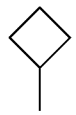 | 2 | 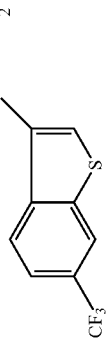 | H | N | 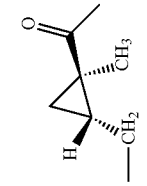 | H | 72.6 |
| 826075 | 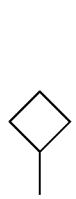 | 2 | 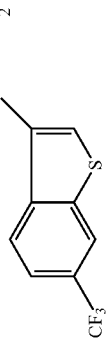 | H | N | 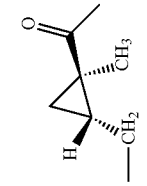 | H | 55.6 |

TABLE 2-continued

| No. | R | n | [structure] | R₁ | A | R₂ | R₃ | d3K₁ |
|---|---|---|---|---|---|---|---|---|
| 826076 | 3-methyl-6-CF₃-benzothiophene | 2 | cyclopropane with CH₃, CH₂ | H | N | cyclohexyl | H | 15 |
| 826077 | 3-methyl-6-CF₃-benzothiophene | 2 | cyclopropane with CH₃, CH₂ | H | N | 2,5-dimethoxybenzyl | H | 88.9 |
| 826078 | 3-methyl-6-CF₃-benzothiophene | 2 | cyclopropane with CH₃, CH₂ | H | N | tetrahydronaphthyl-methyl | H | 162 |
| 822204 | 3-methyl-6-CF₃-benzothiophene | 2 | cyclopropane with CH₃, CH₂ | H | N | benzo[1,3]dioxol-5-ylmethyl | H | 12.6 |

TABLE 2-continued
| No. | R | n | [B-C]— | $R_1$ | A | $R_2$ | $R_3$ | $d3K_i$ |
|---|---|---|---|---|---|---|---|---|
| 826079 | 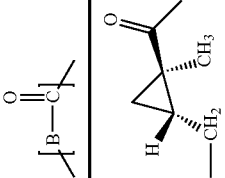 | 2 |  | H | N | 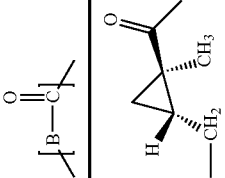 | H | 106 |
| 826080 |  | 2 |  | H | N | 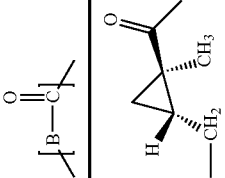 | H | 14.8 |
| 815916 |  | 2 |  | H | N | 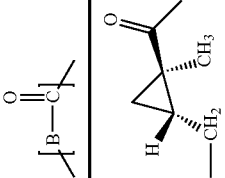 | H | 5 |
| (+)-816589 (S,S) |  | 2 |  | H | N | 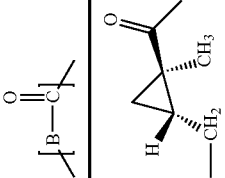 | H | 1070 |
| (−)-817569 (R,R) |  | 2 |  | H | N | 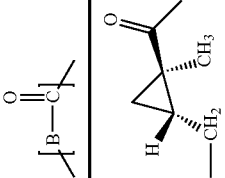 | H | 2.62 |

TABLE 2-continued

| No. | R | n | | R₁ | A | R₂ | R₃ | d3K₁ |
|---|---|---|---|---|---|---|---|---|
| 815917 | 3-methyl-6-CF₃-benzothiophene | 2 | acetyl-cyclopropyl-CH₃,CH₂ | H | N | trans-4-(ethoxycarbonyl)cyclohexyl | H | 18 |
| 815918 | 3-methyl-6-CF₃-benzothiophene | 2 | acetyl-cyclopropyl-CH₃,CH₂ | H | N | trans-4-methylcyclohexyl | H | 15 |
| 826655 | 3-methyl-6-CF₃-benzothiophene | 2 | acetyl-cyclopropyl-CH₃,CH₂ | H | N | -(CH₂)₈- (cyclic) | H | 31 |
| 826656 | 3-methyl-6-CF₃-benzothiophene | 2 | acetyl-cyclopropyl-CH₃,CH₂ | H | N | -CH₂-morpholine | H | 45 |
| 826658 | 3-methyl-6-CF₃-benzothiophene | 2 | acetyl-cyclopropyl-CH₃,CH₂ | H | N | cyclopentyl | H | 17 |

TABLE 2-continued

| No. | R | n | [B-C] | $R_1$ | | A | $R_2$ | $R_3$ | $d3K_i$ |
|---|---|---|---|---|---|---|---|---|---|
| 826884 | 6-CF3-3-methylbenzothiophene | 2 | cyclopropyl(CH3)(CH2) | H | | N | 3,5-dimethylcyclohexyl | H | 15.2 |
| 826885 | 6-CF3-3-methylbenzothiophene | 2 | cyclopropyl(CH3)(CH2) | CH3 | | N | methylcyclohexyl | H | 20.3 |
| 826886 | 6-CF3-3-methylbenzothiophene | 2 | cyclopropyl(CH3)(CH2) | H | phenyl | N | methylcyclohexyl | H | 136 |
| 826887 | 6-CF3-3-methylbenzothiophene | 2 | cyclopropyl(CH3)(CH2) | H | | N | NH-cyclohexyl | H | 83.8 |
| 826888 | 6-CF3-2-methylbenzothiophene | 2 | cyclopropyl(CH3)(CH2) | H | | N | adamantyl | H | 37.2 |

TABLE 2-continued
| No. | R | n | [B-C]= | R₁ | A | R₂ | R₃ | d3K₁ |
|---|---|---|---|---|---|---|---|---|
| 826889 | 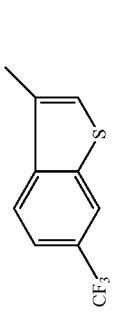 | 2 | 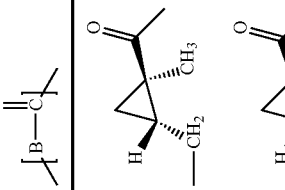 | H | N | 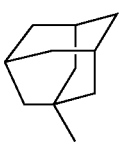 | H | 36.2 |
| 826890 | 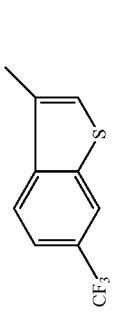 | 2 | 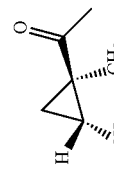 | H | N | 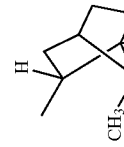 | H | 38 |
| 826891 | 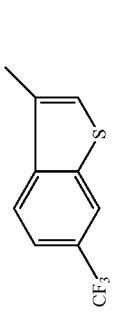 | 2 | 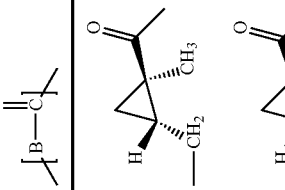 | H | N | 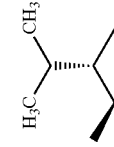 | H | 263 |
| 826892 | 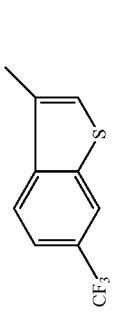 | 2 | 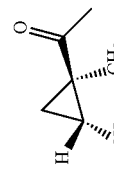 | H | N | 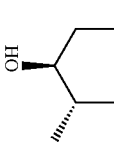 | H | 25.9 |

TABLE 2-continued

| No. | R | n | [B-C] | R₁ | A | R₂ | R₃ | d3K₁ |
|---|---|---|---|---|---|---|---|---|
| 826893 | 3-methyl-6-CF₃-benzothiophene | 2 | cyclopropyl w/ CH₃ and CH₂ | H | N | 3,3,5-trimethylcyclohexyl | H | 20.4 |
| 826894 | 3-methyl-6-CF₃-benzothiophene | 2 | cyclopropyl w/ CH₃ and CH₂ | CH₃CH₂ | N | cyclohexyl | H | 35 |
| 826895 | 3-methyl-6-CF₃-benzothiophene | 2 | cyclopropyl w/ CH₃ and CH₂ | HO(CH₂)₂ | N | cyclohexyl | H | 48.8 |
| 826897 | 3-methyl-6-CF₃-benzothiophene | 2 | cyclopropyl w/ CH₃ and CH₂ | H | N | 2-methylcyclohexyl methyl ester | H | 128 |

TABLE 2-continued

| No. | R | n | [B-C]= | R₁ | A | R₂ | R₃ | d3K$_i$ |
|---|---|---|---|---|---|---|---|---|
| 826898 | 3-methyl-6-CF₃-benzothiophene | 2 | cyclopropyl(COCH₃)(CH₂CH₃) | H | N | 2-methylcyclohexyl CO₂CH₂CH₃ | H | 50.5 |
| 816078A HCl salt | 3-methyl-6-CF₃-benzothiophene | 2 | cyclopropyl(COCH₃)(CH₂CH₃) | H | N | 4-methylcyclohexyl CO₂H | H | 89.7 |
| 826678 | 3-methyl-6-CF₃-benzothiophene | 3 | cyclopropyl(COCH₃)(CH₂CH₃) | H | N | 4-methylcyclohexyl CH₃ | H | 15 |
| 826679 | 3-methyl-6-CF₃-benzothiophene | 3 | cyclopropyl(COCH₃)(CH₂CH₃) | H | N | 4-methylcyclohexyl CO₂CH₂CH₃ | H | 9.1 |
| 826680 | 3-methyl-6-CF₃-benzothiophene | 3 | cyclopropyl(COCH₃)(CH₂CH₃) | H | N | 4-methylcyclohexyl CH₂CH₃ | H | 58 |

TABLE 2-continued

| No. | R | n | [B-C]= | $R_1$ | A | $R_2$ | $R_3$ | $d3K_i$ |
|---|---|---|---|---|---|---|---|---|
| 826681 | | 3 | | H | N | | H | 48 |
| 826682 | | 3 | | H | N | | H | 103 |
| 826684 | | 3 | | H | N | | H | 7.9 |
| 826665 | | 2 | | H | N | | H | 1.9 |
| 826666 | | 2 | | H | N | | H | 6.3 |

TABLE 2-continued

| No. | R | n | B—C | R₁ | A | R₂ | R₃ | d3K₁ |
|---|---|---|---|---|---|---|---|---|
| 826667 | 6-fluoro-3-methylbenzothiophene | 2 | cyclopropane with CH₃ and CH₂ | H | N | trans-4-methylcyclohexylmethyl (CH₃) | H | 2.5 |
| 826668 | 6-fluoro-3-methylbenzothiophene | 2 | cyclopropane with CH₃ and CH₂ | H | N | cyclo-(CH₂)₈ | H | 3.9 |
| 826670 | 6-fluoro-3-methylbenzothiophene | 2 | cyclopropane with CH₃ and CH₂ | H | N | cyclopentyl | H | 4.2 |
| 826677 | 6-fluoro-3-methylbenzothiophene | 2 | cyclopropane with CH₃ and CH₂ | H | N | cyclohexyl | H | 2.3 |
| 826864 | 6-fluoro-3-methylbenzothiophene | 3 | cyclopropane with CH₃ and CH₂ | H | N | trans-4-methylcyclohexyl (CH₃) | H | 2.16 |

TABLE 2-continued

| No. | R | n | [B-C] (acyl group) | $R_1$ | A | $R_2$ | $R_3$ | $d3K_i$ |
|---|---|---|---|---|---|---|---|---|
| 826865 | 6-fluoro-3-methylbenzothiophene | 3 | cyclopropyl with CH₃ and CH₂– | H | N | 4-methylcyclohexyl-CO-O-CH₂CH₃ | H | 3.68 |
| 826866 | 6-fluoro-3-methylbenzothiophene | 3 | cyclopropyl with CH₃ and CH₂– | H | N | 4-methylcyclohexyl-CH₂-CH₃ | H | 1.24 |
| 826867 | 6-fluoro-3-methylbenzothiophene | 3 | cyclopropyl with CH₃ and CH₂– | H | N | 3-methylcyclohexyl | H | 1.89 |
| 826868 | 6-fluoro-3-methylbenzothiophene | 3 | cyclopropyl with CH₃ and CH₂– | CH₃ | N | cyclohexyl | H | 3.49 |
| 826869 | 6-fluoro-3-methylbenzothiophene | 3 | cyclopropyl with CH₃ and CH₂– | CH₃CH₂ | N | cyclohexyl | H | 6.75 |

TABLE 2-continued

| No. | R | n | [B-C] | R₁ | A | R₂ | R₃ | d3K₁ |
|---|---|---|---|---|---|---|---|---|
| 826870 | 6-fluorobenzothiophen-3-yl | 3 | trans-1-acetyl-1-methyl-2-methylcyclopropyl | HO(CH₂)₂ | N | cyclohexyl | H | 7.4 |
| 826880 | 6-fluorobenzothiophen-3-yl | 3 | trans-1-acetyl-1-methyl-2-methylcyclopropyl | H | N | cyclopentyl | H | 2.86 |
| 826881 | 6-fluorobenzothiophen-3-yl | 3 | trans-1-acetyl-1-methyl-2-methylcyclopropyl | H | N | cyclohexyl | H | 2.38 |
| 825825 | 6-fluorobenzothiophen-3-yl | 2 | trans-2-methylcyclopentyl carbonyl | H | N | CH₂-(2-pyridyl) | H | 152 |
| 825826G (Maleate Salt) | 6-fluorobenzothiophen-3-yl | 2 | trans-2-methylcyclopentyl carbonyl | H | N | CH₂-(2-benzimidazolyl) | H | 32.5 |

TABLE 2-continued

| No. | R | n | B-C(=O) (R_1 substituent shown) | R_1 | A | R_2 | R_3 | d3K_i |
|---|---|---|---|---|---|---|---|---|
| 825827 | 6-fluoro-3-methyl-benzothiophene | 2 | 2-methylcyclopentyl-C(=O) | H | N | cyclopropyl | H | 54.8 |
| 825828 | 6-fluoro-3-methyl-benzothiophene | 2 | 2-methylcyclopentyl-C(=O) | H | N | 4-(N,N-dimethylamino)benzyl (p-CH₃ shown as p-OCH₃-like; 4-N(CH_3)_2-benzyl) | H | 21.8 |
| 825829G (Maleate Salt) | 6-fluoro-3-methyl-benzothiophene | 2 | 2-methylcyclopentyl-C(=O) | H | N | cyclopropylmethyl | H | 40.1 |
| 825830 | 6-fluoro-3-methyl-benzothiophene | 2 | 2-methylcyclopentyl-C(=O) | H | N | benzyl | H | 64.6 |

TABLE 2-continued
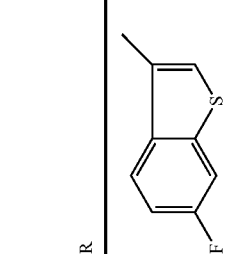
| No. | R | n | B-C | R₁ | A | R₂ | R₃ | d3K_i |
|---|---|---|---|---|---|---|---|---|
| 825831 | 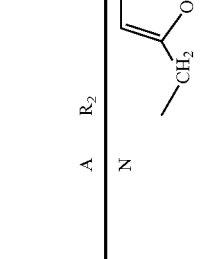 | 2 | 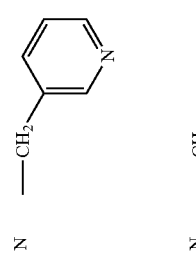 | H | N | 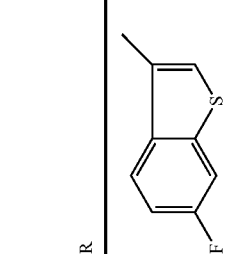 | H | 48.1 |
| 825832 | 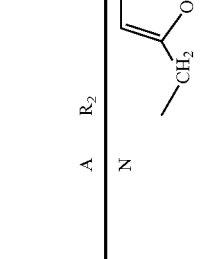 | 2 | 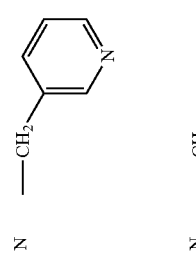 | H | N | 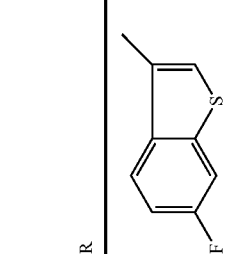 | H | 60.3 |
| 825834G (Maleate Salt) | 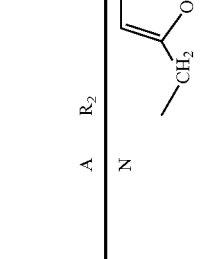 | 2 | 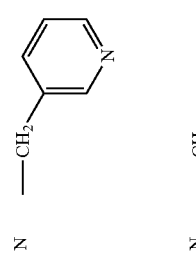 | H | N | 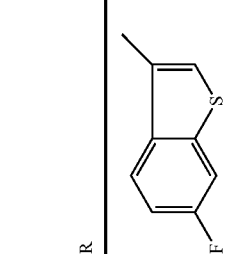 | H | 6.9 |
| 825900 | 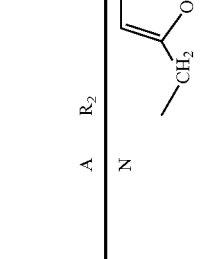 | 2 | 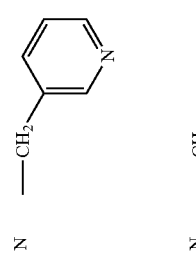 | H | N |  | H | 22.4 |

TABLE 2-continued
| No. | R | n | | R₁ | A | R₂ | R₃ | d3K_i |
|---|---|---|---|---|---|---|---|---|
| 826057 | 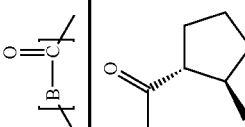 | 2 |  | H | N | 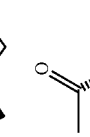 | H | 90.9 |
| 826058 | 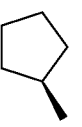 | 2 | 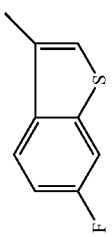 | H | N | 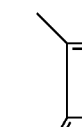 | H | 45.2 |
| 826059 | 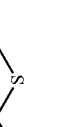 | 2 | 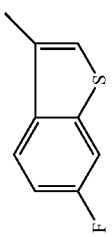 | H | N | 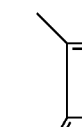 | H | 27.1 |
| 826060 | 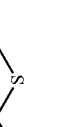 | 2 | 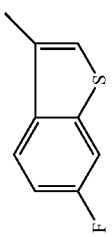 | H | N | 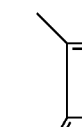 | H | 40.2 |

TABLE 2-continued

| No. | R | n | [B-C]= | $R_1$ | A | $R_2$ | $R_3$ | d3K$_i$ |
|---|---|---|---|---|---|---|---|---|
| 826061 | 6-fluoro-3-methylbenzothiophene | 2 | acetyl-(2-methylcyclopentyl) | H | N | —CH$_2$-(2,5-dimethoxyphenyl) | H | |
| 826062 | 6-fluoro-3-methylbenzothiophene | 2 | acetyl-(2-methylcyclopentyl) | H | N | 8-methyl-tetrahydronaphthyl | H | |
| 826063 | 6-fluoro-3-methylbenzothiophene | 2 | acetyl-(2-methylcyclopentyl) | H | N | —CH$_2$-(benzo[1,3]dioxol-5-yl) | H | |
| 826064 | 6-fluoro-3-methylbenzothiophene | 2 | acetyl-(2-methylcyclopentyl) | H | N | 3-methylpyridyl | H | |

TABLE 2-continued

| No. | R | n | [structure] | R₁ | A | R₂ | R₃ | d3K₁ |
|---|---|---|---|---|---|---|---|---|
| 826086 | 3-CF₃-benzothiophene | 2 | trans-2-methylcyclohexyl acetyl | H | N | -CH₂-C₆H₄-4-N(CH₃)₂ | H | 103 |
| 826092 | 3-CF₃-benzothiophene | 2 | trans-2-methylcyclohexyl acetyl | H | N | -CH₂-C₆H₄-3-CH₃ | H | 293 |
| 826098 | 3-CF₃-benzothiophene | 2 | trans-2-methylcyclohexyl acetyl | H | N | -CH₂-(3,4-methylenedioxyphenyl) | H | 451 |
| 826100 | 3-CF₃-benzothiophene | 2 | trans-2-methylcyclohexyl acetyl | H | N | 3-pyridyl | H | 193 |

TABLE 2-continued

| No. | R | n | [B]— | R₁ | A | R₂ | R₃ | d3K₁ |
|---|---|---|---|---|---|---|---|---|
| 826102 | 3-methyl-6-CF₃-benzothiophene | 2 | cyclohexyl-acetyl (CH₂) | H | N | 2-ethyl-benzimidazole | H | 210 |
| 826104 | 3-methyl-6-CF₃-benzothiophene | 2 | cyclohexyl-acetyl (CH₂) | H | N | 4-(N,N-dimethylamino)benzyl | H | 16.8 |
| 826105 | 3-methyl-6-CF₃-benzothiophene | 2 | cyclohexyl-acetyl (CH₂) | H | N | cyclopropyl | H | 690 |
| 826106 | 3-methyl-6-CF₃-benzothiophene | 2 | cyclohexyl-acetyl (CH₂) | H | N | benzyl | H | 230 |

TABLE 2-continued
| No. | R | n | B-C | R1 | A | R2 | R3 | d3K1 |
|---|---|---|---|---|---|---|---|---|
| 826108 | 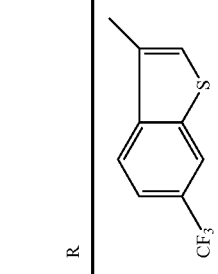 | 2 |  | H | N | 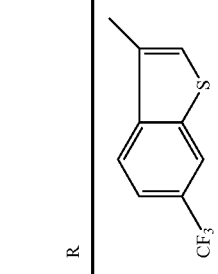 | H | 100 |
| 826113 |  | 2 | 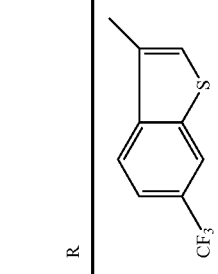 | H | N | 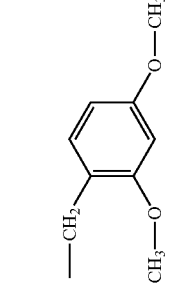 | H | 200 |
| 826114 | 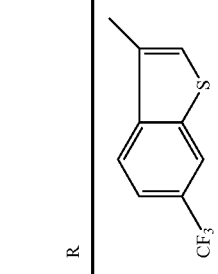 | 2 | 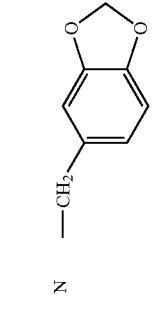 | H | N | | H | 133 |
| 826115 | | 2 | | H | N | | H | 72.3 |

TABLE 2-continued
| No. | R | n | B | R₁ | A | R₂ | R₃ | d3K₁ |
|---|---|---|---|---|---|---|---|---|
| 826616 | 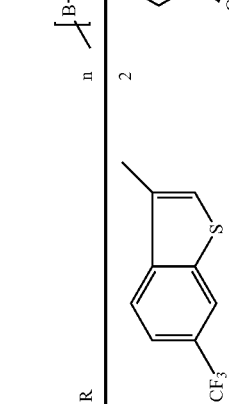 | 2 |  | H | N | 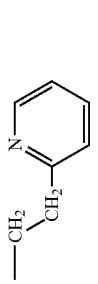 | H | 59.9 |
| 826617 | 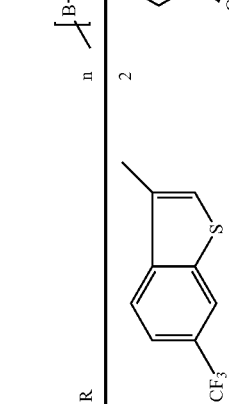 | 2 |  | H | N | 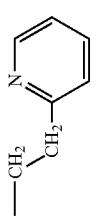 | H | 241 |
| 826118 | 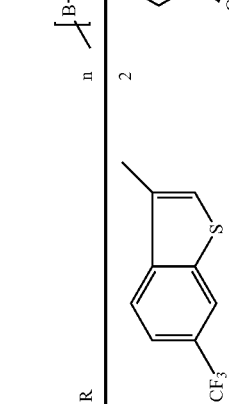 | 2 |  | H | N | 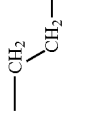 | H | 568 |
| 826120 | 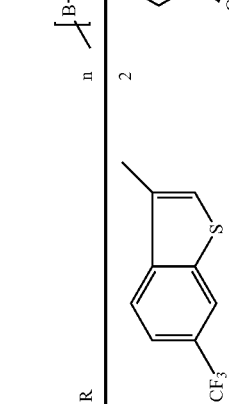 | 2 |  | H | N | 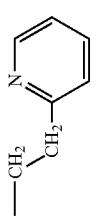 | H | 487 |

TABLE 2-continued

| No. | R | n | [B-C] | R₁ | A | R₂ | R₃ | d3K_i |
|---|---|---|---|---|---|---|---|---|
| 826121 | 3-methyl-6-CF₃-benzothiophene | 2 | trans-2-methylcyclohexyl acetyl | H | N | cyclopropyl | H | 502 |
| 826122 | 3-methyl-6-CF₃-benzothiophene | 2 | trans-2-methylcyclohexyl acetyl | H | N | furan-2-ylmethyl | H | 130 |
| 816592 | 3-methyl-6-CF₃-benzothiophene | 2 | (1S,2S)-2-methylcyclopropyl acetyl | H | N | trans-4-hydroxycyclohexyl | H | 11 |
| 816593 | 3-methyl-6-CF₃-benzothiophene | 2 | (1S,2S)-2-methylcyclopropyl acetyl | H | N | trans-4-(hydroxymethyl)cyclohexyl | H | 7.47 |

TABLE 2-continued

| No. | R | n | B | R₁ | A | R₂ | R₃ | d3K₁ |
|---|---|---|---|---|---|---|---|---|
| 827173 | 3-Cl-phenyl | 2 | (1S,2R)-2-methylcyclopropyl C(=O) | H | N | trans-4-methylcyclohexyl | H | 2.78 |
| 827174 | 4-CH₃-phenyl | 2 | (1S,2R)-2-methylcyclopropyl C(=O) | H | N | trans-4-methylcyclohexyl | H | 8.7 |
| 827176 | 2-CH₃-phenyl-O-CH₂CH₃ | 2 | (1S,2R)-2-methylcyclopropyl C(=O) | H | N | trans-4-methylcyclohexyl | H | 1.18 |
| 827177 | 2-Cl-phenyl-CH₃ | 2 | (1S,2R)-2-methylcyclopropyl C(=O) | H | N | trans-4-methylcyclohexyl | H | 1 |
| 827178 | 4-Cl-phenyl | 2 | (1S,2R)-2-methylcyclopropyl C(=O) | H | N | trans-4-methylcyclohexyl | H | 12.4 |

TABLE 2-continued

| No. | R | n | [structure at R₁ position] | R₁ | A | R₂ | R₃ | d3K_i |
|---|---|---|---|---|---|---|---|---|
| 827179 | 2-methoxyphenyl (with CH₃O) | 2 | cyclopropyl-acetyl (trans, CH₂-CH₃) | H | N | trans-4-methylcyclohexyl | H | 1.04 |
| 827180 | 3-methylphenyl | 2 | cyclopropyl-acetyl (trans, CH₂-CH₃) | H | N | trans-4-methylcyclohexyl | H | 2.47 |
| 827181 | 3-CF₃, 4-Cl-phenyl | 2 | cyclopropyl-acetyl (trans, CH₂-CH₃) | H | N | trans-4-methylcyclohexyl | H | 97.2 |
| 827182 | 5-CF₃, 2-methylpyridyl | 2 | cyclopropyl-acetyl (trans, CH₂-CH₃) | H | N | trans-4-methylcyclohexyl | H | 73 |
| 827183 | 3-CF₃, 2-methylpyridyl | 2 | cyclopropyl-acetyl (trans, CH₂-CH₃) | H | N | trans-4-methylcyclohexyl | H | 3.29 |

TABLE 2-continued

| No. | R | n | [B-C]=O | R₁ | A | R₂ | R₃ | d3K_i |
|---|---|---|---|---|---|---|---|---|
| 827185 | 3,4-diCl-phenyl | 2 | cyclopropyl-CH₂-CH₃ | H | N | trans-4-methylcyclohexyl | H | 4.89 |
| 827186 | 2,5-diMe-phenyl | 2 | cyclopropyl-CH₂-CH₃ | H | N | trans-4-methylcyclohexyl | H | 8.21 |
| 827187 | 2-methylpyrazinyl | 2 | cyclopropyl-CH₂-CH₃ | H | N | trans-4-methylcyclohexyl | H | 10.6 |
| 827189 | 2-methylfuryl | 2 | cyclopropyl-CH₂-CH₃ | H | N | trans-4-methylcyclohexyl | H | 126 |
| 827190 | 3-CF₃-phenyl | 2 | cyclopropyl-CH₂-CH₃ | H | N | trans-4-methylcyclohexyl | H | 2.42 |

TABLE 2-continued

| No. | R | n | [B-C] | R₁ | A | R₂ | R₃ | d3K₁ |
|---|---|---|---|---|---|---|---|---|
| 827191 | phenyl | 2 | cyclopropyl-CH₂CH₃ acetyl | H | N | 4-methylcyclohexyl | H | 0.724 |
| 827193 | 2,4-dimethylphenyl | 2 | cyclopropyl-CH₂CH₃ acetyl | H | N | 4-methylcyclohexyl | H | 40.6 |
| 827194 | 4-methoxyphenyl | 2 | cyclopropyl-CH₂CH₃ acetyl | H | N | 4-methylcyclohexyl | H | 24.4 |
| 827195 | 3-methoxyphenyl | 2 | cyclopropyl-CH₂CH₃ acetyl | H | N | 4-methylcyclohexyl | H | 8.18 |
| 827175 | 2-pyridyl | 2 | cyclopropyl-CH₂CH₃ acetyl | H | N | 4-methylcyclohexyl | H | 4.0 |

TABLE 2-continued
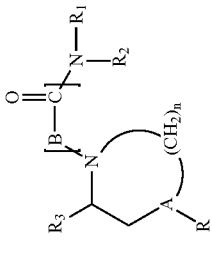
| No. | R | n | B-C | R₁ | A | R₂ | R₃ | d3K$_i$ |
|---|---|---|---|---|---|---|---|---|
| 827197 | 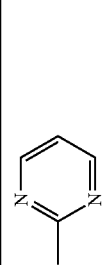 | 2 | 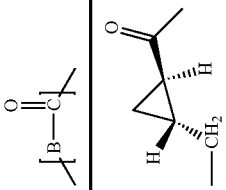 | H | N |  | H | 27.6 |
| 827199 | 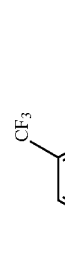 | 2 | 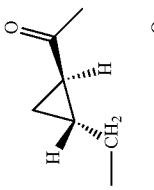 | H | N |  | H | 4.34 |
| 827200 | 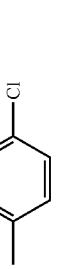 | 2 | 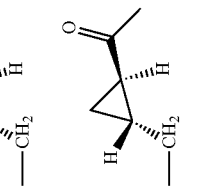 | H | N |  | H | 119 |
| 827205 | 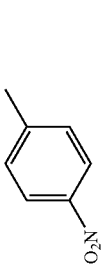 | 2 | 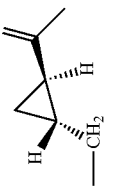 | H | N |  | H | 200 |
| 827206 | 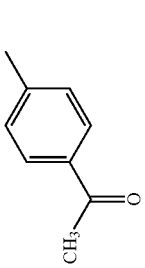 | 2 | 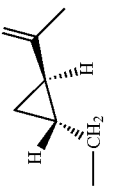 | H | N |  | H | 59.7 |

TABLE 2-continued

| No. | R | n | R₁ | A | R₂ | R₃ | d3K₁ |
|---|---|---|---|---|---|---|---|
| 827212 | 3-Cl-phenyl | 2 | cyclopropyl-acetyl with CH₂ | N | trans-4-methylcyclohexylmethyl | H | 1.2 |
| 827213 | 4-CH₃-phenyl | 2 | cyclopropyl-acetyl with CH₂ | N | trans-4-methylcyclohexylmethyl | H | 11.1 |
| 827215 | 2-(OCH₂CH₃)-phenyl | 2 | cyclopropyl-acetyl with CH₂ | N | trans-4-methylcyclohexylmethyl | H | 0.229 |
| 827216 | 2-Cl-phenyl | 2 | cyclopropyl-acetyl with CH₂ | N | trans-4-methylcyclohexylmethyl | H | 2.16 |
| 827218 | 2-OCH₃-phenyl | 2 | cyclopropyl-acetyl with CH₂ | N | trans-4-methylcyclohexylmethyl | H | 1.22 |

TABLE 2-continued

| No. | R | n | B-C | $R_1$ | A | $R_2$ | $R_3$ | d3$K_i$ |
|---|---|---|---|---|---|---|---|---|
| 827219 | 3-methylphenyl | 2 | cyclopropyl-CH₂ | H | N | 4-methylcyclohexyl-CH₃ | H | 2.63 |
| 817480 (Racemic) | 3-chloro-2-methyl-5-CF₃-pyridyl | 2 | cyclopropyl-CH₂ | H | N | 4-methylcyclohexyl-CH₃ | H | 3.07 |
| 827221 | 2-methyl-5-CF₃-pyridyl | 2 | cyclopropyl-CH₂ | H | N | 4-methylcyclohexyl-CH₃ | H | 99.2 |
| 827222 | 2-methyl-3-CF₃-pyridyl | 2 | cyclopropyl-CH₂ | H | N | 4-methylcyclohexyl-CH₃ | H | 2.09 |
| 828393 | 3,4-dichloro-5-methylphenyl | 2 | cyclopropyl-CH₂ | H | N | 4-methylcyclohexyl-CH₃ | H | 3.45 |

TABLE 2-continued

| No. | R | n | [B-C] | R₁ | A | R₂ | R₃ | d3K_i |
|---|---|---|---|---|---|---|---|---|
| 817570 (Racemic) | 2,4-dimethylphenyl | 2 | cyclopropyl-CH₂- (with H stereochem) | H | N | trans-4-methylcyclohexyl-CH₂-CH₃ | H | 6.24 |
| 827226 | 5-methylpyrazinyl | 2 | cyclopropyl-CH₂- | H | N | trans-4-methylcyclohexyl-CH₂-CH₃ | H | 16.1 |
| 827228 | 2-acetylfuranyl | 2 | cyclopropyl-CH₂- | H | N | trans-4-methylcyclohexyl-CH₂-CH₃ | H | 62 |
| 827229 | 3-(trifluoromethyl)phenyl | 2 | cyclopropyl-CH₂- | H | N | trans-4-methylcyclohexyl-CH₂-CH₃ | H | 1.71 |
| 827230 | phenyl | 2 | cyclopropyl-CH₂- | H | N | trans-4-methylcyclohexyl-CH₂-CH₃ | H | 2.09 |

TABLE 2-continued

| No. | R | n | [B-C(=O)] | R₁ | A | R₂ | R₃ | d3K$_i$ |
|---|---|---|---|---|---|---|---|---|
| 817571 (racemic) | 2,4-dimethylphenyl | 2 | cyclopropyl-CH₂- with H stereochem | H | N | trans-4-ethylcyclohexyl (CH₃) | H | 2.85 |
| 827233 | 4-methoxyphenyl | 2 | cyclopropyl-CH₂- with H stereochem | H | N | trans-4-ethylcyclohexyl (CH₃) | H | 27.7 |
| 827234 | 3-methoxyphenyl | 2 | cyclopropyl-CH₂- with H stereochem | H | N | trans-4-ethylcyclohexyl (CH₃) | H | 3.15 |
| 827235 | 4-fluorophenyl | 2 | cyclopropyl-CH₂- with H stereochem | H | N | trans-4-ethylcyclohexyl (CH₃) | H | 4.49 |
| 827214 | 2-pyridyl | 2 | cyclopropyl-CH₂- with H stereochem | H | N | trans-4-ethylcyclohexyl (CH₃) | H | 6.13 |

TABLE 2-continued

| No. | R | n | | $R_1$ | A | $R_2$ | $R_3$ | $d3K_i$ |
|---|---|---|---|---|---|---|---|---|
| 827236 | 2-methylpyrimidinyl | 2 | cyclopropyl-CH2-C(O)- | H | N | trans-4-methylcyclohexyl-CH2 | H | 12.9 |
| 827238 | 5-CF3, 4-Cl-phenyl (approx) | 2 | cyclopropyl-CH2-C(O)- | H | N | trans-4-methylcyclohexyl-CH2 | H | 2.48 |
| 827239 | 2,6-dimethylphenyl | 2 | cyclopropyl-CH2-C(O)- | H | N | trans-4-methylcyclohexyl-CH2 | H | 90.8 |
| 827244 | 4-methyl-2-nitrophenyl | 2 | cyclopropyl-CH2-C(O)- | H | N | trans-4-methylcyclohexyl-CH2 | H | 197 |
| 827245 | 4-methylphenyl-C(O)-CH3 | 2 | cyclopropyl-CH2-C(O)- | H | N | trans-4-methylcyclohexyl-CH2 | H | 43 |

TABLE 2-continued

| No. | R | n | R₁ | A | R₂ | R₃ | d3K_i |
|---|---|---|---|---|---|---|---|
| 818675 (Racemic) | 2-CH₃-phenyl | 2 | acetyl-cyclopropyl-CH₂- | N | trans-4-methylcyclohexyl-CH₂- (CH₃) | H | 0.771 |
| 817478 (Racemic) | 2-CH₃-phenyl | 2 | acetyl-cyclopropyl-CH₂- | N | trans-4-methylcyclohexyl- (CH₃) | H | 1.46 |

| CMPD NUMBER | R | n | [B-C(=O)] | A | R₁R₂N | R₃ | d3K$_i$ |
|---|---|---|---|---|---|---|---|
| 826811 | 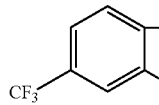 CF₃-benzothiophene-3-yl | 2 | 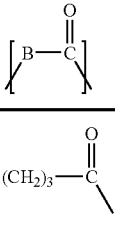 (CH₂)₃C(=O) | N | 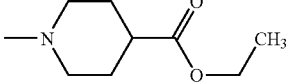 N-methylpiperidine-4-carboxylic acid ethyl ester | H | 40.4 |
| 826816 | 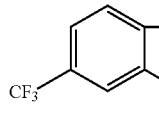 CF₃-benzothiophene-3-yl | 2 | 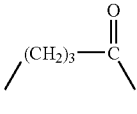 (CH₂)₃C(=O) | N | 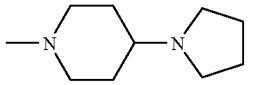 1-methyl-4-(pyrrolidin-1-yl)piperidine | H | 26.3 |
| 826817 | 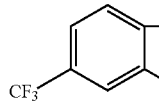 CF₃-benzothiophene-3-yl | 2 | 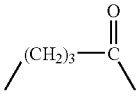 (CH₂)₃C(=O) | N | 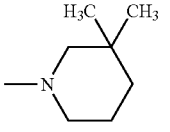 1,3,3-trimethylpiperidine | H | 20 |
| 826818 | 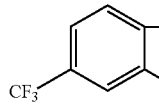 CF₃-benzothiophene-3-yl | 2 | 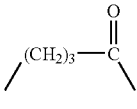 (CH₂)₃C(=O) | N | 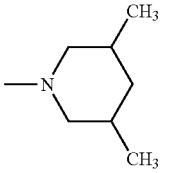 1,3,5-trimethylpiperidine | H | 29.3 |
| 826819 | 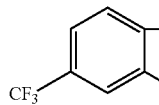 CF₃-benzothiophene-3-yl | 2 | 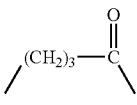 (CH₂)₃C(=O) | N | 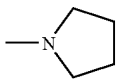 1-methylpyrrolidine | H | 11.6 |
| 826822 | 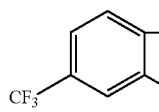 CF₃-benzothiophene-3-yl | 2 | 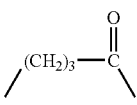 (CH₂)₃C(=O) | N | 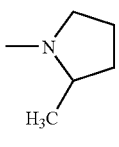 1,2-dimethylpyrrolidine | H | 2.79 |
| 826823 | 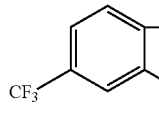 CF₃-benzothiophene-3-yl | 2 | 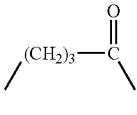 (CH₂)₃C(=O) | N | 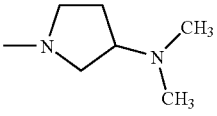 1-methyl-3-(dimethylamino)pyrrolidine | H | 19 |
| 826831 | 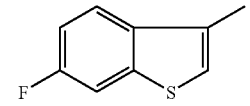 F-benzothiophene-3-yl | 3 | 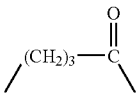 (CH₂)₃C(=O) | N | 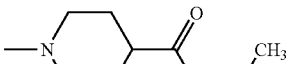 N-methylpiperidine-4-carboxylic acid ethyl ester | H | 2.55 |
| 826832 | 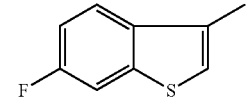 F-benzothiophene-3-yl | 3 | 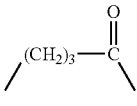 (CH₂)₃C(=O) | N | 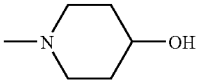 1-methyl-4-hydroxypiperidine | H | 16.1 |
| 826833 | 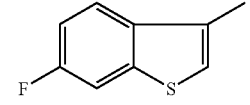 F-benzothiophene-3-yl | 3 | 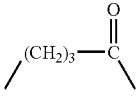 (CH₂)₃C(=O) | N | 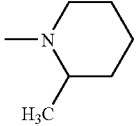 1,2-dimethylpiperidine | H | 0.872 |
| 826834 | 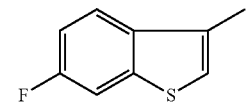 F-benzothiophene-3-yl | 3 | 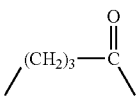 (CH₂)₃C(=O) | N | 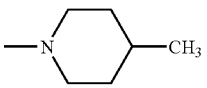 1,4-dimethylpiperidine | H | 8.01 |

-continued
| CMPD NUMBER | R | n | [B—C(=O)]  | A | R₁R₂N | R₃ | d3K$_i$ |
|---|---|---|---|---|---|---|---|
| 826835 | 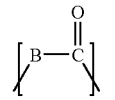 | 3 | 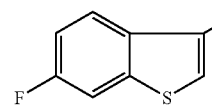 | N | 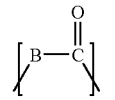 | H | 2.12 |
| 826836 | 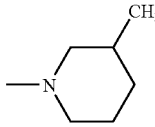 | 3 | 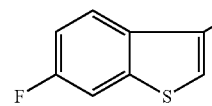 | N | 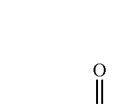 | H | 2.23 |
| 826837 | 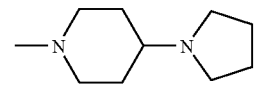 | 3 | 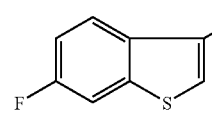 | N |  | H | 8.8 |
| 826838 | 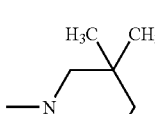 | 3 | 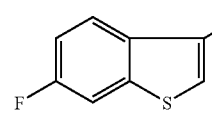 | N | 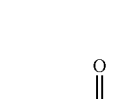 | H | 14.6 |
| 826839 | 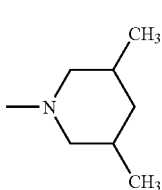 | 3 | 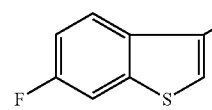 | N | 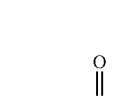 | H | 9.37 |
| 826842 | 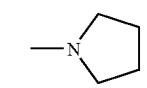 | 3 | 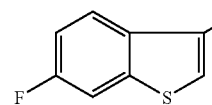 | N |  | H | 3.66 |
| 826843 | 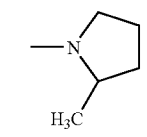 | 3 | 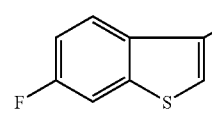 | N |  | H | 126 |
| 826851 | 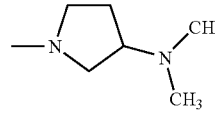 | 2 | 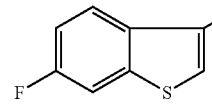 | N | 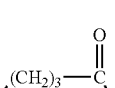 | H | 2.77 |
| 826852 | 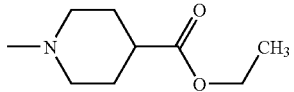 | 2 | 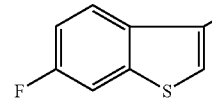 | N | 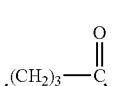 | H | 3.54 |
| 826853 |  | 2 | 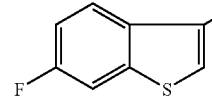 | N | 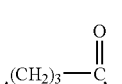 | H | 0.128 |
| 826854 | 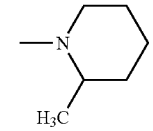 | 2 | 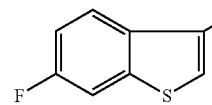 | N | 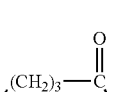 | H | 0.116 |

-continued

| CMPD NUMBER | R | n | [B—C(=O)] | A | R₁R₂N | R₃ | d3K$_i$ |
|---|---|---|---|---|---|---|---|
| 826855 | 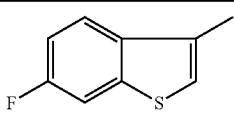 6-F-benzothiophen-3-yl | 2 | 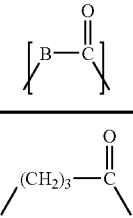 -(CH₂)₃-C(=O)- | N | 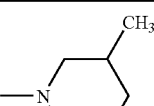 1,3-dimethylpiperidine | H | 0.58 |
| 826856 | 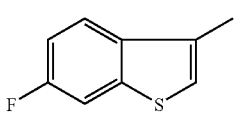 6-F-benzothiophen-3-yl | 2 | 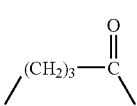 -(CH₂)₃-C(=O)- | N | 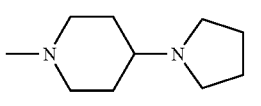 1-methyl-4-(pyrrolidin-1-yl)piperidine | H | 1.8 |
| 826857 | 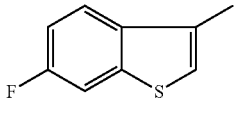 6-F-benzothiophen-3-yl | 2 | 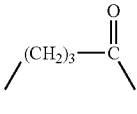 -(CH₂)₃-C(=O)- | N | 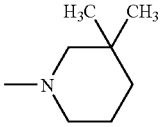 1,3,3-trimethylpiperidine | H | 0.817 |
| 826858 | 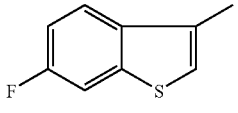 6-F-benzothiophen-3-yl | 2 | 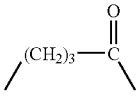 -(CH₂)₃-C(=O)- | N | 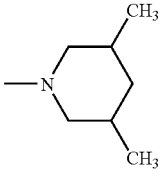 1,3,5-trimethylpiperidine | H | 3.71 |
| 826859 | 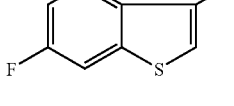 6-F-benzothiophen-3-yl | 2 | 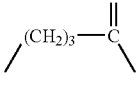 -(CH₂)₃-C(=O)- | N | 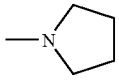 1-methylpyrrolidine | H | 3.53 |
| 826862 | 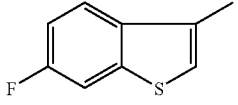 6-F-benzothiophen-3-yl | 2 | 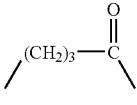 -(CH₂)₃-C(=O)- | N | 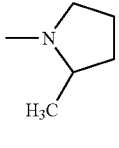 1,2-dimethylpyrrolidine | H | 0.951 |
| 825868 | 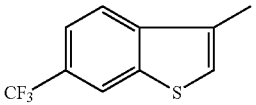 6-CF₃-benzothiophen-3-yl | 2 | 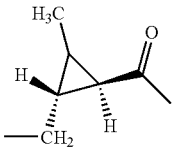 methyl-ethyl-cyclopropyl ketone | N | 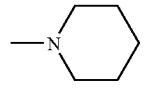 1-methylpiperidine | H | 13 |
| 825891 | 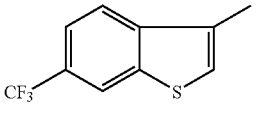 6-CF₃-benzothiophen-3-yl | 2 | 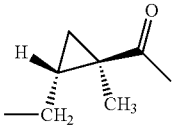 methyl-ethyl-cyclopropyl ketone | N | 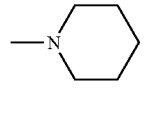 1-methylpiperidine | H | 118 |
| 826081 | 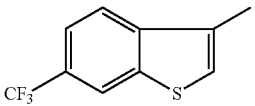 6-CF₃-benzothiophen-3-yl | 2 | 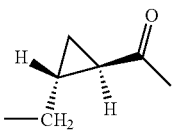 ethyl-cyclopropyl ketone | N | 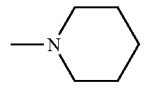 1-methylpiperidine | H | 18.6 |
| 826657 | 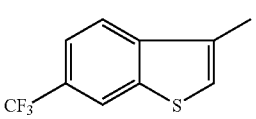 6-CF₃-benzothiophen-3-yl | 2 | 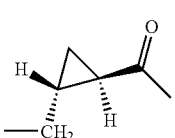 ethyl-cyclopropyl ketone | N | 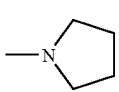 1-methylpyrrolidine | H | 14 |

-continued
| CMPD NUMBER | R | n | [B-C] with O | A | R₁R₂N | R₃ | d3Kᵢ |
|---|---|---|---|---|---|---|---|
| 826659 | 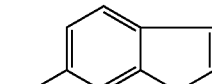 | 2 | 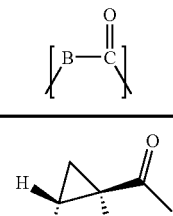 | N | 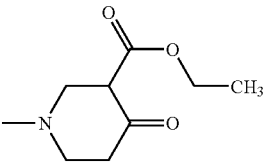 | H | 140 |
| 826660 |  | 2 | 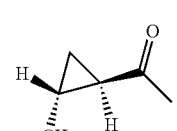 | N | 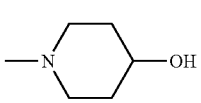 | H | 53 |
| 826661 | 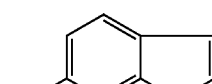 | 2 | 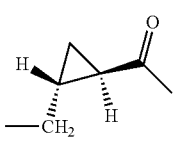 | N | 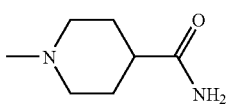 | H | 25 |
| 826662 | 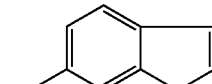 | 2 | 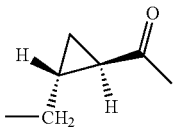 | N | 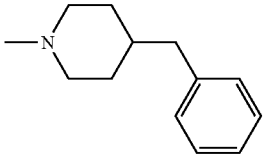 | H | 69 |
| 826664 | 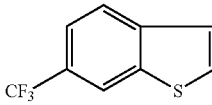 | 2 | 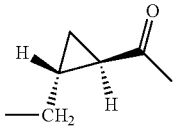 | N | 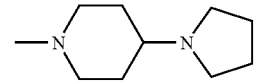 | H | 9.4 |
| 826896 | 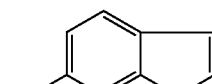 | 2 | 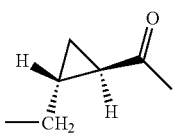 | N | 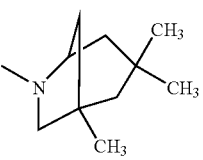 | H | 89.5 |
| 826899 | 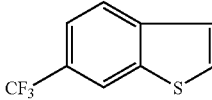 | 2 | 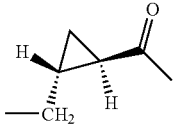 | N | 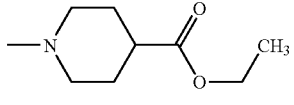 | H | 45.5 |
| 826900 | 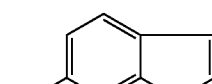 | 2 | 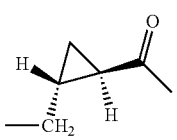 | N | 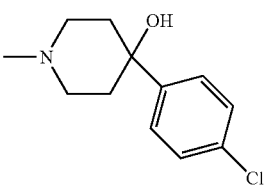 | H | 181 |
| 826901 | 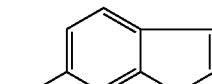 | 2 | 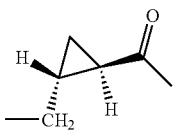 | N | 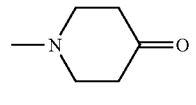 | H | 42.4 |

-continued
| CMPD NUMBER | R | n | B-C (with O) | A | R₁R₂N | R₃ | d3K$_i$ |
|---|---|---|---|---|---|---|---|
| 826902 | 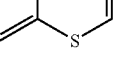 | 2 | 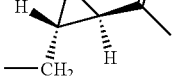 | N | 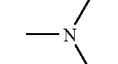 | H | 13.1 |
| 826903 | 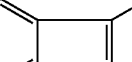 | 2 |  | N | 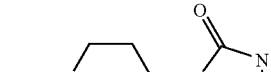 | H | 7.47 |
| 826904 |  | 2 |  | N |  | H | 39.4 |
| 826905 |  | 2 |  | N | 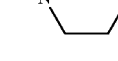 | H | 14.5 |
| 826906 |  | 2 | 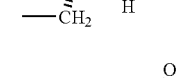 | N | 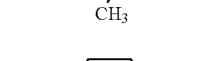 | H | 39.5 |
| 826907 |  | 2 | 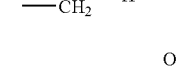 | N |  | H | 18.8 |
| 826908 |  | 2 | 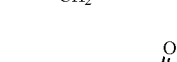 | N | 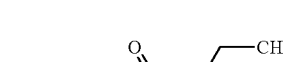 | H | 7.06 |
| 826909 |  | 2 |  | N | 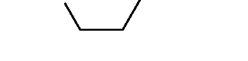 | H | 28.9 |
| 826910 |  | 2 | 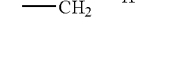 | N | 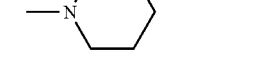 | H | 17.5 |

-continued
| CMPD NUMBER | R | n | [B—C(=O)] | A | R₁R₂N | R₃ | d3$K_i$ |
|---|---|---|---|---|---|---|---|
| 826911 | 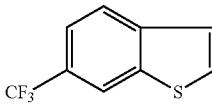 | 2 | 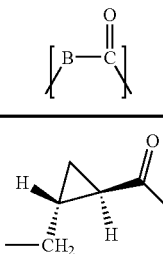 | N | 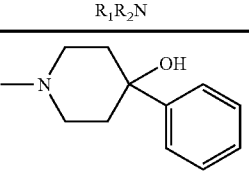 | H | 93 |
| 826912 | 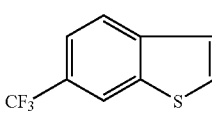 | 2 | 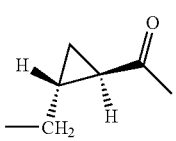 | N | 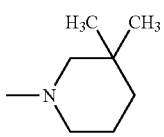 | H | 58.5 |
| 826913 | 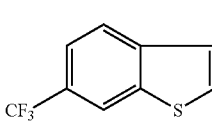 | 2 | 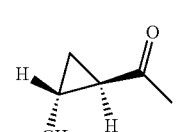 | N | 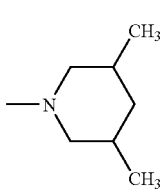 | H | 86.1 |
| 826914 | 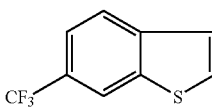 | 2 | 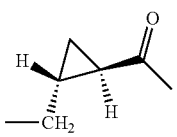 | N | 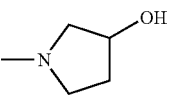 | H | 101 |
| 826916 | 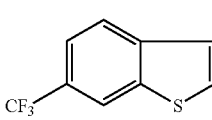 | 2 | 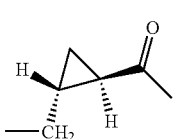 | N | 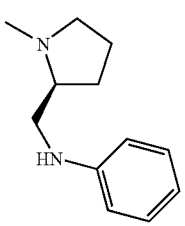 | H | 157 |
| 826917 | 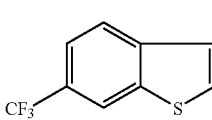 | 2 | 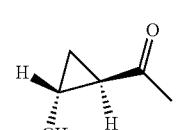 | N | 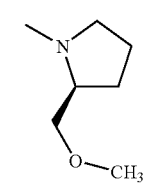 | H | 196 |
| 826918 | 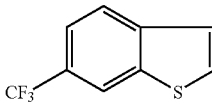 | 2 | 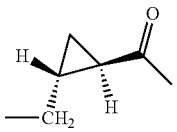 | N | 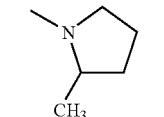 | H | 30.3 |
| 826919 | 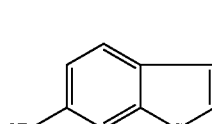 | 2 | 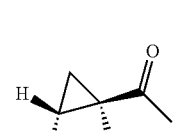 | N | 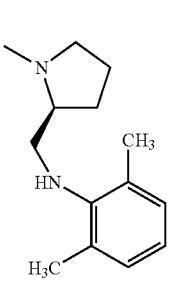 | H | 329 |

-continued
| CMPD NUMBER | R | n | [B—C(=O)] | A | R₁R₂N | R₃ | d3K$_i$ |
|---|---|---|---|---|---|---|---|
| 826920 | 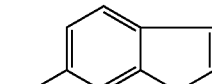 | 2 | 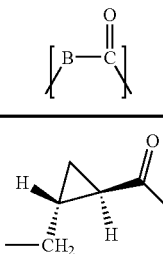 | N | 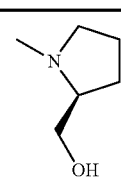 | H | 67.6 |
| 826921 | 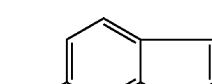 | 2 |  | N | 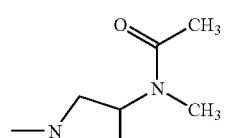 | H | 183 |
| 826922 | 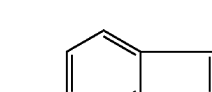 | 2 |  | N | 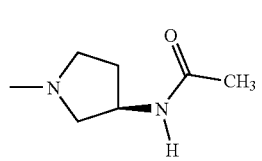 | H | 183 |
| 826923 |  | 2 |  | N | 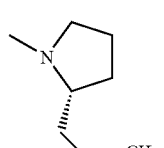 | H | 141 |
| 826924 | 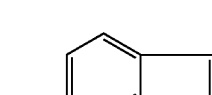 | 2 |  | N | 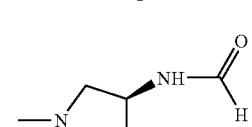 | H | 256 |
| 826926 |  | 2 |  | N | 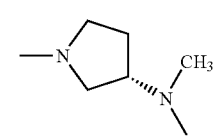 | H | 86.5 |
| 826928 | 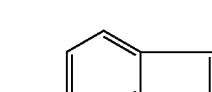 | 2 |  | N | 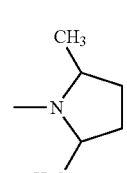 | H | 11.2 |
| 826683 | 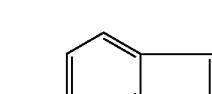 | 3 |  | N | 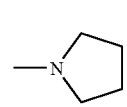 | H | 3.7 |
| 826685 |  | 3 |  | N | 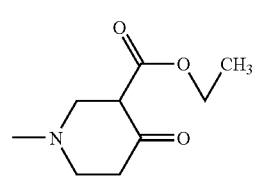 | H | 154 |

-continued
| CMPD NUMBER | R | n | 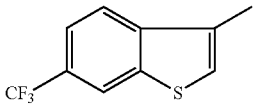 | A | $R_1R_2N$ | $R_3$ | $d3K_i$ |
|---|---|---|---|---|---|---|---|
| 826686 | 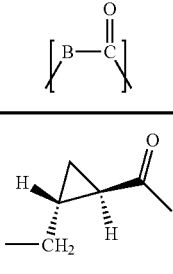 | 3 |  | N | 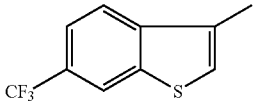 | H | 26 |
| 826687 | 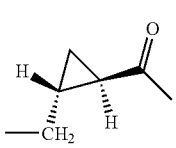 | 3 | 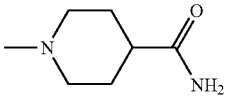 | N | 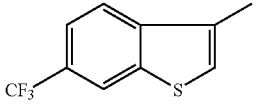 | H | 132 |
| 826688 | 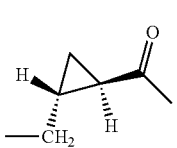 | 3 | 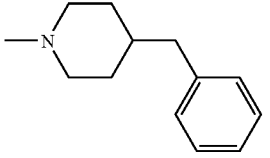 | N | 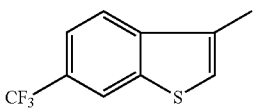 | H | 217 |
| 826689 | 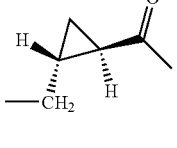 | 3 | 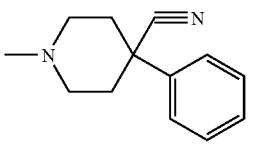 | N | 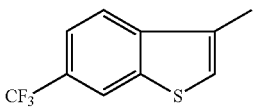 | H | 674 |
| 826691 | 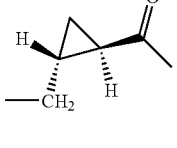 | 3 | 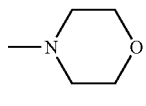 | N | 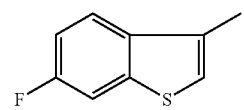 | H | 35 |
| 826669 | 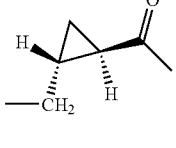 | 2 | 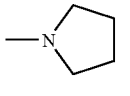 | N | 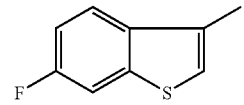 | H | 0.24 |
| 826671 | 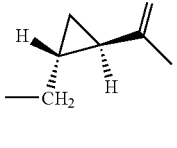 | 2 | 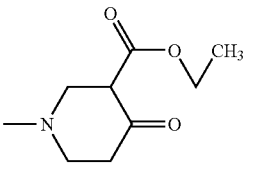 | N | 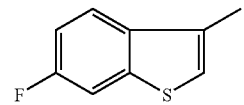 | H | 6.8 |
| 826672 | 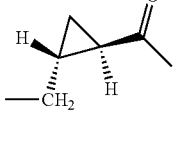 | 2 | 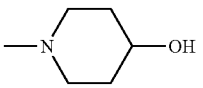 | N | 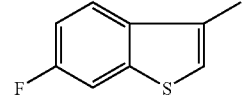 | H | 0.64 |
| 826673 | 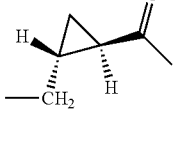 | 2 | 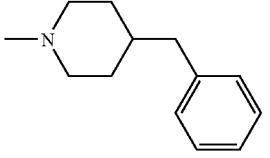 | N |  | H | 7.9 |

-continued
| CMPD NUMBER | R | n | [B—C(=O)] | A | R₁R₂N | R₃ | d3K$_i$ |
|---|---|---|---|---|---|---|---|
| 826674 | 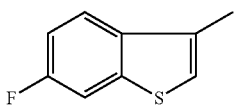 | 2 | 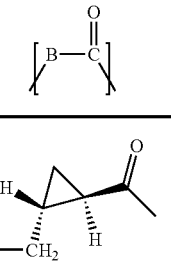 | N | 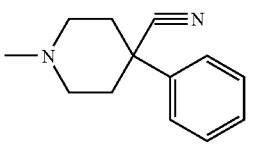 | H | 48 |
| 826675 | 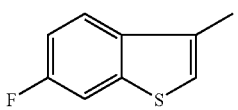 | 2 | 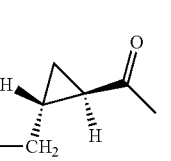 | N | 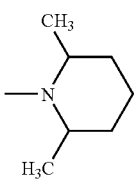 | H | 8 |
| 826676 | 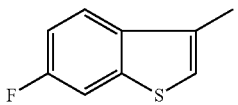 | 2 | 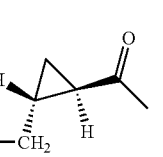 | N | 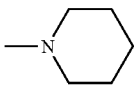 | H | 2 |
| 826871 | 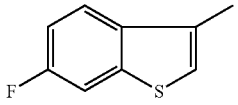 | 3 | 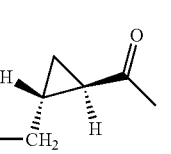 | N | 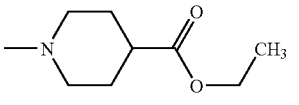 | H | 10.7 |
| 826872 | 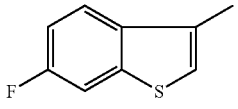 | 3 | 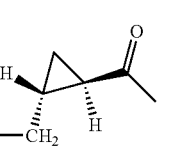 | N | 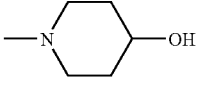 | H | 3.66 |
| 826873 | 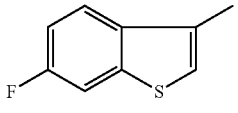 | 3 | 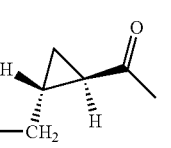 | N | 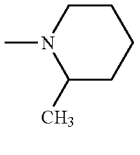 | H | 1.31 |
| 826874 | 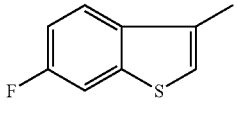 | 3 | 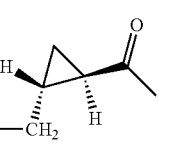 | N | 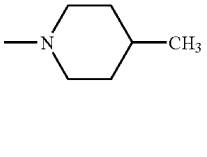 | H | 1.72 |
| 826875 | 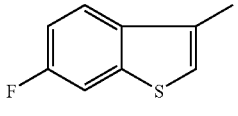 | 3 | 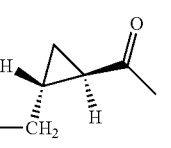 | N | 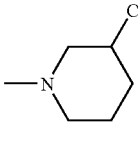 | H | 2.79 |
| 826876 | 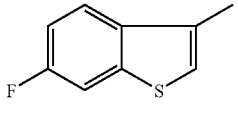 | 3 | 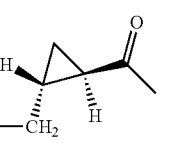 | N | 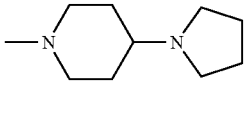 | H | 2.72 |

-continued
| CMPD NUMBER | R | n | [B-C(=O)] | A | R₁R₂N | R₃ | d3K$_i$ |
|---|---|---|---|---|---|---|---|
| 826877 | 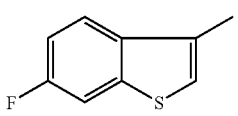 | 3 | 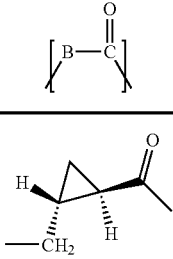 | N | 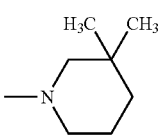 | H | 4.72 |
| 826878 | 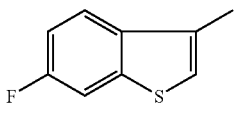 | 3 | 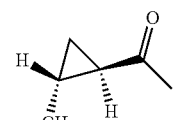 | N | 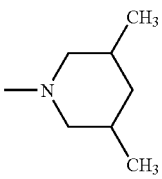 | H | 7.95 |
| 826879 | 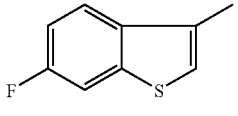 | 3 | 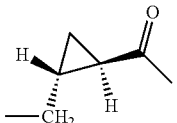 | N | 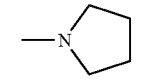 | H | 1.59 |
| 826882 | 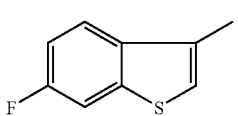 | 3 | 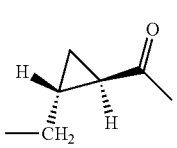 | N | 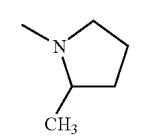 | H | 2.93 |
| 826883 | 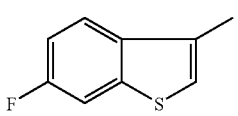 | 3 | 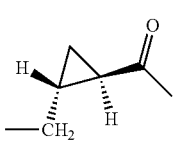 | N | 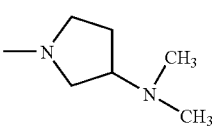 | H | 13.4 |
| 826056 | 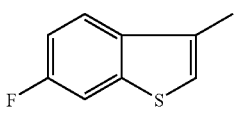 | 2 | 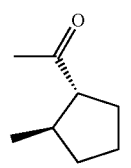 | N | 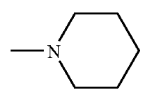 | H | 5.4 |
| 826119 | 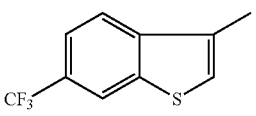 | 2 | 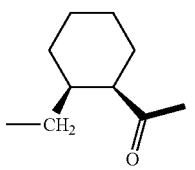 | N | 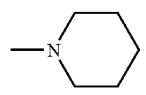 | H | 219 |
| 826812 | 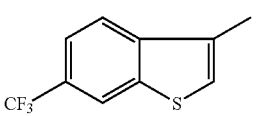 | 2 | 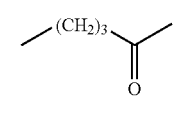 | N | 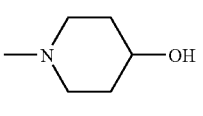 | H | 7.29 |
| 826813 | 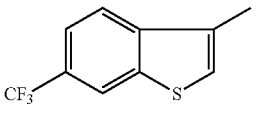 | 2 | 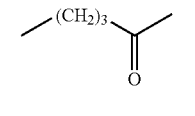 | N | 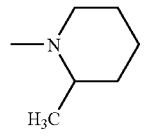 | H | 5.16 |

-continued
| CMPD NUMBER | R | n | B | A | R₁R₂N | R₃ | d3Kᵢ |
|---|---|---|---|---|---|---|---|
| 826814 | 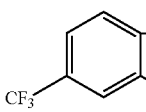 | 2 | 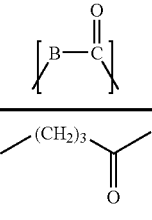 | N |  | H | 10.3 |
| 826815 | 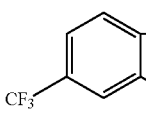 | 2 | 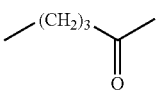 | N | 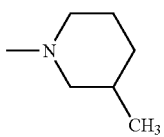 | H | 31.7 |
| 826863 | 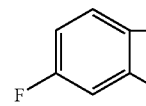 | 2 | 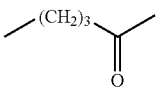 | N | 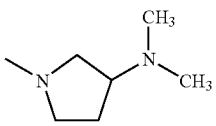 | H | 26.6 |
| 827064 | 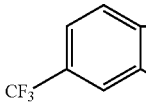 | 2 | 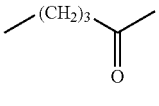 | N | 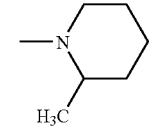 | PhCH₂ | 245 |
| 827065 | 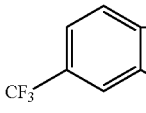 | 2 | 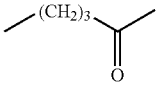 | N | 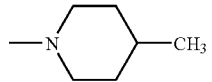 | PhCH₂ | 168 |
| 827066 | 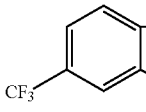 | 2 | 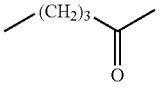 | N | 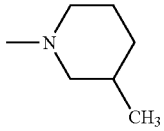 | PhCH₂ | 209 |
| 827067 | 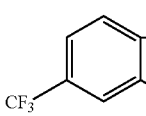 | 2 | 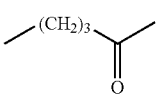 | N | 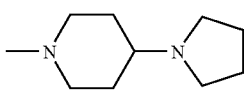 | PhCH₂ | 268 |
| 827068 | 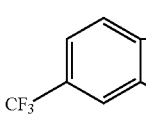 | 2 | 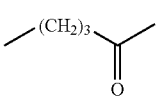 | N | 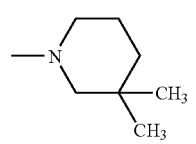 | PhCH₂ | 197 |
| 827063 | 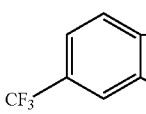 | 2 | 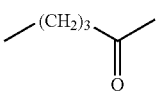 | N | 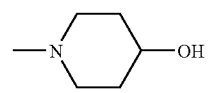 | PhCH₂ | 373 |
| 827082 | 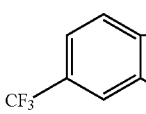 | 2 | 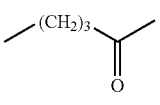 | N | 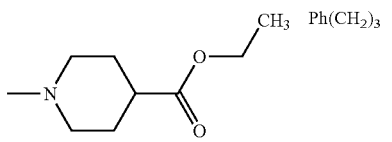 | Ph(CH₂)₃ | 303 |
| 827084 | 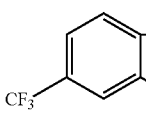 | 2 | 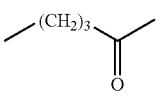 | N | 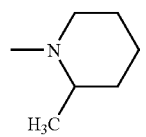 | Ph(CH₂)₃ | 266 |

-continued

| CMPD NUMBER | R | n | [B—C(=O)] | A | R₁R₂N | R₃ | d3$K_i$ |
|---|---|---|---|---|---|---|---|
| 827092 | 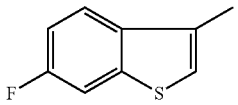 | 2 | 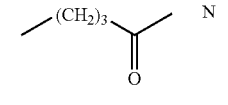 —(CH₂)₃—C(=O)— | N | 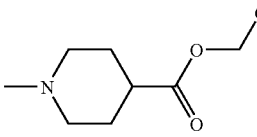 N-methylpiperidine-4-carboxylic acid ethyl ester | PhCH₂ | 316 |
| 827093 | 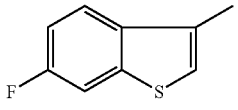 | 2 | 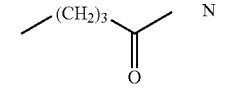 —(CH₂)₃—C(=O)— | N | 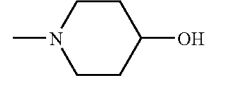 1-methyl-4-hydroxypiperidine | PhCH₂ | 84 |
| 827094 | 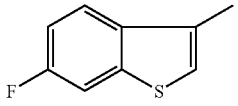 | 2 | 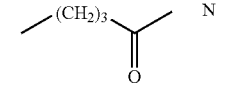 —(CH₂)₃—C(=O)— | N | 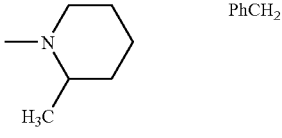 1,2-dimethylpiperidine | PhCH₂ | 34.6 |
| 827095 | 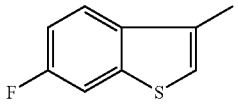 | 2 | 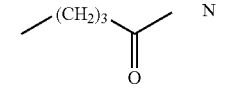 —(CH₂)₃—C(=O)— | N | 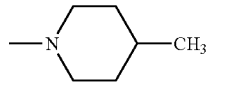 1,4-dimethylpiperidine | PhCH₂ | 37.8 |
| 827096 | 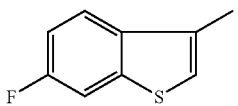 | 2 | 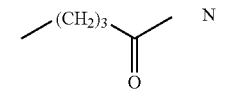 —(CH₂)₃—C(=O)— | N | 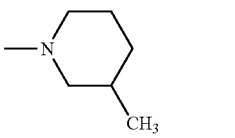 1,3-dimethylpiperidine | PhCH₂ | 44.7 |
| 827097 | 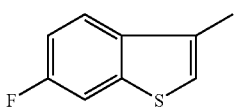 | 2 | 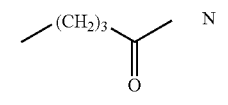 —(CH₂)₃—C(=O)— | N | 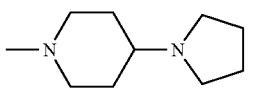 1-methyl-4-pyrrolidinopiperidine | PhCH₂ | 51.5 |
| 827098 | 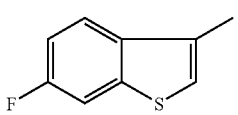 | 2 | 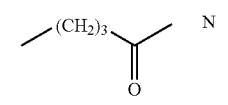 —(CH₂)₃—C(=O)— | N | 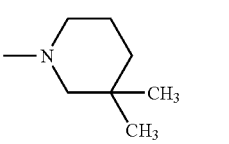 1,3,3-trimethylpiperidine | PhCH₂ | 82.9 |
| 827099 | 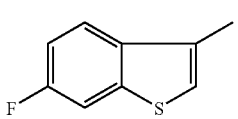 | 2 | 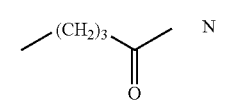 —(CH₂)₃—C(=O)— | N | 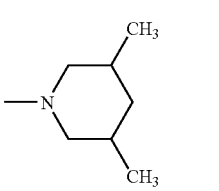 1,3,5-trimethylpiperidine | PhCH₂ | 144 |
| 827100 | 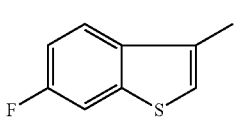 | 2 | 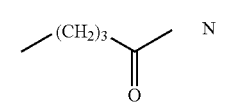 —(CH₂)₃—C(=O)— | N | 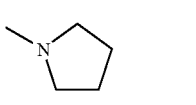 1-methylpyrrolidine | PhCH₂ | 63.5 |
| 827103 | 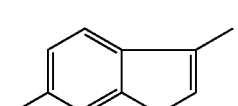 | 2 | 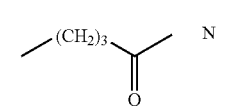 —(CH₂)₃—C(=O)— | N | 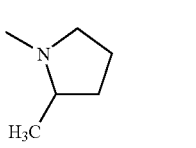 1,2-dimethylpyrrolidine | PhCH₂ | 81.7 |

-continued

| CMPD NUMBER | R | n | [B-C(=O)] A | R₁R₂N | R₃ | d3Kᵢ |
|---|---|---|---|---|---|---|
| 827104 | 6-fluorobenzo[b]thiophen-3-yl | 2 | (CH₂)₃-C(=O) | N | 1-methyl-3-(dimethylamino)pyrrolidine | PhCH₂ | 141 |
| 827112 | 6-fluorobenzo[b]thiophen-3-yl | 2 | (CH₂)₃-C(=O) | N | ethyl 1-methylpiperidine-4-carboxylate | Ph(CH₂)₃ | 126 |
| 827113 | 6-fluorobenzo[b]thiophen-3-yl | 2 | (CH₂)₃-C(=O) | N | 1-methyl-4-hydroxypiperidine | Ph(CH₂)₃ | 95 |
| 827114 | 6-fluorobenzo[b]thiophen-3-yl | 2 | (CH₂)₃-C(=O) | N | 1,2-dimethylpiperidine | Ph(CH₂)₃ | 120 |
| 826690 (racemic) | 6-(trifluoromethyl)benzo[b]thiophen-3-yl | 3 | trans-2-ethylcyclopropyl-C(=O) | N | 1-methyl-4-(pyrrolidin-1-yl)piperidine | H | 83% Inh @ 0.1 nM |

| MDL # | D3 KI (nM) | Chirality | n | X | R1 | R2 | R3 |
|---|---|---|---|---|---|---|---|
| 817274 | 4.49 | Racemic | 1 | N | 4-methyl-6-propyl-2-tert-butylpyrimidin-2-yl | H | N-methyl-trans-4-ethylcyclohexylamine |
| 817275 | 3.34 | Racemic | 1 | N | 4-methyl-6-propyl-2-tert-butylpyrimidin-2-yl | H | N-methyl-trans-4-methylcyclohexylamine |
| 827184 | 237 | Racemic | 1 | N | t-Boc | H | N-methyl-trans-4-methylcyclohexylamine |

-continued

| MDL # | D3 KI (nM) | Chirality | n | X | R1 | R2 | R3 |
|---|---|---|---|---|---|---|---|
| 827192 | 150 | Racemic | 1 | N | 4-MeO-C6H4- | Me | trans-N(Me)-cyclohexyl-CH3 |
| 827202 | 177 | Racemic | 1 | N | —CH2Ph | H | trans-N(Me)-cyclohexyl-CH3 |
| 827209 | 30.4 | Racemic | 1 | CH | —CH2Ph | H | trans-N(Me)-cyclohexyl-CH3 |
| 827211 | 353 | Racemic | 1 | CH | 1-methyl-benzimidazol-2(3H)-one-3-yl | H | trans-N(Me)-cyclohexyl-CH3 |
| 827223 | 159 | Racemic | 1 | N | t-Boc | H | trans-N(Me)-cyclohexyl-CH2CH3 |
| 827226 | 16.1 | Racemic | 1 | N | pyrazin-2-yl | H | trans-N(Me)-cyclohexyl-CH2CH3 |
| 827229 | 1.71 | Racemic | 1 | N | 3-CF3-C6H4- | H | trans-N(Me)-cyclohexyl-CH2CH3 |
| 827231 | 60.6 | Racemic | 1 | N | 4-MeO-C6H4- | CH3 | trans-N(Me)-cyclohexyl-CH2CH3 |
| 827237 | 153 | Racemic | 1 | N | —CH2CH2Ph | H | trans-N(Me)-cyclohexyl-CH2CH3 |
| 827240 | 152 | Racemic | 1 | N | benzo[1,3]dioxol-5-yl-CH2- | H | trans-N(Me)-cyclohexyl-CH2CH3 |

-continued

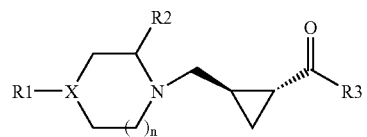

| MDL # | D3 KI (nM) | Chirality | n | X | R1 | R2 | R3 |
|---|---|---|---|---|---|---|---|
| 827241 | 89.5 | Racemic | 1 | N | —CH₂Ph | H | N-cyclohexyl-CH₃ (methylamino, trans-4-ethylcyclohexyl) |
| 827248 | 19.4 | Racemic | 1 | CH | —CH₂Ph | H | N-cyclohexyl-CH₃ |
| 827250 | 45.2 | Racemic | 1 | CH | 3-methyl-2-oxo-benzimidazolyl | H | N-cyclohexyl-CH₃ |
| 828716 | 2.38 | R,R | 1 | N | 6-fluoro-3-methyl-benzothiophenyl | H | 1-methylpiperidin-4-ol |
| 829006DA | 12.4 | R,R | 1 | N | 6-trifluoromethyl-3-methyl-benzothiophenyl | H | N-cyclohexyl-CH₃ |
| 829363 | 63.9 | Racemic | 1 | CH | 6-chloro-3-methyl-benzisoxazolyl | H | N-cyclohexyl-CH₃ |
| 830046 | 16.5 | Racemic | 1 | N | 3-methyl-1-(4-trifluoromethylphenyl)-indazolyl | H | N-cyclohexyl-CH₃ |
| 830112 | 54 | Racemic | 1 | CH | 7-bromo-5-methoxy-2-methyl-benzofuranyl | H | N-cyclohexyl-CH₃ |

-continued

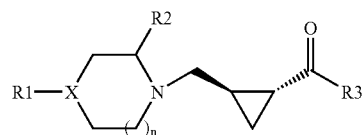

| MDL # | D3 KI (nM) | Chirality | n | X | R1 | R2 | R3 |
|---|---|---|---|---|---|---|---|
| 830114 | 5.42 | Racemic | 1 | N | 3-methyl-1-(2-fluorophenyl)-1H-indazole | H | N-methyl-trans-4-methylcyclohexyl |
| 830116 | 13.1 | Racemic | 1 | N | 3-methyl-1H-indazole | H | N-methyl-trans-4-methylcyclohexyl |
| 830121 | 47.1 | Racemic | 1 | N | 3-methyl-4,5-dihydronaphtho[1,2-c]isoxazole | H | N-methyl-trans-4-methylcyclohexyl |
| 830122 | 67.6 | Racemic | 2 | N | 6-methyl-1H-pyrazolo[3,4-b]pyridine-3-carbonitrile | H | N-methyl-trans-4-ethylcyclohexyl |
| 830123 | 73.8 | Racemic | 2 | N | 3-methyl-4,5-dihydronaphtho[2,1-d]isoxazole | H | N-methyl-trans-4-methylcyclohexyl |
| 830124 | 1.84 | Racemic | 1 | N | 6-chloro-3-methyl-1H-indazole | H | N-methyl-trans-4-methylcyclohexyl |
| 830128 | 69.7 | Racemic | 2 | N | ethyl 6-methylbenzo[b]thiophene-2-carboxylate | H | N-methyl-trans-4-ethylcyclohexyl |

-continued

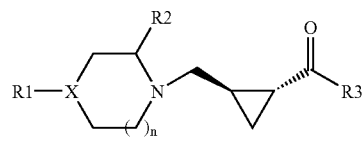

| MDL # | D3 KI (nM) | Chirality | n | X | R1 | R2 | R3 |
|---|---|---|---|---|---|---|---|
| 830129 | 4.16 | Racemic | 1 | N | 6-fluoro-1-phenyl-3-methyl-1H-indazole | H | N-methyl-trans-4-ethylcyclohexyl |
| 830131 | 34.1 | Racemic | 2 | N | 8-methoxy-3-methyl-4,5-dihydronaphtho[1,2-c]isoxazole | H | N-methyl-trans-4-ethylcyclohexyl |
| 830132 | 9.26 | Racemic | 1 | CH | 2-benzylphenyl | H | N-methyl-trans-4-ethylcyclohexyl |
| 830133 | 176 | Racemic | 1 | CH | 1-(4-trifluoromethylphenyl)-3-methyl-1H-indazole | H | N-methyl-trans-4-ethylcyclohexyl |
| 830134 | 0.602 | Racemic | 1 | CH | 6-fluoro-7-methoxy-3-methylbenzo[d]isoxazole | H | N-methyl-trans-4-methylcyclohexyl |
| 830439 | 17.6 | Racemic | 1 | N | 6-methoxy-3-methyl-1H-indazole | H | N-methyl-trans-4-methylcyclohexyl |
| 831147 | 40.8 | S,S | 1 | CH | 2-methylbenzo[b]thiophene | H | N-methyl-trans-4-methylcyclohexyl |

-continued

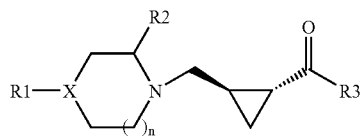

| MDL # | D3 KI (nM) | Chirality | n | X | R1 | R2 | R3 |
|---|---|---|---|---|---|---|---|
| 831148 | 0.454 | R,R | 1 | CH | 2-methylbenzo[b]thiophene | H | N-methyl-(trans-4-methylcyclohexyl) |
| 831226 | 26.7 | R,R | 1 | N | 3-methyl-1-[4-(trifluoromethyl)phenyl]-1H-indazole | H | N-methyl-(trans-4-ethylcyclohexyl) |
| 831269 | 4.08 | R,R | 1 | N | 3-methyl-6-(trifluoromethyl)benzo[b]thiophene | H | N-methyl-3-(1H-imidazol-1-yl)propyl |
| 831270 | 17.8 | R,R | 1 | N | 3-methyl-6-(trifluoromethyl)benzo[b]thiophene | H | —NH—(CH$_2$)$_3$—Ph |
| 831271 | 6.57 | R,R | 1 | N | 3-methyl-6-(trifluoromethyl)benzo[b]thiophene | H | N-methyl-2-(1H-indol-3-yl)ethyl |
| 831309 | 40.6 | R,R | 1 | CH | 6-fluoro-7-methoxy-3-methylbenzo[d]isoxazole | H | N-methyl-3-(1H-imidazol-1-yl)propyl |
| 831310 | 103 | R,R | 1 | CH | 6-fluoro-7-methoxy-3-methylbenzo[d]isoxazole | H | —NH—(CH$_2$)$_3$—Ph |

-continued
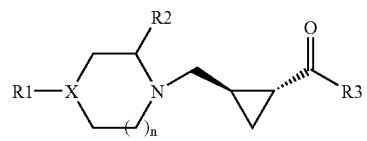
| MDL # | D3 KI (nM) | Chirality | n | X | R1 | R2 | R3 |
|---|---|---|---|---|---|---|---|
| 831311 | 38.7 | R,R | 1 | CH | 3-methyl-1-(4-trifluoromethylphenyl)-1H-indazol-1-yl | H | N-methyl-3-(1H-imidazol-1-yl)propylamino |
| 831312 | 214 | R,R | 1 | CH | 3-methyl-1-(4-trifluoromethylphenyl)-1H-indazol-1-yl | H | —NH—(CH$_2$)$_3$—Ph |
| 831313 | 134 | R,R | 1 | N | 5-methoxy-3-methyl-1-(4-trifluoromethylphenyl)-1H-indazol-1-yl | H | N-methyl-3-(1H-imidazol-1-yl)propylamino |
| 831314 | 133 | R,R | 1 | N | 5-methoxy-3-methyl-1-(4-trifluoromethylphenyl)-1H-indazol-1-yl | H | —NH—(CH$_2$)$_3$—Ph |

-continued

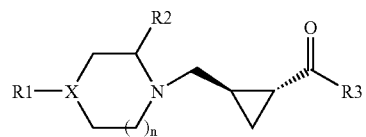

| MDL # | D3 KI (nM) | Chirality | n | X | R1 | R2 | R3 |
|---|---|---|---|---|---|---|---|
| 831360 | 17.1 | S,S | 1 | CH | 3-methyl-6-fluoro-7-methoxy-benzisoxazole | H | N-methyl-trans-4-methylcyclohexyl |
| 831361 | 1.75 | R,R | 1 | CH | 3-methyl-6-fluoro-7-methoxy-benzisoxazole | H | N-methyl-trans-4-methylcyclohexyl |
| 831488 | 0.725 | R,R | 1 | CH | 2-methylbenzothiophene | H | N-methyl-3-(imidazol-1-yl)propyl |
| 831489 | 16.9 | R,R | 1 | CH | 2-methylbenzothiophene | H | —NH—$(CH_2)_3$—Ph |
| 831491 | 0.187 | R,R | 1 | N | 3-methyl-6-trifluoromethyl-benzothiophene | H | N-methyl-3-(piperidin-1-yl)propyl |
| 831492 | 0.432 | R,R | 1 | N | 3-methyl-6-trifluoromethyl-benzothiophene | H | N-methyl-3-(morpholin-4-yl)propyl |
| 831768 | 0.904 | R,R | 1 | N | 5-methoxy-1,3-dimethyl-indazole | H | N-methyl-trans-4-methylcyclohexyl |
| 831808 | 3.84 | R,R | 1 | N | 5-methoxy-1,3-dimethyl-indazole | H | N-methyl-3-(imidazol-1-yl)propyl |
| 831809 | 0.0284 | R,R | 1 | CH | 3-methyl-7-methoxy-benzisoxazole | H | N-methyl-trans-4-methylcyclohexyl |

-continued
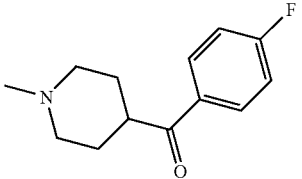
| MDL # | D3 KI (nM) | Chirality | n | X | R1 | R2 | R3 |
|---|---|---|---|---|---|---|---|
| 831810 | 124 | R,R | 1 | CH | 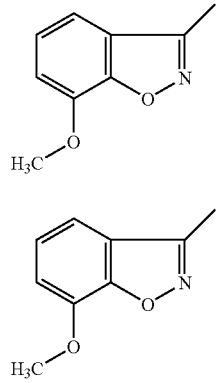 | H | 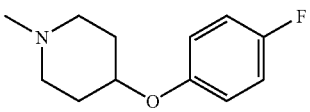 |
| 831878 | 189 | R,R | 1 | CH | 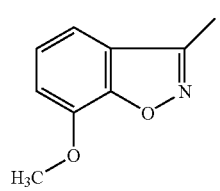 | H | 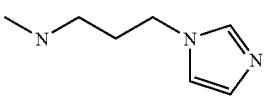 |
| 831880 | 100 | R,R | 1 | CH | 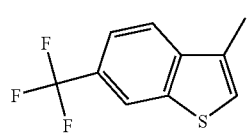 | H | 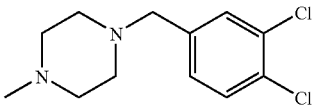 |
| 831881 | 109 | R,R | 1 | N | 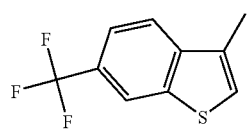 | H | 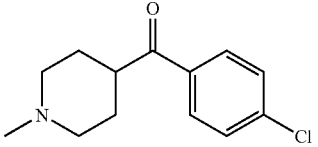 |
| 831882 | 57.3 | R,R | 1 | N | 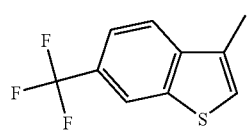 | H | 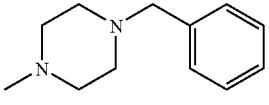 |
| 831883 | 48.1 | R,R | 1 | N | 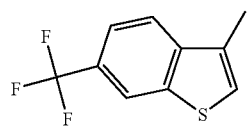 | H | 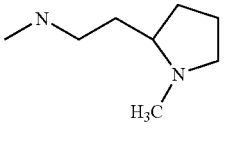 |
| 831884 | 1.94 | R,R, (R,S) | 1 | N | 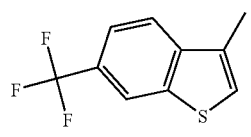 | H | 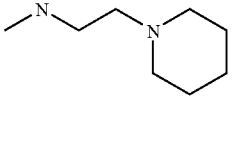 |
| 831885 | 35.3 | R,R | 1 | N | 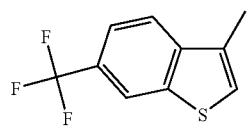 | H | 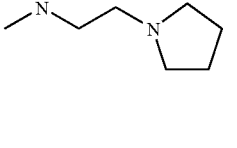 |
| 831886 | 16.8 | R,R | 1 | N | | H | |

-continued
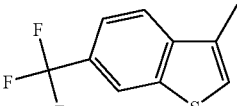
| MDL # | D3 KI (nM) | Chirality | n | X | R1 | R2 | R3 |
|---|---|---|---|---|---|---|---|
| 831887 | 6.5 | R,R | 1 | N | 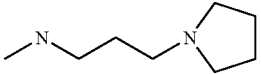 | H | 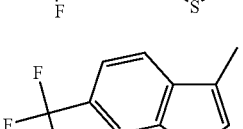 |
| 831888 | 17.5 | R,R | 1 | N | 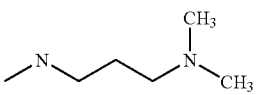 | H | 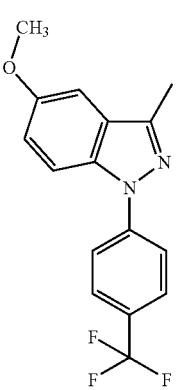 |
| 831949 | 29 | R,R | 1 | N | 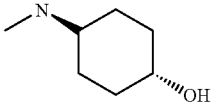 | H | 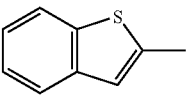 |
| 831950 | 5.48 | R,R | 1 | CH | 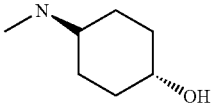 | H | 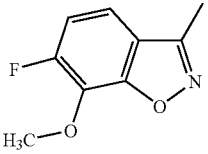 |
| 831952 | 42.8 | R,R | 1 | CH | 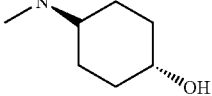 | H | 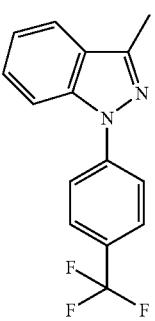 |
| 831953 | 37.4 | R,R | 1 | CH | 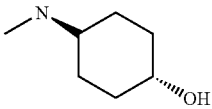 | H | 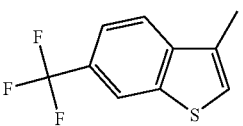 |
| 831958 | 13 | R,R | 1 | N | 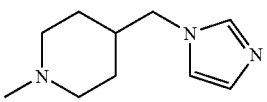 | H | 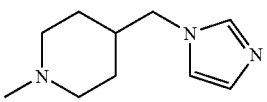 |

-continued

| MDL # | D3 KI (nM) | Chirality | n | X | R1 | R2 | R3 |
|---|---|---|---|---|---|---|---|
| 832102 | 81.5 | R,R | 1 | CH | 3-methyl-7-methoxy-1,2-benzisoxazole | H | —NH—(CH$_2$)$_3$—Ph |
| 832104 | 619.7 | R,R | 1 | CH | 3-methyl-7-methoxy-1,2-benzisoxazole | H | N-methyl-3-(pyridin-3-yl)propylamine |
| 832108 | 178 | R,R | 1 | CH | 3-methyl-7-methoxy-1,2-benzisoxazole | H | N-methyl-3-(piperidin-1-yl)propylamine |
| 832203 | 4.76 | R,R | 1 | CH | 3-methyl-7-trifluoromethyl-1,2-benzisoxazole | H | trans-N-methyl-4-methylcyclohexylamine |
| 832216 | 76.5 | R,R,R | 1 | N | 3-methyl-6-trifluoromethyl-benzo[b]thiophene | H | (R)-N-methyl-2-(1-methylpyrrolidin-2-yl)ethylamine |
| 832217 | 44.1 | R,R,S | 1 | N | 3-methyl-6-trifluoromethyl-benzo[b]thiophene | H | (S)-N-methyl-2-(1-methylpyrrolidin-2-yl)ethylamine |
| 832268 | 2.62 | R,R, (R,S) | 1 | N | 3-methyl-6-trifluoromethyl-benzo[b]thiophene | H | N-methyl-3-((imidazol-1-yl)methyl)piperidine |
| 832271 | 112.29 | R,R | 1 | CH | 3-methyl-7-trifluoromethyl-1,2-benzisoxazole | H | trans-N-methyl-4-hydroxycyclohexylamine |

-continued

| MDL # | D3 KI (nM) | Chirality | n | X | R1 | R2 | R3 |
|---|---|---|---|---|---|---|---|
| 832272 | 144.72 | R,R | 1 | CH | 3-methyl-7-(trifluoromethyl)-1,2-benzisoxazole | H | N-propyl-piperidine |
| 832273 | 205 | R,R | 1 | CH | 3-methyl-7-(trifluoromethyl)-1,2-benzisoxazole | H | N-propyl-morpholine |
| 832274 | 52.4 | R,R | 1 | CH | 7-methoxy-3-methyl-1,2-benzisoxazole | H | N-propyl-imidazole |
| 832494 | 25 | R,R | 1 | N | 3-methyl-6-(trifluoromethyl)-benzothiophene | H | N-propyl-1H-pyrrole |
| 832495 | 63.6 | R,R | 1 | N | 3-methyl-6-(trifluoromethyl)-benzothiophene | H | 1-methylpiperidin-4-yl-(4-chlorophenyl)amine |
| 832496 | 3.66 | R,R | 1 | N | 3-methyl-6-(trifluoromethyl)-benzothiophene | H | piperidinyl-methyl-guanidine |
| 832497 | 38 | R,R | 1 | N | 3-methyl-6-(trifluoromethyl)-benzothiophene | H | N-ethyl-S-(4-chlorophenyl)thio |
| 832498 | 70.3 | R,R | 1 | N | 3-methyl-6-(trifluoromethyl)-benzothiophene | H | N-ethyl-imidazolidin-2-one |
| 832499 | 19.7 | R,R | 1 | N | 3-methyl-6-(trifluoromethyl)-benzothiophene | H | 4-(tert-butoxycarbonyl)piperidinyl-methyl |

-continued

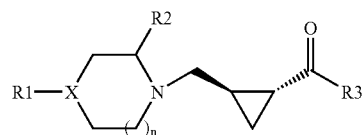

| MDL # | D3 KI (nM) | Chirality | n | X | R1 | R2 | R3 |
|---|---|---|---|---|---|---|---|
| 832500 | 161 | R,R (R,S) | 1 | N | 6-trifluoromethyl-3-methyl-benzothiophene | H | N-methyl-2-(1-Boc-piperidin-2-yl)ethylamine |
| 832501 | 41.4 | R,R (R,S) | 1 | N | 6-trifluoromethyl-3-methyl-benzothiophene | H | N-methyl-(1-Boc-piperidin-3-yl)methylamine |
| 832502 | 2.67 | R,R | 1 | N | 6-trifluoromethyl-3-methyl-benzothiophene | H | N-methyl-4-piperidinylamine |
| 832503 | 11.1 | R,R (R,S) | 1 | N | 6-trifluoromethyl-3-methyl-benzothiophene | H | N-methyl-2-(piperidin-2-yl)ethylamine |
| 832504 | 5.77 | R,R (R,S) | 1 | N | 6-trifluoromethyl-3-methyl-benzothiophene | H | N-methyl-(piperidin-3-yl)methylamine |
| 832510 | 25 | R,R | 1 | N | 6-trifluoromethyl-3-methyl-benzothiophene | H | 1-methyl-4-(pyrrolidin-1-yl)piperidine |
| 832511 | 12.3 | R,R | 1 | N | 6-trifluoromethyl-3-methyl-benzothiophene | H | N-methyl-3-(azepan-1-yl)propylamine |
| 832512 | 15.7 | R,R | 1 | N | 6-trifluoromethyl-3-methyl-benzothiophene | H | N-methyl-3-(4,5-dichloro-2-methyl-imidazol-1-yl)propylamine |

-continued

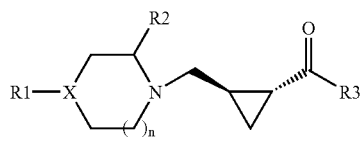

| MDL # | D3 KI (nM) | Chirality | n | X | R1 | R2 | R3 |
|---|---|---|---|---|---|---|---|
| 832577 | 1.85 | R,R | 1 | N | 6-trifluoromethyl-3-methylbenzothiophene | H | 1-methyl-4-(dimethylamino)piperidine |
| 832578 | 25.8 | R,R, (R,S) | 1 | N | 6-trifluoromethyl-3-methylbenzothiophene | H | N-methyl-3-(2-methylpiperidin-1-yl)propylamine |
| 832759 | 6.29 | R,R | 1 | N | 6-trifluoromethyl-3-methylbenzothiophene | H | N-methyl-3-(4-methylpiperazin-1-yl)propylamine |
| 832580 | 28.83 | R,R | 1 | N | 6-trifluoromethyl-3-methylbenzothiophene | H | 1-methyl-4-[2-(dimethylamino)ethyl]piperazine |
| 832581 | 67.35 | R,R | 1 | N | 6-trifluoromethyl-3-methylbenzothiophene | H | 2-[4-(4-methylpiperazin-1-yl)ethoxy]ethanol |
| 832852 | 25 | R,R | 1 | N | 6-trifluoromethyl-3-methylbenzothiophene | H | 2-(4-methylpiperazin-1-yl)-N-isopropylacetamide |
| 832583 | 1.61 | R,R | 1 | N | 6-trifluoromethyl-3-methylbenzothiophene | H | N-methyl-4-[(1H-imidazol-2-yl)methyl]piperidin-4-amine |
| 832654 | 4.72 | R,R | 1 | CH | 1-methyl-3-methyl-7-trifluoromethyl-1H-indazole | H | N-methyl-3-(1H-imidazol-1-yl)propylamine |
| 832714 | 12.4 | R,R | 1 | CH | 2-methylbenzothiophene | H | N-methyl-3-(piperidin-1-yl)propylamine |

-continued

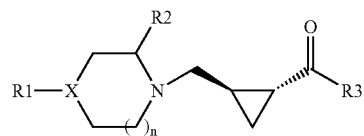

| MDL # | D3 KI (nM) | Chirality | n | X | R1 | R2 | R3 |
|---|---|---|---|---|---|---|---|
| 832715 | 166.46 | R,R | 1 | CH | 2-benzothiophene | H | 1-methylpiperidin-4-yl pyrrolidine |
| 832716 | 7.54 | R,R | 1 | CH | 2-benzothiophene | H | N-methyl-1-(3,4-dichlorobenzyl)piperidin-4-amine |
| 832734 | 9.85 | R,R | 1 | N | 3-methyl-6-(trifluoromethyl)benzothiophene | H | N-methyl-1-(cyclopropylmethyl)piperidin-4-amine |
| 832735 | 36.8 | R,R | 1 | N | 3-methyl-6-(trifluoromethyl)benzothiophene | H | 4-methylpiperazin-1-yl ethanol |
| 832736 | 2.74 | R,R | 1 | N | 3-methyl-6-(trifluoromethyl)benzothiophene | H | N-methyl-1-(3-fluorobenzyl)piperidin-4-amine |
| 832737 | 5.42 | R,R | 1 | N | 3-methyl-6-(trifluoromethyl)benzothiophene | H | N-methyl-1-(4-chlorobenzyl)piperidin-4-amine |
| 832738 | 3.26 | R,R | 1 | N | 3-methyl-6-(trifluoromethyl)benzothiophene | H | N-methyl-1-(4-fluorobenzyl)piperidin-4-amine |
| 832739 | 2.89 | R,R | 1 | N | 3-methyl-6-(trifluoromethyl)benzothiophene | H | N-methyl-1-(2-methoxybenzyl)piperidin-4-amine |
| 832740 | 30.2 | R,R | 1 | N | 3-methyl-6-(trifluoromethyl)benzothiophene | H | N-methyl-1-(3-chlorobenzyl)piperidin-4-amine |

-continued

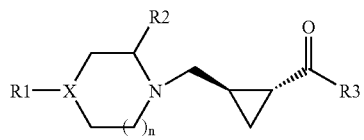

| MDL # | D3 KI (nM) | Chirality | n | X | R1 | R2 | R3 |
|---|---|---|---|---|---|---|---|
| 832741 | 6.03 | R,R | 1 | N | 3-methyl-6-(trifluoromethyl)benzothiophene | H | N-methyl-1-(2-chlorobenzyl)piperidin-4-amine |
| 832742 | 5.75 | R,R | 1 | N | 3-methyl-6-(trifluoromethyl)benzothiophene | H | N-methyl-1-(cyclohexylmethyl)piperidin-4-amine |
| 832743 | 2.36 | R,R | 1 | N | 5-methoxy-1,3-dimethyl-1H-indazole | H | N-methyl-1-(cyclohexylmethyl)piperidin-4-amine |
| 832744 | 1.37 | R,R | 1 | N | 5-methoxy-1,3-dimethyl-1H-indazole | H | N-methyl-1-(cyclopropylmethyl)piperidin-4-amine |
| 832745 | 15.04 | R,R | 1 | N | 5-methoxy-1,3-dimethyl-1H-indazole | H | N,N,1-trimethylpiperidin-4-amine |
| 832747ES | 1.05 | R,R | 1 | N | 5-methoxy-1,3-dimethyl-1H-indazole | H | N-methyl-trans-4-ethylcyclohexylamine |
| 832748FH | 79.07 | R,R | 1 | N | 5-methoxy-1,3-dimethyl-1H-indazole | H | 1-(2-methoxyethyl)-4-methylpiperazine |
| 832789 | 3.05 | R,R | 1 | N | 3-methyl-6-(trifluoromethyl)benzothiophene | H | N-methyl-1-(3-methylbenzyl)piperidin-4-amine |

-continued

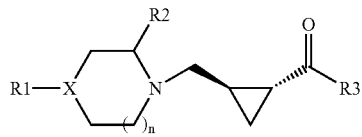

| MDL # | D3 KI (nM) | Chirality | n | X | R1 | R2 | R3 |
|---|---|---|---|---|---|---|---|
| 832833 | 18.2 | R,R | 1 | N | 3-methyl-6-(trifluoromethyl)benzothiophene | H | 4-methyl-1-(propan-2-yl)piperazine |
| 832834 | 12.2 | R,R | 1 | N | 3-methyl-6-(trifluoromethyl)benzothiophene | H | 1-allyl-4-methylpiperazine |
| 832835 | 18.1 | R,R | 1 | N | 3-methyl-6-(trifluoromethyl)benzothiophene | H | 1-(2-methoxyethyl)-4-methylpiperazine |
| 832859 | 14.3 | R,R | 1 | N | 3-methyl-6-(trifluoromethyl)benzothiophene | H | N-methyl-1-(piperidin-4-yl)methanamine |
| 833062 | 55.4 | R,R | 1 | N | 3-methyl-6-(trifluoromethyl)benzothiophene | H | N-methyl-1-(3-(trifluoromethoxy)phenyl)methanamine |
| 833064 | 28.8 | R,R, (R,S) | 1 | N | 3-methyl-6-(trifluoromethyl)benzothiophene | H | 1-(2-(2-(methylamino)ethyl)piperidin-1-yl)ethanone |
| 833065 | 692.37 | R,R | 1 | N | 3-methyl-6-(trifluoromethyl)benzothiophene | H | 1-(4-((methylamino)methyl)piperidin-1-yl)ethanone |
| 833080 | 22.9 | R,R | 1 | CH | 1,3-dimethyl-7-(trifluoromethyl)-1H-indazole | H | trans-4-(methylamino)cyclohexanol |

-continued

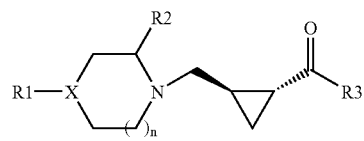

| MDL # | D3 KI (nM) | Chirality | n | X | R1 | R2 | R3 |
|---|---|---|---|---|---|---|---|
| 833090 | 41.85 | R,R | 1 | CH | 3-methyl-7-(trifluoromethyl)-1-methyl-1H-indazole | H | N-propyl-piperidine |
| 833091 | 117.7 | R,R | 1 | CH | 3-methyl-7-(trifluoromethyl)-1-methyl-1H-indazole | H | 1-methyl-4-piperidinyl-piperidine |
| 833092 | 33.47 | R,R | 1 | CH | 3-methyl-7-(trifluoromethyl)-1-methyl-1H-indazole | H | N-propyl-3-pyridyl |
| 833097 | 0.9 | R,R,S | 1 | N | 3-methyl-6-(trifluoromethyl)benzothiophene | H | 1-methyl-3-(imidazol-1-ylmethyl)piperidine |
| 833098 | 8.84 | R,R,R | 1 | N | 3-methyl-6-(trifluoromethyl)benzothiophene | H | 1-methyl-3-(imidazol-1-ylmethyl)piperidine |
| 833120 | 138 | R,R | 1 | N | 5-methoxy-3-methyl-1-methyl-1H-indazole | H | N-propyl-piperidine |
| 833121 | 26.5 | R,R | 1 | N | 5-methoxy-3-methyl-1-methyl-1H-indazole | H | N-propyl-piperidine |

-continued

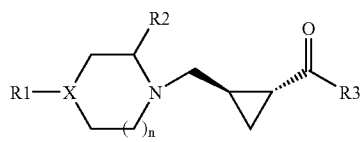

| MDL # | D3 KI (nM) | Chirality | n | X | R1 | R2 | R3 |
|---|---|---|---|---|---|---|---|
| 833122 | 52.89 | R,R | 1 | N | 5-methoxy-1,3-dimethyl-1H-indazole | H | 4-methyl-1-isopropylpiperazine |
| 833123 | 26.26 | R,R | 1 | N | 5-methoxy-1,3-dimethyl-1H-indazole | H | 1-methyl-4-(1H-imidazol-1-yl)piperidine |
| 833124 | 26.83 | R,R | 1 | N | 5-methoxy-1,3-dimethyl-1H-indazole | H | 1-methyl-4-(4-chlorobenzyl)piperazine |
| 833125 | 70.76 | R,R | 1 | N | 5-methoxy-1,3-dimethyl-1H-indazole | H | 1-methyl-4-(4-methylbenzyl)piperazine |
| 833136 | 14.3 | R,R | 1 | N | 5-methoxy-1,3-dimethyl-1H-indazole | H | N-methyl-(piperidin-4-yl)methylamine |
| 833151 | 11.2 | R,R | 1 | CH | 3-methyl-7-(trifluoromethyl)benzo[b]thiophene | H | 4-(methylamino)cyclohexyl pivalate |

-continued

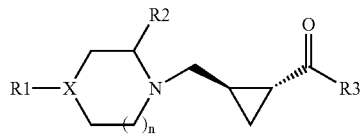

| MDL # | D3 KI (nM) | Chirality | n | X | R1 | R2 | R3 |
|---|---|---|---|---|---|---|---|
| 833157 | 43.88 | R,R | 1 | CH | 6-fluoro-3-methyl-1-(4-fluorophenyl)-1H-indazol-1-yl | H | N-methyl-3-(piperidin-1-yl)propylamine |
| 833197 | 45.38 | R,R | 1 | N | 5-methoxy-1,3-dimethyl-1H-indazol-1-yl | H | (1-acetylpiperidin-4-yl)methyl-N-methyl |
| 833277 | 16.7 | R,R | 1 | N | 3-methyl-6-(trifluoromethyl)benzo[b]thiophen-1-yl | H | tert-butyl 4-(2-(methylamino)ethyl)piperazine-1-carboxylate |
| 833278 | 7.04 | R,R | 1 | N | 3-methyl-6-(trifluoromethyl)benzo[b]thiophen-1-yl | H | tert-butyl (2-(4-methylpiperazin-1-yl)ethyl)carbamate |
| 833305 | 8.81 | R,R | 1 | CH | 1,3-dimethyl-7-(trifluoromethyl)-1H-indazol-1-yl | H | trans-N,4-dimethylcyclohexan-1-amine |
| 833322 | 12.8 | R,R | 1 | N | 3-methyl-6-(trifluoromethyl)benzo[d]isothiazol-1-yl | H | N-methyl-2-(piperazin-1-yl)ethylamine |
| 833323 | 3.46 | R,R | 1 | N | 3-methyl-6-(trifluoromethyl)benzo[b]thiophen-1-yl | H | 2-(4-methylpiperazin-1-yl)ethanamine |

-continued

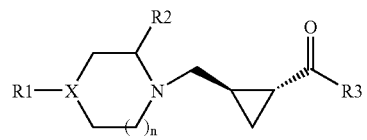

| MDL # | D3 KI (nM) | Chirality | n | X | R1 | R2 | R3 |
|---|---|---|---|---|---|---|---|
| 833512 | 2.17 | R,R | 1 | N | 6-trifluoromethyl-3-methylbenzothiophene | H | N-methyl-4-(N-(3,4-difluorobenzyl))piperidinyl |
| 833513 | 43.1 | R,R | 1 | N | 6-trifluoromethyl-3-methylbenzothiophene | H | 1-methyl-4-(imidazol-1-yl)piperidinyl |
| 833514 | 0.36 | R,R | 1 | N | 6-trifluoromethyl-3-methylbenzothiophene | H | 1-methyl-4-(2-(pyrrolidin-1-yl)ethyl)piperidinyl |
| 833515 | 48.3 | R,R | 1 | N | 6-trifluoromethyl-3-methylbenzothiophene | H | N-methyl-4-(4-(1,2,3-thiadiazol-4-yl)phenyl)methyl |
| 833516 | 21.7 | R,R | 1 | N | 6-trifluoromethyl-3-methylbenzothiophene | H | N-methyl-4-(N-(2,4-difluorobenzyl))piperidinyl |
| 833585ES | 5.86 | R,R | 1 | CH | 5-trifluoromethyl-1,3-dimethylindazole | H | N-methyl-3-(piperidin-1-yl)propyl |
| 833625 | 22.2 | R,R,R | 1 | N | 6-trifluoromethyl-3-methylbenzothiophene | H | N-methyl-((3R)-1-Boc-pyrrolidin-3-yl)methyl |
| 833626 | 2.17 | R,R | 1 | N | 5-methoxy-1,3-dimethylindazole | H | N-methyl-4-(N-(3,4-difluorobenzyl))piperidinyl |

-continued

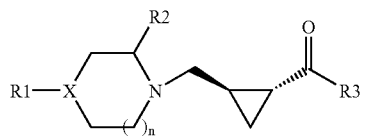

| MDL # | D3 KI (nM) | Chirality | n | X | R1 | R2 | R3 |
|---|---|---|---|---|---|---|---|
| 833627 | 1.63 | R,R | 1 | N | 5-methoxy-1,3-dimethyl-1H-indazole | H | N-methyl-N-(1-(2,4-difluorobenzyl)piperidin-4-yl)amine |
| 833628 | 95.82 | R,R | 1 | N | 5-methoxy-1,3-dimethyl-1H-indazole | H | 1-methyl-4-(2-(pyrrolidin-1-yl)ethyl)piperidine |
| 833629 | 2.69 | R,R | 1 | N | 5-methoxy-1,3-dimethyl-1H-indazole | H | N-methyl-N-(4-fluorophenethyl)amine |
| 833630 | 52.09 | R,R,R | 1 | N | 5-methoxy-1,3-dimethyl-1H-indazole | H | tert-butyl (R)-3-((methylamino)methyl)pyrrolidine-1-carboxylate |
| 833631 | 31.3 | R,R | 1 | N | 5-methoxy-1,3-dimethyl-1H-indazole | H | N,N,N'-trimethylpropane-1,3-diamine |
| 833632 | 4.06 | R,R,R | 1 | N | 5-methoxy-1,3-dimethyl-1H-indazole | H | (R)-N-methyl-1-(pyrrolidin-3-yl)methanamine |
| 833686 | 7.22 | R,R | 1 | CH | 3-methyl-7-(trifluoromethyl)benzo[b]thiophene | H | N-methyl-3-(piperidin-1-yl)propan-1-amine |

-continued

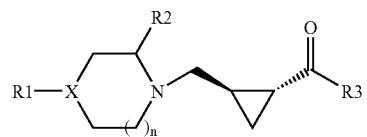

| MDL # | D3 KI (nM) | Chirality | n | X | R1 | R2 | R3 |
|---|---|---|---|---|---|---|---|
| 833690 | 7.97 | R,R | 1 | CH | 3-methyl-7-(trifluoromethyl)benzothiophene | H | trans-4-methyl-N-methylcyclohexylamine |
| 833692 | 72.9 | R,R | 1 | CH | 5-chloro-2-methylbenzoxazole | H | trans-4-methyl-N-methylcyclohexylamine |
| 833693 | 18.4 | R,R | 1 | CH | 6-bromo-1,3-dimethylindazole | H | trans-4-methyl-N-methylcyclohexylamine |
| 833694 | 46.9 | R,R | 1 | CH | 6-bromo-3-methyl-1H-indazole | H | trans-4-methyl-N-methylcyclohexylamine |
| 833695 | 176 | R,R | 1 | CH | 3-methyl-1-(pyridin-3-yl)indazole | H | trans-4-methyl-N-methylcyclohexylamine |
| 833696 | 268 | R,R | 1 | CH | 1,3-dimethyl-6-(trifluoromethyl)indazole | H | trans-4-methyl-N-methylcyclohexylamine |
| 833697 | 105 | R,R | 1 | CH | 1-cyclohexyl-3-methyl-6-(trifluoromethyl)indazole | H | trans-4-methyl-N-methylcyclohexylamine |

-continued

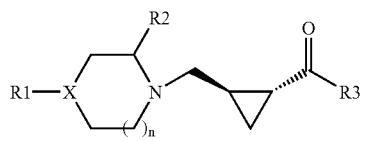

| MDL # | D3 KI (nM) | Chirality | n | X | R1 | R2 | R3 |
|---|---|---|---|---|---|---|---|
| 833698 | 134 | R,R | 1 | CH | 3-methyl-6-(trifluoromethyl)-1-(4-fluorophenyl)-1H-indazole | H | N-methyl-trans-4-methylcyclohexyl |
| 833699 | 7.2 | R,R | 1 | N | 2-methyl-5,6-dihydro-4H-imidazo[4,5,1-ij]quinoline | H | N-methyl-trans-4-methylcyclohexyl |
| 833700 | 3.24 | R,R | 1 | N | 3-methylthieno[2,3-b]pyridine | H | N-methyl-trans-4-methylcyclohexyl |
| 833701 | 1.28 | R,R | 1 | N | 3-methyl-1-(4-fluorophenyl)-1H-indazole | H | N-methyl-trans-4-methylcyclohexyl |
| 833702 | 0.495 | R,R | 1 | N | 1,3-dimethyl-1H-indazole | H | N-methyl-trans-4-methylcyclohexyl |
| 833703 | 1.92 | R,R | 1 | CH | 6-bromo-3-methyl-1,2-benzisothiazole | H | N-methyl-trans-4-methylcyclohexyl |
| 833704 | 2.3 | R,R | 1 | N | 5-methoxy-3-methyl-1H-indazole | H | N-methyl-trans-4-methylcyclohexyl |

-continued

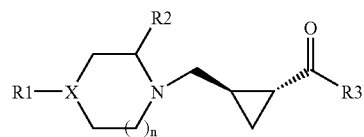

| MDL # | D3 KI (nM) | Chirality | n | X | R1 | R2 | R3 |
|---|---|---|---|---|---|---|---|
| 833769 | 1.63 | R,R | 1 | CH | 5-trifluoromethyl-1,3-dimethyl-1H-indazol-3-yl | H | trans-4-methylcyclohexyl-N-methyl |
| 833821 | 6.91 | R,R | 1 | N | 3-methylthieno[2,3-b]pyridin-2-yl | H | 3-(1H-imidazol-1-yl)propyl-N-methyl |
| 833822 | 0.64 | R,R | 1 | N | 1,3-dimethyl-1H-indazol-3-yl | H | 3-(1H-imidazol-1-yl)propyl-N-methyl |
| 833701 | 1.28 | R,R | 1 | N | 1-(4-fluorophenyl)-3-methyl-1H-indazol-3-yl | H | trans-4-methylcyclohexyl-N-methyl |
| 833702 | 0.495 | R,R | 1 | N | 1,3-dimethyl-1H-indazol-3-yl | H | trans-4-methylcyclohexyl-N-methyl |
| 833703 | 1.92 | R,R | 1 | CH | 6-bromo-3-methylbenzo[d]isothiazol-3-yl | H | trans-4-methylcyclohexyl-N-methyl |
| 833704 | 2.3 | R,R | 1 | N | 5-methoxy-3-methyl-1H-indazol-3-yl | H | trans-4-methylcyclohexyl-N-methyl |

-continued
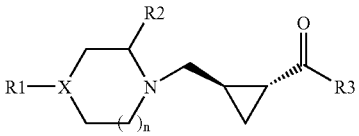
| MDL # | D3 KI (nM) | Chirality | n | X | R1 | R2 | R3 |
|---|---|---|---|---|---|---|---|
| 833769 | 1.63 | R,R | 1 | CH | 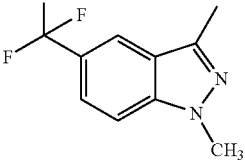 | H | 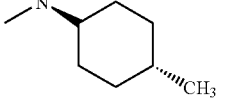 |
| 833821 | 6.91 | R,R | 1 | N | 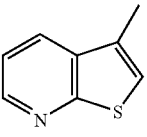 | H | 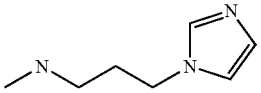 |
| 833822 | 0.64 | R,R | 1 | N | 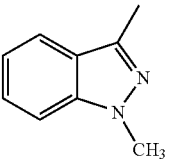 | H | 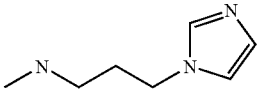 |
| 833823 | 0.637 | R,R | 1 | N | 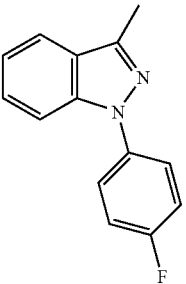 | H | 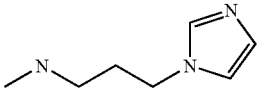 |
| 833834 | 0.333 | R,R | 1 | N | 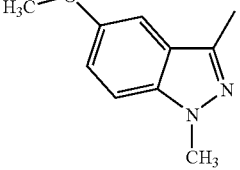 | H | 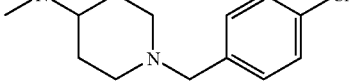 |
| 833835 | 0.499 | R,R | 1 | N | 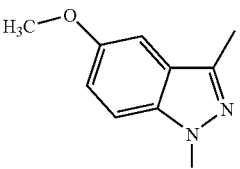 | H | 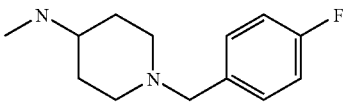 |
| 833836 | 1.36 | R,R | 1 | N | 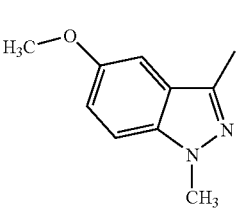 | H |  |

-continued

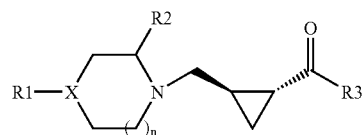

| MDL # | D3 KI (nM) | Chirality | n | X | R1 | R2 | R3 |
|---|---|---|---|---|---|---|---|
| 833910 | 1.09 | R,R, (R,S) | 1 | CH | 7-methoxy-3-methyl-1,2-benzisoxazole | H | (1-methylpiperidin-3-yl)methyl-imidazol-1-yl |
| 833911 | 1.26 | R,R (R,S) | 1 | CH | 3-methyl-7-(trifluoromethyl)-1,2-benzisoxazole | H | (1-methylpiperidin-3-yl)methyl-imidazol-1-yl |
| 833934 | 0.633 | R,R | 1 | CH | 5-(trifluoromethyl)-3-methyl-1H-indazole | H | trans-4-methylcyclohexyl-N-methyl |
| 833941 | 8.98 | R,R | 1 | CH | 6-(trifluoromethyl)-3-methyl-1H-indazole | H | trans-4-methylcyclohexyl-N-methyl |
| 834003 | 3.51 | R,R | 1 | CH | 6-(trifluoromethyl)-3-methylbenzothiophene | H | N-methyl-3-(imidazol-1-yl)propyl |
| 834012 | 0.241 | R,R | 1 | CH | 5-(trifluoromethyl)-3-methyl-1,2-benzisoxazole | H | trans-4-methylcyclohexyl-N-methyl |
| 834015 | 1.24 | R,R | 1 | CH | 6-(trifluoromethyl)-3-methylbenzothiophene | H | N-methyl-3-(piperidin-1-yl)propyl |
| 834016 | 1.63 | R,R | 1 | CH | 6-(trifluoromethyl)-3-methylbenzothiophene | H | trans-4-methylcyclohexyl-N-methyl |

-continued

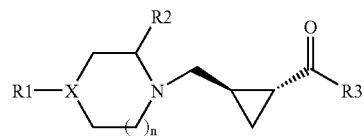

| MDL # | D3 KI (nM) | Chirality | n | X | R1 | R2 | R3 |
|---|---|---|---|---|---|---|---|
| 834017 | 1.62 | R,R | 1 | CH | 3-methyl-6-(trifluoromethyl)benzo[b]thiophene | H | N-methyl-4-((1H-imidazol-1-yl)methyl)piperidine |
| 834054 | 13.8 | R,R | 1 | CH | 7-methoxy-1,3-dimethyl-1H-indazole | H | N-methyl-N-(trans-4-methylcyclohexyl) |
| 834055 | 62 | R,R | 1 | CH | 7-methoxy-1,3-dimethyl-1H-indazole | H | N-methyl-bornyl |
| 834056 | 93.2 | R,R | 1 | CH | 7-methoxy-1,3-dimethyl-1H-indazole | H | N-methyl-3-(piperidin-1-yl)propyl |
| 834057 | 89.4 | R,R | 1 | CH | 7-methoxy-1,3-dimethyl-1H-indazole | H | N-methyl-adamantylmethyl |
| 834058 | 91.4 | R,R | 1 | CH | 7-methoxy-1,3-dimethyl-1H-indazole | H | N-methyl-3-(1H-imidazol-1-yl)propyl |
| 834059 | 2.76 | R,R | 1 | CH | 1,3,5-trimethyl-1H-indazole | H | N-methyl-N-(trans-4-methylcyclohexyl) |
| 834129 | 6.75 | R,R | 1 | CH | 1,3,5-trimethyl-1H-indazole | H | N-methyl-3-(1H-imidazol-1-yl)propyl |

-continued

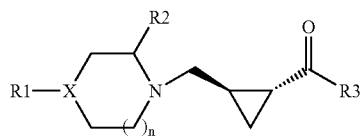

| MDL # | D3 KI (nM) | Chirality | n | X | R1 | R2 | R3 |
|---|---|---|---|---|---|---|---|
| 834171 | 65.2 | R,R | 1 | CH | 7-methoxy-1,3-dimethyl-1H-indazole | H | N-methyl-trimethylbicyclic amine |
| 834172 | 0.837 | R,R | 1 | N | 6-chloro-3-methylbenzo[b]thiophene | H | N-methyl-3-(1H-imidazol-1-yl)propylamine |
| 834173 | 5.15 | R,R (R,S) | 1 | N | 5-methoxy-1,3-dimethyl-1H-indazole | H | (1-methylpiperidin-3-yl)methyl-imidazole |
| A002200835 | 0.4 | R,R (R,S) | 1 | CH | 5-trifluoromethyl-3-methylbenzo[d]isoxazole | H | (1-methylpiperidin-3-yl)methyl-imidazole |
| A002200836 | 1.51 | R,R | 1 | CH | 5-trifluoromethyl-3-methylbenzo[d]isoxazole | H | (1-methylpiperidin-4-yl)methyl-imidazole |
| A002200837 | 0.368 | R,R | 1 | CH | 5-trifluoromethyl-3-methylbenzo[d]isoxazole | H | N-methyl-3-(1H-imidazol-1-yl)propylamine |
| A002200838 | 0.807 | R,R | 1 | CH | 5-trifluoromethyl-3-methylbenzo[d]isoxazole | H | N-methyl-3-(piperidin-1-yl)propylamine |

-continued

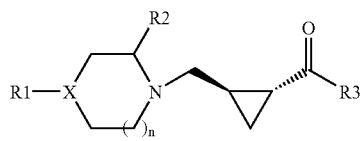

| MDL # | D3 KI (nM) | Chirality | n | X | R1 | R2 | R3 |
|---|---|---|---|---|---|---|---|
| A002243383 | 25.09 | R,R | 1 | N | 5-methoxy-1,3-dimethyl-1H-indazole | H | N-methyl-3-(1H-benzimidazol-1-yl)propylamine |
| A002243384 | 133.36 | R,R | 1 | N | 6-(trifluoromethyl)-3-methylbenzo[b]thiophene | H | N-methyl-3-(1H-benzimidazol-1-yl)propylamine |
| A002287512 | 0.647 | R,R, (R,S) | 1 | CH | 6-(trifluoromethyl)-3-methylbenzo[b]thiophene | H | (1-methylpiperidin-3-yl)methyl-1H-imidazole |
| A002287513 | 3.57 | R,R | 1 | CH | 6-(trifluoromethyl)-3-methylbenzo[b]thiophene | H | N-methyl-piperidin-4-ylamine |
| A002287764 | 0.48 | R,R | 1 | CH | 6-(trifluoromethyl)-3-methylbenzo[d]isoxazole | H | N-methyl-3-(piperidin-1-yl)propylamine |
| A002287765 | 0.011 | R,R | 1 | CH | 6-(trifluoromethyl)-3-methylbenzo[d]isoxazole | H | N-methyl-3-(1H-imidazol-1-yl)propylamine |
| A002287766 | 126.3 | R,R,S | 1 | CH | 6-(trifluoromethyl)-3-methylbenzo[d]isoxazole | H | (1-methylpiperidin-3-yl)methyl-1H-imidazole |

-continued
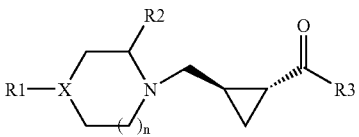
| MDL # | D3 KI (nM) | Chirality | n | X | R1 | R2 | R3 |
|---|---|---|---|---|---|---|---|
| A002328939 | 201.16 | R,R | 1 | CH | 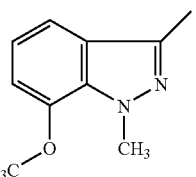 | H | 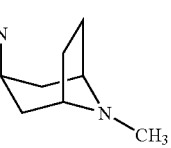 |
| A002328940 | 26.8 | R,R | 1 | CH | 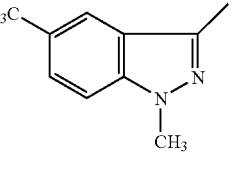 | H | 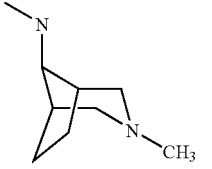 |
| A002328941 | 23.88 | R,R | 1 | CH |  | H | 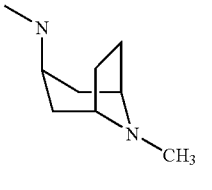 |
| A002329092 | 321.2 | R,R | 1 | CH | 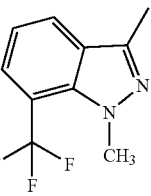 | H | 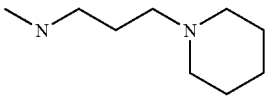 |
| A002329093 | 411.4 | R,R | 1 | CH | 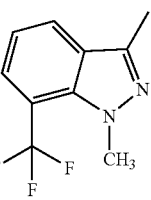 | H | 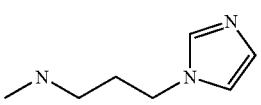 |
| A002329094 | 7.08 | R,R | 1 | CH | 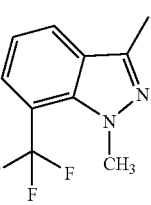 | H | 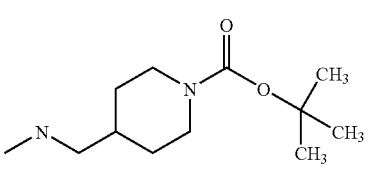 |
| A002329095 | 26.47 | R,R | 1 | CH | 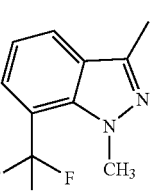 | H | 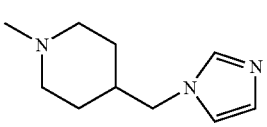 |

-continued

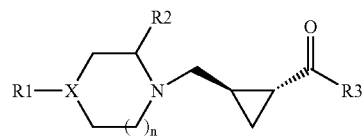

| MDL # | D3 KI (nM) | Chirality | n | X | R1 | R2 | R3 |
|---|---|---|---|---|---|---|---|
| A002329097 | 101.2 | R,R | 1 | CH | 6-bromo-3-methyl-benzisothiazole | H | N-methyl-3-(imidazol-1-yl)propyl |
| A002329098 | 345.2 | R,R | 1 | CH | 6-bromo-3-methyl-benzisothiazole | H | (1-methylpiperidin-4-yl)methyl-imidazol-1-yl |
| A002329099 | 2.06 | R,R (R,S) | 1 | CH | 6-bromo-3-methyl-benzisothiazole | H | (1-methylpiperidin-3-yl)methyl-imidazol-1-yl |
| A002329100 | 6.32 | R,R | 1 | CH | 6-bromo-3-methyl-benzisothiazole | H | N-methyl-3-piperidin-1-yl-propyl |
| A-002436288A | 105.69 | R,R | 1 | CH | 6-trifluoromethyl-1,3-dimethyl-indazole | H | N-methyl-(piperidin-4-yl)methyl |
| A002437094 | 91.93 | R,R | 1 | N | 3-methyl-thieno[2,3-b]pyridine | H | N-methyl-3-piperidin-1-yl-propyl |
| A002437350 | 16.2 | R,R | 1 | N | 2-methyl-lilolidine-imidazo | H | N-methyl-3-(imidazol-1-yl)propyl |
| A002437351 | 32.68 | R,R | 1 | N | 2-methyl-lilolidine-imidazo | H | (1-methylpiperidin-4-yl)methyl-imidazol-1-yl |

-continued

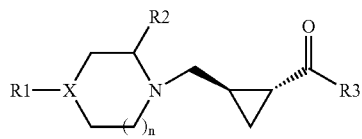

| MDL # | D3 KI (nM) | Chirality | n | X | R1 | R2 | R3 |
|---|---|---|---|---|---|---|---|
| A002437353 | 0.937 | R,R,S | 1 | CH | 3-methyl-6-(trifluoromethyl)-1-methyl-1H-indazol-1-yl | H | (1-methylpiperidin-3-yl)methyl-imidazol-1-yl |
| A002437354 | 1.03 | R,R,S | 1 | CH | 3,5-dimethyl-1-methyl-1H-indazol-1-yl | H | (1-methylpiperidin-3-yl)methyl-imidazol-1-yl |
| A002437355 | 1.87 | R,R,S | 1 | CH | 3-methyl-6-(trifluoromethyl)-1H-indazol-1-yl sec-butyl carbamate | H | (1-methylpiperidin-3-yl)methyl-imidazol-1-yl |
| A002437357 | 14.03 | R,R (R,S) | 1 | N | 3-methyl-6-(trifluoromethyl)benzo[b]thiophen-1-yl | H | (1-methylpiperidin-3-yl)methyl-piperidin-1-yl |
| A002437358 | 8.858 | R,R (R,S) | 1 | N | 3-methyl-6-(trifluoromethyl)benzo[b]thiophen-1-yl | H | (1-methylpiperidin-3-yl)methyl-[1,4]diazepan-1-yl |
| A002437359 | 0.541 | R,R,S | 1 | CH | 3-methyl-7-methoxy-benzo[d]isoxazol-1-yl | H | (1-methylpiperidin-3-yl)methyl-imidazol-1-yl |

-continued
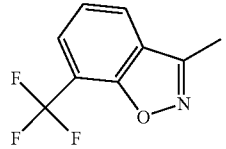
| MDL # | D3 KI (nM) | Chirality | n | X | R1 | R2 | R3 |
|---|---|---|---|---|---|---|---|
| A002437360 | 0.239 | R,R,S | 1 | CH | 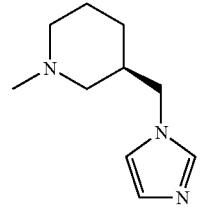 | H | 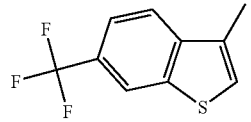 |
| A002437517 | 10.51 | R,R | 1 | CH | 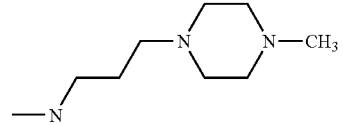 | H | 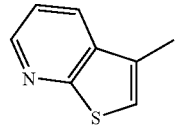 |
| A002437802 | 0.251 | R,R,S | 1 | N | 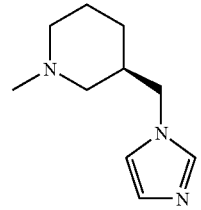 | H | 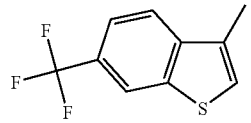 |
| A002438636 | 13.04 | R,R,S | 1 | N | 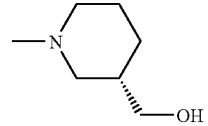 | H | 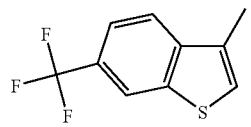 |
| A002438637 | 21.18 | R,R,R | 1 | N | 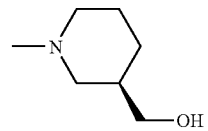 | H | 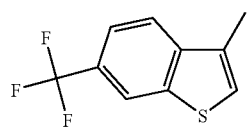 |
| A002438638 | 3.28 | R,R,R | 1 | N | 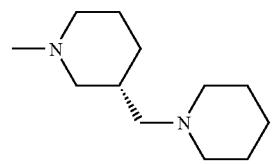 | H | 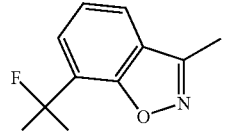 |
| A002438639 | 97.32 | R,R | 1 | CH | 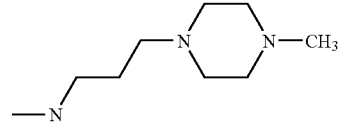 | H | 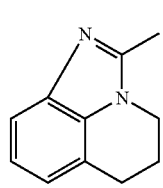 |
| A002438663 | 1.37 | R,R,S | 1 | N | 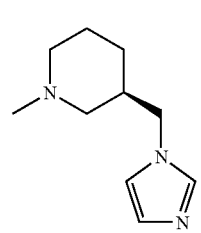 | H |  |

-continued

| MDL # | D3 KI (nM) | Chirality | n | X | R1 | R2 | R3 |
|---|---|---|---|---|---|---|---|
| A002438664 | 6.49 | R,R | 1 | CH | 6-bromo-3-methyl-benzisothiazole | H | N-methyl-N-(3-(4-methylpiperazin-1-yl)propyl)amine |
| A002439099 | 4.91 | R,R | 1 | N | 6-trifluoromethyl-3-methyl-benzothiophene | H | N-methyl-tropane |
| A002439100 | 551.94 | R,R | 1 | N | 2-methyl-5,6-dihydro-4H-imidazo[1,2,3-ij]quinoline | H | N-methyl-N-(3-(4-methylpiperazin-1-yl)propyl)amine |
| A002439258 | 34.08 | R,R | 1 | CH | 1,3-dimethyl-7-trifluoromethyl-indazole | H | tert-butyl 4-(methylaminomethyl)piperidine-1-carboxylate |
| A002439259 | 39.05 | R,R | 1 | CH | 1,3-dimethyl-7-trifluoromethyl-indazole | H | N-methyl-N-(3-(4-methylpiperazin-1-yl)propyl)amine |
| A002439260 | 0.303 | R,R,S | 1 | CH | 1,3-dimethyl-7-trifluoromethyl-indazole | H | (S)-1-methyl-3-(imidazol-1-ylmethyl)piperidine |
| A002439261 | 55.3 | R,R | 1 | CH | 3-methyl-7-trifluoromethyl-benzisoxazole | H | tert-butyl 4-(methylaminomethyl)piperidine-1-carboxylate |

-continued

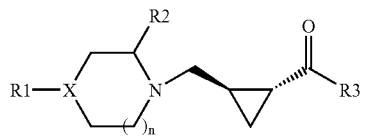

| MDL # | D3 KI (nM) | Chirality | n | X | R1 | R2 | R3 |
|---|---|---|---|---|---|---|---|
| A-002440433A | 180.18 | R,R | 1 | CH | 1-methyl-7-(trifluoromethyl)-3-methyl-1H-indazol-yl | H | (piperidin-4-yl)methylamino |
| A-002440437A | 41.24 | R,R | 1 | CH | 7-(trifluoromethyl)-3-methylbenzo[d]isoxazol-yl | H | (piperidin-4-yl)methylamino |
| A002609935 | 0.142 | R,R,S | 1 | CH | 6-(trifluoromethyl)-3-methylbenzo[b]thiophen-yl | H | (1-methylpiperidin-3-yl)methyl-(1H-imidazol-1-yl) |

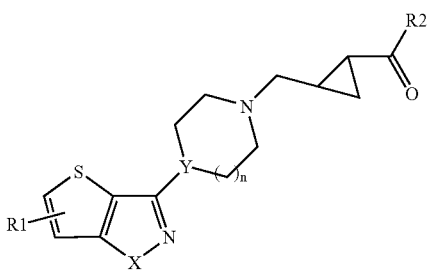

| MDL # | D3 Ki (nM) | Chirality | X | Y | R1 | n | R2 |
|---|---|---|---|---|---|---|---|
| 827393 | 391 | Racemic | O | CH | H | 1 | N-methyl-N-(furan-2-ylmethyl)amino |
| 827394 | 391 | Racemic | O | CH | H | 1 | 4-methyl-1-(pyrimidin-2-yl)piperazin-1-yl |
| 827395 | 31.4 | Racemic | O | CH | H | 1 | N-methyl-(norbornan-2-yl)amino |

-continued
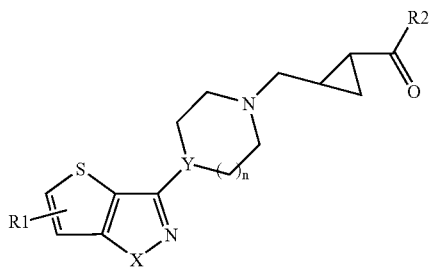
| MDL # | D3 Ki (nM) | Chirality | X | Y | R1 | n | R2 |
|---|---|---|---|---|---|---|---|
| 827397 | 111 | Racemic | O | CH | H | 1 |  |
| 829460 | 158 | R,R | O | CH | H | 1 |  |
| 829461 | 306 | R,R | O | CH | H | 1 |  |
| 829462 | 9.65 | R,R, (R,S) | O | CH | H | 1 |  |
| 829463 | 4.76 | Racemic | O | CH | H | 1 |  |
| 829464 | 22.4 | R,R | O | CH | H | 1 |  |
| 829465 | 80.3 | R,R | O | CH | H | 1 |  |
| 829466 | 24.8 | R,R | O | CH | H | 1 |  |

-continued

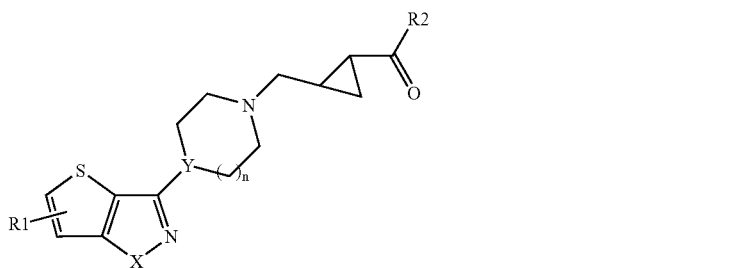

| MDL # | D3 Ki (nM) | Chirality | X | Y | R1 | n | R2 |
|---|---|---|---|---|---|---|---|
| 829467 | 9.01 | R,R | O | CH | H | 1 | (N-methylpiperazine linked via propenyl to phenyl) |
| 829590 | 109 | Racemic | O | CH | H | 1 | (1,4-dimethylpiperazine) |
| 829591 | 72.4 | Racemic | O | CH | H | 1 | (4-methylpiperazin-1-yl cyclohexyl) |
| 829592 | 42.3 | Racemic | O | CH | H | 1 | (N-methyl-N-cyclopentylamine) |
| 829593 | 350 | Racemic | O | CH | H | 1 | (N,N-dimethyl-2-(pyridin-2-yl)ethylamine) |
| 829594 | 364 | Racemic | O | CH | H | 1 | (1-methyl-2,5-dihydropyrrole) |
| 829595 | 201 | Racemic | O | CH | H | 1 | (4-methylcyclohexyl 4-fluorophenyl ether) |
| 829596 | 4.41 | R,R | O | CH | H | 1 | (N-methyl-3-(imidazol-1-yl)propylamine) |

-continued

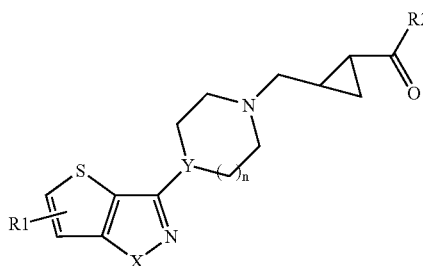

| MDL # | D3 Ki (nM) | Chirality | X | Y | R1 | n | R2 |
|---|---|---|---|---|---|---|---|
| 829597 | 226 | Racemic | O | CH | H | 1 | 1,4-dimethyl-1,4-diazepane |
| 830126 | 23.8 | Racemate | O | N | H | 2 | N-methyl-trans-4-methylcyclohexyl |
| 830127 | 1.66 | Racemate | O | N | H | 1 | N-methyl-trans-4-methylcyclohexyl |
| 830250 | 48.6 | R,R | O | CH | H | 1 | N-methyl-4-hydroxypiperidine |
| 830251 | 11.4 | R,R | O | CH | H | 1 | N-methyl-trans-4-hydroxycyclohexyl |
| 830252 | 110 | R,R | O | CH | H | 1 | 4-(2-pyridyl)-1-methylpiperazine |
| 830827 | 9.85 | R,R | O | CH | 3-CH$_3$ | 1 | N-methyl-3-(imidazol-1-yl)propyl |
| 830828 | 8.57 | R,R | O | CH | H | 1 | —N—(CH$_2$)$_3$-Ph |
| 830829 | 5.3 | R,R | O | CH | H | 1 | —N—(CH$_2$)$_2$-Ph |
| 830830 | 2.58 | R,R | O | CH | H | 1 | N-methyl-2-(indol-3-yl)ethyl |
| 830831 | 3.19 | R,R | O | CH | H | 1 | N-methyl-2-(6-fluoroindol-3-yl)ethyl |
| 830832 | 67.7 | R,R | O | CH | H | 1 | N-methyl-3-(2-oxopyrrolidin-1-yl)propyl |

-continued
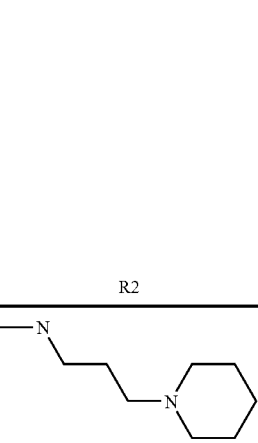
| MDL # | D3 Ki (nM) | Chirality | X | Y | R1 | n | R2 |
|---|---|---|---|---|---|---|---|
| 831045 | 335 | R,R | O | CH | H | 1 | 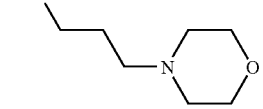 |
| 831046 | 15.5 | R,R | O | CH | H | 1 | 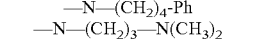 |
| 831047 | 2.87 | R,R | O | CH | H | 1 | —N—(CH$_2$)$_4$-Ph |
| 831048 | 11.3 | R,R | O | CH | H | 1 | —N—(CH$_2$)$_3$—N(CH$_3$)$_2$ |
| 831082 | 38.2 | S,S | O | N | H | 1 |  |
| 831083 | 3.2 | R,R | O | N | H | 1 | 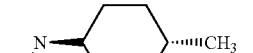 |
| 831192 | 3.44 | R,R | O | CH | H | 1 |  |
| 831193 | 23.8 | R,R | O | CH | H | 1 |  |
| 831194 | 5.06 | R,R | O | CH | H | 1 | 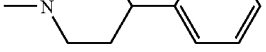 |
| 831195 | 1.84 | R,R | O | CH | H | 1 | 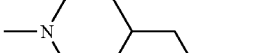 |
| 831196 | 7.81 | R,R | O | CH | H | 1 |  |
| 831197 | 4.17 | R,R | O | CH | H | 1 | 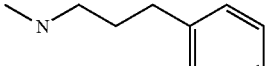 |

-continued
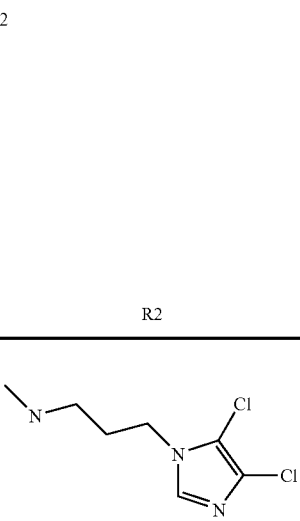
| MDL # | D3 Ki (nM) | Chirality | X | Y | R1 | n | R2 |
|---|---|---|---|---|---|---|---|
| 831198 | 1.76 | R,R | O | CH | H | 1 | 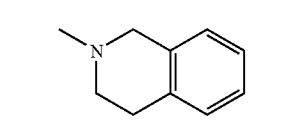 |
| 831199 | 2.78 | R,R | O | CH | H | 1 | 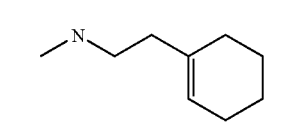 |
| 831215 | 5.92 | R,R | O | CH | H | 1 | 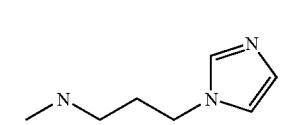 |
| 831267 | 28.3 | R,R | N-Ts | N | H | 1 | 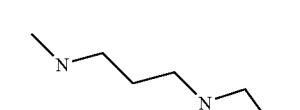 |
| 831272 | 6.22 | R,R | O | CH | H | 1 | 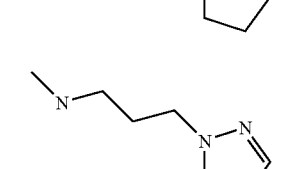 |
| 831273 | 68.6 | R,R | O | CH | H | 1 | 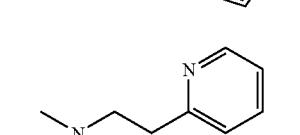 |
| 831274 | 17.4 | R,R | O | CH | H | 1 | 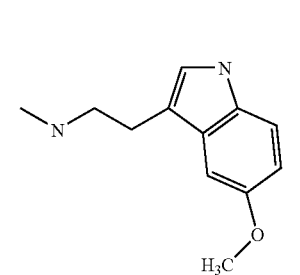 |
| 831275 | 5.15 | R,R | O | CH | H | 1 | |

-continued

| MDL # | D3 Ki (nM) | Chirality | X | Y | R1 | n | R2 |
|---|---|---|---|---|---|---|---|
| 831276 | 3.85 | R,R | O | CH | H | 1 | N-methyl-2-(6-methoxy-1H-indol-3-yl)ethylamine |
| 831277 | 5.38 | R,R | O | CH | H | 1 | N-methyl-2-(5-methyl-1H-indol-3-yl)ethylamine |
| 831278 | 18.1 | R,R | O | CH | H | 1 | N,N-dimethyl-2-(1H-indol-3-yl)ethylamine |
| 831315 | 29.3 | R,R | NH | N | H | 1 | N-methyl-3-(1H-imidazol-1-yl)propylamine |
| 831343 | 13.7 | R,R | O | CH | H | 1 | N-methyl-2-phenoxyethylamine |
| 831344 | 22.1 | R,R | O | CH | H | 1 | N-methyl-2-(4-methoxyphenyl)ethylamine |
| 831345 | 34.4 | R,R | O | CH | H | 1 | 1-methyl-4-(thieno[3,2-d]isoxazol-3-yl)piperidine |
| 831374 | 1.12 | R,R | O | CH | CH₃ | 1 | N-methyl-3-(1H-imidazol-1-yl)propylamine |
| 831375 | 2.9 | R,R | O | CH | CH₃ | 1 | —N—(CH₂)₃-Ph |
| 831376 | 40.3 | R,R | O | CH | H | 1 | N-methyl-3-(1H-pyrrol-1-yl)propylamine |

-continued
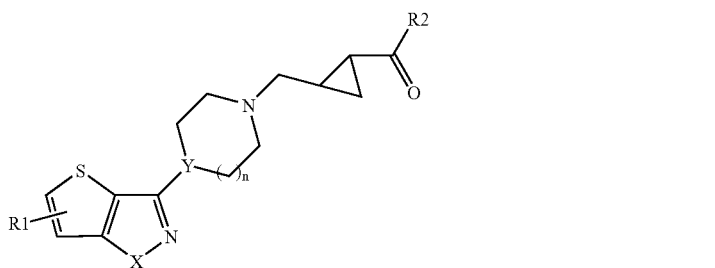
| MDL # | D3 Ki (nM) | Chirality | X | Y | R1 | n | R2 |
|---|---|---|---|---|---|---|---|
| 831377 | 4.68 | R,R | O | CH | H | 1 | |
| 831378 | 35.6 | R,R | O | CH | H | 1 | |
| 831379 | 46.7 | R,R | O | CH | H | 1 | |
| 831385 | 22.7 | Racemic | O | CH | H | 1 | |
| 831390 | 0.861 | Racemic | O | CH | H | 1 | |
| 831453 | 18.3 | Racemic | O | CH | H | 1 | |
| 831454 | 1.86 | Racemic | O | CH | H | 1 | |
| 831455 | 6.79 | Racemic | O | CH | H | 1 | |

-continued

| MDL # | D3 Ki (nM) | Chirality | X | Y | R1 | n | R2 |
|---|---|---|---|---|---|---|---|
| 831456 | 6.21 | Racemic | O | CH | H | 1 | N-methyl-2-(pyridin-3-yl)ethylamine group |
| 831457 | 1.83 | Racemic | O | CH | H | 1 | N-methyl-(1-benzylpiperidin-4-yl)amine group |
| 831458 | 7.43 | Racemic | O | CH | H | 1 | (1-methylpiperidin-4-yl)(4-chlorophenyl)methanone group |
| 831493 | 4.95 | R,R | O | N | H | 1 | N-methyl-3-(imidazol-1-yl)propylamine group |
| 831494 | 28.3 | R,R | O | N | H | 1 | —N—(CH$_2$)$_3$-Ph |
| 831599 | 49.8 | Racemic | O | CH | H | 1 | 1-methyl-4-(4-methoxyphenyl)-1,2,3,6-tetrahydropyridine group |
| 831602 | 19.6 | Racemic | O | CH | H | 1 | 1-methyl-3-phenylpyrrolidine group |
| 831603 | 20.9 | Racemic | O | CH | H | 1 | N-methyl-N'-phenylethylenediamine group |
| 831621 | 70.3 | Racemic | O | CH | H | 1 | benzimidazole carbamate group |
| 831622 | 34.6 | Racemic | O | CH | H | 1 | N-methyl-3-(benzimidazol-2-yl)propylamine group |

-continued

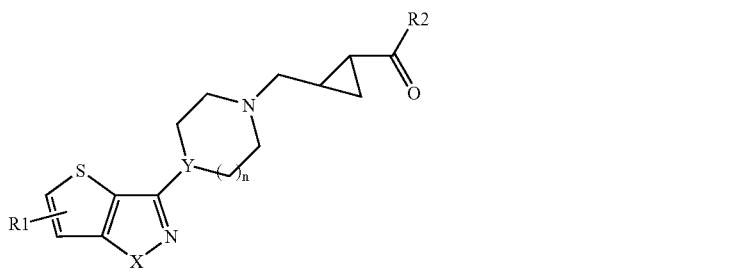

| MDL # | D3 Ki (nM) | Chirality | X | Y | R1 | n | R2 |
|---|---|---|---|---|---|---|---|
| 831649 | 173 | Racemic | O | CH | H | 1 | benzyl N-methyl-N-(2-aminoethyl)carbamate group |
| 831673 | 23.5 | Racemic | N-Me | N | H | 1 | N-methyl-3-(imidazol-1-yl)propylamine group |
| 831686 | 25.3 | Racemic | O | CH | H | 1 | N-methyl-4-(pyridin-3-yl)butylamine group |
| 831687 | 277 | Racemic | O | CH | H | 1 | N-methyl-3-(benzotriazol-1-yl)propylamine group |
| 831689 | 16.4 | Racemic | O | CH | H | 1 | N-methyl-2-((5-chloronaphthalen-1-yl)sulfonyl)ethylamine group |
| 831701 | 55.7 | Racemic | O | CH | H | 1 | N-methyl-2-(4-sulfamoylphenyl)ethylamine group |
| 831702 | 27.9 | Racemic | O | CH | H | 1 | 1-methyl-4-(benzothiazol-2-yl)piperidine group |
| 831703 | 45 | Racemic | O | CH | H | 1 | 1-methyl-4-(5-(thiophen-2-yl)-1H-pyrazol-3-yl)piperidine group |
| 831704 | 47.5 | Racemic | O | CH | H | 1 | 1-methyl-4-(5-(furan-2-yl)-1H-pyrazol-3-yl)piperidine group |

-continued

| MDL # | D3 Ki (nM) | Chirality | X | Y | R1 | n | R2 |
|---|---|---|---|---|---|---|---|
| 831735 | 81.3 | Racemic | O | CH | H | 1 | methylaminomethyl-(3-phenoxyphenyl) |
| 831736 | 291 | Racemic | O | CH | H | 1 | N-methyl-2-(phenylsulfonyl)ethylamine |
| 831737 | 1.25 | Racemic | O | CH | H | 1 | 1-(1-methylpiperidin-4-yl)-1,3-dihydro-2H-benzimidazol-2-one |
| 831738 | 223 | Racemic | O | CH | H | 1 | N,N-diethyl-1-methylpiperidine-4-carboxamide |
| 831740 | 2.96 | Racemic | O | CH | H | 1 | furan-bis(methylamino) derivative |
| 831741 | 125 | Racemic | O | CH | H | 1 | N-methyl-3-(4-methylpiperazin-1-yl)propylamine |
| 831794 | 27.3 | Racemic | O | CH | H | 1 | 4-(4-chlorophenoxy)-1-methylpiperidine |
| 831795 | 1.82 | Racemic | Q | CH | H | 1 | 1-(4-methoxybenzyl)-N-methylpiperidin-4-amine |
| 831798 | 46.3 | Racemic | O | CH | H | 1 | N-methyl-2-(2-chlorophenyl)ethylamine |

-continued

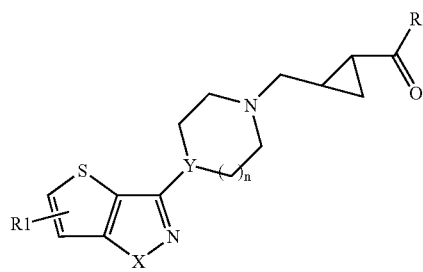

| MDL # | D3 Ki (nM) | Chirality | X | Y | R1 | n | R2 |
|---|---|---|---|---|---|---|---|
| 831799 | 12.1 | Racemic | O | CH | H | 1 | N-CH2CH2-(3-Cl-phenyl), N-methyl |
| 831800 | 5 | Racemic | O | CH | H | 1 | N-CH2CH2-(4-Cl-phenyl), N-methyl |
| 831801 | 11.2 | Racemic | O | CH | H | 1 | N-CH2CH2-(3-F-phenyl), N-methyl |
| 831802 | 13.4 | Racemic | O | CH | H | 1 | N-CH2CH2-(4-F-phenyl), N-methyl |
| 831803 | 7.44 | Racemic | O | CH | H | 1 | N-CH2CH2-(4-CH3-phenyl), N-methyl |
| 831804 | 9.89 | Racemic | O | CH | H | 1 | N-CH2CH2-(3-OCH3-phenyl), N-methyl |
| 831805 | 10.2 | Racemic | O | CH | H | 1 | N-CH2CH2-(2-OCH3-phenyl), N-methyl |
| 831818 | 0.117 | Racemic | O | CH | H | 1 | 4-(N-methyl)-1-(2-naphthylmethyl)piperidine |
| 831819 | 0.1 | Racemic | O | CH | H | 1 | 4-(N-methyl)-1-(3,5-dichlorobenzyl)piperidine |
| 831820 | 6.54 | Racemic | O | CH | H | 1 | 4-(N-methyl)-1-(4-phenoxybenzyl)piperidine |

-continued

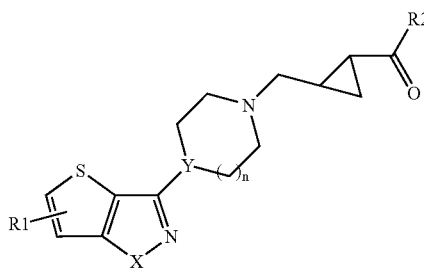

| MDL # | D3 Ki (nM) | Chirality | X | Y | R1 | n | R2 |
|---|---|---|---|---|---|---|---|
| 831821 | 24.1 | Racemic | O | CH | H | 1 | N-methylpiperidine-N-(2,6-dichlorobenzyl) |
| 831822 | 1.38 | Racemic | O | CH | H | 1 | N-methylpiperidine-N-(1-naphthylmethyl) |
| 831823 | 2.37 | Racemic | O | CH | H | 1 | N-methylpiperidine-N-(cyclohexylmethyl) |
| 831830 | 0.76 | R,R | N-Me | N | H | 1 | N-methyl-N-(3-imidazol-1-yl-propyl) |
| 831831 | 6.31 | Racemic | O | CH | H | 1 | N-methylpiperidine-N-(3-trifluoromethylbenzyl) |
| 831835 | 234 | Racemic | O | CH | H | 1 | 4-methylpiperazine-1-sulfonyl-phenyl |
| 831836 | 94.3 | Racemic | O | CH | H | 1 | 4-methylpiperazine-1-sulfonyl-biphenyl |
| 831837 | 491 | Racemic | O | CH | H | 1 | 4-methylpiperazine-1-sulfonyl-benzyl |

-continued
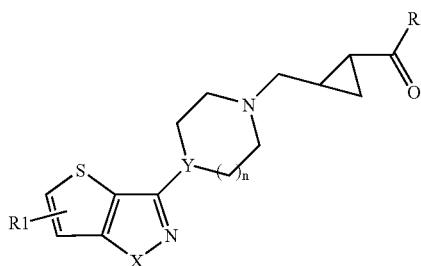
| MDL # | D3 Ki (nM) | Chirality | X | Y | R1 | n | R2 |
|---|---|---|---|---|---|---|---|
| 831838 | 141 | Racemic | O | CH | H | 1 |  |
| 831936 | 34.7 | R,R, (R,S) | O | CH | H | 1 | 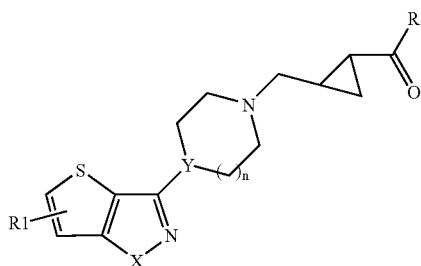 |
| 831937 | 35 | R,R | O | CH | H | 1 |  |
| 831938 | 33 | R,R | O | CH | H | 1 | 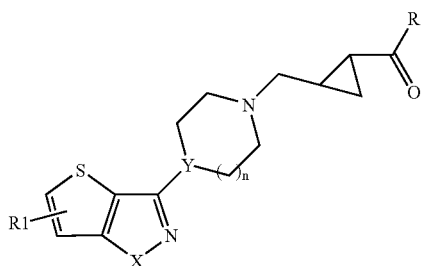 |
| 831951 | 36.7 | R,R | N-Ts | N | H | 1 |  |
| 831954 | 15.6 | R,R | O | CH | CH$_3$ | 1 | 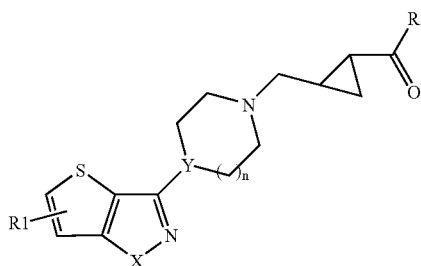 |
| 831955 | 47.3 | R,R | O | N | H | 1 |  |
| 831956DA | 5.91 | R,R | N-Me | N | H | 1 | 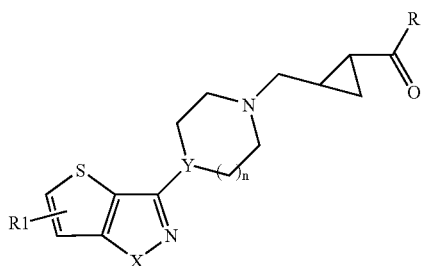 |
| 831957 | 63.2 | R,R | O | CH | H | 1 |  |
| 831991 | 0.722 | Racemic | O | CH | H | 1 | 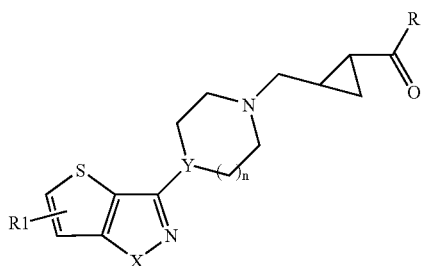 |

-continued

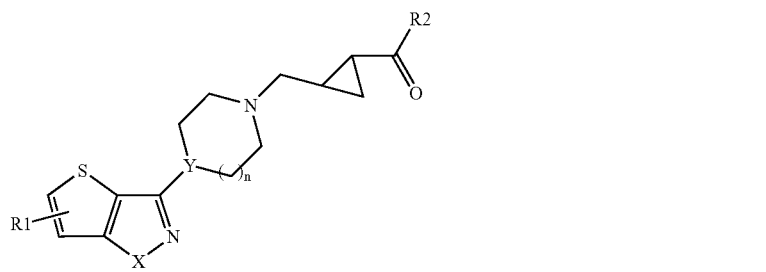

| MDL # | D3 Ki (nM) | Chirality | X | Y | R1 | n | R2 |
|---|---|---|---|---|---|---|---|
| 831992 | 4.81 | Racemic | O | CH | H | 1 | N-methylpiperidine, N-(4-methylbenzyl) |
| 831993 | 2.51 | Racemic | O | CH | H | 1 | N-methylpiperidine, N-(4-fluorobenzyl) |
| 831994 | 2.68 | Racemic | O | CH | H | 1 | N-methylpiperidine, N-(3-fluorobenzyl) |
| 831995 | 4.73 | Racemic | O | CH | H | 1 | N-methylpiperidine, N-(3-chlorobenzyl) |
| 831996 | 7.97 | Racemic | O | CH | H | 1 | N-methylpiperidine, N-(2-chlorobenzyl) |
| 831997 | 3.55 | Racemic | O | CH | H | 1 | N-methylpiperidine, N-(4-chlorobenzyl) |
| 831998 | 7.46 | Racemic | O | CH | H | 1 | N-methylpiperidine, N-(3,4-dichlorobenzyl) |
| 831999 | 473 | Racemic | O | CH | H | 1 | N-methylpiperazine, N-(4-pyridylmethyl) |
| 832000 | 79.6 | Racemic | O | CH | H | 1 | N-methylpiperazine, N-(2-(4-pyridyl)ethyl) |
| 832001 | 157 | Racemic | O | CH | H | 1 | N-methylpiperazine, N-(2-(2-pyridyl)ethyl) |

-continued
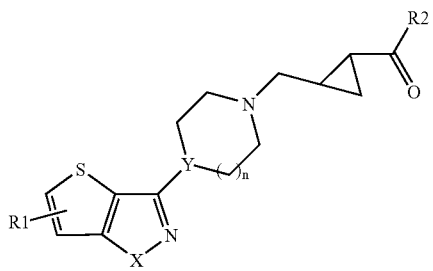
| MDL # | D3 Ki (nM) | Chirality | X | Y | R1 | n | R2 |
|---|---|---|---|---|---|---|---|
| 832044 | 657 | Racemic | O | CH | H | 1 | |
| 832045 | 22 | Racemic | O | CH | H | 1 | |
| 832046 | 35.5 | Racemic | O | CH | H | 1 | |
| 832047 | 25.8 | Racemic | O | CH | H | 1 | |
| 832049 | 6.54 | Racemic | O | CH | H | 1 | |
| 832055 | 112 | Racemic | O | CH | H | 1 | |
| 832057 | 21.7 | Racemic | O | CH | H | 1 | |

-continued

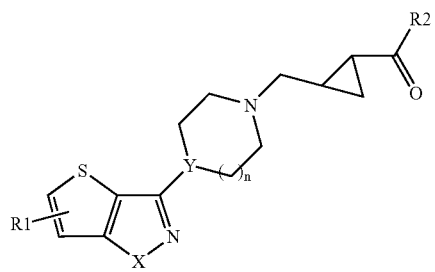

| MDL # | D3 Ki (nM) | Chirality | X | Y | R1 | n | R2 |
|---|---|---|---|---|---|---|---|
| 832058 | 24.2 | Racemic | O | CH | H | 1 | piperazine-N-methyl, N-CH2CH2-cyclohexyl |
| 832059 | 4.13 | Racemic | O | CH | H | 1 | N-methyl piperazine-N-(4-benzyloxyphenyl) |
| 832153 | 30.74 | Racemic | O | CH | H | 1 | N-methyl piperazine-N-benzyl |
| 832154 | 21.86 | Racemic | O | CH | H | 1 | N-methyl piperazine-N-(4-methylbenzyl) |
| 832155 | 0.434 | Racemic | O | CH | H | 1 | N-methyl piperazine-N-(4-methoxybenzyl) |
| 832156 | 0.315 | Racemic | O | CH | H | 1 | N-methyl piperazine-N-(4-chlorobenzyl) |
| 832157 | 0.226 | Racemic | O | CH | H | 1 | N-methyl piperazine-N-(4-tert-butylbenzyl) |
| 832158 | 0.37 | Racemic | O | CH | H | 1 | N-methyl piperazine-N-(3-methylbenzyl) |
| 832164 | 6.6 | Racemic | O | CH | H | 1 | N-methyl piperazine-N-(4-fluorobenzyl) |

-continued
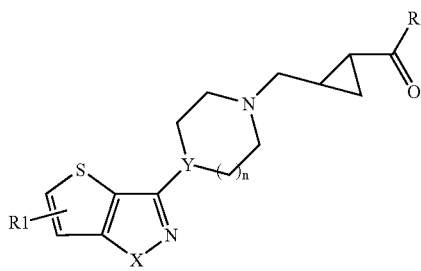
| MDL # | D3 Ki (nM) | Chirality | X | Y | R1 | n | R2 |
|---|---|---|---|---|---|---|---|
| 832165 | 30.13 | Racemic | O | CH | H | 1 | |
| 832185 | 7.87 | Racemic | O | CH | H | 1 | |
| 832186 | 16.06 | Racemic | O | CH | H | 1 | |
| 832187 | 19.14 | Racemic | O | CH | H | 1 | |
| 832188 | 10.1 | Racemic | O | CH | H | 1 | |
| 832189 | 58.47 | Racemic | O | CH | H | 1 | |
| 832190 | 94.61 | Racemic | O | CH | H | 1 | |
| 832191 | 8.06 | Racemic | O | CH | H | 1 | |
| 832192 | 7.81 | Racemic | O | CH | H | 1 | |

-continued

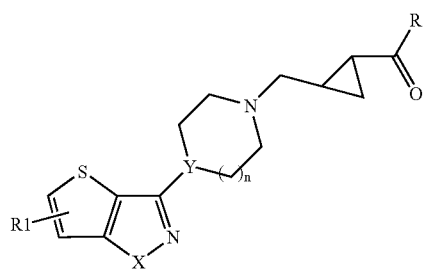

| MDL # | D3 Ki (nM) | Chirality | X | Y | R1 | n | R2 |
|---|---|---|---|---|---|---|---|
| 832193 | 13.1 | Racemic | O | CH | H | 1 | 4-(1-methylpiperidin-4-yl)imidazole |
| 832194 | 23 | Racemic | O | CH | H | 1 | 1-methyl-4-(2,4,6-trimethylbenzyl)piperazine |
| 832195 | 22.8 | Racemic | O | CH | H | 1 | 1-(cyclohexylmethyl)-4-methylpiperazine |
| 832196 | 22.9 | Racemic | O | CH | H | 1 | 1-cyclopentyl-4-methylpiperazine |
| 832197 | 17.1 | Racemic | O | CH | H | 1 | 1-methyl-4-(3-phenylpropyl)piperazine |
| 832198 | 5.81 | Racemic | O | CH | H | 1 | 1-methyl-4-(2-(pyrrolidin-1-yl)ethyl)piperidine |
| 832199 | 18.7 | Racemic | O | CH | H | 1 | N-methyl-1-(3-(trifluoromethyl)pyridin-2-yl)pyrrolidin-3-amine |
| 832207 | 54.84 | R,R | N-Me | N | H | 1 | 4-(1-methylpiperidin-4-yl)imidazole |

-continued

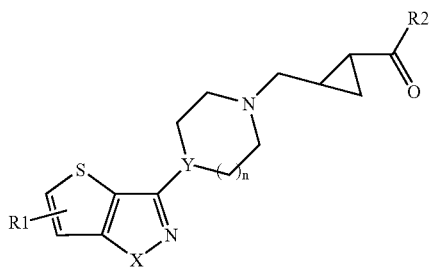

| MDL # | D3 Ki (nM) | Chirality | X | Y | R1 | n | R2 |
|---|---|---|---|---|---|---|---|
| 832269 | 5.1 | R,R, (R,S) | O | CH | H | 1 | methylpiperidinyl-methyl-imidazole |
| 832340 | 11.54 | Racemic | O | CH | H | 1 | N-methyl-piperidinyl-(2,3-difluorobenzyl) |
| 832341 | 2.63 | Racemic | O | CH | H | 1 | N-methyl-piperidinyl-(cyclopropylmethyl) |
| 832342 | 0.077 | Racemic | O | CH | H | 1 | N-methyl-piperidinyl-(3,4-difluorobenzyl) |
| 832343 | 0.718 | Racemic | O | CH | H | 1 | N-methyl-piperidinyl-(3,5-difluorobenzyl) |
| 832344 | 2.76 | Racemic | O | CH | H | 1 | N-methyl-piperidinyl-(2,4-difluorobenzyl) |
| 832345 | 1.46 | Racemic | O | CH | H | 1 | N-methyl-piperidinyl-(2,5-difluorobenzyl) |
| 832346 | 12.88 | Racemic | O | CH | H | 1 | N-methyl-piperidinyl-(2-chloro-5-fluorobenzyl) |

-continued
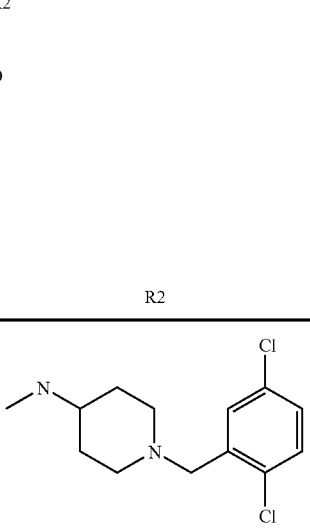
| MDL # | D3 Ki (nM) | Chirality | X | Y | R1 | n | R2 |
|---|---|---|---|---|---|---|---|
| 832347 | 1.88 | Racemic | O | CH | H | 1 | 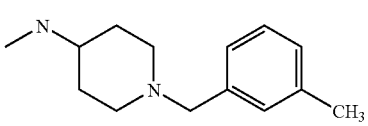 |
| 832348 | 0.465 | Racemic | O | CH | H | 1 | 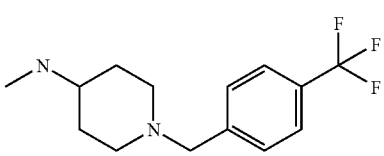 |
| 832349 | 0.843 | Racemic | O | CH | H | 1 | 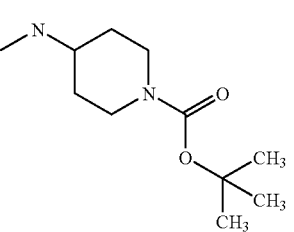 |
| 832391 | 77.93 | Racemic | O | CH | H | 1 | 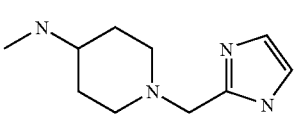 |
| 832392 | 2.29 | Racemic | O | CH | H | 1 | 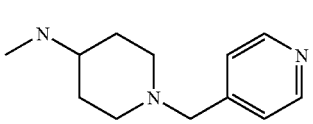 |
| 832393 | 8.44 | Racemic | O | CH | H | 1 | 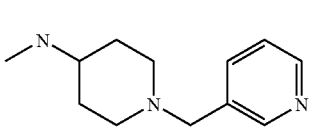 |
| 832394 | 8.32 | Racemic | O | CH | H | 1 | 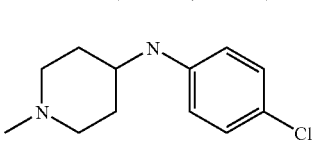 |
| 832395 | 30.2 | Racemic | O | CH | H | 1 | |

-continued
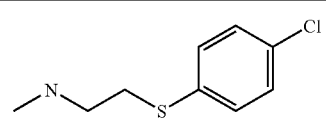
| MDL # | D3 Ki (nM) | Chirality | X | Y | R1 | n | R2 |
|---|---|---|---|---|---|---|---|
| 832397 | 51.94 | Racemic | O | CH | H | 1 | 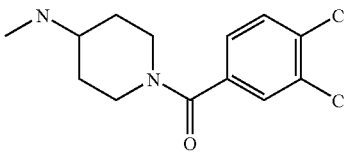 |
| 832464 | 12.8 | Racemic | O | CH | H | 1 | 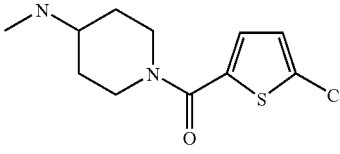 |
| 832487 | 66.1 | Racemic | O | CH | H | 1 | 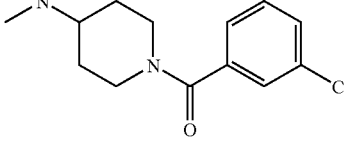 |
| 832488 | 39.5 | Racemic | O | CH | H | 1 | 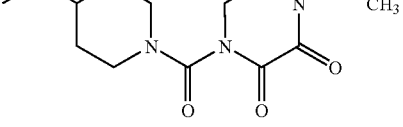 |
| 832489 | 95 | Racemic | O | CH | H | 1 | 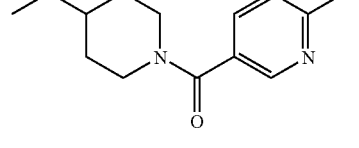 |
| 832505 | 40.6 | Racemic | O | CH | H | 1 | 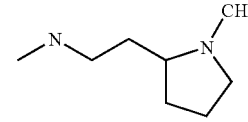 |
| 832513 | 55.4 | R,R (Isomer 1) | O | CH | H | 1 | 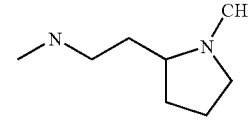 |
| 832514 | 114.6 | S,S, (Isomer 2) | O | CH | H | 1 | |

-continued

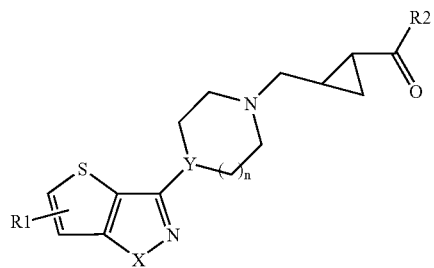

| MDL # | D3 Ki (nM) | Chirality | X | Y | R1 | n | R2 |
|---|---|---|---|---|---|---|---|
| 832527 | 45.4 | R,R | O | CH | H | 1 | 1-methylpiperidin-4-yl benzothiazole |
| 832528 | 48.5 | R,R | O | CH | H | 1 | N-methyl-2-((5-chloronaphthalen-1-yl)sulfonyl)ethanamine |
| 832529 | 145.6 | R,R | O | CH | H | 1 | 1-(2-(methylamino)ethyl)imidazolidin-2-one |
| 832530 | 16 | R,R | O | CH | H | 1 | N-methyl-4-(pyridin-3-yl)butan-1-amine |
| 832531 | 67.67 | R,R | O | CH | H | 1 | 1-(1-methylpiperidin-4-yl)-1H-benzimidazol-2(3H)-one |
| 832532 | 14.4 | R,R | O | CH | H | 1 | 1-(3,4-dichlorobenzyl)-4-methylpiperazine |
| 832533 | 4.12 | R,R, (R,S) | O | CH | H | 1 | tert-butyl 2-(2-(methylamino)ethyl)piperidine-1-carboxylate |

-continued

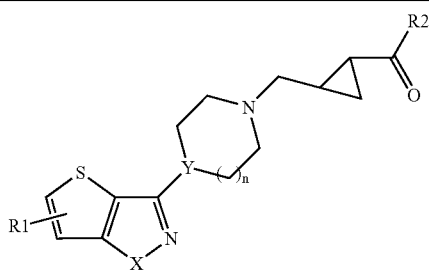

| MDL # | D3 Ki (nM) | Chirality | X | Y | R1 | n | R2 |
|---|---|---|---|---|---|---|---|
| 832565 | 1.45 | R,R | N-(4-fluorophenyl) | N | H | 1 | N-methyl-3-(1-imidazolyl)propylamine |
| 832566 | 1.76 | R,R | N-(4-fluorophenyl) | N | H | 1 | trans-4-(methylamino)cyclohexanol |
| 832573FH | 4.52 | Racemic | O | CH | H | 1 | 1-[2-(3-chlorophenyl)ethyl]-4-(methylamino)piperidine |
| 832574FH | 57.34 | R,R | O | CH | H | 1 | N-methyl-3-(benzimidazol-2-yl)propylamine |
| 832575ES | 4.06 | Racemic | O | CH | H | 1 | 4-(methylamino)-N-(4-chlorophenyl)piperidine-1-carboxamide |
| 832576ES | 17.5 | Racemic | O | CH | H | 1 | 4-(methylamino)-N-(4-fluorophenyl)piperidine-1-carboxamide |
| 832634 | 7.63 | R,R | N-(4-trifluoromethylphenyl) | N | H | 1 | N-methyl-3-(1-imidazolyl)propylamine |

-continued

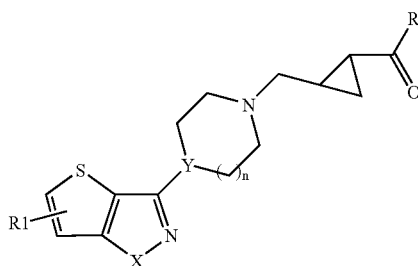

| MDL # | D3 Ki (nM) | Chirality | X | Y | R1 | n | R2 |
|---|---|---|---|---|---|---|---|
| 832648 | 20.8 | R,R | N-(4-trifluoromethylphenyl) | N | H | 1 | trans-4-(methylamino)cyclohexanol |
| 832692 | 7.29 | R,R | N-Ph | N | H | 1 | N-methyl-3-(imidazol-1-yl)propylamine |
| 832723 | 54 | R,R | O | CH | H | 1 | 1-methyl-4-(4-chlorophenoxy)piperidine |
| 832724 | 1.44 | R,R | O | CH | H | 1 | 4-(methylamino)-1-(2-methoxybenzyl)piperidine |
| 832725 | 4.22 | R,R | O | CH | H | 1 | N-methyl-2-(4-fluorophenyl)ethylamine |
| 832726 | 7.05 | R,R | O | CH | H | 1 | N-methyl-2-(3-fluorophenyl)ethylamine |
| 832727 | 1.19 | R,R | O | CH | H | 1 | 4-(methylamino)-1-(3-fluorobenzyl)piperidine |
| 832728 | 3.12 | R,R | O | CH | H | 1 | 4-(methylamino)-1-(3-chlorobenzyl)piperidine |
| 832729 | 1.67 | R,R | O | CH | H | 1 | 4-(methylamino)-1-(4-chlorobenzyl)piperidine |

-continued
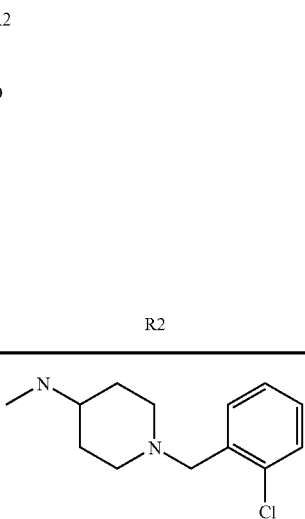
| MDL # | D3 Ki (nM) | Chirality | X | Y | R1 | n | R2 |
|---|---|---|---|---|---|---|---|
| 832730 | 3.62 | R,R | O | CH | H | 1 | 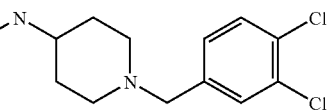 |
| 832731 | 0.699 | R,R | O | CH | H | 1 | 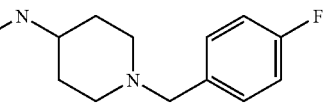 |
| 832732 | 0.74 | R,R | O | CH | H | 1 | 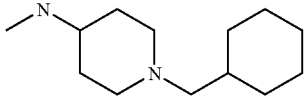 |
| 832733 | 0.656 | R,R | O | CH | H | 1 | 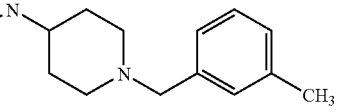 |
| 832788 | 1.84 | R,R | O | CH | H | 1 | 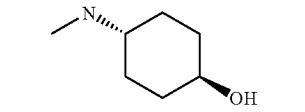 |
| 832816 | 2.57 | R,R | N-Ph | N | H | 1 | 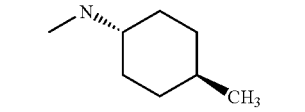 |
| 832849 | 1.12 | R,R | N-Ph | N | H | 1 | 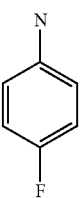 |
| 832850 | 0.264 | R,R | 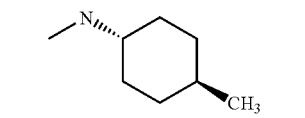 | N | H | 1 | 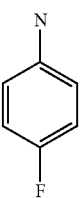 |

-continued

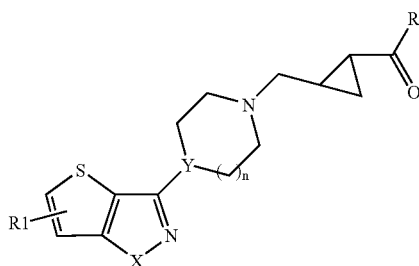

| MDL # | D3 Ki (nM) | Chirality | X | Y | R1 | n | R2 |
|---|---|---|---|---|---|---|---|
| 832881 | 37.86 | R,R | N-(4-trifluoromethylphenyl) | N | H | 1 | N-methyl-trans-4-methylcyclohexylamine |
| 833333 | 8.11 | R,R | N-(4-trifluoromethoxyphenyl) | N | H | 1 | N-methyl-3-(imidazol-1-yl)propylamine |
| 833372 | 1.04 | Racemic | O | CH | H | 1 | N-methyl-1-ethylpiperidin-4-amine |
| 833373 | 65.46 | R,R,S | O | CH | H | 1 | N-methyl-(1-Boc-pyrrolidin-3-yl)methylamine |
| 833374 | 30.6 | R,R (R,S) | O | CH | H | 1 | N-methyl-(1-Boc-piperidin-3-yl)methylamine |
| 833375 | 24.2 | R,R | O | CH | H | 1 | N-methyl-(1-Boc-piperidin-4-yl)methylamine |
| 833382 | 2.32 | R,R | O | CH | H | 1 | N-methyl-1-(imidazol-2-ylmethyl)piperidin-4-amine |

-continued

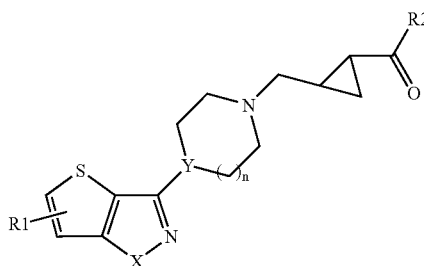

| MDL # | D3 Ki (nM) | Chirality | X | Y | R1 | n | R2 |
|---|---|---|---|---|---|---|---|
| 833383 | 2.57 | R,R | O | CH | H | 1 | 4-(methylamino)piperidine (NH) |
| 833384 | 5.68 | R,R,R | O | CH | H | 1 | (3R)-N-methyl-pyrrolidin-3-ylmethylamine |
| 833385 | 3.31 | R,R (R,S) | O | CH | H | 1 | N-methyl-(piperidin-3-yl)methylamine |
| 833386 | 36.46 | R,R | O | CH | H | 1 | N-methyl-(piperidin-4-yl)methylamine |
| 833482 | 0.962 | R,R | O | CH | H | 1 | 1-(4-methylbenzyl)-4-(methylamino)piperidine |
| 833483 | 0.93 | R,R | O | CH | H | 1 | 1-(cyclopropylmethyl)-4-(methylamino)piperidine |
| 833485 | 2.99 | R,R | O | CH | H | 1 | 1-(pyridin-3-ylmethyl)-4-(methylamino)piperidine |
| 833509 | 41.53 | R,R | O | CH | H | 1 | 1-methyl-4-(2-(pyrrolidin-1-yl)ethyl)piperidine |
| 833714 | 4.16 | R,R | O | CH | H | 1 | 4-(methylamino)-N-(4-chlorophenyl)piperidine-1-carboxamide |
| 833715 | 5.7 | R,R | O | CH | H | 1 | 4-(methylamino)-N-(4-fluorophenyl)piperidine-1-carboxamide |

-continued

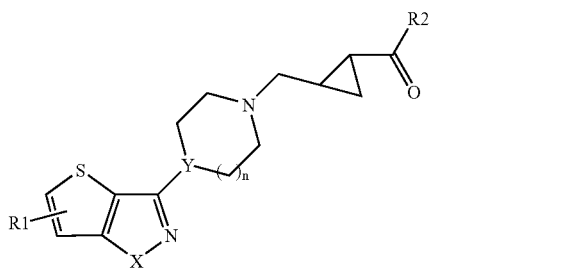

| MDL # | D3 Ki (nM) | Chirality | X | Y | R1 | n | R2 |
|---|---|---|---|---|---|---|---|
| 833748 | 1.38 | R,R | O | CH | H | 1 | N-methyl-4-piperidinyl-N-(2-(3-chlorophenyl)ethyl) |
| 833855 | 12.4 | R,R | N-(4-trifluoromethoxyphenyl) | N | H | 1 | trans-4-(methylamino)cyclohexanol |
| 833856 | 3.01 | R,R | N-(3-fluorophenyl) | N | H | 1 | trans-4-methyl-N-methylcyclohexylamine |
| 833876 | 50.3 | R,R | N-(4-trifluoromethoxyphenyl) | N | H | 1 | trans-4-methyl-N-methylcyclohexylamine |
| 833909 | 1.86 | R,R | N-Ph | CH | H | 1 | trans-4-methyl-N-methylcyclohexylamine |
| 834205 | 90.47 | R,R | N-(4-trifluoromethylphenyl) | N | H | 1 | N-methyl-3-morpholinopropylamine |

-continued
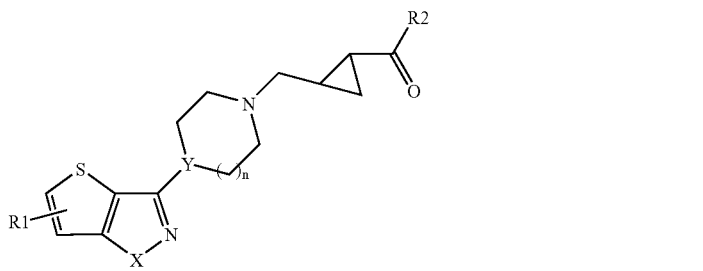
| MDL # | D3 Ki (nM) | Chirality | X | Y | R1 | n | R2 |
|---|---|---|---|---|---|---|---|
| 834206 | 88.82 | R,R | N-(4-trifluoromethylphenyl) | N | H | 1 | -N-(CH2)3-thiomorpholine |
| 834207 | 71.4 | R,R | N-(4-trifluoromethoxyphenyl) | N | H | 1 | -N-(CH2)3-(4-methylpiperidine) |
| A002201942 | 30.2 | R,R | N-(4-trifluoromethylphenyl) | N | H | 1 | -N-(CH2)3-piperidine |
| A002202401 | 205.3 | R,R | N—(CH$_2$)$_3$—CH$_3$ | N | H | 1 | -N-(CH2)3-imidazole |
| A002202402 | 47.33 | R,R | N-Me | N | H | 1 | -N-(CH2)3-morpholine |
| A002202403 | 86.78 | R,R | N-Me | N | H | 1 | -N-(CH2)3-benzimidazole |

-continued

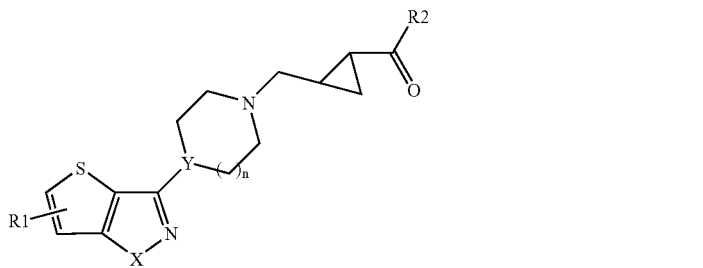

| MDL # | D3 Ki (nM) | Chirality | X | Y | R1 | n | R2 |
|---|---|---|---|---|---|---|---|
| A002243385 | 660.86 | R,R | 4-(OCF₃)-C₆H₄-N | N | H | 1 | N-methyl-3-(benzimidazol-1-yl)propylamine |
| A002243404 | 492.34 | R,R | 3-F-C₆H₄-N | N | H | 1 | trans-4-(methylamino)cyclohexanol |
| A002287757 | 2.41 | R,R | N-Me | N | H | 1 | N-methyl-1-(cyclohexylmethyl)piperidin-4-amine |
| A002287758 | 139.32 | R,R | 4-(OCF₃)-C₆H₄-N | N | H | 1 | N-methyl-3-(4-methylpiperazin-1-yl)propylamine |
| A002287767 | 3.3 | R,R | N—CH₂—CF₃ | CH | H | 1 | N-methyl-3-(imidazol-1-yl)propylamine |
| A002328969 | 137.1 | R,R | N—CH₂—CF₃ | CH | H | 1 | N-methyl-3-(piperidin-1-yl)propylamine |
| A002328970 | 36.2 | R,R | N—CH₂—CF₃ | CH | H | 1 | 1-methyl-4-((imidazol-1-yl)methyl)piperidine |

-continued
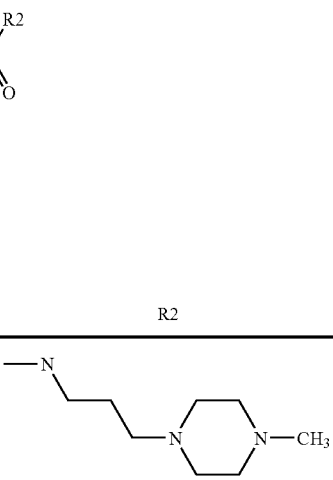
| MDL # | D3 Ki (nM) | Chirality | X | Y | R1 | n | R2 |
|---|---|---|---|---|---|---|---|
| A002329040 | 159.9 | R,R | N-Me | N | H | 1 | 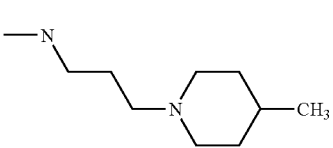 |
| A002350369 | 100.28 | R,R | N-Me | N | H | 1 | 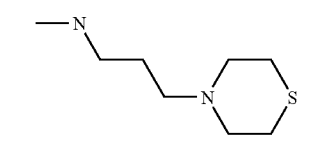 |
| A002350370 | 81.25 | R,R | N-Me | N | H | 1 | 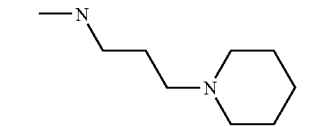 |
| A002436290 | 520.47 | R,R | N-Me | CH | H | 1 | 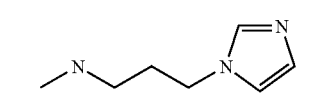 |
| A002436291 | 0.629 | R,R | N-Me | CH | H | 1 | 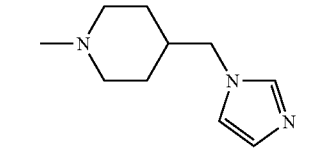 |
| A002436292 | 128.56 | R,R | N-Me | CH | H | 1 | 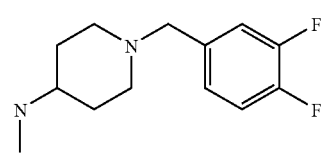 |
| A002436428 | 2.17 | R,R | N-Me | N | H | 1 | 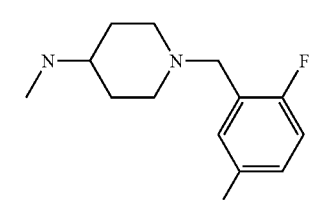 |
| A002436429 | 4.16 | R,R | N-Me | N | H | 1 | |

-continued

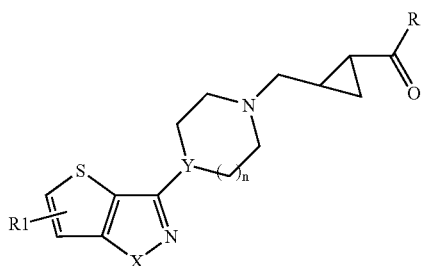

| MDL # | D3 Ki (nM) | Chirality | X | Y | R1 | n | R2 |
|---|---|---|---|---|---|---|---|
| A002437082 | 9.23 | R,R | 4-(trifluoromethoxy)phenyl–N | N | H | 1 | N-methyl-N-[1-(2,5-difluorobenzyl)piperidin-4-yl] |
| A002437083 | 11.03 | R,R | 4-(trifluoromethoxy)phenyl–N | N | H | 1 | N-methyl-N-[1-(3,4-difluorobenzyl)piperidin-4-yl] |
| A002437084 | 7.105 | R,R | 4-(trifluoromethoxy)phenyl–N | N | H | 1 | N-methyl-N-[1-(cyclohexylmethyl)piperidin-4-yl] |
| A002437352 | 1.22 | R,R,S | N-Me | CH | H | 1 | (3)-(1-methylpiperidin-3-yl)methyl-imidazol-1-yl |
| A002438640 | 104.16 | R,R | N-Me | CH | H | 1 | N-methyl-N-[3-(4-methylpiperazin-1-yl)propyl] |
| A002438641 | 62.76 | R,R | N-Me | CH | H | 1 | N-methyl-N-[(1-tert-butoxycarbonylpiperidin-4-yl)methyl] |

-continued

| MDL # | D3 Ki (nM) | Chirality | X | Y | R1 | n | R2 |
|---|---|---|---|---|---|---|---|
| A002439262 | 28.3 | R,R | N-Ph | CH | H | 1 | piperidine-N-CH2- with N-Boc (tert-butyl carbamate) |
| A002439263 | 30.6 | R,R | N-Ph | CH | H | 1 | -N-CH2CH2CH2-N(piperazine)-N-CH3 |
| A002439265 | 87.98 | R,R | N—CH2—CF3 | CH | H | 1 | -N-CH2CH2CH2-N(piperazine)-N-CH3 |
| A002439266 | 66.04 | R,R | N—CH2—CF3 | CH | H | 1 | piperidine-N-CH2- with N-Boc (tert-butyl carbamate) |
| A002440434A | 462.13 | R,R | N-Me | CH | H | 1 | -N-CH2-piperidine-NH |
| A002440435A | 304.55 | R,R | N—CH2—CF3 | CH | H | 1 | -N-CH2-piperidine-NH |
| A002440436A | 11.38 | R,R | N-Ph | CH | H | 1 | -N-CH2-piperidine-NH |
| 833127 | 79.63 | R,R | O | CH | H | 1 | N-methylpiperazine with N-isopropyl |
| 833128 | 28.69 | R,R | O | CH | H | 1 | N-methylpiperazine-CH2-(4-chlorophenyl) |

-continued

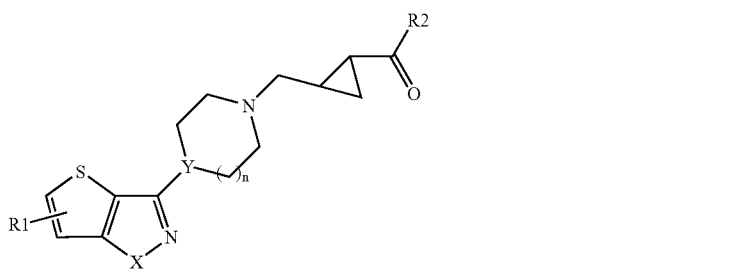

| MDL # | D3 Ki (nM) | Chirality | X | Y | R1 | n | R2 |
|---|---|---|---|---|---|---|---|
| 833129 | 95.34 | R,R | O | CH | H | 1 | N-methyl-N-[2-(4-tert-butylphenyl)ethyl]amine |
| 833130 | 8.85 | R,R | O | CH | H | 1 | N-methyl-N-[2-(3-trifluoromethylphenyl)ethyl]amine |
| 833131 | 16.8 | R,R | O | CH | H | 1 | 4-methyl-1-(3-phenylpropyl)piperazine |
| 833132 | 107.5 | R,R | O | CH | H | 1 | 4-methyl-1-(4-fluorobenzyl)piperazine |
| 833133 | 113.7 | R,R | O | CH | H | 1 | 4-methyl-1-(4-methoxybenzyl)piperazine |
| 833160 | 2.09 | R,R | O | CH | H | 1 | 1-methyl-4-[(4-trifluoromethylbenzyl)amino]piperidine |
| 833163 | 17.5 | R,R | O | CH | H | 1 | 4-methyl-1-[2-(thien-2-yl)ethyl]piperazine |
| 833164 | 52.55 | R,R | O | CH | H | 1 | 1-methyl-4-(imidazol-1-yl)piperidine |
| 833165 | 1.07 | R,R | O | CH | H | 1 | 1-methyl-4-[(3,4-difluorobenzyl)amino]piperidine |

-continued
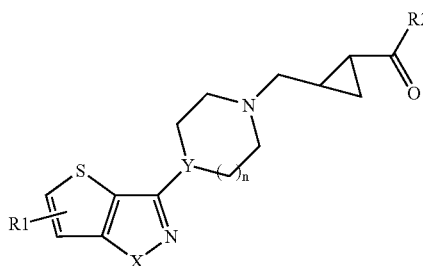
| MDL # | D3 Ki (nM) | Chirality | X | Y | R1 | n | R2 |
|---|---|---|---|---|---|---|---|
| 833166 | 1.72 | R,R | O | CH | H | 1 | (N-methylpiperidine N-benzyl 3,5-difluorophenyl) |
| 833167 | 1.57 | R,R | O | CH | H | 1 | (N-methylpiperidine N-benzyl 2,4-difluorophenyl) |
| 833168 | 3.11 | R,R | O | CH | H | 1 | (N-methylpiperidine N-benzyl 2,5-difluorophenyl) |
| 834126 | 4.9 | R,R | N-Bn | N | H | 1 | (N-methylaminopropyl pyrrole) |
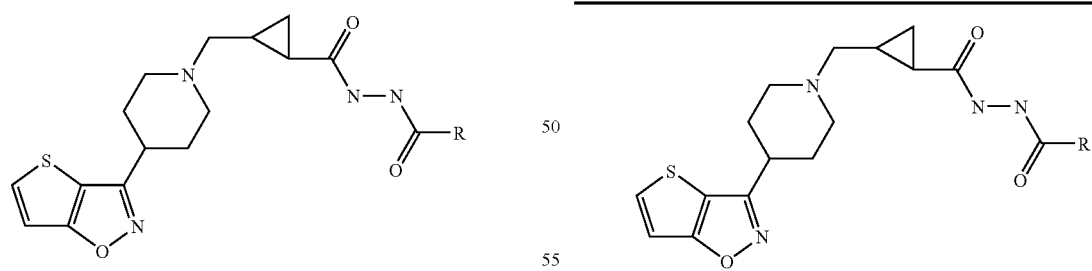
(All Compounds Racemic)
| MDL # | D3 Ki (nM) | R |
|---|---|---|
| 831452 | 115 | Bn |
| 831811 | 819 | 3-OMe-phenyl |
(All Compounds Racemic)
| MDL # | D3 Ki (nM) | R |
|---|---|---|
| 831812 | 453 | 4-Cl-phenyl |

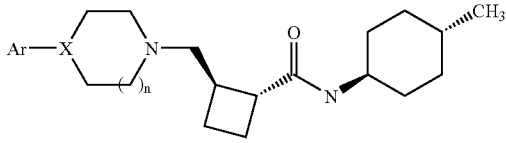
| MDL # | D3 KI (nM) | Chirality | n | X | Ar |
|---|---|---|---|---|---|
| 829997 | 10.4 | Racemic | 2 | N | 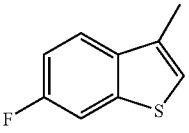 |
| 829830 | 65.3 | Racemic | 1 | CH | 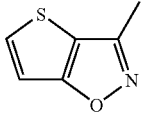 |
-continued
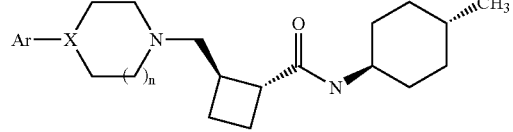
| MDL # | D3 KI (nM) | Chirality | n | X | Ar |
|---|---|---|---|---|---|
| 829996 | 277 | Racemic | 1 | N | 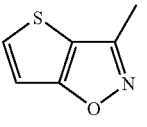 |
| 830000 | 286 | Racemic | 2 | N | 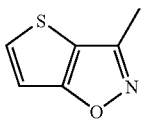 |
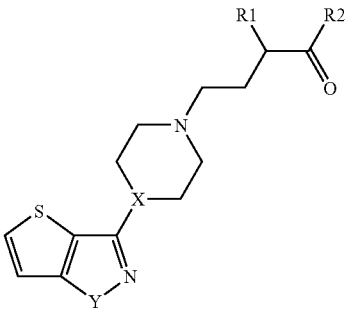
| MDL # | D3 KI (nM) | Chirality | X | Y | R1 | R2 |
|---|---|---|---|---|---|---|
| 830557 | 97.4 | S | CH | O | OH | 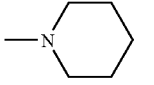 |
| 830558 | 34.2 | R | CH | O | OH | 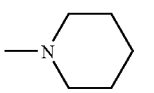 |
| 830573 | 547 | R | CH | O | OH | 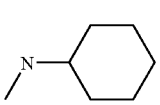 |
| 832212 | 301.8 | n.a. | N | O | H | 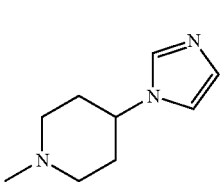 |

-continued

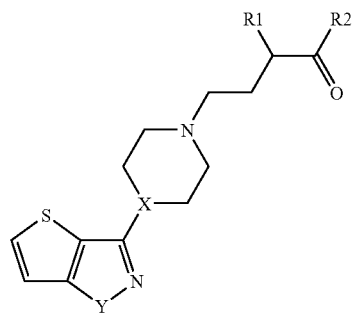

| MDL # | D3 KI (nM) | Chirality | X | Y | R1 | R2 |
|---|---|---|---|---|---|---|
| A002201941 | 119 | n.a. | N | N—CH₃ | H | ![N-methyl-trans-cyclohexyl] |

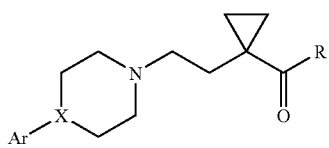

| MDL # | D3 KI (nM) | X | Ar | R |
|---|---|---|---|---|
| 832171 | 4.9 | CH | 3-methyl-thieno[3,2-d]isoxazole | N-methyl-3-(1H-imidazol-1-yl)propylamine |
| 832180 | 91 | CH | 3-methyl-thieno[3,2-d]isoxazole | —NH—(CH₂)₂-Ph |
| 832231 | 6.93 | N | 3-methyl-6-(trifluoromethyl)benzothiophene | N-methyl-3-(1H-imidazol-1-yl)propylamine |
| 832239 | 206.8 | CH | 3-methyl-thieno[3,2-d]isoxazole | N-methylpyrrolidine |
| 832240 | 185.96 | CH | 3-methyl-thieno[3,2-d]isoxazole | N-methyl-3-morpholinopropylamine |

-continued

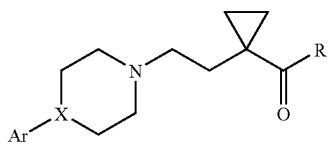

| MDL # | D3 KI (nM) | X | Ar | R |
|---|---|---|---|---|
| 832241A | 51.8 | CH | 3-methyl-thieno[3,2-d]isoxazole | N-methyl-trans-4-methylcyclohexyl |
| 832242A | 436.2 | CH | 3-methyl-thieno[3,2-d]isoxazole | N-methyl-trans-4-ethylcyclohexyl |
| 832317 | 943 | CH | 3-methyl-thieno[3,2-d]isoxazole | N-methyl-trans-4-hydroxycyclohexyl |
| 832517 | 172.58 | N | 3-methyl-6-trifluoromethyl-benzothiophene | N-methyl-trans-4-ethylcyclohexyl |
| 832518 | 98.2 | N | 6-trifluoromethyl-benzothiophen-3-ylmethyl | N-methyl-3-morpholinopropyl |
| 832519 | 97.51 | N | 6-trifluoromethyl-benzothiophen-3-yl | —NH—(CH₂)₂-Ph |
| 832520 | 140.93 | N | 3-methyl-6-trifluoromethyl-benzothiophene | N-methyl-trans-4-hydroxycyclohexyl |
| 833330 | 72.69 | CH | 3-methyl-6-fluoro-7-methoxy-benzisoxazole | N-methyl-trans-4-methylcyclohexyl |

-continued

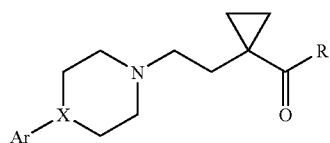

| MDL # | D3 KI (nM) | X | Ar | R |
|---|---|---|---|---|
| 833365 | 166.4 | CH | 3-methyl-6-fluoro-7-methoxy-benzisoxazole | N-methyl-3-piperidinylpropyl |
| 833378 | 23.7 | CH | 3-methyl-6-fluoro-7-methoxy-benzisoxazole | N-methyl-3-imidazolylpropyl |
| 833475 | 22.45 | N | 3-methyl-6-trifluoromethyl-benzothiophene | N-methyl-3-piperidinylpropyl |
| 833476 | 131.37 | CH | 3-methyl-6-fluoro-7-methoxy-benzisoxazole | trans-4-hydroxycyclohexyl-N-methyl |

-continued

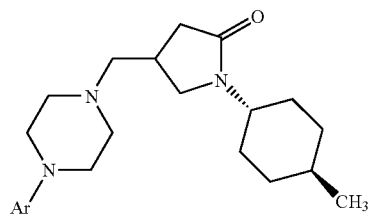

| MDL # | D3 KI (nM) | Chirality | Ar |
|---|---|---|---|
| 832831DA | 153.74 | Racemic | 3-methyl-thieno-isoxazole |

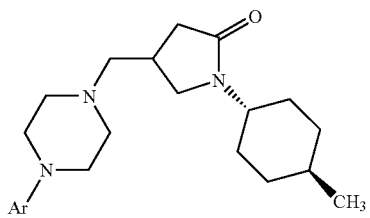

| MDL # | D3 KI (nM) | Chirality | Ar |
|---|---|---|---|
| 833953A | 88.82 | Racemic | 3-methyl-6-trifluoromethyl-benzothiophene |

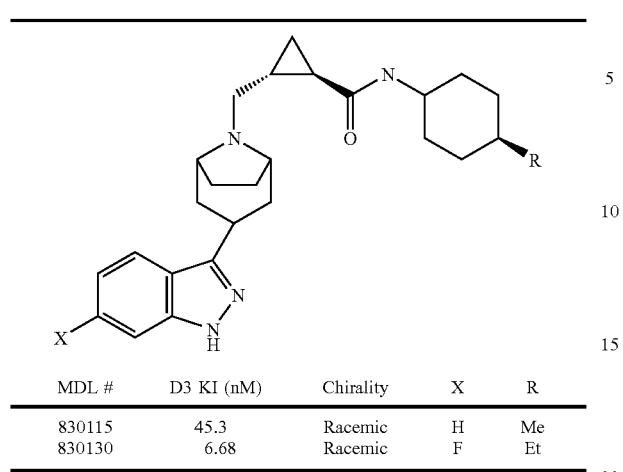

| MDL # | D3 KI (nM) | Chirality | X | R |
|---|---|---|---|---|
| 830115 | 45.3 | Racemic | H | Me |
| 830130 | 6.68 | Racemic | F | Et |

We claim:
1. A compound of the formula (I):

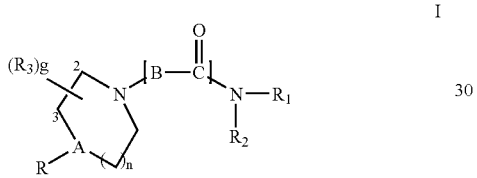

I wherein
  A is N;
  n is 1;
  g is 1 or 2;
  each $R_3$ is independently hydrogen, $C_1$–$C_6$alkyl, or

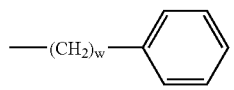

wherein w is 1, 2, or 3;
  R is selected from the group consisting of the following:

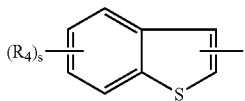 a)

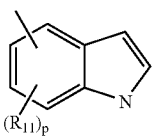 h)

wherein the nitrogen atom is substituted by H

-continued

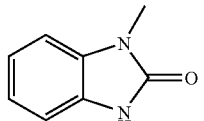 i)

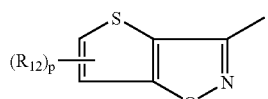 k)

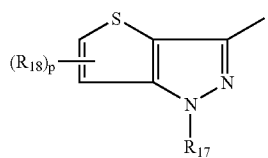 n)

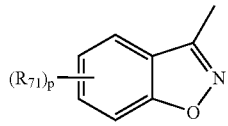 o)

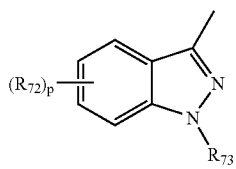 p)

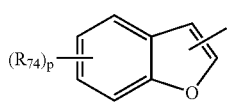 q)

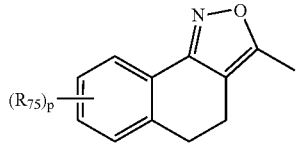 r)

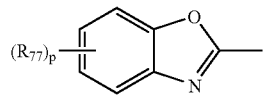 t)

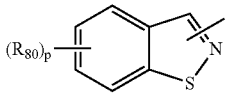 w)

wherein
  each $R_4$, $R_{11}$, $R_{12}$ and $R_{18}$ is independently hydrogen, $C_1$–$C_6$alkyl, halogen, trifluoromethyl, —$CO_2C_1$–$C_6$alkyl or —$CH_2OC_1$–$C_6$alkyl;
  each $R_{71}$, $R_{72}$, $R_{74}$ and $R_{80}$ is independently hydrogen, $C_1$–$C_6$alkyl, $C_1$–$C_6$alkoxy, halogen, trifluoromethyl, —$CO_2C_1$–$C_6$alkyl or —$CH_2OC_1$–$C_6$alkyl;
  $R_{73}$ is hydrogen, alkyl, pyridyl, benzyl, —$CH_2CF_3$, —$CO_2C_1$–$C_6$alkyl, phenyl optionally substituted with halogen, trifluoromethyl, trifluoromethoxy or $R_{73}$ is c)

[cyclopentyl structure with (CR25R26)q— and (R24)t substituents]

wherein
  each R24 is independently hydrogen or C1–C6alkyl;
  each R25, and R26 is independently hydrogen or C1–C6alkyl;
  t is 0 or 1; and
  q is 0 or 1;

R2 is a group selected from (a)–(jj):

—(CH2)z—[ring]—(CR27R28)e  (a)

[phenyl with (M)h and (CR29R30)u substituents]  (b)

—(CR31R32)o—[benzodioxole with (R63)h]  (c)

—(CR33R34)l—[naphthalene with (R64)h]  (d)

—(CR35R36)j—[5-membered heterocycle with X and (R65)h]  (e)

—(CR83R84)w—[benzimidazole with NH-R81]  (f)

[pyridine with (V)h]
—(CR37R38)v—  (g)

—(CR39R40)f—[piperazine with X5]  (h)

[tetrahydronaphthalene]  (i)

HN—[cyclohexyl]—(R66)h  (j)

---

469

[methylcyclopentyl structure with ( )w]

wherein w is 1, 2 or 3;
each R75 is hydrogen, halogen, C1–C6alkyl or C1–C6alkoxy;
each R77 is hydrogen, halogen, C1–C6alkyl or C1–C6alkoxy;
p and s are 0, 1, or 2;
R17 is hydrogen, C1–C6alkyl, Ar, —COAr, —CONHAr or —SO2—Ar wherein Ar is a phenyl group which is optionally mono- or di-substituted with substituents independently selected from C1–C6alkyl, halogen, trifluoromethyl, C1–C6alkoxy, nitro, CN and COC1–C6alkyl; and $$-[B-\overset{O}{\underset{\|}{C}}]-$$

represents a group selected from (b)–(f):

[cyclopropyl with R21, R22, R23 and C=O]  (b)

[cyclobutyl with C=O]  (c)

[cyclopentyl with C=O]  (d)

[cyclohexyl with C=O]  (e)

[cyclopropylmethyl with C=O]  (f)

wherein
  R21, R22, and R23 are each independently hydrogen or C1–C3 linear alkyl;
R1 is a) hydrogen;
  b) C1–C6alkyl optionally mono- or di-substituted with hydroxy; or -continued
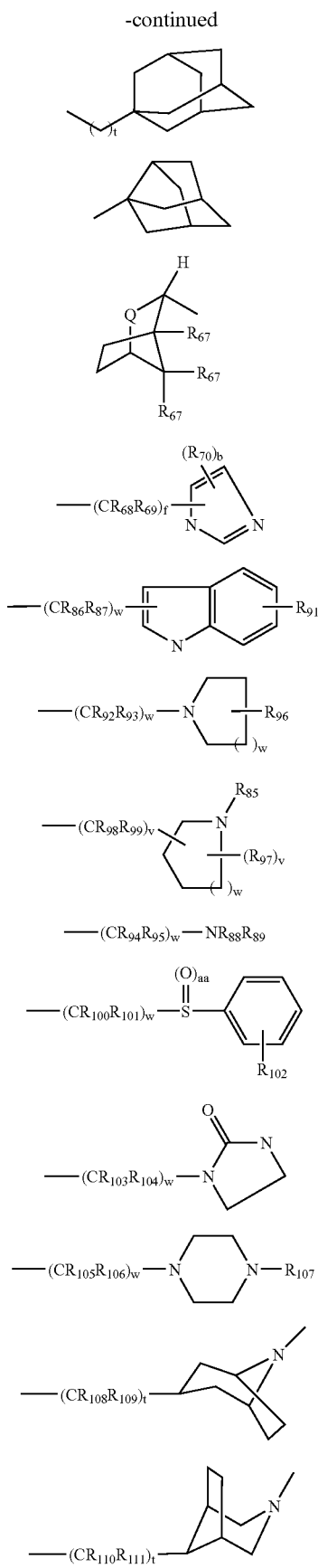
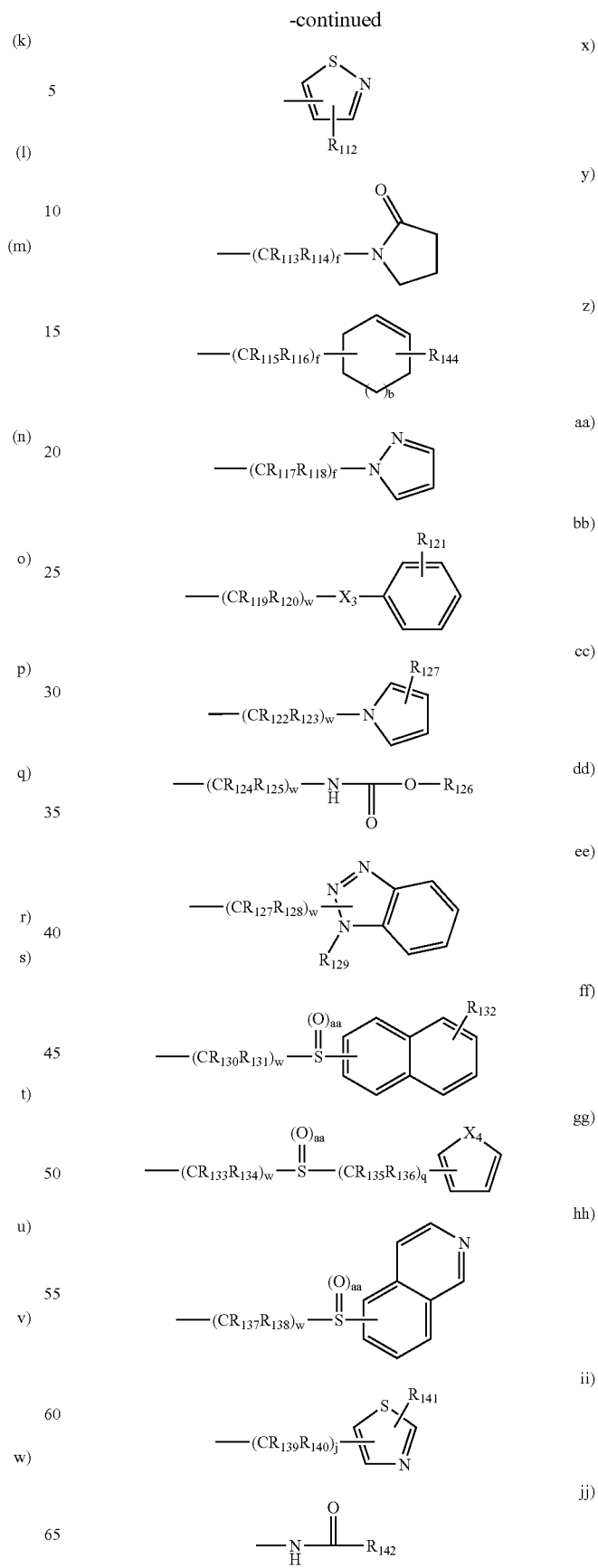

wherein
  each $R_{27}$ and $R_{28}$ is independently selected from:
  (1) hydrogen;
  (2) $C_1$–$C_6$alkyl;
  (3) $C_1$–$C_6$alkoxy;
  (4) —$C_2$—$R_{43}$ wherein $R_{43}$ is hydrogen or $C_1$–$C_6$alkyl;
  (5) hydroxy;
  (6) —$(CH_2)_a$—$OR_{44}$ wherein a is 1, 2 or 3 and $R_{44}$ is hydrogen or $C_1$–$C_6$alkyl;
  (7) —(CO)—$NR_{45}R_{46}$
    wherein $R_{45}$ and $R_{46}$ are each independently hydrogen, $C_1$–$C_2$alkyl, or $R_{45}$ and $R_{46}$ taken together with the nitrogen to which they are attached form

;

z is 0 or 1;
e is 2, 3, 4, 5, 6 or 7;
h is 0, 1, 2 or 3;
u is 0, 1, 2, 3 or 4;
o is 0 or 1;
l is 0 or 1;
j is 0, 1, 2 or 3;
v is 0, 1, 2, 3 or 4;
w is 1, 2 or 3;
f is 1, 2, 3 or 4;
t is 0 or 1;
b is 0, 1 or 2;
q is 0 or 1;
aa is 0 or 2;
X is O, S or $NR_{90}$ wherein $R_{90}$ is hydrogen, $C_1$–$C_6$alkyl, or

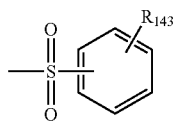

wherein $R_{143}$ is hydrogen or alkyl;
each M and V is a group independently selected from hydrogen, halogen, $C_1$–$C_6$alkyl, $C_1$–$C_6$alkoxy, trifluoromethyl, hydroxy, phenyl, phenoxy, —$SO_2NH_2$ or

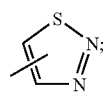

or
—$NR_{48}R_{49}$ wherein $R_{48}$ and $R_{49}$ are each independently hydrogen or $C_1$–$C_2$alkyl;
each $R_{31}$, $R_{32}$, $R_{33}$, $R_{34}$, $R_{35}$, $R_{36}$, $R_{37}$, $R_{38}$, $R_{39}$, $R_{40}$, $R_{68}$, and $R_{69}$ is independently hydrogen or $C_1$–$C_6$alkyl;
each $R_{29}$, $R_{30}$ is independently hydrogen, phenyl or $C_1$–$C_6$alkyl;

each $R_{83}$, $R_{84}$, $R_{86}$, $R_{87}$, $R_{88}$, $R_{89}$, $R_{92}$, $R_{93}$, $R_{98}$, $R_{99}$, $R_{94}$, $R_{95}$, $R_{100}$, $R_{101}$, $R_{103}$, $R_{104}$, $R_{105}$, $R_{106}$, $R_{108}$, $R_{109}$, $R_{110}$, $R_{111}$, $R_{113}$, $R_{114}$, $R_{115}$, $R_{116}$, $R_{117}$, $R_{118}$, $R_{119}$, $R_{120}$, $R_{122}$, $R_{123}$, $R_{124}$, $R_{125}$, $R_{127}$, $R_{128}$, $R_{130}$, $R_{131}$, $R_{133}$, $R_{134}$, $R_{135}$, $R_{136}$, $R_{137}$, $R_{138}$, $R_{139}$ and $R_{140}$ is independently hydrogen or $C_1$–$C_6$alkyl;
each $R_{63}$, $R_{64}$ and $R_{65}$ is independently hydrogen, halogen, $C_1$–$C_6$alkyl or $C_1$–$C_6$alkoxy;
each $R_{66}$ is independently hydrogen, hydroxy, $C_1$–$C_6$alkyl or $C_1$–$C_6$alkoxy;
Q is $CH_2$, CHOH or C=O;
$X_5$ is O or S;
each $R_{67}$ is independently hydrogen or $C_1$–$C_6$alkyl;
$R_{70}$ is hydrogen, $C_1$–$C_6$alkyl, halogen, nitro or a phenyl group optionally mono-substituted with $C_1$–$C_6$alkyl, halogen or trifluoromethyl;
$R_{81}$ is hydrogen, $C_1$–$C_6$alkyl, or —$CO_2C_1$–$C_6$alkyl;
$R_{91}$ is hydrogen, halogen, $C_1$–$C_6$alkyl or $C_1$–$C_6$alkoxy;
$R_{96}$ is hydrogen, $C_1$–$C_6$alkyl or

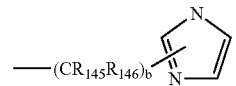

wherein $R_{145}$ and $R_{146}$ are each independently hydrogen or $C_1$–$C_6$alkyl and b is 0, 1 or 2;
$R_{97}$ is hydrogen or $C_1$–$C_6$alkyl;
each $R_{102}$ is independently hydrogen, halogen, $C_1$–$C_6$alkyl or $C_1$–$C_6$alkoxy;
$R_{107}$ is hydrogen or $C_1$–$C_6$alkyl;
each $R_{121}$ is independently hydrogen, halogen, $C_1$–$C_6$alkyl or $C_1$–$C_6$alkoxy;
$R_{127}$ is hydrogen or $C_1$–$C_6$alkyl;
$R_{126}$ is $C_1$–$C_6$alkyl or benzyl;
$R_{129}$ is hydrogen or $C_1$–$C_6$alkyl;
$R_{132}$ is hydrogen, $C_1$–$C_6$alkyl, halogen or $C_1$–$C_6$alkoxy;
$X_3$ is O or —$NR_{127}$ wherein $R_{127}$ is hydrogen or $C_1$–$C_6$alkyl;
$X_4$ is O, S or —$NR_{143}$ wherein $R_{143}$ is hydrogen or $C_1$–$C_6$alkyl;
$R_{141}$ is hydrogen, $C_1$–$C_6$alkyl or amino;
$R_{142}$ is benzyl or phenyl each of which may be optionally substituted with $C_1$–$C_6$alkyl, halogen or $C_1$–$C_6$alkoxy;
$R_{144}$ is hydrogen or $C_1$–$C_6$alkyl;
$R_{85}$ is hydrogen, $C_1$–$C_6$alkoxy, $C_1$–$C_6$alkyl, —$CO_2C_1$–$C_6$alkyl, $C(O)C_1$–$C_6$alkyl or a group selected from the following:

a)
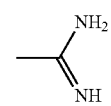

b)
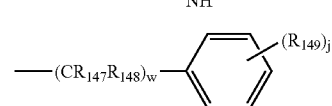

-continued

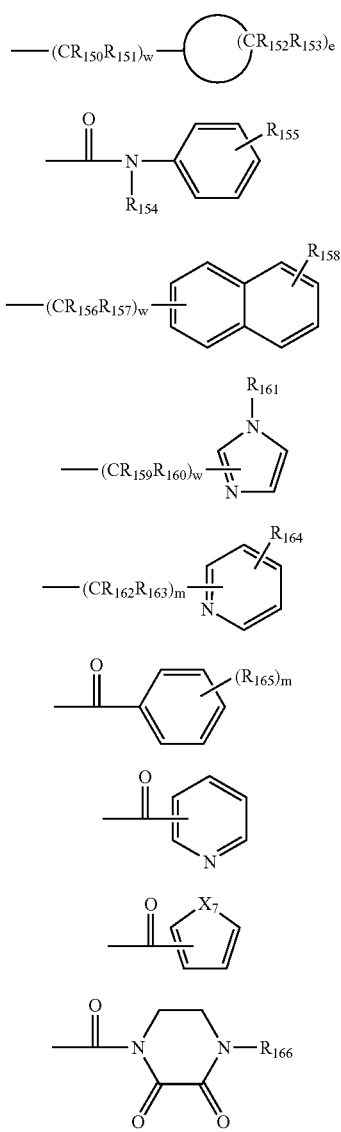

wherein
j is 0, 1, 2 or 3;
w is 1, 2 or 3;
m is 0, 1 or 2;
e is 2, 3, 4, 5, 6 or 7;
each $R_{147}$, $R_{148}$, $R_{150}$, $R_{151}$, $R_{152}$, $R_{153}$, $R_{156}$, $R_{157}$, $R_{159}$, $R_{160}$ $R_{162}$ and
$R_{163}$ is independently hydrogen or $C_1$–$C_6$alkyl;
$R_{149}$ is hydrogen, halogen, $C_1$–$C_6$alkyl, phenoxy, trifluoromethyl or trifluoromethoxy;
$R_{155}$ is hydrogen, halogen or $C_1$–$C_6$alkyl;
$R_{158}$ is hydrogen or $C_1$–$C_6$alkyl;
$R_{161}$ is hydrogen or $C_1$–$C_6$alkyl;
$R_{164}$ is hydrogen, halogen, $C_1$–$C_6$alkyl or trifluoromethyl;
$R_{165}$ is hydrogen, $C_1$–$C_6$alkyl or halogen;
$X_7$ is O or S or —$NR_{167}$ wherein $R_{167}$ is hydrogen or $C_1$–$C_6$alkyl;
$R_{166}$ is hydrogen or $C_1$–$C_6$alkyl;

or $R_1$ and $R_2$ are joined together to form a pyrrolidinyl ring, and in which the ring is optionally mono- or di-substituted, the substituents independently selected from:

(1) $C_1$–$C_6$alkyl;
(2) —$CO_2$—($C_1$–$C_6$alkyl);
(3) —$NR_{50}R_{51}$ wherein $R_{50}$ and $R_{51}$ are each independently hydrogen, $C_1$–$C_6$alkyl, or a phenyl group which is optionally mono- or disubstituted with substituents independently selected from $C_1$–$C_6$alkyl, halogen or trifluoromethyl;
(4) —C(O)phenyl wherein the phenyl group is optionally mono- or disubstituted with substituents independently selected from $C_1$–$C_6$alkyl, halogen or trifluoromethyl;
(5) —$(CH_2)_mOR_{52}$ wherein $R_{52}$ is hydrogen or $C_1$–$C_2$alkyl or a phenyl group which is optionally mono- or disubstituted with substituents independently selected from $C_1$–$C_6$alkyl, halogen or trifluoromethyl, and m is 0, 1 or 2;
(6) —$NR_{54}$—$COR_{53}$ wherein $R_{54}$ is hydrogen or $C_1$–$C_6$alkyl and $R_{53}$ is hydrogen or $C_1$–$C_2$alkyl;
(7) =O;
(8) —CN;

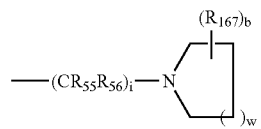 (9)

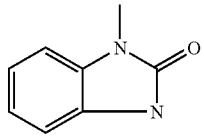 (10)

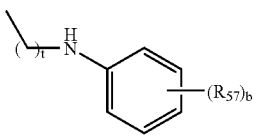 (11)

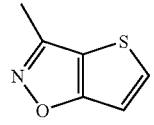 (12)

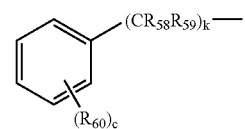 (13)

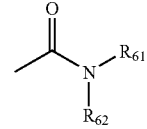 (14)

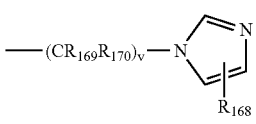 (15)

-continued

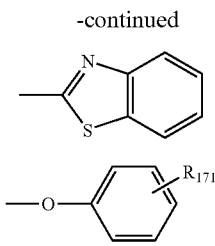
(16)

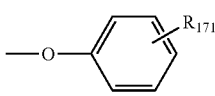
(17)

wherein
b is 0, 1 or 2;
w is 1, 2 or 3;
t is 0 or 1;
i is 0, 1 or 2;
v is 0, 1, 2, 3 or 4;
k is 0 or 1;
c are 0, 1 or 2;
$R_{167}$ is hydrogen or $C_1$–$C_6$alkyl;
each $R_{55}$, $R_{56}$, $R_{58}$, $R_{59}$, $R_{169}$ and $R_{170}$ is independently hydrogen or $C_1$–$C_6$alkyl;
each $R_{57}$ is independently hydrogen, halogen or $C_1$–$C_6$alkyl;
each $R_{60}$ is independently hydrogen, halogen or $C_1$–$C_6$alkyl;
$R_{61}$ and $R_{62}$ are each independently hydrogen or $C_1$–$C_6$alkyl;
$R_{168}$ is hydrogen, thienyl or furanyl;
$R_{171}$ is hydrogen, $C_1$–$C_6$alkyl, halogen, trifluoromethyl or trifluoromethoxy;

or $R_1$ and $R_2$ are joined together to form a group of formula X;

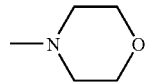
(X)

or $R_1$ and $R_2$ are joined together to form the group of formula (Y)

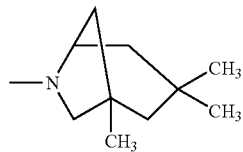
(Y)

or $R_1$ and $R_2$ are joined together to form any of the following groups:

(a)

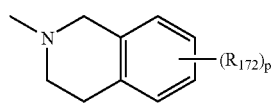
(b)

-continued

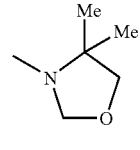
(c)

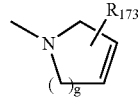
(d)

(e)

wherein
g is 1 or 2;
p is 0, 1 or 2;
$R_{172}$ is hydrogen, $C_1$–$C_6$alkyl or $C_1$–$C_6$alkoxy;
$R_{173}$ is hydrogen, $C_1$–$C_6$alkyl or phenyl optionally mono- or disubstituted with $C_1$–$C_6$alkyl or halogen; and
$R_{82}$ is a substituent selected from the following groups:
(a) $C_1$–$C_6$alkyl optionally substituted with hydroxy;
(b) $C_1$–$C_6$alkenyl;
(c) $C_1$–$C_6$alkoxy;
(d) —(CH$_2$)OC$_1$–$C_6$alkyl;

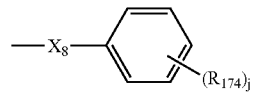
(e)

wherein $X_8$ is —(CR$_{175}$R$_{176}$)$_h$— or —(CR$_{177}$=CR$_{188}$)—
wherein each $R_{174}$ is independently hydrogen, $C_1$–$C_6$alkyl, halogen, trifluoromethyl, $C_1$–$C_6$alkoxy or benzyloxy;
h is 0, 1, 2 or 3 as hereinbefore defined each $R_{175}$, $R_{176}$, $R_{177}$ and $R_{178}$ is independently hydrogen or $C_1$–$C_6$alkyl; and
j is 0, 1, 2 or 3;

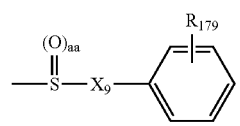
(f)

wherein $X_9$ is —(CR$_{180}$R$_{181}$)$_j$— or —(CR$_{184}$R$_{185}$CR$_{186}$=C$_{187}$)— or —(CR$_{182}$=CR$_{183}$)—
wherein
aa is 0 or 2;
$R_{179}$ is hydrogen, $C_1$–$C_6$alkyl, halogen, trifluoromethyl, $C_1$–$C_6$alkoxy, benzyloxy or phenyl;
each $R_{180}$, $R_{181}$, $R_{182}$, $R_{183}$, $R_{184}$, $R_{185}$, $R_{186}$ and $R_{187}$ is independently hydrogen or $C_1$–$C_6$alkyl;

j is 0, 1, 2, or 3;

(g) 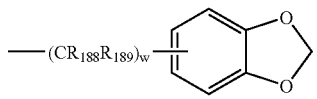

wherein w is 1, 2 or 3;
each $R_{188}$ and $R_{189}$ is independently hydrogen or $C_1$–$C_6$alkyl;

(h) 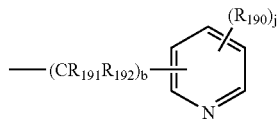

wherein
i is 0, 1 or 2;
each $R_{190}$ is independently hydrogen, alkyl or halogen;
b is 0, 1, or 2;
each $R_{191}$ and $R_{192}$ is independently hydrogen or $C_1$–$C_6$alkyl;

(i) 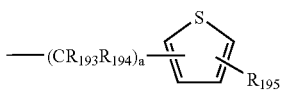

wherein
a is 1, 2 or 3;
each $R_{193}$ and $R_{194}$ is independently hydrogen or $C_1$–$C_6$alkyl;
$R_{195}$ is hydrogen, halogen or $C_1$–$C_6$alkyl;

(j) 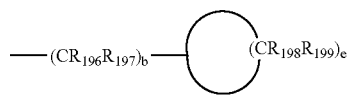

wherein
e is 2, 3, 4, 5 or 6;
b is 0, 1 or 2;
each $R_{196}$ and $R_{197}$ is independently hydrogen or $C_1$–$C_6$alkyl;
each $R_{198}$ and $R_{199}$ is independently hydrogen or $C_1$–$C_6$alkyl;

(k) 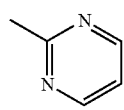

-continued (l) 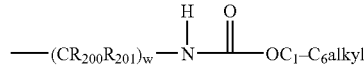

wherein
each $R_{200}$ and $R_{201}$ is independently hydrogen or $C_1$–$C_6$alkyl;
w is 1, 2 or 3;

(m) 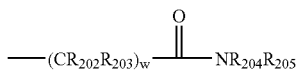

wherein
each $R_{202}$, $R_{203}$, $R_{204}$ and $R_{205}$ is independently hydrogen or $C_1$–$C_6$alkyl; and
w is 1, 2 or 3;

(n) —$(CR_{206}R_{207})_w$—$OC_1$–$C_6$alkyl
wherein
$C_1$–$C_6$alkyl is optionally substituted with hydroxy;
each $R_{206}$ and $R_{207}$ is independently hydrogen or $C_1$–$C_6$alkyl; and
w is 1, 2 or 3;

(o) —$(CR_{208}R_{209})_w$—$NR_{210}R_{211}$
wherein
each $R_{208}$, $R_{209}$, $R_{210}$ and $R_{211}$ is independently hydrogen or $C_1$–$C_6$alkyl;
w is 1, 2 or 3;

(p) 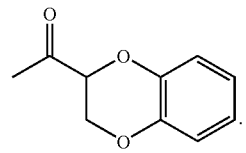

2. The compound of claim 1 wherein R is group (a).
3. The compound of claim 2 wherein $R_4$ is halogen or $CF_3$.
4. The compound of claim 3 wherein $R_2$ is group (a).
5. The compound of claim 4 wherein z is 0 or 1;
e is 5 and each $R_{27}$ and $R_{28}$ is independently selected from hydrogen or $C_1$–$C_6$alkyl.
6. The compound of claim 3 wherein $R_2$ is group (b).
7. The compound of claim 6 wherein M is hydrogen, $C_1$–$C_6$alkoxy or $C_1$–$C_6$alkyl and u is 0 or 1.
8. The compound of claim 3 wherein $R_2$ is group (n).
9. The compound of claim 8 wherein $R_{70}$ is hydrogen and f is 3.
10. The compound of claim 1 wherein R is group (k).
11. The compound of claim 10 wherein $R_{12}$ is hydrogen, $C_1$–$C_6$alkyl, or —$CH_2OC_1$–$C_6$alkyl.
12. The compound of claim 11 wherein wherein $R_2$ is group (a).

13. The compound of claim 12 wherein z is 0 or 1; e is 5 and each $R_{27}$ and $R_{28}$ is independently selected from hydrogen or $C_1$–$C_6$alkyl.

14. The compound of claim 11 wherein $R_2$ is group (b).

15. The compound of claim 14 wherein M is hydrogen, $C_1$–$C_6$alkoxy or $C_1$–$C_6$alkyl and u is 0 or 1.

16. The compound of claim 11 wherein $R_2$ is group (n).

17. The compound of claim 16 wherein $R_{70}$ is hydrogen and f is 3.

18. The compound of claim 1 which is 2-[4-(6-trifluoromethyl-benzo[b]thiophen-3-yl)-piperazin-1-ylmethyl]-trans-cyclopropanecarboxylic acid (trans-4-ethyl-cyclohexyl)-amide.

19. The compound of claim 1 which is 2-[4-(6-trifluoromethyl-benzo[b]thiophen-3-yl)-piperazin-1-ylmethyl]-(2R, 3R)-cyclopropanecarboxylic acid (trans-4-methyl-cyclohexyl)-amide.

20. The compound of claim 1 which is 4-[4-(6-fluoro-benzo[b]thiophen-3-yl)-piperazin-1-yl]-N-(trans-4-methyl-cyclohexyl)-butyramide.

21. The compound of claim 1 which is 2-(4-thieno[2,3-d]isoxazol-3-yl-piperazin-1-ylmethyl)-(2R, 3R)-cyclopropanecarboxylic acid (trans-4-methyl-cyclohexyl)-amide.

22. The compound of claim 1 which is 2R-[4-(1-Methyl-1H-thieno[3,2-c]pyrazol-3-yl)-piperazin-1-ylmethyl]-cyclopropane-1R-carboxylic trans-(4-methyl-cyclohexyl)-amide.

23. The compound of claim 1 which is 2R-(4-Thieno[2,3-d]isoxazol-3-yl-piperazin-1-ylmethyl)-1R-cyclopropanecarboxylic acid (3-imidazol-1-yl-propyl)-amide.

24. The compound of claim 1 which is 1-{2-[4-(6-Trifluoromethyl-benzo[b]thiophen-3-yl)-piperazin-1-yl]-ethyl}-cyclopropanecarboxylic acid (3-imidazol-1-yl-propyl)-amide.

25. A pharmaceutical composition comprising an effective amount of a compound of claim 1 with a pharmaceutically-acceptable carrier or diluent.

26. A pharmaceutical composition comprising an effective amount of a compound of claim 1 with a pharmaceutically-acceptable carrier or diluent in conjunction with one or more dopamine $D_1$, $D_2$, $D_4$, $D_5$ or 5HT receptor antagonists.

27. A process for preparing a compound of formula I of claim 1 which comprises:

(a) reacting a compound of formula (II):

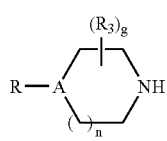

(II)

wherein $R_3$, g, y, R, A and n are as defined in formula I of claim 1;
with a compound of formula (III)

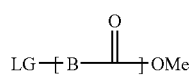

(III)

wherein "LG" is a suitable leaving group selected from chlorine, bromine, iodine and mesyl; and

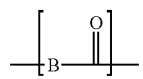

and
is as defined in formula I of claim 1;
to provide a compound of formula (IV)

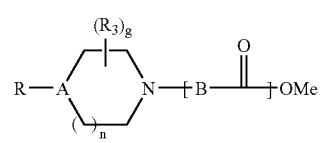

(IV)

(b) hydrolyzing a compound of formula (IV) to provide a compound of formula (V)

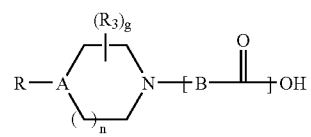

(V)

and (c) reacting a compound of formula (V) with a compound of formula (VI)

(VI)

wherein $R_1$ and $R_2$ are as defined in formula (I) of claim 1;
to provide the compound of formula (I).

28. A process for preparing compounds of formula I of claim 1 which comprises:

(a) reacting a compound of formula (VII)

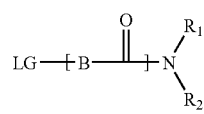

(VII)

wherein "LG" is a suitable leaving group selected from chlorine, bromine, iodine and mesyl; and

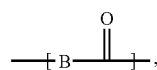

and $R_1$ and $R_2$ are as defined in formula I of claim 1;
with a compound of formula (II)

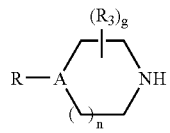

(II)

wherein $R_3$, g, y, R, A and n are as defined in formula I of claim 1;
to provide the compound of formula (I).

29. A process for preparing a compound of formula (XII)

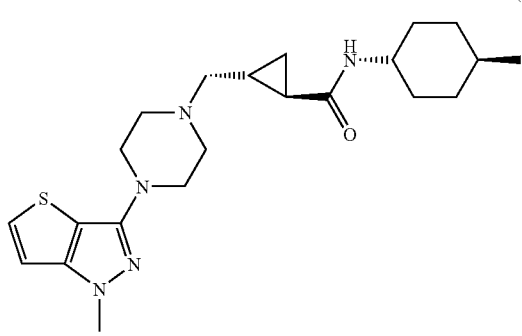

(XII)

comprising the step of coupling a compound of formula (XIII)

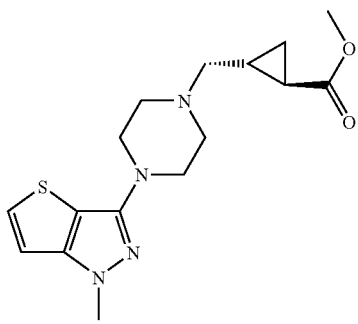

(XIII)

with a compound of formula (XIV)

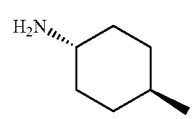

(XIV)

to provide the compound of formula (XII).

30. The compound of claim 1 wherein R is (a).
31. The compound of claim 1 wherein R is (h).
32. The compound of claim 1 wherein R is (i).
33. The compound of claim 1 wherein R is (k).
34. The compound of claim 1 wherein R is (n).
35. The compound of claim 1 wherein R is (o).
36. The compound of claim 1 wherein R is (p).
37. The compound of claim 1 wherein R is (q).
38. The compound of claim 1 wherein R is (r).
39. The compound of claim 1 wherein R is (t).
40. The compound of claim 1 wherein R is (w).

* * * * *